(12) United States Patent
Alphandery

(10) Patent No.: US 11,918,652 B2
(45) Date of Patent: Mar. 5, 2024

(54) NANOPARTICLES SEQUENTIALLY EXPOSED TO LOW INTENSITY ACOUSTIC WAVES FOR MEDICAL OR COSMETIC APPLICATIONS

(71) Applicant: NANOBACTERIE, Paris (FR)

(72) Inventor: Edouard Alphandery, Paris (FR)

(73) Assignee: NANOBACTERIE, Paris (FR)

( * ) Notice: Subject to any disclaimer, the term of this patent is extended or adjusted under 35 U.S.C. 154(b) by 840 days.

(21) Appl. No.: 16/486,574

(22) PCT Filed: Nov. 29, 2018

(86) PCT No.: PCT/IB2018/001460
§ 371 (c)(1),
(2) Date: Aug. 16, 2019

(87) PCT Pub. No.: WO2019/106428
PCT Pub. Date: Jun. 6, 2019

(65) Prior Publication Data
US 2020/0000914 A1    Jan. 2, 2020

(30) Foreign Application Priority Data

Nov. 30, 2017   (EP) .................................... 17020555
Nov. 30, 2017   (EP) .................................... 17020556
(Continued)

(51) Int. Cl.
*A61K 41/00*   (2020.01)
*A61K 9/00*    (2006.01)
(Continued)

(52) U.S. Cl.
CPC ........ *A61K 41/0033* (2013.01); *A61K 9/0009* (2013.01); *A61N 7/02* (2013.01); *G01N 29/09* (2013.01); *G01N 29/11* (2013.01)

(58) Field of Classification Search
CPC ....................................................... A61N 7/02
See application file for complete search history.

(56) References Cited

U.S. PATENT DOCUMENTS

| 9,138,476 | B2 | 9/2015 | Kosheleva et al. |
| 9,427,466 | B2 | 8/2016 | Kosheleva et al. |

(Continued)

FOREIGN PATENT DOCUMENTS

| WO | 2011/061259 A1 | 5/2011 |
| WO | 2017/068252 A1 | 4/2017 |

OTHER PUBLICATIONS

Yu-Wei Chen et al. "A theranostic nrGO@MSN-ION nanocarrier developed to enhance the combination effect of sonodynamic therapy and ultrasound hyperthermia for treating tumor." Nanoscale, vol. 8, 2016, pp. 12648-12657, published Feb. 3, 2016. (Year: 2016).*

(Continued)

*Primary Examiner* — Isaac Shomer
(74) *Attorney, Agent, or Firm* — Maier & Maier, PLLC

(57) ABSTRACT

An acoustic wave medical treatment of a body part of an individual in which nanoparticles are administered to the body part of the individual and the acoustic wave is applied on the body part. The acoustic wave is sequentially applied on the body part, and/or the nanoparticles are magnetosomes. Also, compositions that include these nanoparticles.

28 Claims, 12 Drawing Sheets

(30) Foreign Application Priority Data

Apr. 11, 2018 (EP) .................................... 18020142
Apr. 11, 2018 (EP) .................................... 18020143

(51) Int. Cl.
*A61N 7/02* (2006.01)
*G01N 29/09* (2006.01)
*G01N 29/11* (2006.01)

(56) References Cited

U.S. PATENT DOCUMENTS

| | | | |
|---|---|---|---|
| 2008/0027359 A1* | 1/2008 | Thierman | A61N 7/02 601/3 |
| 2008/0045865 A1* | 2/2008 | Kislev | A61B 5/411 601/3 |
| 2012/0089137 A1* | 4/2012 | Peyman | A61K 49/0093 606/28 |
| 2012/0302819 A1 | 11/2012 | Alphandery et al. | |
| 2014/0212502 A1* | 7/2014 | Liu | A61K 41/0028 424/490 |
| 2014/0335156 A1* | 11/2014 | Kosheleva | A61K 41/0033 424/178.1 |
| 2016/0287911 A1* | 10/2016 | Boer | A61B 5/444 |
| 2020/0000914 A1 | 1/2020 | Alphandery | |

OTHER PUBLICATIONS

Herbert Kent. "Warts and Ultrasound." Archives of Dermatology, vol. 100, Jul. 1969, pp. 79-81. (Year: 1969).*
Wei-Peng Li et al. "Ultrasound-Induced Reactive Oxygen Species Mediated Therapy and Imaging Using a Fenton Reaction Activable Polymersome." ACS Nano, vol. 10, 2016, pp. 2017-2027 and supplemental pp. 1-30 (41 total sheets). Published Dec. 31, 2015. (Year: 2015).*
A. Jozefczak et al. "Magnetic nanoparticles for enhancing the effectiveness of ultrasonic hyperthermia." Applied Physics Letters, vol. 108, 2016, pp. 263701-1 to 263701-5. (Year: 2016).*
Dustin E. Kruse et al. "Spatial and Temporal-Controlled Tissue Heating on a Modified Clinical Ultrasound Scanner for Generating Mild Hyperthermia in Tumors." IEEE Transactions on Biomedical Engineering, vol. 57, No. 1, Jan. 2010, pp. 155-166. (Year: 2010).*
A. Jozefczak, K. Kaczmarek, T. Hornowski, M. Kubovcikova, Z. Rozynek, M. Timko, and A. Skumiel. "Magnetic nanoparticles for enhancing the effectiveness of ultrasonic hyperthermia." Applied Physics Letters, vol. 108, Article 263701, 2016, pp. 263701-1 to 263701-5. (Year: 2016).*
International Preliminary Report on Patentability issued in International Application No. PCT/IB2018/001460; 8 pages.
Search Report dated Jun. 13, 2018 in corresponding European Application No. 17020555.3; 8 pages.
Search Report dated Oct. 29, 2018 in corresponding European Application No. 18020142.8; 8 pages.
International Search Report and Written Opinion of the International Searching Authority dated Apr. 8, 2019 in corresponding International application No. PCT/IB2018/001460; 10 pages.
Józefczak et al., "The Effect of Sonication on Acoustic Properties of Biogenic Ferroparticle Suspension", Archives of Acoustics, Mar. 2016, p. 161-168, vol. 41, No. 1; 8 pages.
Hergt et al., "Magnetic properties of bacterial magnetosomes as potential diagnostic and therapeutic tools", Journal of Magnetism and Magnetic Materials, May 2005, p. 80-86, vol. 293, No. 1; 7 pages.
Józefczak et al., "Magnetic nanoparticles for enhancing the effectiveness of ultrasonic hyperthermia", Applied Physics Letters, 2016, vol. 108; 6 pages.
Office Action dated Nov. 18, 2022, in corresponding Japanese Application No. 2020-528904, 8 pages.
Notice of Allowance dated Apr. 28, 2015, in related U.S. Appl. No. 14/253,977, 10 pages.
Office Action dated Nov. 14, 2022, in corresponding Chinese Application No. 201880076134.8, 11 pages.

* cited by examiner

NANOPARTICLES SEQUENTIALLY EXPOSED TO LOW INTENSITY ACOUSTIC WAVES FOR MEDICAL OR COSMETIC APPLICATIONS

FIELD OF INVENTION

This invention is related to nanoparticles being sequentially exposed to low intensity acoustic waves for medical treatment.

TECHNICAL BACKGROUND

Diseases such as cancers, for example prostate cancer, can currently be treated with ultrasound, usually using high intensity focused ultrasound (HIFU). However, this treatment method presents several drawbacks. To be efficient, HIFU usually requires to heat cancer tissues at relatively high temperatures, which can be damaging for healthy tissues. Using HIFU often necessitates heating the tumor in several spots to eradicate it. To overcome these drawbacks, low intensity ultrasound (LIU) could be used instead of HIFU. In this invention, we propose a method to make LIU efficient for medical treatment. It is based on the use of nanoparticles located in a pathological site, which are sequentially exposed to acoustic waves of low intensity (Nature Reviews Cancer, V. 5, P. 321 (2005)).

SUMMARY

The invention also relates to nanoparticles for use in an acoustic wave medical treatment of a body part of an individual, wherein the nanoparticles are administered to the body part of the individual and the acoustic wave is applied on the body part, wherein:

The acoustic wave is sequentially applied on the body part, and/or

The nanoparticles are magnetosomes.

The invention also relates to nanoparticles for use in radiation medical treatment of a body part of an individual, wherein the nanoparticles are administered to the body part of the individual and the radiation is applied on the body part, wherein:

The radiation is sequentially applied on the body part, and/or

The nanoparticles are magnetosomes.

The invention also relates to nanoparticles for use in radiation or acoustic wave medical treatment of a body part of an individual, wherein the nanoparticles are administered to the body part of the individual and the radiation or acoustic wave is applied on the body part, wherein:

The radiation or acoustic wave is sequentially applied on the body part, and/or

The nanoparticles are synthesized by a living organism, preferentially inside or outside the living organism.

The invention also relates to magnetosomes for use in an acoustic wave medical treatment or radiation medical treatment of a body part of an individual, wherein the magnetosomes are administered to the body part of the individual and the body part is exposed to the acoustics wave or radiation. In some cases, the magnetosomes are administered to the body part of the individual and the body part is exposed to the acoustic wave or radiation.

The invention also relates to nanoparticles for use in an acoustic wave medical treatment of a body part of an individual or in a radiation medical treatment of a body part of an individual, wherein the nanoparticles are administered to a body part of an individual and the acoustic wave or radiation is applied, preferentially sequentially, on the nanoparticles and/or body part.

The invention also relates to a method for treating a body part of an individual, comprising administering an effective amount of nanoparticles to the body part and applying, preferentially sequentially, an effective acoustic wave or radiation to the body part, wherein the nanoparticles are preferentially magnetosomes.

In some cases, the nanoparticles can be administered to the body part of the individual and the body part can be exposed, preferentially sequentially, to the acoustic wave or radiation.

In some cases, it can be equivalent to say that the acoustic wave is applied on the nanoparticles or body part than to say that the nanoparticle or body part is exposed to the acoustic wave or radiation.

The invention will be further described by the following non-limiting figures and examples.

Figure 1:
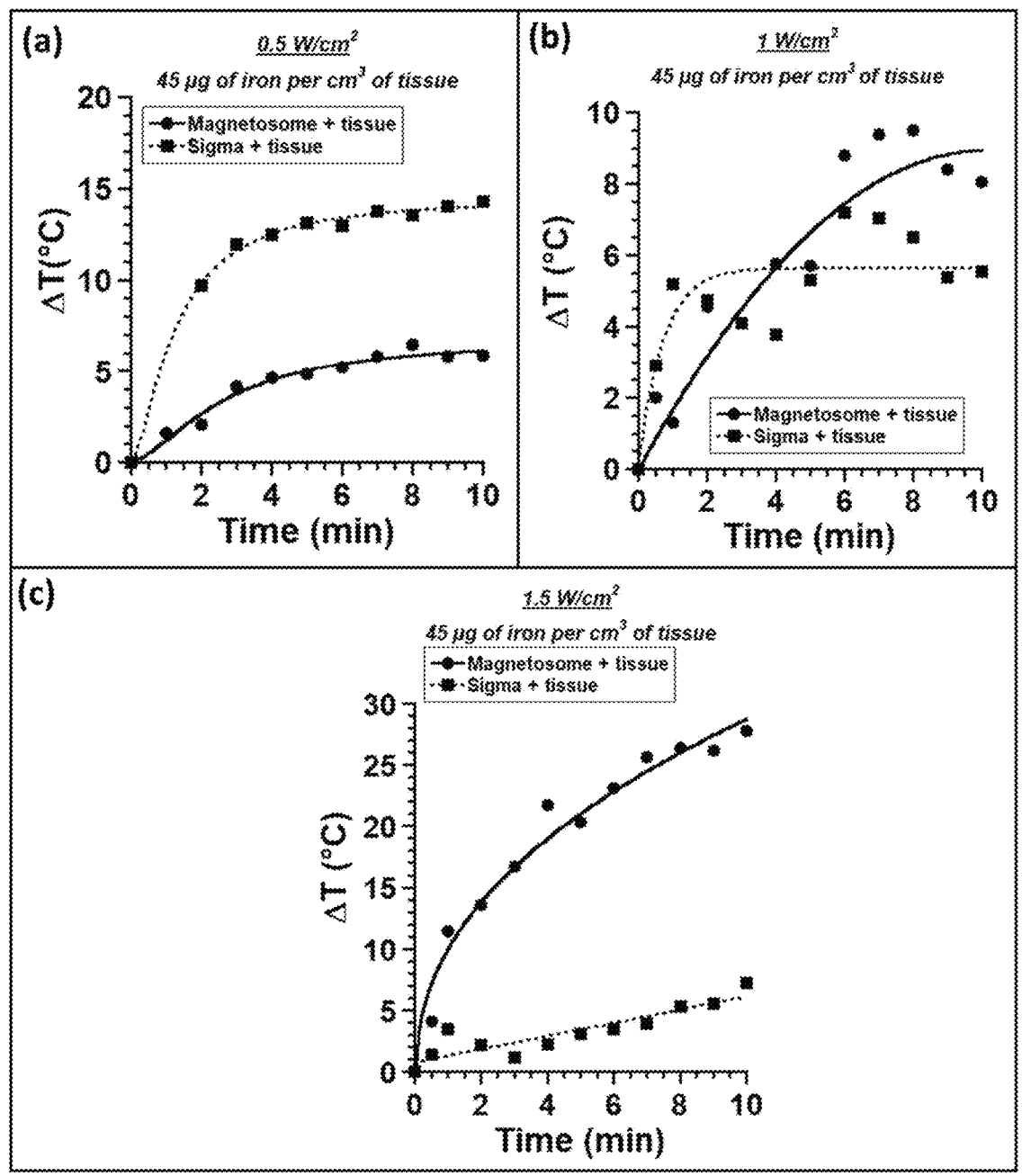
FIG. 1: (a) For 210 µg in iron of nanoparticles (magnetosomes or Sigma) inserted in 4.6 cm$^3$ of tissue exposed to ultrasounds of frequency 3 MHz and power 0.5 W/cm$^2$, ΔT, designing the temperature difference between the temperature measured for the tissue or body part with the nanoparticles and the temperature measured for the tissue or body part without the nanoparticles, as a function of duration of ultrasound application (time in minutes). (b) same as in (a) for an ultrasound power of 1 W/cm$^2$. (c) same as in (a) for an ultrasound power of 1.5 W/cm$^2$.

non-application of the laser during 18.5 seconds resulting in a temperature decrease from 45° C. to 37° C.; twelfth sequence: i) application of the laser an average power at 3 W/cm² during 18 seconds resulting in a temperature increase from 37° C. to 45° C., ii) non-application of the laser during 19.5 seconds resulting in a temperature decrease from 45° C. to 37° C.; thirteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fourteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fifteenth sequence: i) application of the laser of average power 3 W/cm² during 19.5 seconds resulting in a temperature increase from 37° C. to 45° C., ii) non-application of the laser during 21.5 seconds resulting in a temperature decrease from 45° C. to 37° C.; sixteenth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; seventeenth sequence: i) application of the laser of average power 3 W/cm² during 17.5 seconds resulting in a temperature increase from 37° C. to 45° C., ii) non-application of the laser during 19.5 seconds resulting in a temperature decrease from 45° C. to 37° C.; eighteenth sequence: i) application of the laser of average power 3 W/cm² during 17.5 seconds resulting in a temperature increase from 37° C. to 45° C., ii) non-application of the laser during 20 seconds resulting in a temperature decrease from 45° C. to 37° C.; nineteenth sequence: i) application of the laser of average power 3 W/cm² during 19 seconds resulting in a temperature increase from 37° C. to 45° C., ii) non-application of the laser during 18.5 seconds resulting in a temperature decrease from 45° C. to 37° C.

Figure 8:
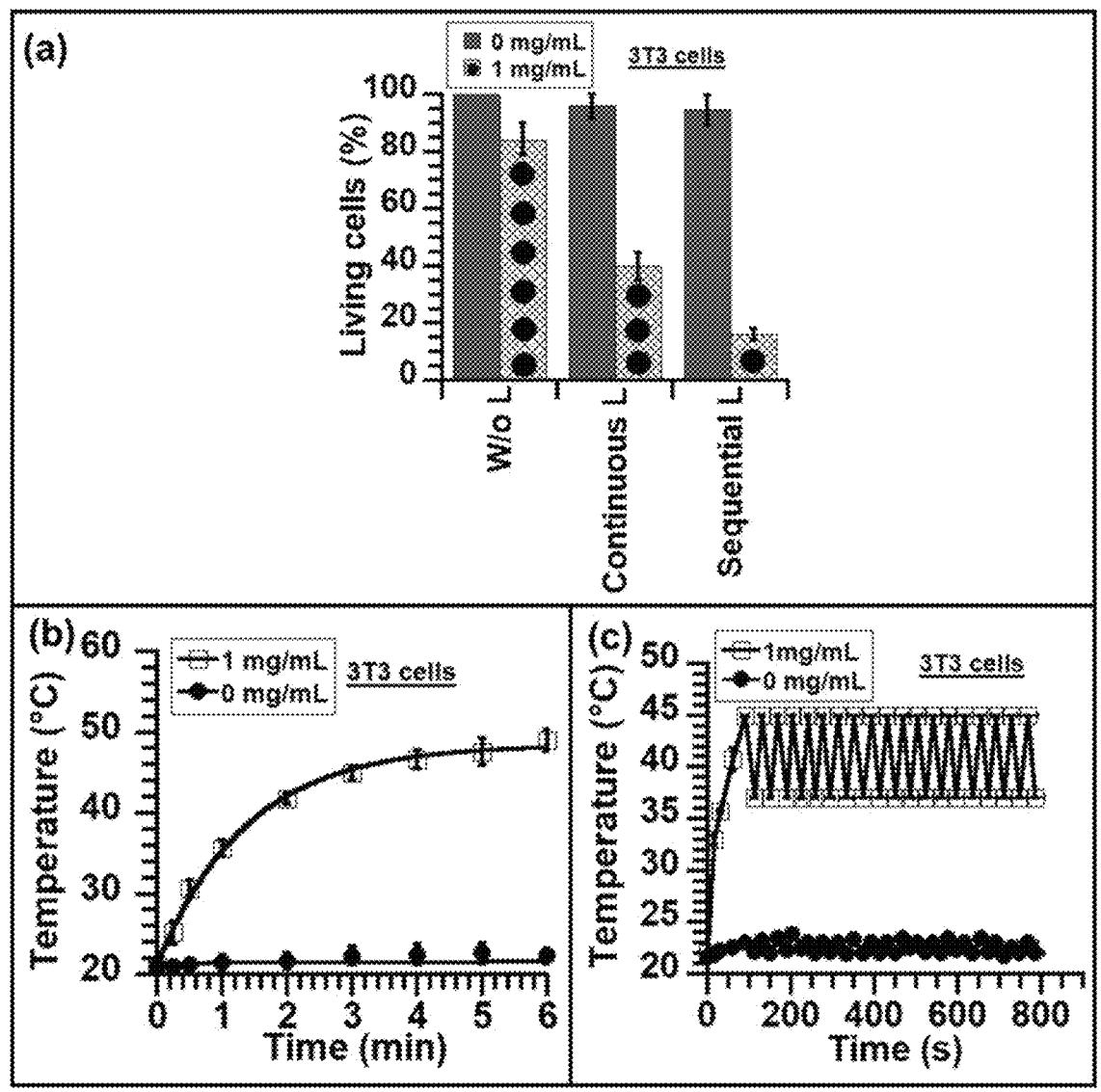
FIG. 8: (a) Percentage of living cells after the following treatment: 3T3 cells are brought into contact with 1 mg/mL in iron of magnetosomes or not brought into contact with magnetosomes (0 mg/mL) and either not exposed to the laser (W/o L), exposed sequentially to the laser with an average power at 3 W/cm², where the details of the sequences are given in the legend of (c) (Sequential L), or exposed continuously to the laser with an average power at 3 W/cm² during 6 minutes (continuous L). (b) Variation as a function of time of the temperature of 3T3 cells brought into contact with 0 mg/mL and 1 mg/mL of magnetosomes and exposed continuously to a laser with an average power at 3 W/cm² during 6 minutes. (c) Variation as a function of time of the temperature of 3T3 cells brought into contact with 0 mg/mL and 1 mg/mL of magnetosomes and sequentially exposed to a laser an average power at 3 W/cm². The details of the sequences are as follows: First sequence: i) application of the laser an average power at 3 W/cm² during 90 seconds until the temperature reaches 45° C., ii) non-application of the laser during 21 seconds resulting in a temperature decrease from 45° C. to 37° C.; Second sequence: i) application of the laser of average power 3 W/cm² during 17.5 seconds resulting in a temperature increase from 37° C. to 45° C., ii) non-application of the laser during 22 seconds resulting in a temperature decrease from 45° C. to 37° C.; Third sequence: i) application of the laser an average power at 3 W/cm² during 17.5 seconds resulting in a temperature increase from 37° C. to 45° C., ii) non-application of the laser during 20.5 seconds resulting in a temperature decrease from 45° C. to 37° C.; Fourth sequence: i) application of the laser of average power 3 W/cm² during 14.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm² during 15.5 seconds resulting in a temperature increase from 37° C. to 45° C., ii) non-application of the laser during 19 seconds resulting in a temperature decrease from 45° C. to 37° C.; sixth sequence: i) application of the laser of average power 3 W/cm² during 15.5 seconds resulting in a temperature increase from 37° C. to 45° C., ii) non-application of the laser during 19.5 seconds resulting in a temperature decrease from 45° C. to 37° C.; seventh sequence: i) application of the laser of average power 3 W/cm² during 18.5 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 18.5 seconds resulting in a temperature increase from 37° C. to 45° C., ii) non-application of the laser during 21 seconds resulting in a temperature decrease from 45° C. to 37° C.; ninth sequence: i) application of the laser of average power 3 W/cm² during 20 seconds resulting in a temperature increase from 37° C. to 45° C., ii) non-application of the laser during 20 seconds resulting in a temperature decrease from 45° C. to 37° C.; tenth sequence: i) application of the laser of average power 3 W/cm² during 18.5 seconds resulting in a temperature increase from 37° C. to 45° C., ii) non-application of the laser during 19.5 seconds resulting in a temperature decrease from 45° C. to 37° C.; eleventh sequence: i) application of the laser of average power 3 W/cm² during 17.5 seconds resulting in a temperature increase from 37° C. to 45° C., ii)
Figure 9:
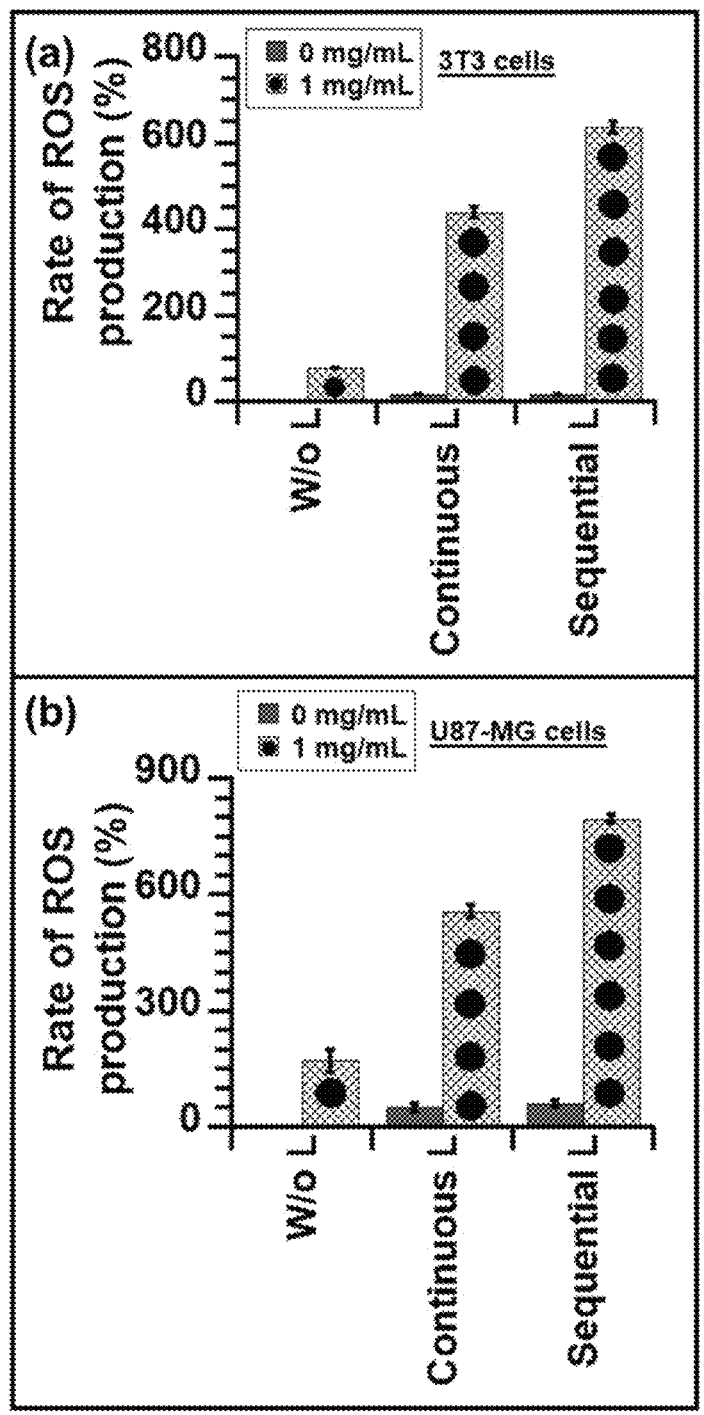

FIG. 9: (a), Rate of ROS production after the following treatment: 3T3 cells are brought into contact with 1 mg/mL in iron of magnetosomes (M-CMD) or not brought into contact with magnetosomes (0 mg/mL) and either not exposed to the laser (W/o L), or exposed continuously to the laser with average power of 3 W/cm2 during 6 minutes, or exposed sequentially to the laser with an average power at 3 W/cm2, where the details of the sequences are given in the legend FIG. 7(c). (b), Rate of ROS production after the following treatment: 3T3 cells are brought into contact with 1 mg/mL in iron of magnetosomes or not brought into contact with magnetosomes (0 mg/mL) and either not exposed to the laser (W/o L), exposed continuously to the laser with an average power at 3 W/cm2 during 6 minutes, exposed sequentially to the laser with an average power at 3 W/cm2, where the details of the sequences are given in FIG. 8(c).

Figure 10:
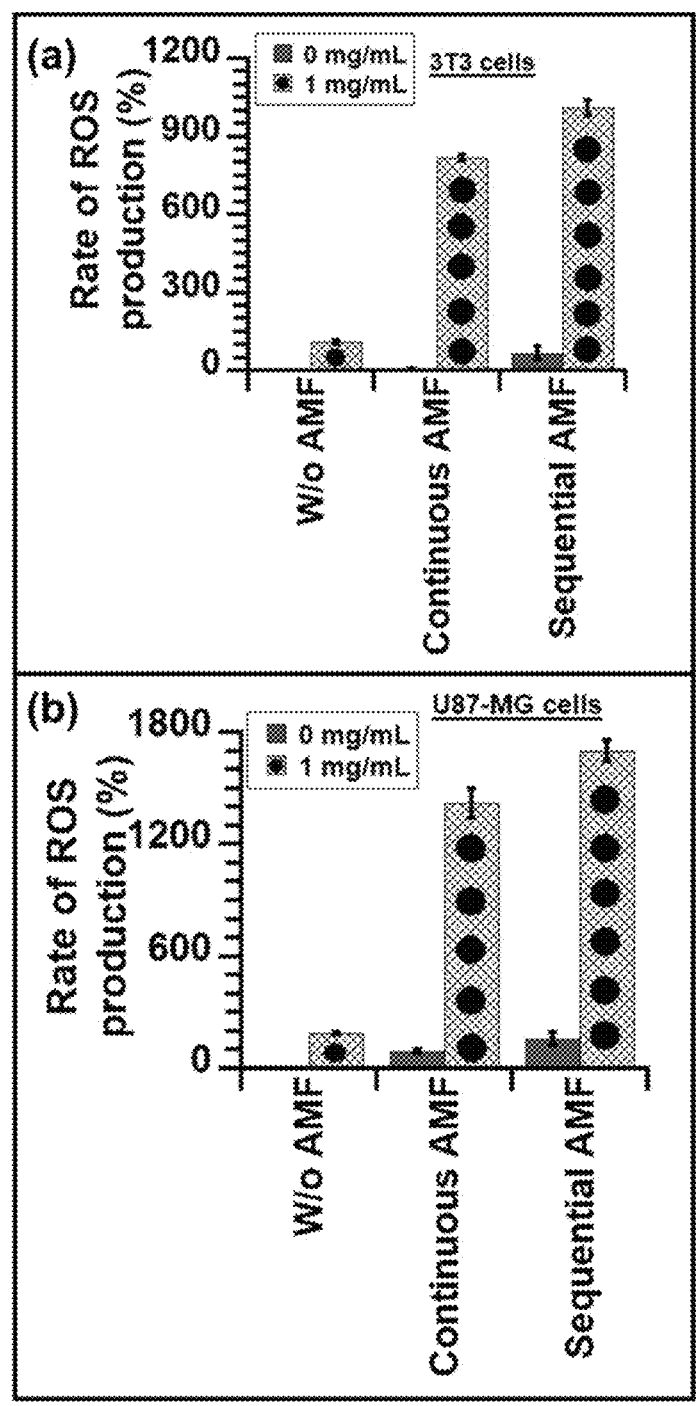

FIG. 10: (a), Rate of ROS production after the following treatment: 3T3 cells are brought into contact with 1 mg/mL in iron of magnetosomes or not brought into contact with magnetosomes (0 mg/mL) and either not exposed to the AMF (alternating magnetic field) (W/o AMF), or exposed continuously to the AMF with a strength of 34-47 mT and a frequency of 198 KHz during 30 minutes, or exposed sequentially to the AMF of strength 34-47 mT and frequency 198 KHz, where the details of the sequences are as follows: First sequence: i) application of the AMF with strength 34-47 mT and frequency 198 KHz during 5 minutes until the temperature reaches 45° C., ii) non-application of the AMF during 2.2 minutes resulting in a temperature decrease from 45° C. to 37° C.; Second sequence: i) application of AMF with strength of 34-47 mT and frequency 198 KHz during 3.7 minutes until the temperature reaches 45° C., ii) non-application of the AMF during 2.7 minutes resulting in a temperature decrease from 45° C. to 37° C.; Third sequence: i) application of the AMF with a strength of 34-47 mT and frequency of 198 KHz during 3.1 minutes until the temperature reaches 45° C., ii) non-application of the AMF during 2.3 minutes resulting in a temperature decrease from 45° C. to 37° C.; Fourth sequence: i) application of the AMF with strength 34-47 mT and frequency 198 KHz during 2.3 minutes until the temperature reaches 45° C., ii) non-application of the AMF during 2.5 minutes resulting in a temperature decrease from 45° C. to 37° C.; Fifth sequence: i) application of the AMF with strength 34-47 mT and frequency 198 KHz during 1.8 minutes until the temperature reaches 45° C., ii) non-application of the AMF during 1.5 minutes resulting in a temperature decrease from 45° C. to 37° C.; sixth sequence: i) application of the AMF with a strength of 34-47 mT and a frequency of 198 KHz during 2.2 minutes until the temperature reaches 45° C., ii) non-application of the AMF during 2.6 minutes resulting in a temperature decrease from 45° C. to 37° C.; seventh sequence: i) application of the AMF with a strength of 34-47 mT and a frequency of 198 KHz during 2.4 minutes until the temperature reaches 45° C., ii) non-application of the AMF during 2.9 minutes resulting in a temperature decrease from 45° C. to 37° C.; eighth sequence: i) application of the AMF of strength 34-47 mT and frequency 198 KHz during 2.8 minutes until the temperature reaches 45° C., ii) non-application of the AMF during 2.7 minutes resulting in a temperature decrease from 45° C. to 37° C.; ninth sequence: i) application of the AMF of strength 34-47 mT and frequency 198 KHz during 2.4 minutes until the temperature reaches 45° C., ii), non-application of the AMF during 2.4 minutes resulting in a temperature decrease from 45° C. to 37° C.; tenth sequence: i) application of the AMF of strength 34-47 mT and frequency 198 KHz during 2.1 minutes until the temperature reaches 45° C., ii), non-application of the AMF during 2.7 minutes resulting in a temperature decrease from 45° C. to 37° C. (b), Rate of ROS production after the following treatment: U87-MG cells were brought into contact with 1 mg/mL in iron of magnetosomes or not brought into contact with magnetosomes (0 mg/mL) and either not exposed to the AMF (W/o AMF), or exposed continuously to the AMF with a strength of 34-47 mT and frequency 198 KHz during 30 minutes, or exposed sequentially to the AMF with a strength of 34-47 mT and a frequency of 198 KHz, where the details of the sequences are as follows: First sequence: i) application of the AMF with a strength of 34-47 mT and a frequency of 198 KHz during 5 minutes until the temperature reaches 45° C., ii), non-application of the AMF during 2.2 minutes resulting in a temperature decrease from 45° C. to 37° C.; Second sequence: i) application of the AMF with a strength of 34-47 mT and a frequency of 198 KHz during 3.7 minutes until the temperature reaches 45° C., ii), non-application of the AMF during 2.7 minutes resulting in a temperature decrease from 45° C. to 37° C.; Third sequence: i) application of the AMF with a strength of 34-47 mT and a frequency of 198 KHz during 3.1 minutes until the temperature reaches 45° C., ii) non-application of the AMF during 2.3 minutes resulting in a temperature decrease from 45° C. to 37° C.; Fourth sequence: i) application of the AMF with a strength of 34-47 mT and a frequency of 198 KHz during 2.3 minutes until the temperature reaches 45° C., ii) non-application of the AMF during 2.5 minutes resulting in a temperature decrease from 45° C. to 37° C.; Fifth sequence: i) application of the AMF of strength 34-47 mT and frequency 198 KHz during 1.8 minutes until the temperature reaches 45° C., ii), non-application of the AMF during 1.5 minutes resulting in a temperature decrease from 45° C. to 37° C.; Sixth sequence: i) application of the AMF of strength 34-47 mT and frequency 198 KHz during 2.2 minutes until the temperature reaches 45° C., ii), non-application of the AMF during 2.6 minutes resulting in a temperature decrease from 45° C. to 37° C.; Seventh sequence: i) application of the AMF of strength 34-47 mT and frequency 198 KHz during 2.4 minutes until the temperature reaches 45° C., ii) non-application of the AMF during 2.9 minutes resulting in a temperature decrease from 45° C. to 37° C.; Eighth sequence: i) application of the AMF of strength 34-47 mT and frequency 198 KHz during 2.8 minutes until the temperature reaches 45° C., ii), non-application of the AMF during 2.7 minutes resulting in a temperature decrease from 45° C. to 37° C.; Ninth sequence: i) application of the AMF of strength 34-47 mT and frequency 198 KHz during 2.4 minutes until the temperature reaches 45° C., ii) non-application of the AMF during 2.4 minutes resulting in a temperature decrease from 45° C. to 37° C.; Tenth sequence: i) application of the AMF of strength 34-47 mT and frequency 198 KHz during 2.1 minutes until the temperature reaches 45° C., ii) non-application of the AMF during 2.7 minutes resulting in a temperature decrease from 45° C. to 37° C.

Figure 11:
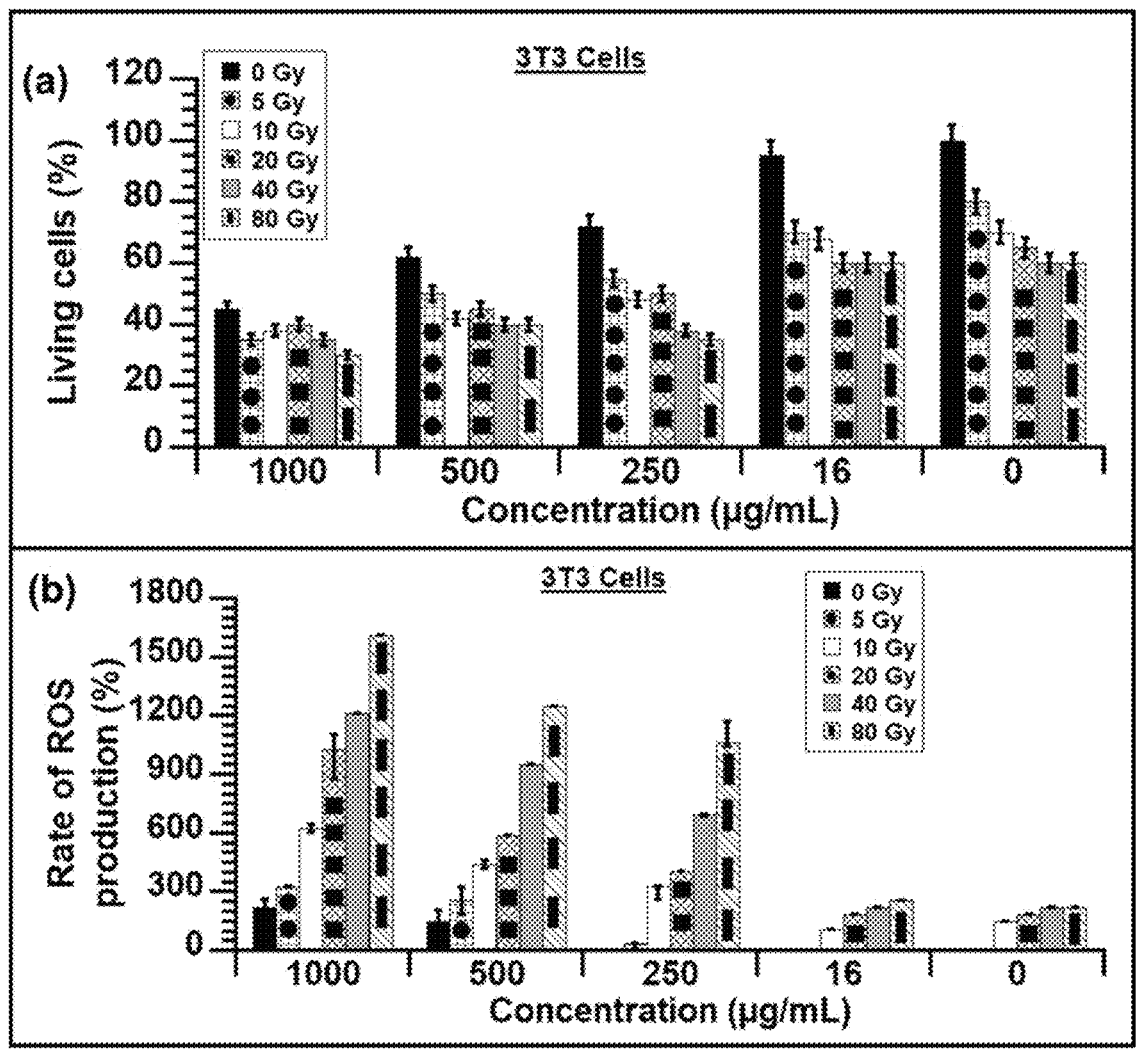

FIG. 11: (a), Percentage of living cells after the following treatment: 3T3 cells are brought into contact with 1000, 500, 250, 16 µg/mL in iron of magnetosomes or not brought into contact with magnetosomes (0 mg/mL) and either not exposed to gamma irradiation (control), exposed to different doses of gamma radiation: 5, 10, 20, 40 and 80 Gy. (b), Rate of ROS production after the following treatment: 3T3 cells are brought into contact with 1000, 500, 250, 16 µg/mL in iron of magnetosomes or not brought into contact with magnetosomes (0 mg/mL) and either not exposed to gamma radiation or exposed to different doses of gamma radiation (5, 10, 20, 40 and 80 Gy).

Figure 12:
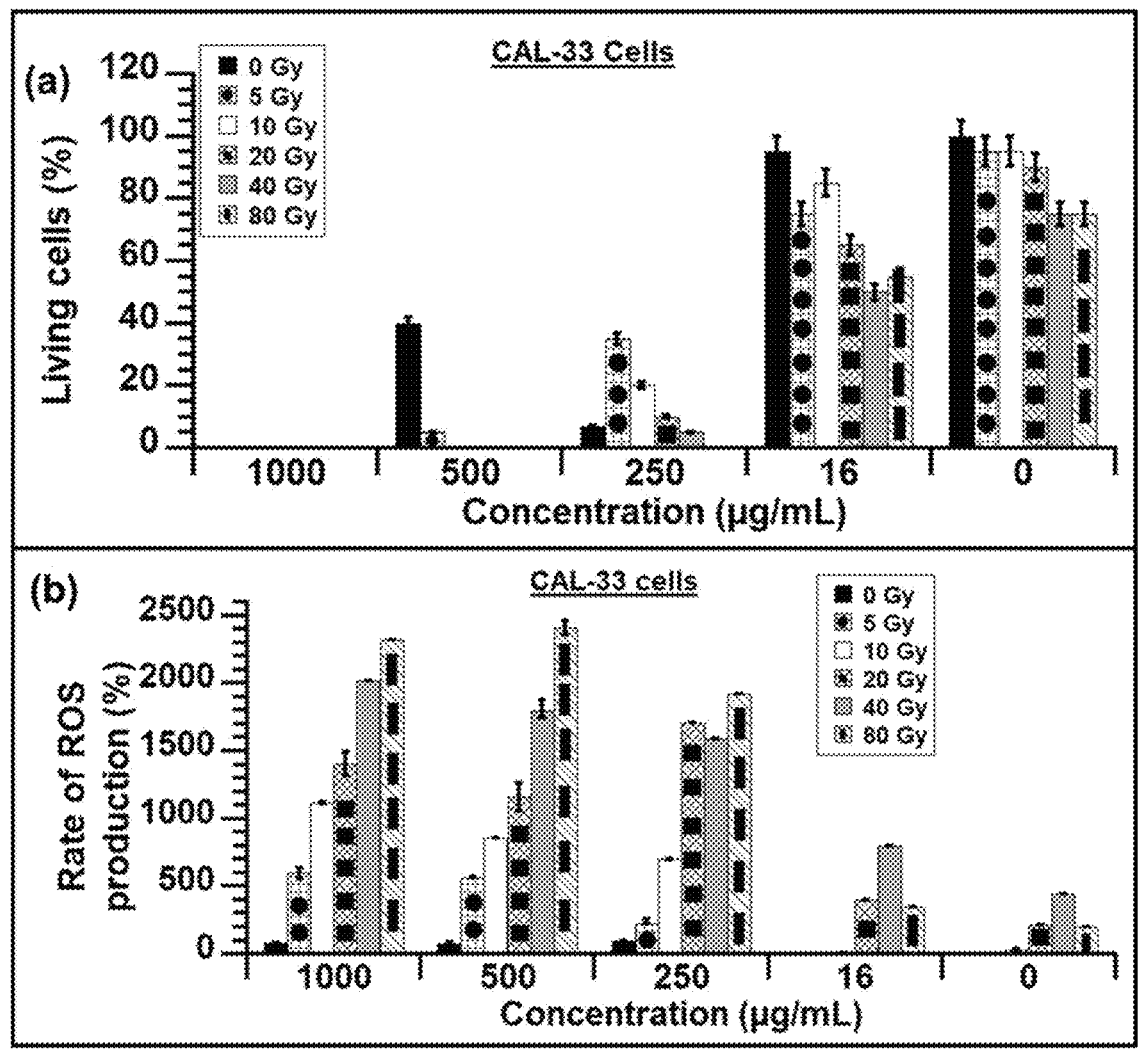

FIG. 12: (a), Percentage of living cells after the following treatment: CAL-33 cells are brought into contact with 1000, 500, 250, 16 µg/mL of magnetosomes or not brought into contact with magnetosomes (0 mg/mL) and either not exposed to gamma irradiation (control), or exposed to different doses of gamma radiation (5, 10, 20, 40 et 80 Gy). (b), Rate of ROS production after the following treatment: CAL-33 cells are brought into contact with 1000, 500, 250, 16 µg/mL in iron of magnetosomes or not brought into contact with magnetosomes (0 mg/mL) and either not to gamma radiation or exposed to different doses of gamma radiation (5, 10, 20, 40 and 80 Gy).

In one embodiment of the invention, the nanoparticle(s) designate(s) more than 1, 10, $10^2$, $10^3$, $10^5$, $10^{10}$ or $10^{50}$ nanoparticle(s) or assembly of nanoparticle(s).

In another other embodiment of the invention, the nanoparticle(s) designate(s) less than $10^{100}$, $10^{50}$, $10^{20}$, $10^{10}$, $10^5$, $10^3$, $10^2$, 50, 10, 5, 2 or 1 nanoparticle(s) or assembly of nanoparticle(s).

In one embodiment of the invention, the nanoparticle region is: i) the portion of the body part comprising the nanoparticles, ii) the volume occupied by the nanoparticles in the body part, or iii) the volume occupied by the nanoparticles outside of the body part.

The invention relates to nanoparticles for use according to the invention, wherein the acoustic wave has at least one of the following properties:

i1) it has a power or power density lower than 1000 W (Watt), i2) it has a power or power density lower than 1000 W per cm, W per $cm^2$, or W per $cm^3$, i3) it has a power or power density lower than 1000 W per cm of body part, W per $cm^2$ of body part, or W per $cm^3$ of body part, i4) it has a power or power density lower than 1000 W per cm of transducer, W per $cm^2$ of transducer, or W per $cm^3$ of transducer, i5) it has a power or power density lower than 1000 W per gram of nanoparticle, ii1) it has an energy or energy density lower than $10^5$ W·sec, ii2) it has an energy or energy density lower than $10^5$ W·sec per cm, W·sec per $cm^2$, or W·sec per $cm^3$, ii3) it has an energy or energy density lower than $10^5$ W·sec per cm of body part, W·sec per $cm^2$ of body part, or W·sec per $cm^3$ of body part, ii4) it has an energy or energy density lower than $10^5$ W·sec per cm of transducer, W·sec per $cm^2$ of transducer, W·sec per $cm^3$ of transducer, ii5) it has an energy or energy density lower than $10^5$ J (Joule), ii6) it has an energy or energy density lower than $10^5$ J per cm, J per $cm^2$, or J per $cm^3$, ii7) it has an energy or energy density lower than $10^5$ J per cm of body part, J per $cm^2$ of body part, or J per $cm^3$ of body part, ii8) it has an energy or energy density lower than $10^5$ J per cm of transducer, J per $cm^2$ of transducer, J per $cm^3$ of transducer, ii9) it has an energy or energy density lower than $10^5$ J per gram of nanoparticle, iii) it has a frequency lower than $10^5$ MHz, iv) it has a penetration depth in the body part larger than $10^{-5}$ cm, v) it is unfocused, and/or vi) it is not a focused ultrasound or a high intensity focused ultrasound.

In one embodiment of this invention, the acoustic wave or radiation irradiates the body part and/or nanoparticle and/or is applied on the body part or nanoparticle can mean that the acoustic wave or radiation covers, targets, is present in, or is located in the body part or nanoparticle or in at least $10^{-9}$, $10^{-7}$, $10^{-5}$, $10^{-3}$, $10^{-1}$, 1, 5, 10, 25, 50, 75 or 80% of the body part or nanoparticle(s) or that the body part or nanoparticle or at least $10^{-100}$, $10^{-50}$, $10^{-10}$, $10^{-9}$, $10^{-7}$, $10^{-5}$, $10^{-3}$, $10^{-1}$, 1, 5, 10, 25, 50, 75 or 80% of the body part or nanoparticle is exposed to the acoustic wave or radiation. This percentage can represent or be the number or volume of nanoparticles or body part exposed to the acoustic wave or radiation divided by the total number or volume of nanoparticles or body part. In some cases, the acoustic wave or radiation can also cover, target, be present, be applied on, or be located outside of the body part or nanoparticle(s), preferentially when the acoustic wave or radiation is of low enough power or energy not to induce toxicity.

In one embodiment of the invention, the excitation by radiation or acoustic wave of the nanoparticles or the irradiation of the body part or nanoparticle by the acoustic wave or radiation or the application of the radiation or acoustic wave, preferentially on the nanoparticles or body part, takes place or occurs in less than 100%, 90%, 70%, 60%, 50%, 40%, 30%, 20%, 10%, 5%, 2%, 1% or 0.1% of the body part. This percentage can be the ratio between the volume onto which the radiation or acoustic wave is applied and the volume of the body part.

In one embodiment of the invention, when the body part or nanoparticle is irradiated by or exposed to the acoustic wave or radiation, the body part or nanoparticle receives or absorbs the energy or power of the acoustic wave or radiation. In some cases, the body part or nanoparticle receives or absorbs at least $10^{-9}$, $10^{-7}$, $10^{-5}$, $10^{-3}$, $10^{-1}$, 1, 5, 10, 25, 50, 75 or 80% of the energy or power of the acoustic wave or radiation. This can be the case when the concentration of the nanoparticle in the body part and/or the energy or power of the acoustic wave or radiation applied on the body part and/or nanoparticle is/are large. In some other cases, the body part or nanoparticle receives or absorbs less than 80, 70, 50, 60, 10, 5 or 1% of the energy or power of the acoustic wave or radiation. This can be the case when the concentration of the nanoparticle in the body part and/or the energy or power of the acoustic wave or radiation applied on the body part and/or nanoparticle is/are small. In some cases, this percentage is: i) the ratio between the power or energy of the acoustic wave or radiation absorbed or received by the body part or nanoparticle divided by the power or energy of the acoustic wave or radiation applied on the body part or nanoparticle or ii) the ratio between the power or energy of the acoustic wave or radiation absorbed or received by the body part or nanoparticle divided by the power or energy of the acoustic wave or radiation generated by the apparatus generating the acoustic wave or radiation.

In this invention, an acoustic wave can be defined as: i) a mechanical wave, which preferentially induces a mechanical perturbation or disturbance of a medium or a body part through which it travels such as compression and/or expansion of the medium, ii) an elastic wave, iii) a wave that can't propagate or exist in empty space, or iv), a wave that induces or is associated with the movement or vibration of a substance, atom, ion, nanoparticle with a non-zero mass or non-zero weight. The acoustic wave is usually not an electromagnetic wave. In some cases, it can however produce or generate an electromagnetic wave, for example if moving/vibrating substances associated to the acoustic wave possess a non-zero charge. An example of radiation produced or resulting from or being associated with an acoustic wave can be an acoustic radiation force. The word "acoustic wave" can designate acoustic wave energy, acoustic wave power, acoustic wave intensity, or acoustic wave frequency. In some cases, acoustic wave intensity can have a similar meaning as acoustic wave power or acoustic wave energy. In other cases, acoustic wave power can have a similar meaning as acoustic wave energy. The acoustic wave can be absorbed by, reflected by, or transmitted through nanoparticles or a body part. The acoustic wave can have a frequency, energy, power, or intensity, which can be designated as the acoustic wave frequency, energy, power, or intensity, respectively. The acoustic wave can designate an assembly of more than 1, 10, $10^2$, $10^3$, $10^5$, $10^{10}$ or $10^{20}$ acoustic wave(s). The acoustic wave energy can represent the acoustic wave power multiplied by the time of application of the acoustic wave. It can be expressed in a power unit, such as Watt, multiplied by a time unit, such as seconds. The energy density of the acoustic wave can represent the energy of the acoustic wave per unit length, such as cm, per unit surface area, such as $cm^2$, or per unit volume, such as $cm^3$. The acoustic wave power can be proportional to the acoustic wave energy per unit time. It can be expressed in a power unit such as Watt. The acoustic wave power density can represent the acoustic wave power per unit length, such as cm, per unit surface area, such as $cm^2$, or per unit volume, such as $cm^3$. The acoustic wave intensity can be proportional to the acoustic wave power per unit surface area, such as $cm^2$. It can be expressed in a power unit, such as Watt, divided by a surface area unit, such as $cm^2$. In some cases, the unit length, unit surface area, and unit volume can represent the length, surface area, and volume of the nanoparticle(s), respectively.

In an embodiment of the invention, the acoustic wave is a wave, which is associated with, or linked with, or which induces, or produces, or originates from, is due to, results in, or is responsible for, or creates the movement, or vibration, or oscillation of a substance or assembly of substances, where the substance(s) has or have: i) a mass that is in some cases larger than $10^{-20}$, $10^{-10}$, $10^{-5}$, $10^{-3}$, $10^{-1}$, 1, 2, 5, 10, $10^5$ or $10^7$ grams or grams per $cm^3$ of body part or grams of nanoparticles, ii) a mass that is in some other cases smaller than $10^9$, $10^7$, $10^5$, $10^3$, $10^2$, 10, 1, $10^{-2}$, $10^{-5}$, $10^{-7}$, $10^{-9}$, $10^{-20}$ or $10^{-50}$ grams or grams per $cm^3$ of body part or grams of nanoparticles, iii) a mass that is between 0 and $10^{20}$, $10^{-20}$ and $10^{20}$, $10^{-10}$ and $10^{10}$, or between $10^{-10}$ and 10 grams or grams per $cm^3$ of body part or grams of nanoparticles iii) a positive charge in some cases, iv) a negative charge in some other cases, and/or v) a neutral charge in still some other cases.

In one embodiment of the invention, the substance is the nanoparticle.

In some cases, the acoustic wave can be due to the movement of more than 2, 5, 10, $10^5$, $10^{10}$ or $10^{20}$ nanoparticles or to a change with time, preferentially within less than $10^{10}$, $10^5$, $10^3$, 10, 5, 2, 1, $10^{-2}$ or $10^{-5}$ minutes, of the nanoparticle concentration, preferentially by a factor of more than 1.1, 2, 5, 10, $10^5$, $10^{10}$ or $10^{20}$, where these changes in nanoparticle movement or concentration preferentially occur in the body part.

In one embodiment of the invention, the movement, or vibration, or oscillation of the substance(s) is periodic or is repeated periodically. In this case, the movement, or vibration, or oscillation of the substance can preferentially be repeated more than 2, 5, 10, $10^3$, $10^6$ or $10^9$ times, where this repetition preferentially means that at least one of the properties associated with the movement, vibration, or oscillation of the substance can be repeated, where this property can be the speed or speed variation with time or space of the substance, the displacement or displacement variation with time or space of the substance, the acceleration or acceleration variation with time or space of the substance.

In this invention, an acoustic wave can be defined as or be an infrasound, a sound, an ultrasound, or a hypersound.

In this invention, the acoustic wave is preferentially an ultrasound, preferentially with: i) a frequency comprised between $10^{-2}$ and 100 MHz, between $10^{-1}$ and 10 MHz or between 1 and 5 MHz, and/or ii) a power between $10^{-2}$ and $10^2$ W per $cm^2$, between $10^{-1}$ and 10 W per $cm^2$ or between 1 and 5 W per $cm^2$.

Preferentially, an infrasound can be defined as an acoustic wave of low frequency. In some cases, the frequency of the infrasound can be lower than 2, 20, 200, 2000 or $10^5$ Hz. In some other cases, the frequency of the infrasound can be larger than $10^{-100}$, $10^{-50}$ or $10^{-10}$ Hz. Most preferentially, an infrasound has a frequency lower than 20 Hz.

Preferentially, a sound can be defined as a sound of frequency: i) in some cases larger than $2.10^{-3}$, $2.10^{-1}$, 2, 20 or 200 Hz, ii) in some other cases lower than 2, 20, 200 or $2.10^5$ kHz. Most preferentially, a sound has a frequency between 16 Hz and 16 kHz.

Preferentially, an ultrasound can be defined as a sound of frequency: i) in some cases larger than $2.10^{-3}$, 2, 20, or 200 kHz, ii) in some other cases of frequency lower than 0.1, 1, 10 or $10^5$ GHz. Most preferentially, an ultrasound has a frequency between 16 kHz at 10 MHz.

Preferentially, a hyper-sound can be defined as a sound of large frequency. In some cases, the frequency of the hypersound can be larger than $10^{-10}$, $10^{-3}$, $10^{-2}$, $10^{-1}$, 1 or 10 GHz. In some other cases, the frequency of the hypersound can be lower than $10^{1000}$, $10^{100}$, $10^{10}$ or $10^5$ GHz.

Most preferentially, a hypersound has a frequency larger than 10 MHz.

In some cases, an acoustic wave, infrasound, sound, ultrasound, or hypersound, can be a wave, preferentially a longitudinal wave, preferentially of frequency comprised between $10^{-100}$ and $10^{100}$ Hz.

In some cases, a large value of the frequency of an acoustic wave can be reached when the acoustic wave travels through a medium and its frequency increases while traveling though this medium.

In some other cases, a low value of the frequency of an acoustic wave can be reached when the acoustic wave travels through a medium and its frequency decreases while traveling through this medium.

In one embodiment of the invention, an ultrasound has a frequency larger than a sound or a hypersound has a frequency larger than an ultrasound, preferentially by a factor that is: i) in some cases larger than 1.001, 1.1, 2, 5, 10 or $10^3$, ii) in some other cases lower than $10^{50}$, $10^{20}$, $10^{10}$, $10^5$, $10^3$, 10, 5 or 2, or iii) in still some other cases between 1.00001 and $10^{50}$. According to the invention, the forms of radiation can be waves, such as electromagnetic waves, sound or acoustic waves, or particle waves. The particles can have: i) a weight or mass in some cases, ii), do not have a weight or mass in some other cases, iii) a movement in some cases, or iv) not a movement in some other cases.

In another embodiment of the invention, the radiation is a wave, which is associated with, or linked with, or which induces, or produces, or results in, or is responsible for, or creates the movement, or vibration, or oscillation of a substance or assembly of substances, where the substance(s) has or have: i) a zero-mass, or ii) a mass that is lower by a factor of more than 1.111, 1.5, 2, 5, 10, $10^3$ or $10^5$ than the mass of the substance(s) associated with, linked with, induced by, produced by, or resulting from the acoustic wave.

According to the invention, the form of radiation can be electromagnetic radiation.

According to the invention, radiation can in some cases be acoustic radiation forces, radiation forces, or radiation pressures.

According to the invention, radiation can be irradiation, preferentially of the body part, with the acoustic wave.

Preferably, the source of radiation is selected from the group consisting of: i) a magnetic or electric field, ii) laser light, iii) light produced by a lamp, iv) light emitted at a single wavelength, v) light emitted at multiple wavelengths, vi) a ionizing radiation, vii) microwave, viii) radiofrequencies, and ix) acoustic wave.

In some cases, the radiation can be selected from the group consisting of: alpha, beta, gamma, X-ray, neutron, proton, electron, ion, neutrino, muon, meson, and photon particles or radiation. Preferably, the radiation can also in some cases be selected from the group consisting of acoustic waves, infrasounds, sounds, ultra-sounds, and hypersounds.

Preferably also, the radiation is or generates or results in or causes or induces a magnetic field or electromagnetic field. In some cases, the strength of the magnetic field or electromagnetic field is larger than 1 µT, 10 µT, 100 µT, 1 mT, 10 mT, 100 mT, 1 T, 5 T, 10 T or 100 T. In some other cases, the strength of the magnetic field or electromagnetic field is lower than $10^{20}$, $10^5$, $10^2$, 10, 1, $10^{-1}$, $10^{-3}$ or $10^{-9}$ T.

In some cases, the radiation according to the invention can have a power larger than $10^{-10}$, $10^{-5}$, $10^{-3}$, 0.01, 0.1, 1, 10, $10^2$, $10^3$, $10^5$ or $10^7$ Gy or Gy per $cm^3$ of body part or Gy per gram of body part or Gy per $cm^3$ of nanoparticle Gy per gram of nanoparticle.

In some other cases, the radiation according to the invention can have a power lower than $10^{100}$, $10^{50}$, $10^{10}$, $10^5$, $10^2$, 10, 1, $10^{-3}$ or $10^{-5}$ Gy or Gy per $cm^3$ of body part or Gy per gram of body part or Gy per $cm^3$ of nanoparticle or Gy per gram of nanoparticle.

In another embodiment of the invention, an acoustic wave is not at least one radiation selected from the group consisting of: i) an electromagnetic radiation, ii) a magnetic field, iii) an electric field, iv) an alternating electric or magnetic field, v) a laser or laser light, vi) a lamp or light produced by a lamp, vii) light emitted at a single wavelength, viii) light emitted at multiple wavelengths, ix) a ionizing radiation, x) microwave, xi) radiofrequency, xii) a photon, and xiii) alpha, beta, gamma, X-ray, neutron, proton, electron, ion, neutrino, muon, meson, photon particles or radiation, and xiv) radiation of particles, substances, or photons originating from an atom or a molecule.

In some cases, the acoustic wave can be or be replaced by acoustic radiation.

In some cases, acoustic wave or radiation can be or represent an assembly of more than 1, 5, 10, $10^3$, $10^5$, $10^{10}$, $10^{20}$ or $10^{50}$ acoustic waves or forms of radiation. In other cases, the acoustic wave or the radiation can be or represent an assembly of less than $10^{100}$, $10^{50}$, $10^{20}$, $10^{10}$, $10^5$, $10^2$, 5 or 2 acoustic waves or forms of radiations.

In this invention, the radiation or acoustic wave can be the radiation or acoustic wave generated or produced by an equipment or apparatus generating or producing the radiation or acoustic wave, preferentially before, during, or after the radiation or acoustic wave has reached or covered or targeted the body part or nanoparticles. In some cases, the equipment or apparatus is different from the nanoparticles and is preferentially fabricated by a human.

In some cases, the equipment generating the acoustic wave is or comprises a transducer, which preferentially transforms an electrical signal into an acoustic wave.

In this invention, the radiation or acoustic wave can in some cases be the radiation or acoustic wave generated by the nanoparticles. In this case, the radiation or acoustic wave may be due to a change in the organization of the nanoparticles, preferentially between before and after nanoparticle administration in the body part or individual. For example, nanoparticles may be organized in chains before their administration to the individual and then be progressively degraded, for example by lysosomes, following their administration to the individual, leading to a variation, preferentially an increase, in the distances between the nanoparticles and therefore to a change in the interactions between the nanoparticles, which could produce an acoustic wave or radiation.

In one embodiment of the invention, the intensity, power, energy, or frequency of the acoustic wave or radiation is the acoustic wave intensity or frequency generated by an apparatus generating acoustic waves or radiation, or by a transducer. It can be the intensity, power, energy, or frequency of the acoustic wave or radiation measured just after the acoustic wave or radiation has left the apparatus generating the acoustic wave or radiation or has left the transducer. It can also be the intensity, power, energy, or frequency of the acoustic wave or radiation measured after the acoustic wave or radiation has left the apparatus generating the acoustic wave or radiation or has left the transducer and travelled through another medium (liquid, gas, solid), such as the body part.

In some cases, equipment detecting an acoustic wave can be an acoustic wave sensor, preferentially comprising a transducer, preferentially converting acoustic wave power or energy into an electric signal.

In some cases, the intensity, strength, or power, of the acoustic wave or radiation can't be detected, because it is too small or undetectable with the acoustic wave or radiation detectors that are available. In this case, the existence of the acoustic wave or radiation can be revealed by the change of the movement, oscillation, size, organization, composition, or charge, of the substances that produce the acoustic wave, such as the nanoparticles.

The invention also relates to nanoparticles for use according to the invention, wherein the intensity, power, or power density of the acoustic wave or radiation is lower than:
i) $10^{100}$, $10^{50}$, $10^{20}$, $10^{10}$, $10^9$, $10^6$, $10^5$, $10^3$, $10^2$, 100, 50, 10, 5, 3, 1, $10^{-1}$ $10^{-2}$, $10^{-3}$, $10^{-5}$ or $10^{-7}$ W (Watt),
ii) $10^{100}$, $10^{50}$, $10^{20}$, $10^{10}$, $10^9$, $10^6$, $10^5$, $10^3$, $10^2$, 100, 50, 10, 5, 3, 1, $10^{-1}$ $10^{-2}$, $10^{-3}$, $10^{-5}$ or $10^{-7}$ W per cm, W per cm$^2$, or W per cm$^3$,
iii) $10^{100}$, $10^{50}$, $10^{20}$, $10^{10}$, $10^9$, $10^6$, $10^5$, $10^3$, $10^2$, 100, 50, 10, 5, 3, 1, $10^{-1}$ $10^{-2}$, $10^{-3}$, $10^{-5}$ or $10^{-7}$ W per cm of body part, W per cm$^2$ of body part, or W per cm$^3$ of body part,
iv) $10^{100}$, $10^{50}$, $10^{20}$, $10^{10}$, $10^9$, $10^6$, $10^5$, $10^3$, $10^2$, 100, 50, 10, 5, 3, 1, $10^{-1}$ $10^{-2}$, $10^{-3}$, $10^{-5}$ or $10^{-7}$ W per cm of transducer, W par cm$^2$ of transducer, or W per cm$^3$ of transducer, or
v) $10^{100}$, $10^{50}$, $10^{20}$, $10^{10}$, $10^9$, $10^6$, $10^5$, $10^3$, $10^2$, 100, 50, 10, 5, 3, 1, $10^{-1}$ $10^{-2}$, $10^{-3}$, $10^{-5}$ or $10^{-7}$ W per gram of nanoparticle.

In some cases, 1 cm$^3$, 1 cm$^2$, and 1 cm can be 1 cm$^3$ of body part, 1 cm$^2$ of body part, and 1 cm of body part, respectively.

In some other cases 1 cm$^3$, 1 cm$^2$, and 1 cm can be 1 cm$^3$ of transducer, 1 cm$^2$ of transducer, and 1 cm of transducer, respectively.

In some cases, transducer can designate the part of the transducer that generates the acoustic wave.

In some other cases, 1 gram of nanoparticles can be 1 gram of nanoparticles exposed to the acoustic wave or radiation or 1 gram of nanoparticles onto which the acoustic wave is applied.

The invention also relates to nanoparticles for use according to the invention, wherein the intensity, power, or power density of the acoustic wave or radiation is larger than:
i) $10^{-100}$, $10^{-50}$, $10^{-20}$, $10^{-10}$, $10^{-7}$, $10^{-5}$, $10^{-3}$, $10^{-2}$, $10^{-1}$, 1, 5, 10, $10^2$, $10^3$, $10^5$, $10^7$ or $10^9$ W (Watt),
ii) $10^{-100}$, $10^{-50}$, $10^{-20}$, $10^{-10}$, $10^{-7}$, $10^{-5}$, $10^{-3}$, $10^{-2}$, $10^{-1}$, 1, 5, 10, $10^2$, $10^3$, $10^5$, $10^7$ or $10^9$ W per cm, W per cm$^2$, or W per cm$^3$,
iii) $10^{-100}$, $10^{-50}$, $10^{-20}$, $10^{-10}$, $10^{-7}$, $10^{-5}$, $10^{-3}$, $10^{-2}$, $10^{-1}$, 1, 5, 10, $10^2$, $10^3$, $10^5$, $10^7$ or $10^9$ W per cm of body part, W per cm$^2$ of body part, or W per cm$^3$ of body part,
iv) $10^{-100}$, $10^{-50}$, $10^{-20}$, $10^{-10}$, $10^{-7}$, $10^{-5}$, $10^{-3}$, $10^{-2}$, $10^{-1}$, 1, 5, 10, $10^2$, $10^3$, $10^5$, $10^7$ or $10^9$ W per cm of transducer, W per cm$^2$ of transducer, or W per cm$^3$ of transducer,
v) $10^{-100}$, $10^{-50}$, $10^{-20}$, $10^{-10}$, $10^{-7}$, $10^{-5}$, $10^{-3}$, $10^{-2}$, $10^{-1}$, 1, 5, 10, $10^2$, $10^3$, $10^5$, $10^7$ or $10^9$ W per gram of nanoparticle.

The invention also relates to nanoparticles for use according to the invention, wherein the intensity, power, or power density of the acoustic wave or radiation is between:
i) 0 and $10^{100}$, $10^{-100}$ and $10^{100}$, $10^{-10}$ and $10^{10}$, $10^{-5}$ and $10^5$, $10^{-3}$ and $10^3$, or between $10^{-1}$ and 10 W (Watt),
ii) 0 and $10^{100}$, $10^{-100}$ and $10^{100}$, $10^{-10}$ and $10^{10}$, $10^{-5}$ and $10^5$, $10^{-3}$ and $10^3$, or between $10^{-1}$ and 10 W per cm, W per cm$^2$, or W per cm$^3$,
iii) 0 and $10^{100}$, $10^{-100}$ and $10^{100}$, $10^{-10}$ and $10^{10}$, $10^{-5}$ and $10^5$, $10^{-3}$ and $10^3$, or between $10^{-1}$ and 10 W per cm of body part, W per cm$^2$ of body part, or W per cm$^3$ of body part,
iv) 0 and $10^{100}$, $10^{-100}$ and $10^{100}$, $10^{-10}$ and $10^{10}$, $10^{-5}$ and $10^5$, $10^{-3}$ and $10^3$, or between $10^{-1}$ and 10 W per cm of transducer, W per cm$^2$ of transducer, or W per cm$^3$ of transducer,
v) 0 and $10^{100}$, $10^{-100}$ and $10^{100}$, $10^{-10}$ and $10^{10}$, $10^{-5}$ and $10^5$, $10^{-3}$ and $10^3$, or between $10^{-1}$ and 10 W per gram of nanoparticle.

The invention also relates to nanoparticles for use according to the invention, wherein the energy or energy density of the acoustic wave or radiation is lower than:
i) $10^9$, $10^6$, $10^5$, $10^3$, 100, 10, 1, $10^{-1}$, $10^{-2}$, or $10^{-5}$ W·sec,
ii) $10^9$, $10^6$, $10^5$, $10^3$, 100, 10, 1, $10^{-1}$, $10^{-2}$, or $10^{-5}$ W·sec/cm, W·sec/cm$^2$, or W·sec/cm$^3$,
iii) $10^9$, $10^6$, $10^5$, $10^3$, 100, 10, 1, $10^{-1}$, $10^{-2}$, or $10^{-5}$ W·sec per cm of body part, W·sec per cm$^2$ of body part, or W·sec per cm$^3$ of body part,
iv) $10^9$, $10^6$, $10^5$, $10^3$, 100, 10, 1, $10^{-1}$, $10^{-2}$, or $10^{-5}$ W·sec per cm of transducer, W·sec per cm$^2$ of transducer, or W·sec per cm$^3$ of transducer,
v) $10^9$, $10^6$, $10^5$, $10^3$, 100, 10, 1, $10^{-1}$, $10^{-2}$, or $10^{-5}$ J (Joule)
vi) $10^9$, $10^6$, $10^5$, $10^3$, 100, 10, 1, $10^{-1}$, $10^{-2}$, or $10^{-5}$ J per cm, J per cm$^2$, or J per cm$^3$,
vii) $10^9$, $10^6$, $10^5$, $10^3$, 100, 10, 1, $10^{-1}$, $10^{-2}$, or $10^{-5}$ J per cm of body part, J per cm$^2$ of body part, or J per cm$^3$ of body part,
viii) $10^9$, $10^6$, $10^5$, $10^3$, 100, 10, 1, $10^{-1}$, $10^{-2}$, or $10^{-5}$ J per cm of transducer, J per cm$^2$ of transducer, or J per cm$^3$ of transducer, or
ix) $10^9$, $10^6$, $10^5$, $10^3$, 100, 10, 1, $10^{-1}$, $10^{-2}$, or $10^{-5}$ J per gram of nanoparticle, In some cases, the acoustic wave can have a low energy when the power of the acoustic wave is low and/or when the time of application of the acoustic is short, preferentially shorter than 24, 12, 6, 3, 2, or 1 hour, or shorter than 50, 30, 15, 10, 5, 2, or 1 minute(s), or shorter than 50, 30, 20, 10, 5, 2, 1, $10^{-1}$, $10^{-3}$, $10^{-6}$ or $10^{-9}$ second(s).

The invention also relates to nanoparticles for use according to the invention, wherein the energy or energy density of the acoustic wave or radiation is larger than:
i) $10^{-50}$, $10^{-10}$, $10^{-5}$, $10^{-3}$, $10^{-1}$, 1, 10, $10^2$, or $10^5$ W·sec,
ii) $10^{-50}$, $10^{-10}$, $10^{-5}$, $10^{-3}$, $10^{-1}$, 1, 10, $10^2$, or $10^5$ W·sec/cm, W·sec/cm$^2$, W·sec/cm$^3$,
iii) $10^{-50}$, $10^{-10}$, $10^{-5}$, $10^{-3}$, $10^{-1}$, 1, 10, $10^2$, or $10^5$ W·sec per cm of body part, W·sec per cm$^2$ of body part, or W·sec per cm$^3$ of body part,
iv) $10^{-50}$, $10^{-10}$, $10^{-5}$, $10^{-3}$, $10^{-1}$, 1, 10, $10^2$, or $10^5$ W·sec per cm of transducer, W·sec per cm$^2$ of transducer, or W·sec per cm$^3$ of transducer,
v) $10^{-50}$, $10^{-10}$, $10^{-5}$, $10^{-3}$, $10^{-1}$, 1, 10, $10^2$, or $10^5$ J (Joule), vi) $10^{-50}$, $10^{-10}$, $10^{-5}$, $10^{-3}$, $10^{-1}$, 1, 10, $10^2$, or $10^5$ J/cm, J/cm$^2$ or J/cm$^3$.

vii) $10^{-50}$, $10^{-10}$, $10^{-5}$, $10^{-3}$, $10^{-1}$, 1, 10, $10^2$, or $10^5$ J per cm of body part, J per cm$^2$ of body part, or J per cm$^3$ of body part, viii) $10^{-50}$, $10^{-10}$, $10^{-5}$, $10^{-3}$, $10^{-1}$, 1, 10, $10^2$, or $10^5$ J per cm of transducer, J per cm$^2$ of transducer, or J per cm$^3$ of transducer, or ix) $10^{-50}$, $10^{-10}$, $10^{-5}$, $10^{-3}$, $10^{-1}$, 1, 10, $10^2$, or $10^5$ J per gram of nanoparticle.

In some cases, the acoustic wave can have a large energy when the power of the acoustic wave is large and/or when the time of application of the acoustic is long, preferentially longer than $10^{-50}$, $10^{-10}$, $10^{-1}$, 1, 5, 10, $10^5$ or $10^{10}$ minute(s).

The invention also relates to nanoparticles for use according to the invention, wherein the energy or energy density of the acoustic wave or radiation is between:

i) $10^{-50}$ and $10^{50}$, $10^{-10}$ and $10^{10}$, $10^{-5}$ and $10^5$, $10^{-1}$ and $10^5$, or between 1 and $10^4$ W·sec, ii) $10^{-50}$ and $10^{50}$, $10^{-10}$ and $10^{10}$, $10^{-5}$ and $10^5$, $10^{-1}$ and $10^5$, or between 1 and $10^4$ W·sec/cm, W·sec/cm$^2$, W·sec/cm$^3$, iii) $10^{-50}$ and $10^{50}$, $10^{-10}$ and $10^{10}$, $10^{-5}$ and $10^5$, $10^{-1}$ and $10^5$, or between 1 and $10^4$ W·sec per cm of body part, W·sec per cm$^2$ of body part, or W·sec per cm$^3$ of body part, iv) $10^{-50}$ and $10^{50}$, $10^{-10}$ and $10^{10}$, $10^{-5}$ and $10^5$, $10^{-1}$ and $10^5$, or between 1 and $10^4$ W·sec per cm of transducer, W·sec per cm$^2$ of transducer, or W·sec per cm$^3$ of transducer, v) $10^{-50}$ and $10^{50}$, $10^{-10}$ and $10^{10}$, $10^{-5}$ and $10^5$, $10^{-1}$ and $10^5$, or between 1 and $10^4$ J (Joule), vi) $10^{-50}$ and $10^{50}$, $10^{-10}$ and $10^{10}$, $10^{-5}$ and $10^5$, $10^{-1}$ and $10^5$, or between 1 and $10^4$ J/cm, J/cm$^2$ or J/cm$^3$, vii) $10^{-50}$ and $10^{50}$, $10^{-10}$ and $10^{10}$, $10^{-5}$ and $10^5$, $10^{-1}$ and $10^5$, or between 1 and $10^4$ J per cm of body part, J per cm$^2$ of body part, or J per cm$^3$ of body part, viii) $10^{-50}$ and $10^{50}$, $10^{-10}$ and $10^{10}$, $10^{-5}$ and $10^5$, $10^{-1}$ and $10^5$, or between 1 and $10^4$ J per cm of transducer, J per cm$^2$ of transducer, or J per cm$^3$ of transducer, or ix) $10^{-50}$ and $10^{50}$, $10^{-10}$ and $10^{10}$, $10^{-5}$ and $10^5$, $10^{-1}$ and $10^5$, or between 1 and $10^4$ J per gram of nanoparticle.

In some cases, the power of the acoustic wave or of the radiation can be equal to 0 Watt or 0 Gray, preferentially before, at the beginning, at the end, or after the acoustic wave medical treatment or after the radiation medical treatment, or during some specific treatments or methods described in this invention such as the treatment of anemia.

In some other cases, the power of the acoustic wave or of the radiation can be larger than 0 Watt or 0 Gray, preferentially during the acoustic wave medical or during the radiation medical treatment.

The invention also relates to nanoparticles for use according to the invention, wherein the frequency of the acoustic wave or radiation is lower than $10^5$ MHz. In some cases, the frequency of the acoustic wave or radiation can be lower than $10^{100}$, $10^{50}$, $10^{30}$, $10^{20}$, $10^{10}$, $10^5$, $10^3$, $10^2$, 10, 1, $10^{-1}$, $10^{-2}$, $10^{-3}$, $10^{-4}$, $10^{-5}$, $10^{-6}$, $10^{-7}$, $10^{-8}$, $10^{-10}$ or $10^{-15}$ MHz or kHz.

In some other cases, the radiation or acoustic wave according to the invention can have a frequency larger than $10^{-100}$, $10^{-50}$, $10^{-20}$, $10^{-10}$, $10^{-8}$, $10^{-7}$, $10^{-6}$, $10^{-5}$, $10^{-4}$, $10^{-3}$, $10^{-2}$, $10^{-1}$, 1, 10, $10^3$, $10^5$ or $10^{10}$ kHz or MHz.

In still some other cases, the radiation or acoustic wave according to the invention can have a frequency between $10^{-15}$ and $10^{15}$ MHz, $10^{-13}$ and $10^{13}$ MHz, $10^{-11}$ and $10^{11}$ MHz, $10^{-9}$ and $10^9$ MHz, $10^{-7}$ and $10^7$ MHz, $10^{-5}$ and $10^5$ MHz, $10^{-3}$ and $10^3$ MHz, or between $10^{-1}$ and 10 MHz.

In some cases, the frequency of the acoustic wave or radiation can be the frequency of oscillation of the acoustic wave or radiation.

The invention also relates to nanoparticles for use, wherein the acoustic wave or radiation has a penetration depth, preferentially in the body part, which is larger than $10^{-10}$, $10^{-5}$, $10^{-3}$, $10^{-1}$, 1, 5, 10, 20, 50 or 500 cm.

The invention also relates to nanoparticles for use, wherein the acoustic wave or radiation has a penetration depth, preferentially in the body part, which is lower than $10^{10}$, $10^5$, $10^3$, 50, 50, 20, 10, 5, 1, 0.1 or 0.001 cm.

In some cases, the acoustic wave or radiation can have a penetration depth, preferentially in the body part, which is between $10^{-10}$ and $10^{10}$, $10^{-5}$ and $10^3$, $10^{-3}$ and $10^3$, $10^{-3}$ and 100, $10^{-2}$ and 10, or between $10^{-2}$ and 10 cm.

The penetration depth is preferentially the penetration of the acoustic wave or radiation through or in the body part or nanoparticle region, or through or in 99, 75, 50, 25, 1, 0.1, $10^{-3}$, $10^{-9}$ or $10^{-20}$% or nanoparticle region, or through or in the region separating the equipment generating the acoustic wave or radiation and the body part or nanoparticle region.

In one embodiment, the intensity, energy, power, frequency of the acoustic wave or radiation decreases, preferentially by a factor of more than 1.1, 1.2, 1.5, 2, 3, 5, 10, $10^2$, $10^3$, $10^5$ or $10^{10}$, with an increase in the penetration depth, preferentially by a factor of more than 1.1, 1.2, 1.5, 2, 3, 5, 10, $10^2$, $10^3$, $10^5$ or $10^{10}$, preferentially of the acoustic wave or radiation.

In one embodiment of the invention, the penetration depth of the acoustic wave or radiation is inversely proportional to the frequency of the acoustic wave or radiation. In some cases, the frequency of the acoustic wave or radiation can be decreased, preferentially by a factor of more than 1.1, 1.2, 1.5, 2, 3, 5, 10, $10^2$, $10^3$, $10^5$ or $10^{10}$, preferentially in order to increase the penetration depth of the acoustic wave or radiation, preferentially by a factor of more than 1.1, 1.2, 1.5, 2, 3, 5, 10, $10^2$, $10^3$, $10^5$ or $10^{10}$. Inversely, the frequency of the acoustic wave or radiation can be increased, preferentially by a factor of more than 1.1, 1.2, 1.5, 2, 3, 5, 10, $10^2$, $10^3$, $10^5$ or $10^{10}$, preferentially in order to decrease the penetration depth of the acoustic wave or radiation, preferentially by a factor of more than 1.1, 1.2, 1.5, 2, 3, 5, 10, $10^2$, $10^3$, $10^5$ or $10^{10}$.

In one embodiment of the invention, an unfocused acoustic wave or radiation is applied on the body part, possibly including or comprising regions comprising the nanoparticles and/or regions not comprising the nanoparticles, possibly including or comprising pathological cells and/or healthy cells.

In one embodiment of the invention, an unfocused acoustic wave or an unfocused radiation covers more than $10^{-5}$, $10^{-3}$, $10^{-1}$, 1, 10, $10^3$ or $10^5$% of the body part, using less than $10^3$, $10^2$, 10, 5, 2 or 1 application(s) or application spot(s). An application spot can be defined as the acoustic volume or radiation volume that can be covered or targeted during a single application of acoustic wave or radiation or during one sequence, preferentially during $t_1$ or $t_3$.

In one embodiment of the invention, an acoustic wave volume or acoustic volume is defined as the volume, which is exposed to the acoustic wave or which receives the acoustic wave energy or which undergoes the effects of the acoustic wave.

In one embodiment of the invention, a radiation volume is defined as the volume, which is exposed to radiation or which receives the radiation energy or which undergoes the effects of the radiation.

The invention also relates to nanoparticles for use according to the invention, wherein the acoustic wave or radiation is unfocused. In some cases an unfocused acoustic wave or radiation can be applied over an acoustic wave volume or radiation volume, which comprises the nanoparticle region or body part, or a portion of the nanoparticle region or body part.

In some cases, an unfocused acoustic wave or radiation can be applied over an acoustic wave volume or radiation volume, which is: i) larger than $10^{-10}$, $10^{-3}$, $10^{-2}$, $10^{-1}$, 1, 10, $10^2$, $10^3$, $10^5$ or $10^{10}$ cm$^3$, ii) larger than the nanoparticle region or body part or healthy site or pathological site, preferentially by a factor larger or equal to than 1.1, 1.5, 2, 5, 10, $10^3$ or $10^5$, or by more than 1, 10, $10^3$, $10^5$ or $10^{10}$ cm$^3$, or iii) larger, preferentially by a factor larger or equal to than 1.1, 1.5, 2, 5, 10, $10^3$ or $10^5$, or by more than 1, 10, $10^3$, $10^5$ or $10^{10}$ cm$^3$, than the acoustic wave volume or radiation volume that is reached by or exists with or results from a focused acoustic wave or radiation or the application of a focused acoustic wave or radiation. In some cases, this situation can occur when an unfocused acoustic wave or radiation is applied over a region comprising healthy cells, preferentially without undamaging or destroying healthy cells, preferentially either because: i) healthy cells are not in contact or mixed with nanoparticles and the application of acoustic wave or radiation on both healthy cell and nanoparticles is preferentially necessary to induce healthy cell destruction, or ii) because healthy cells are less sensitive to or less easily destroyed by the acoustic wave or radiation than pathological cells.

In some other cases, this situation can occur to treat a boy part of large size.

In some other cases, an unfocused acoustic wave or radiation can be applied over an acoustic wave volume or radiation volume, which is: i) lower than $10^{100}$, $10^{50}$, $10^{20}$, $10^{10}$, $10^5$, $10^3$, 10, 5, 2, 1, $10^{-1}$, $10^{-3}$ or $10^{-5}$ cm$^3$, ii) lower than the nanoparticle region or body part or healthy site or pathological site, preferentially by a factor of more than 1.1, 1.5, 2, 5, 10, $10^3$ or $10^5$, or by more than 1, 10, $10^3$, $10^5$ or $10^{10}$ cm$^3$. In some cases, this situation can occur when: i) an unfocused acoustic wave or radiation is applied over a region or volume that is not too large, preferentially to avoid possible toxicity induced by the application of acoustic wave or radiation over a large volume, ii) to treat a body part of small size, or iii) to avoid having to use a too large or too expensive or too energy consuming equipment generating the acoustic wave or radiation.

In some other cases, an unfocused acoustic wave or radiation can be applied over an acoustic wave or radiation volume, which is: i) between $10^{-100}$ and $10^{100}$ cm$^3$, between $10^{-50}$ and $10^{50}$ cm$^3$, or between $10^{-10}$ and $10^{10}$ cm$^3$, or, ii) between a volume that is $10^{100}$, $10^{10}$, $10^5$, $10^3$, 10, 5, or 2 times smaller than the body part, nanoparticle region, pathological site, and/or healthy site, and a volume that is 2, 5, 10, $10^3$, $10^5$, $10^{10}$ or $10^{100}$ larger than the body part, nanoparticle region, pathological site, and/or healthy site.

In some other cases, an unfocused acoustic wave or radiation can be applied over an acoustic wave or radiation volume, which is larger than the acoustic wave or radiation volume of a focused acoustic wave or radiation by a factor: i) between 0 and $10^{50}$ cm$^3$, between 0 and $10^3$ cm$^3$, between 0 and 10 cm$^3$, between $10^{-50}$ and $10^{50}$ cm$^3$, or between $10^{-3}$ and $10^3$ cm$^3$, or ii) between 1 and $10^{50}$, between 1 and $10^5$, between 1.1 and $10^{50}$, or between 1.1 and $10^5$.

The invention also relates to nanoparticles for use according to the invention, wherein the acoustic wave or radiation is focused. In this case, the acoustic wave or radiation is preferentially applied over an acoustic wave volume or radiation volume preferentially comprised in the body part, which is smaller than 0.001, 0.1, 1, 10, $10^2$, $10^3$, $10^5$ or $10^{10}$ cm$^3$.

In one embodiment of the invention, a focused acoustic wave or radiation can cover less than $10^{-5}$, $10^{-3}$, $10^{-1}$, 1, 10, $10^3$ or $10^5$% of the body part, using more than $10^3$, $10^2$, 10, 5, 2 or 1 application(s) or application spot(s).

In some cases, the acoustic wave volume of a focused acoustic wave can be the volume covered by or exposed to a focused ultrasound, preferentially a high intensity focused ultrasound (HIFU). In some cases, the acoustic wave volume can be the focal region of the acoustic wave. For HIFU, a typical focal region, preferentially of one spot, can be: i) an ellipsoid or ellipsoidal volume of 15 mm along the beam axis and 1.5 mm in diameter, ii) or a volume lower than $10^5$, $10^3$, 100, 75 or 50 mm$^3$.

In some cases, a focused acoustic wave or focused ultrasound can be a high intensity focused ultrasound (HIFU).

In one embodiment of the invention, the acoustic wave is not a focused acoustic wave or a HIFU.

In one embodiment of the invention, the radiation or acoustic wave has a strength, power, intensity, wavelength, or frequency that does not vary as a function of time and/or space.

In another embodiment of the invention, the radiation has a strength, power, intensity, wavelength, or frequency that varies as a function of time and/or space.

In one embodiment of the invention, the radiation or acoustic wave has a strength, power or frequency that varies spatially. In some cases the strength, power, or frequency of the radiation varies by more than $10^{-50}$, $10^{-20}$, $10^{-10}$, $10^{-5}$, $10^{-2}$, 1, 10, $10^2$, $10^3$, $10^5$ or $10^{10}$ T per cm or T per cm$^2$ or μT per cm$^3$ or μT per gram of nanoparticle or Watt per cm or Watt per cm$^2$ or Watt per cm$^3$ or Watt per gram of nanoparticle or Hz per cm$^2$ or Hz per cm$^3$ or Hz per cm or Hz per gram of nanoparticle.

In some other cases the strength, power, or frequency of the radiation varies by less than $10^{50}$, $10^{20}$, $10^{10}$, $10^5$, $10^2$, 1, 10, $10^{-2}$, $10^{-3}$, $10^{-5}$ or $10^{-10}$ μT per cm or μT per cm$^2$ or μT per cm$^3$ or μT per gram of nanoparticle or Watt per cm or Watt per cm$^2$ or Watt per cm$^3$ or Watt per gram of nanoparticle or Hz per cm$^2$ or Hz per cm$^3$ or Hz per cm or Hz per gram of nanoparticle.

In some cases, cm, cm$^2$, and cm$^3$, can designate or be cm of body part, cm$^2$ of body part, and cm$^3$ of body part, respectively.

In some other cases, 1 cm$^3$ of body part can designate or be 1 gram of body part.

In some cases, the radiation or acoustic wave can have a power, strength, and/or frequency, which is sufficiently large, preferentially to heat the nanoparticles or to induce the generation of radical or reactive species by the nanoparticles, preferentially a strength larger than $10^{-100}$, $10^{-50}$, $10^{-20}$, $10^{-10}$, $10^{-3}$, $10^{-2}$, $10^{-1}$, 1 or 10 mT, preferentially a frequency larger than $10^{-100}$, $10^{-3}$, $10^{-2}$, $10^{-1}$, 10, 50, 100 or 200 KHz, and/or preferentially a power larger than $10^{-100}$, $10^{-6}$, $10^{-3}$, $10^{-1}$, 1, 10, $10^3$ or $10^{10}$ W (Watt) or W per cm or W per cm$^2$ or W per cm$^3$ or W per gram of body part or W per gram of nanoparticle or Gy or Gy per cm or Gy per cm$^2$ or Gy per cm$^3$ or Gy per gram of body part or Gy per gram of nanoparticle.

In some other cases, the radiation or acoustic wave can have a power, strength, and/or frequency, which is/are kept below a certain threshold, preferentially to avoid toxicity, such as that induced by Foucault currents or a too large heating or a too large production of radical or reactive species, preferentially induced or produced outside of the body part. The strength of the radiation can be lower or kept below than $10^{100}$, $10^{50}$, $10^{10}$, $10^5$, 10, 1, $10^{-1}$ or $10^{-5}$ mT. The frequency of the radiation or acoustic wave can be lower than or kept below $10^{100}$, $10^{50}$, $10^{10}$, $10^5$, $10^3$, 10, 1 or $10^{-3}$ kHz. The power of the radiation or acoustic wave can be lower or kept below than $10^{100}$, $10^{50}$, $10^{20}$, $10^{10}$, $10^5$, $10^3$, 10, 1, $10^{-1}$, $10^{-3}$ or $10^{-6}$ W or or W per cm or W par $cm^2$ or W per $cm^3$ or W per gram of body part or W per gram of nanoparticle or Gy or or Gy per cm or Gy per $cm^2$ Gy per $cm^3$ or Gy per gram of body part or Gy per gram of nanoparticle.

In one embodiment of the invention, the excitation by radiation or acoustic wave of the nanoparticle or the application of radiation or acoustic wave, preferentially on the nanoparticles or body part, is continuous. In some cases, a continuous application of radiation or acoustic wave is an application of radiation or acoustic wave that is not stopped during a lapse of time larger than $10^{-100}$, $10^{-50}$, $10^{-20}$, $10^{-10}$, $10^{-6}$, $10^{-3}$, $10^{-1}$, 1 or $10^3$ seconds, preferentially larger than $t_1$. In some other cases, a continuous application of radiation or acoustic wave is an application of radiation that is not stopped during a lapse of time smaller than $10^{100}$, $10^{50}$, $10^{20}$, $10^{10}$, $10^5$, $10^3$, 10, 1, $10^{-1}$ or $10^{-5}$ seconds or hours or days or months or years.

In some other cases, the nanoparticle can be the nanoparticle exposed to the radiation or acoustic wave.

In one embodiment of this invention, the nanoparticle is or belongs to or is comprised in the group of nanoparticles selected from: a nanosphere, a nanocapsule, a dendrimer, a carbon nanotube, a lipid/solid nanoparticle, a lipid or protein or DNA or RNA based nanoparticle, a nanoparticle with an inner aqueous environment surrounded by a layer, preferentially a stabilizing layer, most preferentially a phospholipid layer, a multilayer nanoparticle, a polymeric nanoparticle, a quantum dot, a metallic nanoparticle, a polymeric micelle or nanoparticle, a carbon based nano-structure, a nanobubble, a nanosome, a pharmacyte, a niosome, a nanopore, a microbivore, a liposome, a virus, preferentially recombinant, a herbal nanoparticle, an antibody, and a vesicle.

In another embodiment of this invention, the nanoparticle is not or does not belong to or is not comprised in at least one nanoparticle belonging to the group of: a nanosphere, a nanocapsule, a dendrimer, a carbon nanotube, a lipid/solid nanoparticle, a lipid or protein or DNA or RNA based nanoparticle, a nanoparticle with an inner aqueous environment surrounded by a layer, preferentially a stabilizing layer, most preferentially a phospholipid layer, a multilayer nanoparticle, a polymeric nanoparticle, a quantum dot, a metallic nanoparticle, a polymeric micelle or nanoparticle, a carbon based nano-structure, a nanobubble, a nanosome, a pharmacyte, a niosome, a nanopore, a microbivore, a liposome, a virus, preferentially recombinant, a herbal nanoparticle, an antibody, and a vesicle.

In some cases, the nanoparticle can be in a liquid, gaseous, or solid state, preferentially before, during or after its presence or administration in the body part.

In some other cases, the nanoparticle can't be in one or two of the liquid, gaseous, or solid states, preferentially before, during or after its presence or administration in the body part.

In still some other cases, the nanoparticles can be assimilated to or be comprised in a ferrofluid, a chemical or biological ferrofluid, wherein chemical and biological ferrofluids are fluids containing iron, preferentially forming nanoparticles, which are fabricated through a chemical or biological synthesis, respectively.

In still some other cases, the ferrofluid or nanoparticle assembly can comprise the nanoparticles and an excipient, a solvent, a matrix, a gel, which preferentially enables the administration of the nanoparticles to the individual or body part.

In still some other cases, the nanoparticle can comprise synthetic material and/or biological material and/or inorganic material and/or organic material.

In one embodiment of the invention, (the) nanoparticle(s) is/are or designate: i) a suspension of nanoparticles, ii) a composition comprising nanoparticles, iii) an assembly of nanoparticles,
  iv) a nanoparticle region, v) the mineral part of the nanoparticle, vi) the organic part of the nanoparticle, vii) the inorganic part of the nanoparticle, viii) or the coating of the nanoparticle.

In one embodiment of the invention, nanoparticle(s) or the nanoparticle(s) represent(s) or is or are an assembly or suspension or composition of more or comprising more than $10^{-100}$, $10^{-50}$, $10^{-10}$, $10^{-5}$, $10^{-1}$, 1, 10, $10^2$, $10^3$, $10^5$, $10^{10}$, $10^{20}$ or $10^{50}$ nanoparticle(s) or mg of nanoparticle(s) or mg of iron comprised in nanoparticle(s) or mg of nanoparticle(s) per $cm^3$ or mg of nanoparticle(s) per $cm^3$ of body part or mg of iron comprised in nanoparticle(s) per $cm^3$ or mg of iron comprised in nanoparticle(s) per $cm^3$ of body part. In some cases, an assembly or suspension or composition comprising a large number of nanoparticles can be used to induce or produce a temperature increase, radical or reactive species, or the dissociation of a compound from the nanoparticles.

In another embodiment of the invention, nanoparticle(s) or the nanoparticle(s) represent(s) or is or are an assembly or suspension or composition of less or comprising less than $10^{100}$, $10^{50}$, $10^{20}$, $10^{10}$, $10^5$, $10^2$, 10, 1, 5, 2, 1, $10^{-1}$, $10^{-5}$, $10^{-10}$ or $10^{-50}$ nanoparticle(s) or mg of nanoparticle(s) or mg of iron comprised in nanoparticle(s) or mg of nanoparticle(s) per $cm^3$ or mg of nanoparticle(s) per $cm^3$ of body part or mg of iron comprised in nanoparticle(s) per $cm^3$ or mg of iron comprised in nanoparticle(s) per $cm^3$ of body part. In some cases, an assembly or suspension or composition of nanoparticles comprising a low number of nanoparticle(s) can be used to prevent toxicity.

In one embodiment of the invention, the nanoparticle(s) or nanoparticle(s) or nanoparticle assembly can represent or be the region, also designated as nanoparticle region, volume, surface, length, which comprises the nanoparticles or where nanoparticles are located. In some cases, the volume of the region occupied by the nanoparticles in the body part is designated as nanoparticle region.

In some cases, the nanoparticle region can be the volume occupied by an assembly of nanoparticles in the body part, where the nanoparticles are preferentially separated by less than $10^9$, $10^6$, $10^3$ or 10 nm.

In some cases, the nanoparticle assembly is a more general term than nanoparticle region, which could designate any type of nanoparticle assembly, before, during, or after nanoparticle administration to or in the body part.

In some cases, the separating distance between the nanoparticles within the nanoparticle assembly or nanoparticle region can correspond to the average or maximum distance separating the nanoparticles within this assembly.

In some cases, the distribution in separating distances between nanoparticles can highlight the presence of a minority of nanoparticles, i.e. preferentially less than 50, 10, 1, $10^{-2}$ or $10^{-5}$% of the total number of nanoparticles in the individual, with either small separating distances, i.e separating distances preferentially lower than $10^9$, $10^6$, $10^3$ or 10 nm, or with large separating distances, i.e. separating distances preferentially larger than $10^9$, $10^6$, $10^3$ or 10 nm. In this case, the presence of this minority of nanoparticles is preferentially not taken into consideration to estimate the average or maximum separating distance between the nanoparticles.

The invention also relates to nanoparticles for use according to the invention, wherein the nanoparticles are crystallized, metallic, or magnetic.

In an embodiment of the invention, the nanoparticles are crystallized. In this case, they preferentially possess more than or at least 1, 2, 10, $10^2$, $10^3$, $10^6$ or $10^9$ crystallographic plane(s) or regular atomic arrangement(s), preferentially observable by electron microscopy.

In one embodiment of the invention, the nanoparticles are metallic. In this case, they contain at least 1, 10, $10^3$, $10^5$ or $10^9$ metallic atom(s) or contain at least 1, 10, 50, 75 or 90% of metallic atoms, where this percentage can be the ratio between the number or mass of metallic atoms in the nanoparticle divided by the total number or mass of all atoms in the nanoparticle. The nanoparticles, preferentially metal oxide nanoparticles, can also contain at least 1, 10, $10^3$, $10^5$ or $10^9$ oxygen atom(s), or contain at least 1, 10, 50, 75 or 90% of oxygen atoms, where this percentage can be the ratio between the number or mass of oxygen atoms in the nanoparticles divided by the total number or mass of all atoms in the nanoparticles.

In another embodiment of the invention, the metal or metal atom is selected in the list consisting of: Lithium, Beryllium, Sodium, Magnesium, Aluminum, Potassium, Calcium, Scandium, Titanium, Vanadium, Chromium, Manganese, Iron, Cobalt, Nickel, Copper, Zinc, Gallium, Rubidium, Strontium, Yttrium, Zirconium, Niobium, Molybdenum, Technetium, Ruthenium, Rhodium, Palladium, Silver, Cadmium, Indium, Tin, Cesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Polonium, Francium, Radium, Actinium, Thorium, Protactinium, Uranium, Neptunium, Plutonium, Americium, Curium, Berkelium, Californium, Einsteinium, Fermium, Mendelevium, Nobelium, Lawrencium, Rutherfordium, Dubnium, Seaborgium, Bohrium, Hassium, Meitnerium, Darmstadtium, Roentgenium, Copernicium, Nihonium, Flerovium, Moscovium, and Livermorium or Livermorium atom.

In another embodiment of the invention, the nanoparticle contains less than 1, 10, $10^3$, $10^5$ or $10^9$ metallic atom(s) or contains less than 1, 10, 50, 75 or 90% of metallic atoms, where this percentage can be the ratio between the number or mass of metallic atoms in the nanoparticle divided by the total number or mass of all atoms in the nanoparticle. It can also contain less than 1, 10, $10^3$, $10^5$ or $10^9$ oxygen atom(s), or contain less than 1, 10, 50, 75 or 90% of oxygen atoms, where this percentage can be the ratio between the number or mass of oxygen atoms in the nanoparticle divided by the total number or mass of all atoms in the nanoparticle.

In one embodiment of the invention, the nanoparticle is magnetic when it has a magnetic behavior or property, where the magnetic behavior or property is preferentially selected from the group consisting of a diamagnetic, superparamagnetic, paramagnetic, ferromagnetic, and ferrimagnetic behavior or property.

In some cases, the magnetic behavior or property can be observed or exists at a temperature, which is lower than: i) $10^5$, $10^3$, 500, 350, 200, 100, 50, 20, 10, 1, 0.5 or 1 K (Kelvin), ii) the Curie temperature, or iii) the blocking temperature.

In some other cases, the magnetic behavior or property can be observed or exists at a temperature, which is larger than: i) 0.5, 1, 10, 20, 50, 100, 200, 350, 500, $10^3$ or $10^5$ K, ii) the Curie temperature, or iii) the blocking temperature.

In still some other cases, the magnetic behavior or property can be observed or exists at a temperature, which is between $10^{-20}$ and $10^{20}$ K, or between 0.1 and 1000 K.

In one embodiment of the invention, the nanoparticles have or are characterized by at least one of the following properties: i) the presence of a core, preferentially magnetic, preferentially mineral, preferentially composed of a metallic oxide such as iron oxide, most preferentially maghemite or magnetite, or an intermediate composition between maghemite and magnetite, ii) the presence of a coating that surrounds the core and preferentially prevents nanoparticle aggregation, preferentially enabling nanoparticle administration in an organism or in the body part or stabilizing the nanoparticle core, where coating thickness may preferably lie between 0.1 nm and 10 µm, between 0.1 nm and 1 µm, between 0.1 nm and 100 nm, between 0.1 nm and 10 nm, or between 1 nm and 5 nm, iii) magnetic properties leading to diamagnetic, paramagnetic, superparamagnetic, ferromagnetic, or ferrimagnetic behavior, iv) a coercivity larger than 0.01, 0.1, 1, 10, 100, $10^3$, $10^4$, $10^5$, $10^9$ or $10^{20}$ Oe, v) a ratio between remanent and saturating magnetization larger than 0.01, 0.1, 0.2, 0.3, 0.4, 0.5, 0.75, 0.9 or 0.99, vi) a saturating magnetization larger than 0.1, 1, 5, 10 or 50 emu/g, vii) magnetic properties such as coercivity, remanent and saturating magnetization, preferentially measured or observed at a temperature larger than 0.1 K, 1 K, 10 K, 20 K, 50 K, 100 K, 200 K, 300 K, 350 K or 3000 K, viii) a crystallinity, i.e. nanoparticles preferentially possessing at least 1, 2, 5, 10 or 100 crystalline plane(s), preferentially observable or measured by electron microscopy, ix) the presence of a single domain, x) a size that is larger than 0.1, 0.5, 1.5, 10, 15, 20, 25, 30, 50, 60, 70, 80, 100, 120, 150 or 200 nm, xi) a size lying between 0.1 nm and 10 µm, between 0.1 nm and 1 µm, between 0.1 nm and 100 nm, between 1 nm and 100 nm, or between 5 nm and 80 nm, xii) a non-pyrogenicity or apyrogenicity, which preferentially means that nanoparticles possess an endotoxin concentration lower than $10^{20}$, 10000, 1000, 100, 50, 10, 5, 2 or 1 EU (endotoxin unit) per mg of nanoparticle or per mg of iron comprised in nanoparticles, or which means that nanoparticles do not trigger fever or an increase in whole body temperature larger than 100, 50, 6.6, 5, 3, 2 or 1° C. following their administration to a living organism or body part, xiii) a synthesis by a synthetizing living organism, preferentially by bacteria, xiv) a chemical synthesis, xv) the presence of less than 50, 25, 15, 10, 5, 2 or 1% of organic or carbon material originating from the synthetizing living organism, xv), the presence of more than 99, 95, 80, 70, 60, 50 or 25% of mineral material originating from the synthetizing living organism, or xvi) a specific absorption rate (SAR) that is larger than 1, 10, 1000 or $10^4$ Watt per gram of nanoparticle, preferentially measured under the application of an alternating magnetic field of strength preferentially larger than 0.1, 1, 10 or 100 mT, and/or frequency larger than 1, 10, 100 or 1000 KHz, alternatively preferentially measured under the application of the acoustic wave, alternatively under the application of a radiation such as an electromagnetic acoustic, or light radiation.

In some cases, the synthetizing living organism can be magnetotactic bacteria, other types bacteria than magnetotactic bacteria or enzymes of certain bacteria, preferentially synthetizing nanoparticles extra-cellularly, such as *Mycobacterium paratuberculosis, Shewanella oneidensi, Geothrix fermentans*, ants, fungi, or various plants.

In another embodiment of the invention, the nanoparticles have or are characterized by at least one of the following properties: i) a coercivity lower than 0.01, 0.1, 1, 10, 100, $10^3$, $10^4$, $10^5$, $10^9$ or $10^{20}$ Oe, ii) a ratio between remanent and saturating magnetization lower than 0.01, 0.1, 0.2, 0.3, 0.4, 0.5, 0.75, 0.9 or 0.99, iii) a saturating magnetization lower than 0.1, 1, 5, 10, 50, 200, 1000 or 5000 emu/g, iv) magnetic properties preferentially measured or observed at a temperature lower than 0.1 K, 1 K, 10 K, 20 K, 50 K, 100 K, 200 K, 300 K, 350 K or 3000 K, v) a size that is lower than 0.1, 0.5, 1.5, 10, 15, 20, 25, 30, 50, 60, 70, 80, 100, 120, 150 or 200 nm, vi) the presence of more than 50, 25, 15, 10, 5, 2 or 1% of organic or carbon material originating from the synthetizing living organism, vii) the presence of less than 99, 95, 80, 70, 60, 50 or 25% of mineral material originating from the synthetizing living organism, or xi) a specific absorption rate (SAR) that is lower than 1, 10, 1000 or $10^4$ Watt per gram of nanoparticle, preferentially measured under the application of an alternating magnetic field of strength preferentially lower than 0.1, 1, 10, or 100, 200, 500, $10^3$ or $10^5$ mT, and/or of frequency preferentially lower than 1, 10, 100, $10^3$, $10^5$ or $10^9$ KHz, alternatively preferentially measured under the application of the acoustic wave, alternatively under the application of a radiation such as an electromagnetic acoustic, or light radiation.

In some cases, the mineral can be the part of the nanoparticle or magnetosome that does not comprise organic material or comprises a low percentage in mass of organic material, preferentially less than 100, 99, 50, 20, 10, 5, 1, $10^{-1}$ or $10^{-2}$ percent or percent in mass of organic material. The mineral is preferentially the core of the nanoparticle.

In some other cases, the mineral can comprise a percentage in mass of organic material larger than 0, $10^{-50}$, $10^{-10}$, $10^{-2}$, $10^{-1}$ or 1 percent or percent in in mass of organic material. This can be the case when the purification step unsuccessfully removes the organic material or when organic material is added to the mineral after the purification step.

In some cases, the nanoparticles can be surrounded by a coating. The coating can be made of a synthetic, organic, or inorganic material or of a substance comprising a function selected in the group consisting of carboxylic acids, phosphoric acids, sulfonic acids, esters, amides, ketones, alcohols, phenols, thiols, amines, ether, sulfides, acid anhydrides, acyl halides, amidines, amides, nitriles, hydroperoxides, imines, aldehydes, and peroxides. In some cases, the coating can be made of carboxy-methyl-dextran, citric acid, phosphatidylcholine (DOPC), or oleic acid. In some cases, the coating can enable the dispersion of the nanoparticles in a matrix or solvent such as water, preferentially without aggregation or sedimentation of the nanoparticles.

In some cases, the coating can enable internalization of the nanoparticles in cells. In some other cases, the coating can enable: i) to bind two or more nanoparticle(s) together preferentially in a chain, ii) to prevent nanoparticle aggregation and/or, iii) to obtain uniform nanoparticle distribution.

In one embodiment of the invention, the nanoparticles are non-pyrogenic. Non-pyrogenic nanoparticles preferentially: i) comprise less than $10^{100}$, $10^{50}$, $10^{20}$, $10^8$, $10^5$, $10^3$, or 10 EU (endotoxin unit) or EU per $cm^3$ of body part or EU per mg of nanoparticle or EU per $cm^3$ of body part per mg of nanoparticle, or ii) induce a temperature increase of the individual or body part of less than $10^5$, $10^3$, $10^2$, 50, 10, 5, 4, 3, 2 or 1° C., preferentially above physiological temperature, preferentially before, after or without the application of the acoustic wave or radiation on the nanoparticle.

In one embodiment of this invention, the nanoparticle or compound is composed of or comprises a chemical element of the families selected from the group consisting of: metals (alkali metal, alkaline earth metal, transition metals), semi-metal, non-metal (halogens element, noble gas), chalcogen elements, lanthanide, and actinide.

In another embodiment of the invention, the nanoparticle or compound is composed of or comprises a chemical element selected from the group consisting of: hydrogen, lithium, sodium, potassium, rubidium, caesium, francium, beryllium, magnesium, calcium, strontium, barium, radium, scandium, yttrium, lanthanide, actinide, titanium, zirconium, hafnium, rutherfordium, vanadium, niobium, tantalum, dubnium, chromium, molybdenum, tungsten, seaborgium, manganese, technetium, rhenium, bohrium, iron, ruthenium, osmium, hessium, cobalt, rhodium, iridium, meitherium, nickel, palladium, platinum, darmstadtium, copper, silver, gold, roentgenium, zinc, cadmium, mercury, copernicum, boron, aluminium, gallium, indium, thallium, ununtrium, carbon, silicon, germanium, tin, lead, fleovium, nitrogen, phosphorus, arsenic, antimony, bismuth, ununpentium, oxygen, sulphur, selenium, tellurium, polonium, livermorium, fluorine, chlorine, bromine, iodine, astatine, ununseptium, helium, neon, argon, krypton, xenon, radon, ununoctium, lanthanum, cerium, praseodymium, neodymium, promethium, samarium, europium, gadolinium, terbium, dysprosium, holmium, erbium, thulium, ytterbium, lutetium, actinium, thorium, proctactinium, uranium, neptunium, plutonium, americium, curium, berkelium, californium, einsteinium, fermium, mendelevium, nobelium, and lawrencium.

In some cases, the nanoparticle or compound can also be composed of or comprise an alloy, a mixture, or an oxide of this(these) chemical element(s).

In some cases, the nanoparticle or compound can be composed of more than $10^{-50}$, $10^{-20}$, $10^{-10}$, $10^{-5}$, $10^{-2}$, 1, 5, 10, 50, 75, 80, 90, 95 or 99% of one or several of this(these) element(s), where this percentage can represent the mass or number of this(these) chemical elements comprised in the nanoparticle or compound divided by the total number or total mass of all chemical elements comprised in the nanoparticle or compound or by the total mass of the nanoparticle or compound.

In some other cases, the nanoparticle or compound can be composed of or comprise less than $10^{-50}$, $10^{-20}$, $10^{-10}$, $10^{-5}$, $10^{-2}$, 1, 5, 10, 50, 75, 80, 90, 95 or 99% of one or several of this(these) chemical element(s).

In still some other cases, this(these) chemical element(s) is(are) comprised inside the nanoparticle or compound, or at the surface of the nanoparticle or compound, or in the mineral or central part of the nanoparticle or compound, or in the coating of the nanoparticle or compound.

In one embodiment of this invention, the nanoparticle or compound is not composed of or does not comprise at least one chemical element belonging to the family selected from the group consisting of: metals (alkali metal, alkaline earth metal, transition metals), semimetal, non-metal (halogens element, noble gas), chalcogen elements, lanthanide, actinide.

In another embodiment of the invention, the nanoparticle or compound is devoid of or does not comprise at least one chemical element selected from the group consisting of: hydrogen, lithium, sodium, potassium, rubidium, caesium, francium, beryllium, magnesium, calcium, strontium, barium, radium, scandium, yttrium, lanthanide, actinide, titanium, zirconium, hafnium, rutherfordium, vanadium, niobium, tantalum, dubnium, chromium, molybdenum, tungsten, seaborgium, manganese, technetium, rhenium, bohrium, iron, ruthenium, osmium, hessium, cobalt, rhodium, iridium, meitherium, nickel, palladium, platinum, darmstadtium, copper, silver, gold, roentgenium, zinc, cadmium, mercury, copernicum, boron, aluminium, gallium, indium, thallium, ununtrium, carbon, silicon, germanium, tin, lead, fleovium, nitrogen, phosphorus, arsenic, antimony, bismuth, ununpentium, oxygen, sulphur, selenium, tellurium, polonium, livermorium, fluorine, chlorine, bromine, iodine, astatine, ununseptium, helium, neon, argon, krypton, xenon, radon, ununoctium, lanthanum, cerium, praseodymium, neodymium, promethium, samarium, europium, gadolinium, terbium, dysprosium, holmium, erbium, thulium, ytterbium, lutetium, actinium, thorium, proctactinium, uranium, neptunium, plutonium, americium, curium, berkelium, californium, einsteinium, fermium, mendelevium, nobelium, and lawrencium.

In another embodiment of the invention, the nanoparticle or compound is not composed of or does not comprise an alloy, a mixture, or an oxide of this(these) chemical element(s).

In one embodiment of the invention, the nanoparticle is defined as a particle with a size in one dimension, which is larger than $10^{-1}$, 1, 2, 5, 10, 20, 50, 70, 100, 200 or 500 nm. A nanoparticle with a large size can have a larger coercivity and/or a larger remanent magnetization and/or can more strongly or more efficiently absorb the energy or power of the acoustic wave than a nanoparticle with a small size. In some cases, the amount of energy or power absorbed by a nanoparticle is increased by a factor of more than 1.001, 1.01, 1.1, 1.2, 1.5, 2, 5, 10, $10^3$, $10^5$ or $10^7$ by increasing the size of the nanoparticle by a factor of more than 1.001, 1.01, 1.1, 1.2, 1.5, 2, 5, 10, $10^3$, $10^5$ or $10^7$.

In another embodiment of the invention, the nanoparticle is defined as a particle with a size in one dimension, which is lower than $10^4$, $10^3$, $10^2$, 10, 1 or $10^{-1}$ nm. A nanoparticle with a small size can more easily be administered, for example intravenously, or can enable the avoidance of some toxicity effects, such as embolism.

In still another embodiment of the invention, the nanoparticle size lies between $10^{-2}$ and $10^{20}$ nm, $10^{-2}$ and $10^4$ nm, between $10^{-1}$ and $10^3$ nm, or between 1 and $10^2$ nm. This can be the case when the nanoparticle or nanoparticle assembly possesses a well-defined, preferentially narrow, distribution in sizes.

In still another embodiment of the invention, the nanoparticle size distribution is lower than 1000, 100, 75, 50, 25, 10, 5, 2 or 1 nm. A narrow nanoparticle size distribution may be desired to prevent aggregation, or to favor an organization in chains of the nanoparticles.

In another embodiment of the invention, the nanoparticle size distribution is larger than 1000, 100, 75, 50, 25, 10, 5, 2 or 1 nm. A large nanoparticle size distribution may in some cases enable nanoparticles to be eliminated more rapidly.

In another embodiment of the invention, the nanoparticle has a surface charge, which is larger than −200, −100, −50, −10, −5, 0.1, 1, 2, 5, 10, 50 or 100 mV, preferentially at a pH lower than 0.1, 1, 2, 3, 4, 5, 6, 7, 8, 9, 10, 11, 12, 13 or 14. Preferentially, a nanoparticle can have a large surface charge at low pH when it is surrounded by a coating that enables to reach such charge without being destroyed.

In another embodiment of the invention, the nanoparticle has a surface charge, which is lower than −200, −100, −50, −10, −5, 0.1, 1, 2, 5, 10, 50 or 100 mV, preferentially at a pH larger than 0.1, 1, 2, 3, 4, 5, 6, 7, 8, 9, 10, 11, 12, 13 or 14. A nanoparticle can have a low surface charge at high pH when it is surrounded by a coating that enables to reach such charge without being destroyed.

In still another embodiment of the invention, the nanoparticle has a surface charge comprised between +200 and −200 mV, +100 and −100 mV, +50 and −50 mV, +40 et−40 mV, +20 and −20, +10 and −10 mV, or between +5 and −5 mV, preferentially at a pH lower than 0.1, 1, 2, 3, 4, 5, 6, 7, 8, 9, 10, 11, 12, 13 or 14.

In still another embodiment of the invention, the nanoparticle has a surface charge comprised between +200 and −200 mV, +100 and −100 mV, +50 and −50 mV, +40 et−40 mV, +20 and −20, +10 and −10 mV, or between +5 and −5 mV, preferentially at a pH larger than 0.1, 1, 2, 3, 4, 5, 6, 7, 8, 9, 10, 11, 12, 13 or 14.

In another embodiment of the invention, the nanoparticle has a weight or a mass, preferentially expressed in unit such as gram (g), kilogram (kg), or milligram (mg). A gram of nanoparticle can be a gram of metal such as iron comprised in the nanoparticle. The mass or weight of the nanoparticle can correspond to the mass or weight of one nanoparticle or to the mass or weight of an assembly of nanoparticles.

In an embodiment, the mass of the nanoparticle is larger than $10^{-20}$, $10^{-10}$, $10^{-5}$, $10^{-2}$, 1, 10, $10^3$, $10^9$ or $10^{20}$ gram. In some cases, a large nanoparticle mass may be desired to increase the quantity of acoustic wave energy absorbed by the nanoparticle.

In an embodiment, the mass of the nanoparticle is lower than $10^{-20}$, $10^{-10}$, $10^{-5}$, $10^{-2}$, 1, 10, $10^3$, $10^9$ or $10^{20}$ gram. In some cases, a low nanoparticle mass may be desired to prevent or minimize nanoparticle toxicity.

In one embodiment of the invention, the nanoparticle, the suspension, composition, or assembly of nanoparticle is stable, preferentially during a lapse of time, preferentially being its stability duration, which is larger than $10^{-10}$, 5, 10, $10^{50}$ or $10^{100}$ minute(s). In some cases, the nanoparticle, the suspension, composition, or assembly of nanoparticle can be stable at a concentration of nanoparticles larger than 1, 5, 10, 50, 100, 200, 500 or 1000 mg of nanoparticles per mL of solvent, matrix, or body part surrounding or comprising the or nanoparticle. In some cases, the nanoparticle, the suspension, composition, or assembly of nanoparticle can be stable when: i) the nanoparticle is not degraded or does not lose partly or fully its coating or can be administered to the body part, or ii) the optical density of the nanoparticle, the suspension, composition, or assembly of nanoparticle, preferentially measured at 480 nm or at another fixed wavelength, does not decrease by more than 1, 5, 10, 50, 75 or 90% or by more than $10^{-10}$, $10^{-3}$, $10^{-1}$, 0.5 or 0.7, within 1, 5, 10, $10^3$, $10^7$ or $10^{20}$ seconds following homogenization or mixing or optical density measurement or absorption measurement of this suspension or composition. This percentage can be equal to $(OD_B - OD_A)/OD_B$ or $OD_A/OD_B$, where $OD_B$ is the optical density of the nanoparticle, the suspension, composition, or assembly of nanoparticle measured before the homogenization or mixing or optical density measurement or absorption measurement of the nanoparticle, the suspension, composition, or assembly of nanoparticle and $OD_A$ is the optical density of the nanoparticle, the suspension, composition, or assembly of nanoparticle measured after the homogenization or mixing or optical density measurement or absorption measurement of the nanoparticle, the suspension, composition, or assembly of nanoparticle.

In some cases, the nanoparticle can be suspended in a liquid or dispersed in a matrix or body part to yield a homogenous nanoparticle dispersion or a highly stable nanoparticle composition or suspension.

In one embodiment of the invention, the nanoparticles are arranged in chains comprising more than 1, 2, 3, 4, 5, 6, 7, 8, 9, 10, 15, 20, 25, 30, 35 or 40 nanoparticles.

In another embodiment of the invention, the nanoparticles are arranged in chains, which have:
i) a length smaller than $2.10^{10}$, $2.10^5$, $2.10^3$ or $2.10^2$ nm, or ii) a number of nanoparticles in each chain smaller than 2, 5, 10, $10^2$ or $10^3$. In some cases, short chains of nanoparticles may be desired or obtained, for example to favor nanoparticle internalization in cells or after partial or total destruction of long chains.

In another embodiment of the invention, the nanoparticles are arranged in chains, which have: i) a length longer than $10^{-1}$, 1, 5, 10, $2.10^2$, $2.10^3$ or $2.10^5$, or ii) a number of nanoparticles in each chain larger than 2, 5, 10, $10^2$ or $10^3$. In some cases, long chains of nanoparticles may be desired or obtained to increase the quantity of heat or compounds dissociated from the nanoparticles under the application of an acoustic wave or radiation or to prevent nanoparticle aggregation or enable uniform nanoparticle distribution.

In still another embodiment of the invention, the nanoparticles are arranged in chains, which have: i) a length between $10^{-1}$ and $10^{10}$ nm, or between 1 and $10^5$ nm, or ii) a number of nanoparticles in each chain between 2 and $10^5$, 2 and $10^3$, 2 and $10^2$, or 2 and 50.

In still another embodiment of the invention, the nanoparticles are arranged in chains when they are bound or linked to each other or when the crystallographic directions of two adjacent nanoparticles in the chain are aligned, wherein such alignment is preferentially characterized by an angle between two crystallographic directions belonging to two adjacent nanoparticles in the chains of less than 90, 80, 70, 60, 50, 20, 10, 3, or 2° (degree).

Preferentially when the nanoparticles are biologically synthesized, the nanoparticles can be arranged in chains: i) inside the organism that synthesizes them, also designated as synthetizing living organism, or ii) outside this organism. Preferentially, nanoparticles are arranged in chains after or before their extraction or isolation from this organism.

In one embodiment of the invention, the nanoparticles are not arranged in chains.

In another embodiment of the invention, the nanoparticles are synthesized chemically or are not synthesized by a living organism when less than 1, 2, 5, 10 or 100 step(s) of their production, such as crystallization of iron oxide, stabilization of the iron oxide mineral, organization of the nanoparticles, involves or is due to a living organism. In some cases, a chemical synthesis can be defined as a synthesis involving a majority of steps, or more than 1, 2, 5 or 10 steps, or more than 1, 2, 5, 25, 50, 75 or 90% of steps, which involve chemical reactions occurring without the involvement of living organisms, or parts of living organisms such as DNA, RNA, proteins, enzymes, lipids.

In another embodiment of the invention, a chemical synthesis can be used to produce a chemical substance or compound that mimics, copies, or reproduces the compartment, organelle, or other biological material, wherein this chemical synthesis or chemical substance can be used or can result in the production of the nanoparticles. In some cases, the compartment, organelle, or other biological material, can be a lysosome, an endosome, a vesicle, preferentially biological material that has the capacity or the function either to dissolve or transform crystallized iron into free iron or to transform free iron into crystalized iron. In some cases, this transformation is partial and preferentially results in the destruction or formation of partly crystallized assembly of iron atoms or ions, or preferentially results in a mixture of crystallized iron and non-crystallized iron. In some cases, crystallized iron can be defined as an assembly of iron atoms or ions that leads to the presence of crystallographic planes, preferentially observable using a technique such as transmission or scanning electron microscopy as a characterization method, and free iron can preferentially be defined as one of several iron atoms or ions that do not lead to the presence of crystallographic planes, preferentially highlighted by the absence of diffraction patterns, using for example transmission or scanning electron microscopy as a characterization method.

In one embodiment of the invention, the nanoparticles are synthesized biologically or by a living organism, designated as synthetizing living organism, which preferentially consists or comprises at least 1, 2, 5, 10, $10^3$, $10^6$ or $10^9$ eukaryotic cell(s), prokaryotic cell(s), or part of these cells. In some cases, part of eukaryotic or prokaryotic cell(s) can be biological material originating or produced by these cells such as RNA, DNA, organelle, nucleolus, nucleus, ribosome, vesicle, rough endoplasmic reticulum, Golgi apparatus, cytoskeleton, smooth endoplasmic reticulum, mitochondrion, vacuole, cytosol, lysosome, centrosome, cell membrane. In some cases, a biological synthesis can be defined as a synthesis involving a majority of steps, or more than 1, 2, 5 or 10 steps, or more than 1, 2, 5, 25, 50, 75 or 90% of steps, which involve chemical reactions occurring with the involvement of at least 1, 2, 10, $10^3$, $10^6$ or $10^9$ living organisms, or parts of living organisms such as DNA, RNA, proteins, enzymes, lipids.

In still another embodiment of the invention, the nanoparticles are synthesized or produced or crystallized or assembled or transformed into a nanoparticle by a compartment, organelle, or other biological material, such as protein, lipid, enzyme, DNA, or RNA, which is preferentially produced by or originates from an eukaryotic or prokaryotic cell.

In another embodiment of the invention, the nanoparticles are synthesized by or in at least one eukaryotic cell, prokaryotic cell, or part of this cell.

In another embodiment of the invention, the nanoparticles are synthesized by or in: i) the matrix or medium or environment located outside of at least one eukaryotic cell, prokaryotic cell, or part of this cell, or ii) the extracellular matrix.

In one embodiment of the invention, the nanoparticles are synthesized by a living organism when at least 1, 2, 5, 10 or 100 step(s) of their production, such as crystallization of iron oxide, stabilization of the iron oxide mineral, organization of the nanoparticles, for example in chains or aggregates, involves or is due to a living organism.

The invention also relates to the nanoparticles for use, wherein the nanoparticles are magnetosomes synthesized by, originating from, extracted from, or isolated from magnetotactic bacteria.

In one embodiment of the invention, the magnetosome is synthesized by, produced by, originates from, extracted from, isolated from magnetotactic bacteria.

In one embodiment of the invention, magnetotactic bacteria are selected from the group consisting of: *Magnetospirillum magneticum* strain AMB-1, magnetotactic coccus strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anaerobic magnetotactic spirillum, *Magnetospirillum magneticum* strain MGT-1, and an obligate anaerobe, and *Desulfovibrio magneticus* RS-1.

In one embodiment of the invention, a magnetotactic bacterium is defined as a bacterium able to synthesize magnetosomes, wherein these magnetosomes are preferentially characterized by at least one of the following properties: i) they are produced intracellularly, ii) they are magnetic, iii) they comprise a mineral, iv) their core is preferentially composed of a metallic oxide such as iron oxide, v) their core is surrounded by biological material such as lipids, proteins, endotoxins, which can preferentially be removed, vi) they are arranged in chains, vii) they produce heat under the application of an alternating magnetic field.

In one embodiment of the invention, the magnetosomes possess one or several property(ies) in common with the nanoparticles such as at least one magnetic, size, composition, chain arrangement, charge, core, mineral, coating, or crystallinity property.

In one embodiment of the invention, magnetosomes comprise the mineral part synthesized by magnetotactic bacteria, i.e. preferentially the crystallized iron oxide produced by these bacteria. In this case, magnetosomes or magnetosome mineral parts preferentially do not comprise proteins, lipids, endotoxins, or biological materials comprising carbon or do not comprise more or comprise less than 0.1, 1, 10, 30, 50 or 75% or percent in mass of carbon, which is/are produced by these bacteria.

The invention also relates to nanoparticles for use, wherein nanoparticles are or are assimilated to chemical analogues of magnetosomes, such as iron oxide nanoparticles designated as Sigma nanoparticles (ref: 637106-25G), SPION20 (Nanomag®-D-spio 20, Ref: 79-02-201), SPION50 (synomag-D50, Ref: 104-000-501), SPION100 (Nanomag®-D-spio 100, Ref: 79-00-102) or nanoparticles synthesized using a similar method as for these nanoparticles but yielding improved or additional properties such as an arrangement in chains.

In some cases, chemical analogues of magnetosomes can be synthesizes chemically and/or are not synthesized by magnetotactic bacteria.

In some cases, chemical analogues of magnetosomes possess at least 1, 2, 3, 4, 5, 6, 7, 8, 9, or 10 common property(ies) with the magnetosomes, where these common properties are preferentially a ferrimagnetic behavior, preferentially a coercivity larger that $10^{-50}$, $10^{-10}$, $10^{-2}$, 1, 5, 10 or 100 Oe at a temperature preferentially larger than 0, 5, 10, 50, 100, 200, 300, 500 or 1000 K, a large size, preferentially a size larger than 1, 5, 10, 20, 50 or 70 nm, and/or a chain arrangement, preferentially an arrangement of more than 1, 2, 5 or 10 nanoparticles in chain.

In one embodiment of the invention, the nanoparticles or magnetosomes are purified to remove more than 10, 50 or 90 percent or percent in mass of endotoxins and/or other biological material such as proteins or lipids originating from the synthesizing living organism or magnetotactic bacteria. In some other cases, the nanoparticles or magnetosomes are purified to remove less than 100, 99.9, 99, 95 or 90 percent or percent in mass of endotoxins and/or other biological material. This purification step preferentially yields purified nanoparticles or magnetosomes.

In some cases, this percentage can be equal to $[Q_{BP}-Q_{AP}]/Q_{BP}$ or $Q_{AP}/Q_{BP}$, where $Q_{BP}$ and $Q_{AP}$ are the quantities of endotoxins, biological material, proteins, or lipids before and after the purification step, respectively.

In some cases, the purification step can consist in using a method or detergent(s) such as NaOH and/or KOH, which is/are preferentially mixed with the synthetizing living organism or magnetotactic bacteria or bacterial debris, preferentially to remove organic material or separate the organic material from the inorganic material comprised in the nanoparticles or magnetosomes and preferentially then be able to harvest the nanoparticle or magnetosome mineral, preferentially comprised in the nanoparticles or magnetosomes.

In some cases, the purified nanoparticles or magnetosomes are nanoparticle or magnetosome minerals.

In an embodiment of the invention, the nanoparticles according to the invention are drugs, medical devices, cosmetic products, biological products, products used for research purposes, or products used to determine the properties of biological samples.

In one embodiment of the invention, nanoparticles are sonosensitizers, preferentially used in sonodynamic therapy.

In one embodiment of the invention, a sonosensitizer is defined as a substance that enhances the effect of acoustic waves, i.e. that increases the number of biological material(s), preferentially pathological cell(s), which is(are) dead, destroyed, denatured, or inactivated, preferentially by a factor of 1.2, 1.5, 2, 5, 10, $10^3$ or $10^5$ and/or that decreases the number of healthy cell(s), which is(are) dead, destroyed, denatured, or inactivated, preferentially by a factor of 1.2, 1.5, 2, 5, 10, $10^3$ or $10^5$, preferentially during the treatment. A sonosensitizer can in some cases also be defined as a substance that leads to a temperature increase under the application of the acoustic wave, which is larger in the presence than in the absence of the sonosensitizers, i.e. a temperature increase that is preferentially $10^{-100}$, $10^{-50}$, $10^{-10}$, $10^{-5}$, 0.1, 1, 2, 5, 10, 20 or 50° C. larger in the presence than in the absence of the sonosensitizer, where the concentration of the sonosensitizer is preferentially larger than $10^{-50}$, $10^{-9}$, $10^{-6}$, $10^{-3}$, $10^{-1}$, 1, 10, 100 or $10^3$ mg as measured per mL or per $cm^3$ of body part. A sonosensitizer can in some other cases also be defined as a substance that leads to the dissociation of the compound under the application of the acoustic wave, which is larger in the presence than in the absence of the sonosensitizers, i.e. a percentage of dissociated compounds that is preferentially 0.1, 1, 2, 5, 10, 20, 50, 75, 80 or 90% larger in the presence than in the absence of the sonosensitizer, where the concentration of the sonosensitizer is preferentially larger than $10^{-9}$, $10^{-6}$, $10^{-3}$, $10^{-1}$, 1, 10, 100 or $10^3$ mg as measured per mL or per $cm^3$ of body part.

In another embodiment of the invention, the nanoparticle, nanoparticle suspension or assembly or composition, has a concentration, preferentially expressed in unit such as gram (g), kilogram (kg), or milligram (mg) of nanoparticle, metal, metallic chemical element, iron, iron oxide, maghemite, magnetite, per unit volume such as liter (l), milliliter (ml), $cm^3$, or $m^3$ or per unit surface area or per unit length. It preferentially has a concentration before or after administration in the body part, wherein the volume, surface area, or length, is preferentially the volume, surface area, or length of the suspension, assembly, or composition of nanoparticles before or after administration in the body part, or the volume, surface area, or length of the body part.

The invention also relates to nanoparticles for use according to the invention, wherein the concentration of nanoparticles, preferentially exposed to the acoustic wave or radiation or onto which the acoustic wave or radiation is applied, preferentially located in the body part or nanoparticle region, is lower than 10 g of nanoparticles per $cm^3$ of body part or of g iron comprised in nanoparticles per $cm^3$ of body part. In some cases, the nanoparticle concentration can be smaller than $10^{50}$, $10^{20}$, $10^{10}$, $10^5$, $10^3$, $10^2$, 10, 5, 2, 1, $10^{-3}$, $10^{-6}$ or $10^{-9}$ nanoparticle(s) as measured per $cm^3$ or per $cm^3$ of body part or gram (g) of nanoparticle as measured per $cm^3$ or per $cm^3$ of body part. In some cases, a low concentration of nanoparticles may be necessary or desired to prevent toxicity possibly arising at high nanoparticle concentration.

The invention also relates to nanoparticles for use according to the invention, wherein the concentration of nanoparticles, preferentially exposed to the acoustic wave or radiation or onto which the acoustic wave or radiation is applied, preferentially located in the body part or nanoparticle region, is larger than $10^{-50}$, $10^{-20}$, $10^{-10}$, $10^{-9}$, $10^{-6}$, $10^{-3}$, 1, 2, 5, 10, $10^2$, $10^5$, $10^{10}$, $10^{20}$ or $10^{50}$ nanoparticle(s) as measured per $cm^3$ or per $cm^3$ of body part or gram (g) of nanoparticle as measured per $cm^3$ or per $cm^3$ of body part. A large concentration of nanoparticles may be necessary to lead to an effect of the application of the acoustic wave on the nanoparticles, such as a temperature increase or the dissociation of the compound from the nanoparticles. In some cases, the nanoparticle concentration is the concentration in at least one substance comprised in the nanoparticle such as iron, oxide, iron oxide, or another metal than iron.

The invention also relates to nanoparticles for use according to the invention, wherein the concentration of nanoparticles, preferentially exposed to the acoustic wave or radiation or onto which the acoustic wave or radiation is applied, preferentially located in the body part or nanoparticle region, is between $10^{-50}$ and $10^{50}$, $10^{-20}$ and $10^{20}$, $10^{-3}$ and $10^3$, 0 and $10^{50}$, 1 and $10^{100}$, 1 and $10^{20}$, or between 1 and $10^5$ nanoparticle(s) as measured per $cm^3$ or per $cm^3$ of body part or gram (g) of nanoparticle as measured per $cm^3$ or per $cm^3$ of body part.

In still another embodiment of the invention, the nanoparticle concentration is comprised between a minimum value and a maximum value. In some cases, the minimum value is sufficiently large to enable the production of heat by the nanoparticle or the dissociation of the compound from the nanoparticle, preferentially under the application of laser radiation. In some other cases, the maximum value is sufficiently low to enable the imaging of the body part.

The invention also relates to nanoparticles for use according to the invention, having or resulting in at least one of the following properties:
i) the production of a slope of the initial variation, preferentially increase, of temperature with time, which is larger than $10^{-9}$ or $10^{-50}$ °C. per second as measured per gram of nanoparticle or $cm^3$ of body part or gram of nanoparticle per $cm^3$ of body part.
ii) a specific absorption rate that is larger than $10^{-9}$ Watt per gram of nanoparticle or Watt per $cm^3$ of body part, and/or
iii) a specific absorption rate, which increases which increases with increasing power of the acoustic wave applied on the nanoparticles at a rate that can increase with decreasing nanoparticle concentration.

In some cases, the slope of the initial variation, preferentially increase, of temperature with time can be measured or obtained by applying the acoustic wave on the nanoparticle or body part.

In some cases, $(\Delta T/\delta t)_{(N)}$ can be the initial variation of temperature with time of the body part comprising the nanoparticles, In some cases, $(\Delta T/\delta t)_{(WN)}$ can be the initial variation of temperature with time of the body part not comprising the nanoparticles.

In some cases, the abbreviation N for nanoparticle(s) can be replaced by the abbreviation M for magnetosome(s).

In some cases, $(\Delta T/\delta t)_{real}$, $(\Delta T/\delta t)_{(N)}$, or $(\Delta T/\delta t)_{(WN)}$ can represent a temperature variation by more than 1, 5, 10, 50, 75, $10^2$ or $10^3$%, during the initial time of application of the acoustic wave or radiation, designated as $t_i$, where this percentage can be the ratio between the temperature variation reached during $t_i$ and the initial temperature just before the application of the acoustic wave or radiation.

In some cases, $(\Delta T/\delta t)_{real}$ can be equal to $(\Delta T/\delta t)_{(N)} - (\Delta T/\delta t)_{(WN)}$.

In some cases, $(\Delta T/\delta t)_{real}$, $(\Delta T/\delta t)_{(N)}$, and/or $(\Delta T/\delta t)_{(WN)}$ can be the slopes of the initial temperature variation with time measured: i) during the first $10^{-9}$, $10^{-6}$, $10^{-3}$, $10^{-1}$, 1, 10, $10^3$, or $10^5$ minute(s) of the application of the acoustic wave, ii) during less than $10^3$, $10^2$, 10, 1, $10^{-2}$, $10^{-3}$, $10^{-6}$ or $10^{-9}$ seconds, preferentially following the beginning of the application of the acoustic wave or radiation, iii) when the temperature varies linearly with time, iv) before the saturating temperature has been reached, v) during an initial time of heating or heating step, which represents less than 1, 5, 10, 25, 50, 75, 80, 90, 95, or 99% of the total duration of heating or heating step.

In one embodiment of the invention, the values of $(\Delta T/\delta t)_{(N)}$, $(\Delta T/\delta t)_{(WN)}$, and/or $(\Delta T/\delta t)_{real}$ are larger than $10^{-100}$, $10^{-50}$, $10^{-20}$, $10^{-9}$, $10^{-7}$, $10^{-6}$, $10^{-5}$, $10^{-3}$, $10^{-1}$, 1, $10^3$, $10^5$, $10^6$ or $10^{9}$° C./sec or ° C./sec. In some cases, $(\Delta T/\delta t)_{(N)}$ and/or $(\Delta T/\delta t)_{real}$ are large when the nanoparticles have a large heating power, or the acoustic wave or radiation applied on the nanoparticles has a large power.

In another embodiment of the invention, the values of $(\Delta T/\delta t)_{(N)}$, $(\Delta T/\delta t)_{(WN)}$, and/or $(\Delta T/\delta t)_{real}$ are smaller than $10^{100}$, $10^{50}$, $10^{20}$, $10^9$, $10^6$, $10^3$, 1, $10^{-1}$, $10^{-3}$, $10^{-6}$ or $10^{-9}$° C./sec. In some cases, $(\Delta T/\delta t)_{(N)}$ and/or $(\Delta T/\delta t)_{real}$ are low when the nanoparticles have a low heating power, or the acoustic wave or radiation applied on the nanoparticles has a low power.

In still another embodiment of the invention, the values of $(\Delta T/\delta t)_{(N)}$, $(\Delta T/\delta t)_{(WN)}$, and/or $(\Delta T/\delta t)_{real}$ are between than $10^{-100}$ and $10^{100}$, $10^{-10}$ and $10^{10}$, $10^{-5}$ and $10^5$, or between $10^{-5}$ and 10, $10^{-5}$ and ° C./sec.

In some cases, the unit ° C./sec can be replaced by ° C./sec as measured per gram of nanoparticle, per gram of body part, per $cm^3$ of nanoparticle, per $cm^2$ of nanoparticle, per cm of nanoparticle, per $cm^3$ of body part, per $cm^2$ of body part, or per cm of body part.

In one embodiment of the invention, $(\Delta T/\delta t)_{(N)}$ is larger than $(\Delta T/\delta t)_{(WN)}$ by a factor $\alpha$, where $\alpha$ is: i) in some cases larger than 1.00001, 1.1, 1.2, 1.5, 2, 5, 10, $10^3$, $10^5$ or $10^9$, or larger than $10^{-100}$, $10^{-50}$, $10^{-20}$, $10^{-9}$, $10^{-6}$, $10^{-3}$, $10^{-1}$, 1, $10^3$, $10^6$ or $10^{9}$° C./sec, ii) in some other cases smaller than $10^5$, $10^3$, $10^2$, 5, 2 or 1.1 or smaller than $10^{100}$, $10^{50}$, $10^5$, $10^2$, 5, 2 or 1.5, or iii) in still some other cases comprised between $10^{-100}$ and $10^{100}$, $10^{-5}$ and $10^5$, $10^{-1}$ and 10, or between $10^{-100}$ and $10^{100}$° C./sec, or between $10^{-10}$ and $10^{50}$° C./sec.

In one embodiment of the invention, a suitable range of values for $(\Delta T/\delta t)_{(M)}$, is between 0.09° C./sec and 0.7° C./sec. The minimum value of this range (0.09° C./sec) was estimated by exposing 45 μg of magnetosomes or nanoparticles per cm$^3$ of tissue to an acoustic wave of 0.5 W/cm$^2$. In some cases, this minimum value can be decreased by a factor of more than 1.5, 2, 5, 10, 50, 10$^2$, 10$^5$, 10$^7$, 10$^9$, or 10$^{20}$, preferentially by decreasing the magnetosome or nanoparticle concentration by a factor of more than 1.5, 2, 5, 10, 50, 10$^2$, 10$^5$, 10$^7$, 10$^9$, or 10$^{20}$ or by decreasing the intensity, power, or frequency of the acoustic wave by a factor of more than 1.5, 2, 5, 10, 50, 10$^2$, 10$^5$, 10$^7$, 10$^9$, or 10$^{20}$. The maximum value of this range (0.7° C./sec) was estimated by exposing 100 μg of magnetosomes mixed in 100 μL of water to an acoustic wave of 1.5 W/cm$^2$. In some cases, this maximum value can be increased by a factor of more than 1.5, 2, 5, 10, 50, 10$^2$, 10$^5$, 10$^7$, 10$^9$ or 10$^{20}$, preferentially by increasing the magnetosome or nanoparticle concentration by a factor of more than 1.5, 2, 5, 10, 50, 10$^2$, 10$^5$, 10$^7$, 10$^9$ or 10$^{20}$ or by increasing the intensity, power, or frequency of the acoustic wave by a factor of more than 1.5, 2, 5, 10, 50, 10$^2$, 10$^5$, 10$^7$, 10$^9$ or 10$^{20}$.

In another embodiment of the invention, a suitable range of values for $(\Delta T/\delta t)_{(WM)}$ is between 0.063° C./sec and 0.645° C./sec. The minimum value of this range (0.063° C./sec) was estimated by applying an acoustic wave of 0.5 W/cm$^2$ to a piece of tissue. In some cases, this minimum value can be decreased by a factor of more than 1.5, 2, 5, 10, 50, 10$^2$, 10$^5$, 10$^7$, 10$^9$, or 10$^{20}$ by decreasing the intensity, power, or frequency of the acoustic wave by a factor of more than 1.5, 2, 5, 10, 50, 10$^2$, 10$^5$, 10$^7$, 10$^9$, or 10$^{20}$. The maximum value of this range (0.645° C./sec) was estimated by applying an acoustic wave of 1.5 W/cm$^2$ to a water solution. In some cases, this maximum value can be increased by a factor of more than 1.5, 2, 5, 10, 50, 10$^2$, 10$^5$, 10$^7$, 10$^9$, or 10$^{20}$ by increasing the intensity, power, or frequency of the acoustic wave by a factor of more than 1.5, 2, 5, 10, 50, 10$^2$, 10$^5$, 10$^7$, 10$^9$, or 10$^{20}$ or by using a body part that absorbs less the acoustic wave.

In one embodiment of the invention, the specific absorption rate (SAR) of the nanoparticles, also designated as SAR, is the specific absorption rate of the nanoparticles comprised, mixed or inserted in the body part. It can be expressed in a power unit such as Watt divided by a mass unit such as gram or in a power unit divided by a length, surface area, or volume unit such as cm, cm$^2$, or cm$^3$.

Preferentially, the SAR is measured under the application of an acoustic wave or radiation that produces a temperature increase preferentially in the presence of the nanoparticles. In some cases, such radiation or acoustic wave can have: i) a power or power density larger than 10$^{-9}$, 10$^{-5}$, 10$^{-3}$, 10$^{-1}$, 1, 10 or 10$^3$ W/cm, W/cm$^2$, or W/cm$^3$, ii) a frequency larger than 10$^{-6}$, 10$^{-3}$, 10$^{-1}$, 1, 10, 10$^3$ or 10$^6$ MHz. In some other cases, such radiation can be an alternating magnetic field, preferentially of: i) frequency larger than 10$^{-9}$, 10$^{-6}$, 10$^{-3}$, 1, 10$^3$, 10$^6$ or 10$^9$ kHz, and/or ii) strength larger than 10$^{-9}$, 10$^{-6}$, 10$^{-3}$, 10$^{-1}$, 1, 10, 10$^3$ or 10$^6$ mT. In still some other cases, such radiation can be a laser, preferentially of power or power density larger than 10$^{-9}$, 10$^{-5}$, 10$^{-3}$, 10$^{-1}$, 1, 10 or 10$^3$ W/cm, W/cm$^2$, or W/cm$^3$.

Preferentially, the SAR measured in adiabatic conditions or in conditions in which heat exchanges are minimized, preferentially between: i) the portion of the body part comprising the nanoparticles and the portion of the body part not comprising the nanoparticles or the region outside the body part comprising the nanoparticles, or ii) the container or tube containing the nanoparticles and the exterior of this container or tube. Preferentially, heat exchanges are minimized when they produce a temperature decrease of less than 75, 60, 50, 25, 10, 5, 2, 1 or 0.1° C.

In one embodiment of the invention, the SAR is estimated by exposing nanoparticles, preferentially comprised in the body part, to the acoustic wave or radiation. In some cases, the SAR can be equal or proportional to the specific heat capacity of the medium surrounding the nanoparticles, preferentially times the initial slope of the temperature variation with time resulting from the application of the acoustic wave or radiation, preferentially divided by the nanoparticle concentration.

In another embodiment of the invention, the SAR does not correspond to or is not associated with or is not the SAR estimated by exposing the nanoparticles to an alternating magnetic field or to another source of excitation than an acoustic wave or radiation.

The invention also relates to nanoparticles for use according to the invention, wherein the nanoparticles possess a specific absorption rate (SAR), preferentially measured in the body part, which is larger than 10$^{-100}$, 10$^{-50}$, 10$^{-20}$, 10$^{-9}$, 10$^{-6}$, 10$^{-3}$, 1, 10$^3$, 10$^6$ or 10$^9$ W (Watt) as measured per gram of nanoparticles (W/g$_{nano}$), per cm$^3$ of nanoparticles (W/cm$^3_{nano}$), per gram of body part (W/g$_{bp}$), or per cm$^3$ of body part (W/cm$^3_{bp}$). In some cases, large SAR values may be obtained in some specific conditions, for example using acoustic waves or radiation of high power or frequency or using high nanoparticle concentration or combining the application of the acoustic wave with the application of another source of energy or combining the application of different types of acoustic waves or radiation.

The invention also relates to nanoparticles for use according to the invention, wherein the nanoparticles possess a specific absorption rate (SAR), preferentially measured in the body part, which is lower than 10$^{100}$, 10$^{50}$, 10$^{20}$, 10$^{-9}$, 10$^{-6}$, 10$^{-3}$, 1, 10$^3$, 10$^6$ or 10$^9$ Watt as measured per gram of nanoparticles (W/g$_{nano}$), per cm$^3$ of nanoparticles (W/cm$^3_{nano}$), per gram of body part (W/g$_{bp}$), or per cm$^3$ of body part (W/cm$^3_{bp}$).

The invention also relates to nanoparticles for use according to the invention, wherein the nanoparticles possess a specific absorption rate (SAR), preferentially measured in the body part, which is between 10$^{-100}$ and 10$^{100}$, 10$^{-10}$ and 10$^{10}$, 10$^{-5}$ and 10$^5$, 10$^{-3}$ and 10$^3$, 0 and 10$^{100}$, 10 and 10$^{10}$, 10 and 10$^4$ W, as measured per gram of nanoparticles (W/g$_{nano}$), per cm$^3$ of nanoparticles (W/cm$^3_{nano}$), per gram of body part (W/g$_{bp}$), or per cm$^3$ of body part (W/cm$^3_{bp}$).

In one embodiment of the invention, a suitable range of nanoparticle SAR, preferentially measured under the application of the acoustic wave, is between 1.2 Watt per gram of nanoparticle, preferentially in iron, and 424 Watt per gram of nanoparticle, preferentially in iron. In some cases, the minimum value of this range (1.2 W/g$_M$) can be lower, for example by a factor of more than 1.5, 2, 5, 10, 10$^3$, 10$^5$, 10$^7$ or 10$^9$, preferentially when the viscosity of the body part is increased or when the thermal diffusion of the body part is decreased or when nanoparticle diffusion away from the body part is increased or when the power of the acoustic wave is decreased or when the heat produced by the acoustic wave in the absence of the nanoparticles is increased. In some other cases, the maximum value of this range (424 W/g$_M$) can be larger, for example by a factor of more than 1.5, 2, 5, 10, 10$^3$, 10$^5$, 10$^{10}$ or 10$^9$, preferentially when the viscosity of the body part is decreased or when the thermal diffusion of the body part is increased or when nanoparticle concentration in the body part is increased or when the power of the acoustic wave is increased or when the heat produced by the acoustic wave in the absence of the nanoparticles is decreased.

In another embodiment of the invention, the lowest values of the SAR can be justified by the fact that SAR values may decrease with decreasing nanoparticle concentration or nanoparticle number, preferentially by a factor of more than 1.1, 2, 5, 10, $10^2$, $10^3$, $10^5$ or $10^{10}$, when the nanoparticle concentration or nanoparticle number decreases by a factor of more than 1.1, 2, 5, 10, $10^2$, $10^3$, $10^5$ or $10^{10}$. For example, a SAR of 1 W per gram of nanoparticle for $10^7$ nanoparticles can lead to a SAR value of $10^{-7}$ W per gram of nanoparticles for a single nanoparticle. This behavior may be explained by a collective effect in which the SAR values of the individual nanoparticles would add to yield a SAR for the assembly of the nanoparticles, which is the sum of or is proportional to the SAR value of a single nanoparticle.

In still another embodiment of the invention, the small nanoparticles with a size preferentially lower than 500, 200, 100, 50, 20, 10 or 1 nm, do not possess a SAR, or possess a SAR that is lower than $10^5$, $10^3$, 10, 1, $10^{-1}$, $10^{-3}$, $10^{-6}$ or $10^{-9}$ Watt per gram of nanoparticle.

In still another embodiment of the invention, the large nanoparticles with a size preferentially larger than 1, 10, 20, 50, 100, 200 or 500 nm, possess a SAR preferentially larger than $10^{-9}$, $10^{-6}$, $10^{-3}$, $10^{-1}$, 1, 10, $10^3$ or $10^5$ Watt per gram of nanoparticle.

The invention also relates to nanoparticles for use according to the invention, wherein the nanoparticles possess a specific absorption rate, which increases with increasing power of the acoustic wave applied on the nanoparticles at a rate that can increase with decreasing nanoparticle concentrations.

In some cases, the SAR can increase, preferentially by a factor of more than 1.01, 1.1, 2, 5, 10, $10^2$, $10^3$, $10^5$ or $10^{10}$, when the power of the acoustic wave or radiation applied on nanoparticles increases, preferentially by a factor of more than 1.1, 2, 5, 10, $10^2$, $10^3$, $10^5$ or $10^{10}$, preferentially at a rate that increases by a factor of more than 1.01, 1.1, 2, 5, 10, $10^2$, $10^3$, $10^5$ or $10^{10}$, when the nanoparticle concentration decreases, preferentially by a factor of more than 1.01, 1.1, 2, 5, 10, $10^2$, $10^3$, $10^5$ or $10^{10}$. To meet this feature, the nanoparticle concentration should preferentially be comprised between $10^{-9}$ and $10^9$, $10^{-5}$ and $10^5$, $10^{-2}$ and $10^2$, or between $10^{-1}$ and 10 mg of nanoparticles per mL or per $cm^3$ of body part.

In an embodiment of the invention, the rate of SAR increase with increasing intensity of the acoustic wave or radiation corresponds to the percentage of SAR increase, i.e. $(SAR_{I2}-SAR_{I1})/SAR_{I1}$, where $SAR_{I1}$ and $SAR_{I2}$ are the SAR measured at two different intensities of the acoustic wave or radiation $I_1$ and $I_2$ where $I_2 \geq I_1$, preferentially divided by $I_2/I_1$.

In still another embodiment of the invention, the SAR of the nanoparticles does not vary or decrease by more than $10^5$, 500, 90, 70, 50, 25, 10, 5 or 2% between different nanoparticle concentrations, where this percentage can represent $C_2-C_1/C_1$, where $C_1$ and $C_2$ are two different nanoparticle concentrations. In some cases, the situation occurs when the nanoparticle concentration is between $10^{-6}$ and $10^6$, $10^{-5}$ and $10^5$, $10^{-3}$ and $10^3$, or between $10^{-2}$ and $10^2$ mg per mL or mg per $cm^3$ of body part. In some other cases, this situation occurs when the nanoparticle concentration is lower than 1000, 100, 10, 1, 0.1 or 0.01 mg per mL or mg per $cm^3$ of body part. In still some other cases, the situation occurs when the nanoparticle concentration is larger than 1000, 100, 10, 1, 0.1 or 0.01 mg per mL or mg per $cm^3$ of body part.

In one embodiment of the invention, the nanoparticles possess a specific absorption rate, which increases when the nanoparticle concentration decreases. In some cases, the nanoparticle specific absorption rate increases by a factor of more than 1.1, 2, 5, 10, $10^2$, $10^3$, $10^5$ or $10^{10}$ when the nanoparticle concentration decreases by a factor of 1.1, 2, 5, 10, $10^2$, $10^3$, $10^5$ or $10^{10}$.

To meet this feature, the nanoparticle concentration should preferentially be comprised between $10^{-9}$ and $10^9$, $10^{-5}$ and $10^5$, $10^{-2}$ and $10^2$, or between $10^{-1}$ and 10 mg of nanoparticles per mL, or the nanoparticle concentration should be lower than $10^{-9}$, $10^{-7}$, $10^{-5}$, $10^{-2}$, $10^{-1}$, 1, 10 or 100 mg of nanoparticle per mL. This behavior is interesting since it is the opposite of that observed when the SAR is measured by applying an alternating magnetic field.

In some cases, the SAR can designate $(SAR)_{(real)}$.

In some cases, $(SAR)_{(real)}$ can be the specific absorption rate of the nanoparticles taking into consideration the initial slopes of the temperature variation of the body part with and without the nanoparticles.

In an embodiment of the invention, a suitable range of rate of SAR increase with increasing acoustic wave power is between 15% and 440%. The minimum and maximum values of this range were estimated using the values of $SAR_{real}(M)$ given in tables 2 and 1, respectively. In some cases, the minimum value of this range can be decreased, preferentially by a factor of more than 2, 5, 10, $10^3$ or $10^5$, by decreasing the intensity of the acoustic wave or by changing the maximum concentration or body part. In some other cases, the maximum value of this range can be increased, preferentially by a factor of more than 2, 5, 10, $10^3$ or $10^5$, by increasing the intensity of the acoustic wave or by changing the maximum concentration or body part.

In some cases, $SAR_{(real)}$ can be estimated using the formula: $SAR_{(real)} = \alpha_{real}[(\Delta T/\delta t)_{(real)}]$, where $\alpha_{real}$ is a proportionality coefficient, which can be equal to $C_v/C_{nano}$, where $C_v$ is the specific heat capacity, preferentially of the body part, tissue, water, medium comprising the nanoparticles, and $C_{nano}$ is the nanoparticle concentration or quantity or number of nanoparticles preferentially comprised in the body part.

In another embodiment of the invention, a suitable range of values for $SAR_{(real)}$ is between 5 W/g and 427 W/g. The minimum value of this range (5 W/g) was estimated by applying an acoustic wave of 1 $W/cm^2$ to 45 µg of magnetosomes per $cm^3$ of tissue. In some cases, this minimum value can be decreased by a factor of more than 1.5, 2, 5, 10, 50, $10^2$, $10^5$, $10^7$, $10^9$ or $10^{20}$ by decreasing the intensity, power, or frequency of the acoustic wave by a factor of more than 1.5, 2, 5, 10, 50, $10^2$, $10^5$, $10^7$, $10^9$ or $10^{20}$. The maximum value of this range (427 W/g) was estimated by applying an acoustic wave of 1 $W/cm^2$ to a water solution comprising 100 µg of magnetosomes mixed in 100 µl of water. In some cases, this maximum value can be increased by a factor of more than 1.5, 2, 5, 10, 50, $10^2$, $10^5$, $10^7$, $10^9$ or $10^{20}$ by increasing the intensity, power, or frequency of the acoustic wave by a factor of more than 1.5, 2, 5, 10, 50, $10^2$, $10^5$, $10^7$, $10^9$ or $10^{20}$, or by using a body part that absorbs less the acoustic wave.

In some other cases, SAR can be equal to $SAR_{(N)}$.

In some cases, $SAR_{(N)} = \alpha_N \cdot (\Delta T/\delta t)_{(N)}$, where $\alpha_N$ can be equal to $C_v/C_{mag}$.

In another embodiment of the invention, a suitable range of values for $SAR_{(N)}$ is between 37 W/g and 3124 W/g. The minimum value of this range (37 W/g) was estimated by applying an acoustic wave of 0.5 W/cm² to 45 µg of magnetosomes per cm³ of tissue. In some cases, this minimum value can be decreased by a factor of more than 1.5, 2, 5, 10, 50, $10^2$, $10^5$, $10^7$, $10^9$, or $10^{20}$ by decreasing the intensity, power, or frequency of the acoustic wave by a factor of more than 1.5, 2, 5, 10, 50, $10^2$, $10^5$, $10^7$, $10^9$, or $10^{20}$. The maximum value of this range (3124 W/g) was estimated by applying an acoustic wave of 1.5 W/cm² to a water solution comprising 100 µg of magnetosomes mixed in 100 µl of water. In some cases, this maximum value can be increased by a factor of more than 1.5, 2, 5, 10, 50, $10^2$, $10^5$, $10^7$, $10^9$, or $10^{20}$ by increasing the intensity, power, or frequency of the acoustic wave by a factor of more than 1.5, 2, 5, 10, 50, $10^2$, $10^5$, $10^7$, $10^9$, or $10^{20}$ or by using a body part that absorbs less the acoustic wave.

In still another embodiment of the invention, the values of $\alpha_N$ and/or $\alpha_{WN}$ is(are) smaller than $10^{-9}$, $10^{-6}$, $10^{-3}$, 1, $10^3$, $10^6$ or $10^9$ (sec/° C.)·(W/$g_{nano}$) or (sec/° C.)·(W/$g_{bp}$) or (sec/° C.)·(W/cm³$_{bp}$) or (sec/° C.)·(W/cm³$_{nano}$).

In still another embodiment of the invention, the value(s) of $\alpha_N$ and/or $\alpha_{WN}$ is(are) larger than $10^{-9}$, $10^{-6}$, $10^{-3}$, 1, $10^3$, $10^6$ or $10^9$ (sec/° C.)·(W/$g_{nano}$) or (sec/° C.)·(W/$g_{bp}$) or (sec/° C.)·(W/cm³$_{bp}$) or (sec/° C.)·(W/cm³$_{nano}$).

In still some other cases, the SAR can be equal to $SAR_{AW}$, which is the SAR measured by applying the acoustic wave on the nanoparticles. $SAR_{AW}$ can be different from the SAR measured by applying an alternating magnetic field, designated as $SAR_{AMF}$. In some cases, $SAR_{AW}$ differs from $SAR_{AMF}$ by at least $10^{-9}$, $10^{-7}$, $10^{-5}$, $10^{-3}$, $10^{-1}$, 1, 10, $10^3$, $10^5$, $10^7$ or $10^9$%, where this percentage can be equal to $(SAR_{AW}-SAR_{AMF})/SAR_{AW}$, where this percentage is preferentially measured for a given nanoparticle concentration, which is preferentially: i) in some cases, lower than $10^9$, $10^7$, $10^5$, $10^3$, 10, 1, $10^{-3}$, $10^{-5}$, $10^{-7}$ or $10^{-9}$ mg of nanoparticles as measured per cm³ or cm³ of body part, ii) in some other cases, larger than $10^{-9}$, $10^{-7}$, $10^{-5}$, $10^{-3}$, $10^{-1}$, 1, $10^3$, $10^5$, $10^7$ or $10^9$ mg of nanoparticles as measured per cm³ or cm³ of body part, or iii) in still some other cases comprised between $10^{-9}$ and $10^9$, $10^{-7}$ and $10^7$, $10^{-5}$ and $10^5$, $10^{-3}$ and $10^3$, or between $10^{-1}$ and 10 mg of nanoparticle as measured per cm³ or cm³ of body part.

In one embodiment of the invention, the SAR is not measured in the presence of a magnetic field or an alternating magnetic field applied on nanoparticles. In some cases, the SAR is preferentially not due to hysteresis losses, or to Brownian motion, or to Néel relaxation, or to a movement of the nanoparticles under the application of the acoustic wave, or to the inversion of the magnetic moment of the nanoparticles under the application of the acoustic wave, or to a coupling of the nanoparticle magnetic moment with the acoustic wave.

In another embodiment of the invention, $SAR_{AW}$ is not due or not only due or not mainly due to Brownian motion, Néel relaxation or hysteresis losses. In some cases, $SAR_{AW}$ is due, preferentially partly or mainly, to the absorption of the acoustic wave by the nanoparticle(s) or body part comprising the nanoparticles. In some cases, $SAR_{AW}$ is due, preferentially partly or mainly, to the absorption of the acoustic wave by the body part without or not comprising the nanoparticles, preferentially followed by heat diffusion between the body part without or not comprising the nanoparticles and the body part with or comprising the nanoparticles.

In one embodiment of this invention, the body part is divided between a portion of the body part comprising the nanoparticles and a portion of the body part not comprising the nanoparticles.

In one embodiment of the invention, the portion of the body part comprising the nanoparticles is the nanoparticle region or the portion of the body part in which the nanoparticles, nanoparticle assembly, or nanoparticle suspension is or has been administered.

In another embodiment of the invention, the portion of the body part without the nanoparticles is the portion of the body part in which the nanoparticles, nanoparticle assembly, or nanoparticle suspension is not or has not been administered, for example the portion of the body part before nanoparticle administration or outside of the nanoparticle region.

In some cases, the portion of the body part comprising the nanoparticles can absorb more than $10^{-9}$, $10^{-7}$, $10^{-5}$, $10^{-3}$, $10^{-1}$, 1, 5, 10, 25, 50, 75 or 80% of the energy of the acoustic wave or radiation and the portion of the body part not comprising the nanoparticles can preferentially absorb less than $10^{-9}$, $10^{-7}$, $10^{-5}$, $10^{-3}$, $10^{-1}$, 1, 5, 10, 25, 50, 75 or 80% of the energy of the acoustic wave or radiation. In some other cases, the portion of the body part comprising the nanoparticles can absorb less than $10^{-9}$, $10^{-7}$, $10^{-5}$, $10^{-3}$, $10^{-1}$, 1, 5, 10, 25, 50, 75 or 80% of the energy of the acoustic wave or radiation and the portion of the body part not comprising the nanoparticles can preferentially absorb more than $10^{-9}$, $10^{-7}$, $10^{-5}$, $10^{-3}$, $10^{-1}$, 1, 5, 10, 25, 50, 75 or 80% of the energy of the acoustic wave or radiation. The percentages mentioned in this embodiment and in the previous embodiment can represent or be the energy of the acoustic wave or radiation applied on the nanoparticles divided by the energy of the acoustic wave or radiation applied on the body part or the energy of the acoustic wave or radiation applied on the nanoparticles or body part divided by the energy of the acoustic wave or radiation produced by the equipment generating the acoustic wave or radiation.

In some cases, the body part can designate the portion of the body part or the portion of the body part comprising the nanoparticle.

In some other cases, the body part can designate the portion of the body part or the portion of the body part not comprising the nanoparticle.

In still some other cases, the body part can designate both the portion of the body part comprising the nanoparticle or nanoparticle region and the portion of the body part not comprising the nanoparticle or nanoparticle region.

In some cases, the body part can comprise: i) more than $10^{-9}$, $10^{-7}$, $10^{-5}$, $10^-$, $10^{-1}$, 1, 10, $10^3$, $10^5$, $10^7$ or $10^9$ mg of nanoparticles, preferentially per mm³ or per cm³ of body part or per pathological or healthy cell, or ii) more than $10^{-9}$, $10^{-7}$, $10^{-5}$, $10^{-3}$, $10^{-1}$, 1, 10, $10^3$, $10^5$, $10^7$ or $10^9$ pathological or healthy cells, preferentially per mm³ or per cm³ of body part.

In some other cases, the body part can comprise: i) less than $10^{-9}$, $10^{-7}$, $10^{-5}$, $10^{-3}$, $10^{-1}$, 1, 10, $10^3$, $10^5$, $10^{10}$ or $10^9$ mg of nanoparticles, preferentially per mm³ or per cm³ of body part or per pathological or healthy cell, or ii) less than $10^{-9}$, $10^{-7}$, $10^{-10}$, $10^{-3}$, $10^{-1}$, 1, 10, $10^3$, $10^5$, $10^7$ or $10^9$ pathological or healthy cells, preferentially per mm³ or per cm³ of body part.

The invention also relates to nanoparticles for use according to the invention, wherein the concentration of the administered nanoparticles is larger than $10^{-3}$ mg per mm³ of body part. In some cases, the nanoparticle concentration is larger than $10^{-9}$, $10^{-7}$, $10^{-5}$, $10^-$, $10^{-1}$, 1, 10, $10^3$, $10^5$, $10^7$ or $10^9$ gram or milligram as measured per mm³ of body part, per mL of suspension, or per mm$^3$ of matrix or body part (biological or not) comprising the nanoparticles.

In one embodiment of the invention, a suitable range of nanoparticle concentration comprised in the body part is between 1 ng of nanoparticle, preferentially in iron, per mm$^3$ of body part and 1 gram of nanoparticle, preferentially in iron, per mm$^3$ of body part. The minimum value of this range (1 ng/mm$^3$) was estimated by calculating the lowest concentration of a magnetosome or nanoparticle suspension that can be administered in the body part, i.e. the lowest magnetosome or nanoparticle concentration that can typically be detected. In some cases, it is possible that this minimum value is decreased, for example by a factor larger than 10, $10^3$, $10^6$ or $10^9$, if more sensitive detection methods are used or developed to detect the presence of the magnetosomes or nanoparticles or if part of the magnetosomes or nanoparticles have diffused away from the body part following their administration in the body part. The maximum value of this range (1 g/mm$^3$) was estimated by calculating the largest magnetosome or nanoparticle concentration that yields a stable suspension. It is possible that this maximum value is larger, for example by a factor of 10, $10^3$, $10^6$ or $10^9$, for example if magnetosomes or nanoparticles are inserted in a matrix or solvent that is solid, semi-solid, or more viscous than water, or if magnetosomes have concentrated in the body part following their administration in the body part yielding a larger concentration in the body part than in the magnetosome or nanoparticle suspension used for injection.

In another embodiment of the invention, the nanoparticles remain in the body part during the treatment, preferentially during more than 1, 2, 5, 10, 20, 50, 100, $10^3$ or $10^4$ sequence(s) or session(s), preferentially during more than 1, 2, 5, 10, 50, 100 or $10^3$ day(s).

In another embodiment of the invention, the nanoparticles remain in the body part during the treatment, preferentially during less than 1, 2, 5, 10, 20, 50, 100, $10^3$ or $10^4$ sequence(s) or session(s), preferentially during less than 1, 2, 5, 10, 50, 100 or $10^3$ day(s).

In some cases, the nanoparticles remain in the body part during the treatment without decreasing in size by more than $10^{-4}$, $10^{-1}$, 1, 10, 20, 50, 100, 500, $10^3$ or $10^4$%, preferentially compared with the size of the nanoparticles before administration in the body part or before the beginning of the treatment. In some cases, this percentage can be equal to the ratio between the site of the nanoparticle after administration in the body part and the size of the nanoparticle before administration in the body part.

In some cases, the body part is the body part exposed to the radiation or acoustic wave.

In this invention, the body part or nanoparticles exposed to the acoustic wave or radiation can mean that the acoustic wave or radiation covers, targets, is present in, is applied in or on, or is located in, preferentially at least $10^{-9}$, $10^{-7}$, $10^{-5}$, $10^{-3}$, $10^{-1}$, 1, 5, 10, 25, 50, 75, or 80% of the body part or nanoparticles. This percentage can represent the number or volume of nanoparticles or body part exposed to the acoustic wave or radiation divided by the total number or volume of nanoparticles or body part. In some cases, the acoustic wave or radiation can also cover, target, be present, be applied in or on, or be located outside of the body part or nanoparticles, preferentially when these acoustic waves or radiation are of low enough power or energy not to induce toxicity.

Furthermore, in some cases the body part or nanoparticles can be exposed to the acoustic wave or radiation when an acoustic wave or radiation is applied on the body part or nanoparticles or when the body part or nanoparticles are subjected to the application of the acoustic wave or radiation or when the body part or nanoparticles undergo the acoustic wave or radiation or when the body part or nanoparticles undergo the effects of the acoustic wave or radiation or when the body part or nanoparticles undergo the disturbance created by the acoustic wave or radiation or when the body part or nanoparticles undergo the disturbance of the acoustic wave or radiation.

In an embodiment of the invention, the body part is or is associated with: i) the body part exposed to the acoustic wave(s) or radiation, or ii) the body part receiving the energy or power of the acoustic wave or radiation, or iii) the body part absorbing the energy or power of the acoustic wave or radiation.

In some cases, the body part can also be or be associated to: i) the body part not exposed to the acoustic wave(s) or radiation, or ii) the body part not receiving the energy or power of the acoustic wave or radiation, or iii) the body part not absorbing the energy or power of the acoustic wave or radiation.

The invention also relates to nanoparticles for use according to the invention, wherein the application of acoustic waves or radiation on the body part leads to a temperature increase of the body part, preferentially larger than $10^{-10}$, $10^{-5}$, $10^{-3}$, $10^{-1}$, 1, 5, 10 or $10^{3}$° C.

In some cases, the temperature increase can be at least $10^{-10}$, $10^{-5}$, $10^{-1}$, 1, 2, 5, 10, 50, 75 or 80% larger in the presence than in the absence of the nanoparticle in the body part. In some cases, this percentage can be the ratio between the temperature increase of the body part without the nanoparticle and the temperature increase of the body part with the nanoparticle.

The invention also relates to nanoparticles for use according to the invention, wherein the temperature increase of the body part, temperature decrease of the body part, or dissociation of the compound from the nanoparticle, occurs within less than $10^{20}$, $10^{10}$, $10^5$, $10^3$, 500, 200, 90, 70, 50%, 10 or 1% of the body part. This percentage can be the ratio between the volume in which the temperature increase of the body part, temperature decrease of the body part, or dissociation of the compound from the nanoparticle, occurs and the total volume of the body part.

In some other cases, the temperature increase of the body part, temperature decrease of the body part, or dissociation of the compound from the nanoparticle, can occur within more than $10^{-10}$, $10^{-5}$, $10^{-1}$, 1, 10, 50, 70, 90, 200, 500, $10^3$, $10^5$ or $10^{20}$% of the body part.

The invention also relates to nanoparticles for use according to the invention, wherein the temperature increase of the body part, temperature decrease of the body part, or dissociation of the compound from the nanoparticle occurs within more than $10^{-10}$, $10^{-5}$, $10^{-1}$, 1, 10, 50, 70, 90, 200, 500, $10^3$, $10^5$, $10^{10}$ or $10^{20}$% of the volume occupied by the nanoparticles in the body part.

This percentage can be the ratio between the volume in which the temperature increase of the body part, temperature decrease of the body part, or dissociation of the compound from the nanoparticle, occurs and the total volume occupied by the nanoparticles in the body part.

In some other cases, the temperature increase of the body part, temperature decrease of the body part, or dissociation of the compound from the nanoparticle, can occur within less than $10^{20}$, $10^{10}$, $10^5$, $10^3$, 500, 200, 90, 70, 50%, 10 or 1% of the volume occupied by the nanoparticles in the body part.

In an embodiment of the invention, the body part comprises more than or at least 1, 2, 5, 10, or 100 similar or different organism(s), apparatus, organ(s), tissue(s), cell(s), or biomolecule(s).

In some cases, the body part can be all or part of the head, neck, shoulder, arm, leg, knee, foot, hand, ankle, elbow, trunk, inferior members, or superior members. In some other cases, the body part can be or belong to an organ, the musculoskeletal, muscular, digestive, respiratory, urinary, female reproductive, male reproductive, circulatory, cardiovascular, endocrine, circulatory, lymphatic, nervous (peripheral or not), ventricular, enteric nervous, sensory, or integumentary system, reproductive organ (internal or external), sensory organ, endocrine glands. The organ or body part can be human skeleton, joints, ligaments, tendons, mouth, teeth, tongue, salivary glands, parotid glands, submandibular glands, sublingual glands, pharynx, esophagus, stomach, small intestine, duodenum, jejunum, ileum, large intestine, liver, gallbladder, mesentery, pancreas, nasal cavity, pharynx, larynx, trachea, bronchi, lungs, diaphragm, kidneys, ureters, bladder, urethra, ovaries, fallopian tubes, uterus, vagina, vulva, clitoris, placenta, testes, epididymis, vas deferens, seminal vesicles, prostate, bulbourethral glands, penis, scrotum, pituitary gland, pineal gland, thyroid gland, parathyroid glands, adrenal glands, pancreas, heart, arteries, veins, capillaries, lymphatic vessel, lymph node, bone marrow, thymus, spleen, gut-associated lymphoid tissue, tonsils, brain, cerebrum, cerebral hemispheres, diencephalon, brainstem, midbrain, pons, medulla, oblongata, cerebellum, spinal cord, choroid plexus, nerves, cranial nerves, spinal nerves, ganglia, eye, cornea, iris, ciliary body, lens, retina, ear, outer ear, earlobe, eardrum, middle ear, ossicles, inner ear, cochlea, vestibule of the ear, semicircular canals, olfactory epithelium, tongue, taste buds, mammary glands, or skin. The body part or organ can belong to the blood circulation or circulatory system.

In some cases, the body part can be or comprise at least one tumor, cancer, virus, bacterium, or pathological cell.

In one embodiment of the invention, the body part is or comprises water, an excipient, a solution, a suspension, at least one chemical element, organic material, or gel, which can be synthetic or produced by a living organism.

Preferably, the body part of an individual, also designated as the body part, represents or is part of an individual or a whole individual, where the individual is preferentially a human, an animal, or an organism, preferentially a living or inactivated or dead organism, comprising at least one prokaryotic or eukaryotic cell.

In one embodiment of the invention, the body part is alive (or not), is any tissue, water, medium, substance, cell, organelle, organ protein, lipid, DNA, RNA, biological material, preferentially localized in a specific region of an individual, preferentially originating or extracted from such region.

In an embodiment of the invention, the body part comprises a pathological site, a healthy site, and/or a nanoparticle region.

In one embodiment of the invention, the body part is or comprises a pathological site or pathological cells.

In some cases, the pathological site can be defined as an unhealthy site, or a site that is in a different condition from a site of a healthy individual, or the site of an unhealthy individual. It can comprise pathological cells, such as tumor cells, bacteria, eukaryotic or prokaryotic cells, as well as viruses or other pathological material. Pathological cells can be cells that are: i) not arranged or working as they usual do in a healthy individual, ii) dividing more quickly than healthy cells, iii) healthy cells having undergone a transformation or modification, iv) dead, sometimes due to the presence of a virus or to other organisms, or v), in contact, in interaction, with foreign material not belonging to the individual, such as viruses, where viruses can possibly penetrate, colonize, or replicate in these cells. In some cases, pathological cells can be assimilated to viruses or to other organisms or entities that colonize cells or target cells or destroy cells or use cells or enter in interaction with cells, preferentially to enable their own reproduction, multiplication, survival, or death. In some cases, a pathological site can comprise healthy cells, preferentially with a lower number, activity or proliferation, than that of pathological cells.

In one embodiment of the invention, the body part is or comprises a healthy site or healthy cells. In some cases, the healthy site can be defined as a site or region that comprises healthy cell(s), where a healthy cell can be defined as a cell that belongs to a healthy individual or to the body part of a healthy individual.

In some cases, the healthy site can surround the pathological site when it is located at a distance of less than 1, $10^{-1}$, $10^{-3}$, $10^{-6}$ or $10^{-9}$ m from the pathological site.

In some cases, the number of pathological or healthy cells, preferentially comprised in the body part or volume exposed to the acoustic wave or radiation, can be lower than $10^{100}$, $10^{50}$, $10^{20}$, $10^{10}$, $10^5$, 10, 5, 2 or 1 cell(s) preferentially per $cm^3$ of body part.

In some other cases, the number of pathological or healthy cells, preferentially comprised in the body part or volume exposed to the acoustic wave or radiation, can be larger than 1, 10, $10^3$, $10^5$, $10^7$, $10^9$, $10^{20}$, $10^{50}$ or $10^{100}$ cell(s) preferentially per $cm^3$ of body part.

In still some other cases, the ratio between the number of pathological cells and the number of healthy cells, preferentially comprised in the body part or volume exposed to the acoustic wave or radiation, can be lower than $10^{100}$, $10^{50}$, $10^{20}$, $10^{10}$, $10^5$, $10^3$, $10^2$, 10, 5, 2 or 1. In still some other cases, the ratio between the number of pathological cells and the number of healthy cells, preferentially comprised in the body part or volume exposed to the acoustic wave or radiation, can be larger than 1, 2, 5, 10, $10^3$, $10^5$, $10^{20}$ or $10^{100}$.

In another embodiment of the invention, the body part, healthy or pathological site, or nanoparticle region, has a length, surface area, or volume, which is larger than 103, 1, $10^{-1}$, $10^{-2}$, $10^{-3}$, $10^4$, $10^{-5}$, $10^{-6}$, $10^{-7}$, $10^{-8}$, or $10^{-9}$ or $10^{-20}$ measured in m, $m^2$, or $m^3$, respectively.

In another embodiment of the invention, the body part, healthy or pathological site, or nanoparticle region, has a length, surface area, or volume, which is lower than $10^3$, 1, $10^{-1}$, $10^{-2}$, $10^{-3}$, $10^4$, $10^{-5}$, $10^{-6}$, $10^{-7}$, $10^{-8}$, or $10^{-9}$ measured in m, $m^2$, or $m^3$, respectively.

In one embodiment of the invention, the nanoparticles are administered to or in the body part, when they are directly administered to the body part or when they are administered close to the body part, preferentially less than 1, $10^{-1}$, $10^{-2}$, $10^{-3}$, $10^{-4}$, $10^{-5}$, $10^{-6}$ or $10^{-9}$ m away from the body part. In this case, the nanoparticles may not need to be transported or diffuse from the region where they are administered to the body part.

In another embodiment of the invention, the nanoparticles are administered to or in the body part, when they are administered far from the body part, preferentially more than 1, $10^{-1}$, $10^{-2}$, $10^{-3}$, $10^{-4}$, $10^{-5}$, $10^{-6}$ or $10^{-9}$ m away from the body part. In this case, the nanoparticles may be transported or diffuse from the region where they are administered to the body part.

In another embodiment of the invention, the nanoparticles are administered to or in the body part when they are injected in, or mixed with, or introduced in, or inserted in the body part.

In another embodiment of the invention, the nanoparticles are administered to or in the body part when they occupy more than $10^{-9}$, $10^{-7}$, $10^{-5}$, $10^{-3}$, 1, 10, 25, 50 or 75% of the body part, where this percentage can be the ratio between the volume of the region occupied by the nanoparticles in the body part or nanoparticle region and the volume of the body part. This occupation can correspond to that measured $10^{-5}$, $10^{-3}$, $10^{-1}$, 1, 10, $10^{3}$ or $10^{5}$ minutes following nanoparticle administration.

In another embodiment of the invention, the nanoparticles are administered to or in the body part following at least one of the following administration routes: local, enteral, gastrointestinal, parenteral, topical, oral, inhalation, intramuscular, subcutaneous, intra-tumor, in an organ, in a vein, in arteries, in blood, or in tissue.

In one embodiment of the invention, the thermal conductivity or density of the body part, the velocity of the acoustic wave, attenuation of the acoustic wave, absorption of the acoustic wave, elasticity of the acoustic wave, or acoustic impedance of the acoustic wave, is at least 1.001, 1.01, 1.1, 1.2, 1.5, 2, 5, 10, 50, $10^{2}$, $10^{3}$ or $10^{5}$ larger in the portion of the body part comprising the nanoparticles than in the portion of the body part without the nanoparticles.

In one embodiment of the invention, the thermal conductivity or density of the body part, the velocity of the acoustic wave, attenuation of the acoustic wave, absorption of the acoustic wave, elasticity of the acoustic wave, or acoustic impedance of the acoustic wave, is at least 1.001, 1.01, 1.1, 1.2, 1.5, 2, 5, 10, 50, $10^{2}$, $10^{3}$ or $10^{5}$ lower in the portion of the body part comprising the nanoparticles than in the portion of the body part without the nanoparticles.

In one embodiment of the invention, the thermal conductivity of the body part is at least $10^{20}$, $10^{10}$, $10^{5}$, $10^{3}$, $10^{2}$, 50, 10, 5, 2, 1, $10^{-1}$, $10^{-2}$, $10^{-3}$, $10^{-5}$, $10^{-10}$ or $10^{-20}$ W/m·K (Watt/meter·kelvin) larger in the body part comprising the nanoparticles than in the body part without the nanoparticles.

In one embodiment of the invention, the thermal conductivity of the body part is at least $10^{20}$, $10^{10}$, $10^{5}$, $10^{3}$, $10^{2}$, 50, 10, 5, 2, 1, $10^{-1}$, $10^{-2}$, $10^{-3}$, $10^{-5}$, $10^{-10}$ or $10^{-20}$ W/m·K (Watt/meter·kelvin) lower in the portion of the body part comprising the nanoparticles than in the portion of the body part without the nanoparticles.

In one embodiment of the invention, the density of the body part is at least $10^{-9}$, $10^{-6}$, $10^{-3}$, $10^{-1}$, 1, 2, 5, 10, $10^{3}$ or $10^{6}$ g/cm$^{3}$ larger in the portion of the body part comprising the nanoparticles than in the portion of the body part without the nanoparticles.

In one embodiment of the invention, the density of the portion of the body part is at least $10^{-9}$, $10^{-6}$, $10^{-3}$, $10^{-1}$, 1, 2, 5, 10, $10^{3}$ or $10^{6}$ g/cm$^{3}$ lower in the body part comprising the nanoparticles than in the portion of the body part without the nanoparticles.

In one embodiment of the invention, the velocity of the acoustic wave is at least $10^{-5}$, $10^{-3}$, $10^{-1}$, 1, 10, 100, 1000, 1500, 2000, 3000, 5000, $10^{4}$ or $10^{6}$ m/s larger in the portion of the body part comprising the nanoparticles than in the portion of the body part without the nanoparticles.

In one embodiment of the invention, the velocity of the acoustic wave is at least $10^{-5}$, $10^{-3}$, $10^{-1}$, 1, 10, 100, 1000, 1500, 2000, 3000, 5000, $10^{4}$ or $10^{6}$ m/s lower in the portion of the body part comprising the nanoparticles than in the portion of the body part without the nanoparticles.

In one embodiment of the invention, the attenuation of the acoustic wave is at least $10^{-5}$, $10^{-3}$, $10^{-1}$, 1, 10, 100, $10^{3}$ or $10^{5}$ dB/cm larger in the portion of the body part comprising the nanoparticles than in the portion of the body part without the nanoparticles.

In one embodiment of the invention, the attenuation of the acoustic wave is at least $10^{-5}$, $10^{-3}$, $10^{-1}$, 1, 10, 100, $10^{3}$ or $10^{5}$ dB/cm lower in the portion of the body part comprising the nanoparticles than in the portion of the body part without the nanoparticles.

In one embodiment of the invention, the acoustic impedance of the acoustic wave is at least $10^{-3}$, $10^{-2}$, $10^{-1}$, 0.5, 1, 1.5, 2, 5, 10, $10^{2}$, $10^{4}$, $10^{6}$, $10^{9}$ or $10^{20}$ MRayl or Kg·m$^{-2}$s$^{-1}$ larger in the portion of the body part comprising the nanoparticles than in the portion of the body part without the nanoparticles.

In one embodiment of the invention, the acoustic impedance of the acoustic wave is at least $10^{-3}$, $10^{-2}$, $10^{-1}$, 0.5, 1, 1.5, 2, 5, 10, $10^{2}$, $10^{4}$, $10^{6}$, $10^{9}$ or $10^{20}$ MRayl or Kg·m$^{-2}$s$^{-1}$ lower in the portion of the body part comprising the nanoparticles than in the portion of the body part without the nanoparticles.

In another embodiment of the invention, the increase, decrease, or variation of thermal conductivity or density of the body part, the velocity of the acoustic wave, attenuation of the acoustic wave, absorption of the acoustic wave, elasticity of the acoustic wave, or acoustic impedance of the acoustic wave, between the portion of the body part without the nanoparticles and the portion of the body part with the nanoparticles, is due to at least one of the following properties: i) a nanoparticle concentration in the body part that is larger than $10^{-9}$, $10^{-7}$, $10^{-5}$, $10^{-3}$, $10^{-1}$, 1, 10, $10^{3}$, $10^{5}$, $10^{7}$ or $10^{9}$ mg per mm$^{3}$ or per cm$^{3}$ of body part, ii) a nanoparticle size that is larger than $10^{-6}$, $10^{-3}$, $10^{-1}$, 1, 20, 50, $10^{3}$ or $10^{6}$ nm, iii) a nanoparticle arrangement in chains, or iv), nanoparticles forming aggregates.

In another embodiment of the invention, the increase, decrease, or variation of thermal conductivity or density of the body part, the velocity of the acoustic wave, attenuation of the acoustic wave, absorption of the acoustic wave, elasticity of the acoustic wave, or acoustic impedance of the acoustic wave, between the body part without the nanoparticles and the body part with the nanoparticles, is due to at least one of the following properties: i) a nanoparticle concentration in the body part that is lower than $10^{-9}$, $10^{-7}$, $10^{-5}$, $10^{-3}$, $10^{-1}$, 1, 10, $10^{3}$, $10^{5}$, $10^{7}$ or $10^{9}$ mg per mm$^{3}$ or per cm$^{3}$ of body part, ii) a nanoparticle size that is lower than $10^{-6}$, $10^{-3}$, $10^{-1}$, 1, 20, 50, $10^{3}$ or $10^{6}$ nm.

In one embodiment of the invention, an acoustic wave medical treatment is a medical treatment, also designated as medical treatment or treatment. In some cases, the treatment uses or is due to acoustic wave energy, intensity, or power, preferentially applied on nanoparticles or a body part. In some cases, the treatment can involve or be due to or caused by acoustic waves, preferentially applied on nanoparticles. In some cases, the treatment triggers a medical, pharmaceutical, immunological, metabolic, diagnostic, medical device, drug, biological, or cosmetic effect. In some cases, a medical treatment can be the treatment of an illness such as an infectious disease, a cancer, or a therapeutic treatment. It can be the treatment of a disease due to the malfunction of an organ or body part. It can be due to the malfunction of a body part of an individual. In some cases, it can be a diagnostic of a disease or a cosmetic treatment. In some cases, it can induce the death, destruction, denaturation, or inactivation of at least 1, 10, $10^{3}$, $10^{6}$, or $10^{9}$ biological material(s), such as cell(s), preferentially pathological cell(s), RNA, DNA, protein(s), lipid(s), or enzyme(s), where the death of cell(s) can occur through apoptosis or necrosis, preferentially apoptosis.

The invention also relates to nanoparticles for use according to the invention, wherein the medical treatment is the treatment of a disease or disorder selected from the group consisting of: a disease associated with a proliferation of cells that is different from the cellular proliferation in a healthy individual, a disease associated with the presence of pathological cells in the body part, a disease associated with the presence of a pathological site in an individual or body part, a disease or disorder or malfunction of the body part, a disease associated with the presence of radio-resistant or acoustic-resistant cells, an infectious disease, an auto-immune disease, a neuropathology, a cancer, a tumor, a disease comprising or due to at least one cancer or tumor cell, a cutaneous condition, an endocrine disease, an eye disease or disorder, an intestinal disease, a communication disorder, a genetic disorder, a neurological disorder, a voice disorder, a vulvovaginal disorder, a liver disorder, a heart disorder, a heating disorder, a mood disorder, anemia, preferentially iron anemia, and a personality disorder.

In some cases, the disease or disorder can be the disease or disorder of or belonging to the individual or body part, or the disease or disorder from which the individual is suffering.

In one embodiment of the invention, the cancer or tumor selected from the group consisting of: the cancer of an organ, cancer of blood, cancer of a system of a living organism, adrenal cancer, anal cancer, bile duct cancer, bladder cancer, bone cancer, brain cancer, breast cancer, cervical cancer, colon/rectum cancer, endometrial cancer, esophagus cancer, eye cancer, gallbladder cancer, heart cancer, kidney cancer, laryngeal and hypopharyngeal cancer, leukemia, liver cancer, lung cancer, nasal cavity and paranasal sinus cancer, nasopharyngeal cancer, neuroblastoma, non-Hodgkin lymphoma, oral cavity and oropharyngeal cancer, osteosarcoma cancer, ovarian cancer, pancreatic cancer, pancreatic penile cancer, prostate cancer, retinoblastoma, rhabdomyosarcoma, salivary gland cancer, sarcoma, skin cancer, small intestine cancer, stomach cancer, testicular cancer, thymus cancer, thyroid cancer, uterine cancer, uterine sarcoma cancer, vaginal cancer, vulvar cancer, waldenstrom macroglobulinemia wilms tumor, castleman disease ewing family of tumor, gastrointestinal carcinoid tumor, gastrointestinal stromal tumor, myelodysplastic syndrome pituitary tumor, and a cancerous disease such as gestational trophoblastic disease, Hodgkin disease, kaposi sarcoma, malignant mesothelioma, and multiple myeloma.

In one embodiment, the disorder or malfunction of the body part is associated with the malfunction of cells, which divide more rapidly or enter in an apoptotic or necrotic state for example, or with the malfunction of the immune system or immune cell(s).

In one embodiment of the invention, the medical treatment is or comprises the detection or diagnosis of a disease such as those mentioned in the previous embodiments.

In one embodiment of the invention, the medical treatment is the treatment of an anemia or the nanoparticles are used for the treatment of anemia, preferentially an anemia of a substance comprised in the body part or compound, preferentially an anemia in iron or in a substance comprised in the core and/or coating of the nanoparticles. In some cases, the anemia can be defined as a concentration in a substance comprised in an individual, which is more than 1.001, 1.01, 1.1, 2, 5, 10, $10^2$, $10^5$, $10^{10}$ or $10^{20}$ times lower in the individual suffering from anemia than in a healthy individual.

In some cases, anemia of a substance comprised in the body part is defined as a concentration of a substance comprised in the nanoparticle or compound, such as iron or oxide, which is lower, preferentially 1.001, 1.01, 1.1, 2, 5, 10, $10^2$, $10^5$, $10^{10}$ or $10^{20}$ times lower, in the body part before or without nanoparticle administration than after or with nanoparticle administration.

The invention also relates to a method for the treatment of anemia or anemia disease or to nanoparticles, in particular magnetosomes, for use in the treatment of anemia disease, preferentially iron anemia disease, wherein magnetosomes are administered to the body part of an individual, preferentially to reduce or stop anemia.

The invention also relates to a method for the treatment of an anemia disease, wherein this disease is selected from the group consisting of: Iron deficiency anemia, Vitamin deficiency anemia, Anemia of chronic disease, Aplastic anemia, Anemia associated with bone marrow disease, Hemolytic anemia, Sickle cell anemia, Thalassaemia, Pernicious anaemia, Fanconi anaemia, Sideroblastic Anemia, Congenital Dyserythropoietic Anemia (CDA), Diamond-Blackfan Anemia, and Megaloblastic Anemia. In some cases, anemia Anemia is a decrease in the total amount of red blood cells (RBCs) or hemoglobin in the blood, or a lowered ability of the blood to carry oxygen. In some other cases, The invention also relates to the method for the treatment of anemia or anemia disease, wherein the treatment is due to or involves or is caused by the release or dissociation of iron or free iron from the nanoparticles, in particular magnetosomes. In some cases, the percentage of iron released by the nanoparticles, in particular magnetosomes, is larger than $10^{-5}$, $10^{-3}$, $10^{-1}$, 1, 5, 10, 50, 75, 90 or 99%. In some other cases, the percentage of iron released by nanoparticles, in particular magnetosomes, is lower than 100, 99, 90, 75, 50, 10, 5, 1 or 1%. In some cases, this percentage can be the ratio $Q_{FI}/Q_{IM}$, where $Q_{FI}$ is the quantity of free iron released by the nanoparticles, in particular magnetosomes, and $Q_{IM}$ is the total quantity of iron comprised in the nanoparticles, in particular magnetosomes. In some other cases, this percentage can be the ratio $S_{MFI}/S_M$, where $S_{MFI}$ is the size of the nanoparticles, in particular magnetosomes, measured after free iron has been released from the nanoparticles, in particular magnetosomes, and $S_M$ is the size of the nanoparticles, in particular magnetosomes, measured before free iron has been released from the nanoparticles, in particular magnetosomes.

The invention also relates to the method for the treatment of anemia or anemia disease, wherein the quantity of free iron dissociated or released from the nanoparticles, in particular magnetosomes, is larger than the quantity of iron comprised in the body part of the individual.

In some cases, the quantity of free iron dissociated or released from the nanoparticles, in particular magnetosomes, is larger by a factor of more than 1.00001, 1.1, 2, 5, 10 or 50, than the quantity of iron comprised in the body part of the individual, preferentially before the treatment has started. In some other cases, the quantity of free iron dissociated or released from the nanoparticles, in particular magnetosomes, is larger than $10^{-100}$, $10^{-50}$, $10^{-20}$, $10^{-10}$, $10^{-5}$, $10^{-2}$, $10^{-1}$, 1, 10 or $10^3$ gram of free iron per nanoparticles, in particular magnetosomes, or gram of free iron per gram of nanoparticles, in particular magnetosomes, or gram of free iron per $cm^3$ of body part preferentially comprising the nanoparticles, in particular magnetosomes.

The invention also relates to the method for the treatment of anemia or anemia disease, wherein the quantity of free iron dissociated or released from the nanoparticles, in particular magnetosomes, is lower than $10^{100}$, $10^{50}$, $10^{20}$, $10^{10}$, $10^5$, $10^3$, 10, 1, $10^{-1}$, $10^{-5}$, $10^{-10}$ or $10^{-50}$ gram of free iron per nanoparticles, in particular magnetosomes, or gram of free iron per gram of nanoparticles, in particular magnetosomes, or gram of free iron per cm$^3$ of body part preferentially comprising the nanoparticles, in particular magnetosomes.

The invention also relates to the method for the treatment of anemia or anemia disease, wherein the treatment is due to or involves or is caused by:
i) Internalization of nanoparticles in cells,
ii) Externalization of nanoparticles from cells,
iii) A change in structure, geometry, composition, size, size distribution, surface charge of nanoparticles, and/or
iv) The application of a radiation or acoustic wave on nanoparticles.

In some cases, the change in a property of the nanoparticles, where the property of the nanoparticles can be the structure, geometry, composition, size, size distribution, or surface charge of the nanoparticles, is a variation by more than $10^{-50}$, $10^{-10}$, 1, 5, 10 or 50% of this property. In some other cases, the change in a property of the nanoparticles is a variation by less than 100, 99, 90, 80, 70, 50, 25, 10 or 5% of this property. In some cases, this percentage can be equal to $P_{AT}/P_{BT}$, where $P_{AT}$ and $P_{BT}$ are the values of this property after and before anemia treatment, respectively.

The invention also relates to the method for the treatment of anemia or anemia disease, wherein the radiation is selected from the group consisting of: X-rays, light waves, microwaves, radio waves, and acoustic waves. In some cases, the application of the radiation on the nanoparticles increases the quantity of free iron dissociated or released from the nanoparticles, preferentially by a factor larger than 1.0001, 1.1, 2, 5, 10, 103, 105 or 1010, where this factor can be equal to $Q_{FIR}/Q_{FI}$, where $Q_{FIR}$ and $Q_{FI}$ are the quantities of free iron released or dissociated from the nanoparticles after and before the application of the radiation on the nanoparticles, respectively.

The invention also relates to the method for the treatment of anemia or anemia disease, wherein the power of the radiation is between $10^{-10}$ and $10^{10}$ Watt or Watt per cm$^3$ or Watt per cm$^3$ of body part or Watt per cell.

The invention also relates to the method for the treatment of anemia or anemia disease, wherein the radiation is applied sequentially on the nanoparticles, wherein a sequence comprises the following steps:
i) during a time $t_1$: the application of a radiation,
ii) during a time $t_2$: the non-application of a radiation or the application of a radiation of lower power than during $t_1$.

In some cases, the sequential application of the radiation on the nanoparticles or magnetosomes increases the quantity of free iron dissociated or released from the nanoparticles or magnetosomes, preferentially by a factor larger than 1.0001, 1.1, 2, 5, 10, $10^3$, $10^5$ or $10^{10}$, where this factor can be equal to $Q_{FISR}/Q_{FIR}$, where $Q_{FISR}$ and $Q_{IR}$ are the quantities of free iron released or dissociated from the nanoparticles or magnetosomes after the sequential application of the radiation on the nanoparticles or magnetosomes and the non-sequential application of the radiation on the nanoparticles or magnetosomes, respectively.

In one embodiment of the invention, the treatment according to the invention is sonodynamic therapy.

In some cases, sonodynamic therapy can be defined as a therapy, which triggers a therapeutic activity by: i) applying low intensity acoustic wave on the nanoparticle or body part, or ii) by using the nanoparticle as a sonosensitizer. In some cases, sonodynamic therapy is defined as a therapy, in which the temperature increase is lower than $10^{50}$, $10^5$, $10^3$, 500, 200, 100, 50, 25, 10, 5, 2 or 1° C., and/or the percentage of dissociation of the compound is larger than $10^{-5}$, $10^{-2}$, $10^{-1}$, 1, 10, $10^3$ or $10^7$%.

In some cases, the percentage of dissociation of the compounds or percentage of dissociated compounds can be defined as the ratio between: i) the number or mass of compounds that are not linked or not bound to the nanoparticles or that have dissociated, preferentially following the application of the acoustic wave or radiation, and ii) the number or mass compounds that are linked or not dissociated to the nanoparticle, preferentially before or without the application of the acoustic wave or radiation.

In some other cases, sonodynamic therapy is defined as a therapy, in which the temperature increase is larger than $10^5$, $10^3$, 500, 200, 100, 50, 25, 10, 5, 2 or 1° C., and/or the percentage of dissociation of the compound is lower than $10^{-5}$, $10^{-2}$, $10^{-1}$, 1, 10, $10^3$ or $10^7$%.

The invention also relates to nanoparticles for use according to the invention, wherein the application of the acoustic wave or radiation on the nanoparticle or body part induces a temperature increase of the body part or nanoparticle, which is between $10^{-10}$ and $10^{10}$, $10^{-5}$ and $10^5$, $10^{-1}$ and $10^{4}$° C., or between 1 and 30 (degree Celsius). In some cases, the temperature of the body part or nanoparticle increases by a temperature increase, which is between $10^{-10}$ and $10^{10}$, $10^{-5}$ and $10^5$, or between $10^{-1}$ and $10^{4}$° C.

In some other cases, the temperature can be measured at the nanoscopic scale, i.e. a scale that comprises less than 2, 5, 10, $10^3$, $10^5$ or $10^9$ nanoparticles or a scale smaller than: i) the size of 1, 2, 5, 10, $10^3$, $10^5$ or $10^9$ nanoparticle(s) or ii) or $10^5$, $10^3$, $10^2$, 10 or 1 nm.

In some cases, the temperature can be measured at the macroscopic scale, i.e. a scale: i) larger by a factor of at least 1.001, 1.1, 1.2, 1.5, 5, 10, $10^3$ or $10^5$ than the nanoscopic scale, ii) larger than the size of 1, 10, $10^3$, $10^5$ or $10^9$ nanoparticle(s), or iii) comprising more than 2, 5, 10, $10^3$, $10^5$ or $10^9$ nanoparticle(s).

In one embodiment of the invention, the temperature increase of the body part or nanoparticle exposed to the acoustic waves, $\Delta T$, is the temperature increase above the physiological temperature or above the temperature of the body part of nanoparticle reached before the application of the acoustic wave or radiation. In some cases, $\Delta T=T_{NPBP}-T_{BP}$, where $T_{NPBP}$ is the temperature or temperature increase of the body part comprising the nanoparticles exposed to the acoustic waves or radiation and $T_{BP}$ is: i) the temperature or temperature increase of the body part not comprising the nanoparticles exposed to the acoustic waves or radiation, or ii) the temperature or temperature increase of the body part not comprising the nanoparticles not exposed to the acoustic waves or radiation. In some other cases, $\Delta T$ can occur or be measured: i), in the body part with the nanoparticles, ii), in the nanoparticle region, iii) in the body part without the nanoparticles, iv) in the body part without the nanoparticle and in the nanoparticle region, or v) in the nanoparticle region and not in the body part without the nanoparticles. It can be preferred that a larger temperature increase occurs in the body part with the nanoparticles or in the nanoparticle region than in the body part without the nanoparticles. In some cases, the temperature increase $\Delta T$ can be the difference between: the temperature measured or occurring for the acoustic wave or radiation sequentially applied on the nanoparticles and the temperature measured or occurring for the acoustic wave or radiation continuously applied on the nanoparticles.

The invention also relates to nanoparticles for use according to the invention, wherein the application of the acoustic wave or radiation on the nanoparticle or body part induces a temperature increase of the body part or nanoparticle, which is larger than 0.01, 0.1, 1, 2, 5, 10, 30, 50, 100 or 1000° C. In some cases, the temperature of the body part or nanoparticle increases by more than 0.01, 0.1, 1, 2, 5, 10, 30, 50, 100, or 1000° C. when the acoustic wave or radiation is applied on the nanoparticle or body part.

In one embodiment of the invention, the acoustic wave or radiation, preferentially the acoustic wave or radiation frequency, is thermal. In this case, the acoustic wave or radiation induces an increase in temperature, preferentially larger than 0.1, 1, 2, 5, 10, $10^2$ or $10^{3°}$ C. A thermal acoustic wave frequency is preferentially larger than $10^{-20}$, $10^{-10}$, $10^{-5}$, $10^{-3}$, $10^{-1}$, 1, 10, $10^3$, $10^5$, $10^{10}$ or $10^{20}$ Hz.

The invention also relates to nanoparticles for use according to the invention, wherein the application of the acoustic wave or radiation on the nanoparticle or body part induces a temperature increase of the body part or nanoparticle, which is lower than $10^{100}$, $10^{50}$, $10^{20}$, $10^{10}$, $10^5$, $10^3$, $10^2$, 50, 30, 10, 5, 2, 1, 0.1 or 0.01° C. In some cases, the temperature of the body part or nanoparticle increases by less than $10^3$, $10^2$, 50, 30, 10, 5, 2, 1 or 0.1° C., when the acoustic wave or radiation is applied on the nanoparticle or body part.

In one embodiment of the invention, the frequency of the acoustic wave or radiation is non-thermal. In this case, the frequency of the acoustic wave or radiation is such that it does not induce an increase in temperature or it induces an increase in temperature lower than $10^3$, $10^2$, 10, 5, 2, 1 or 0.1° C. In this case, the frequency of the acoustic wave or radiation is preferentially lower than $10^{20}$, $10^{10}$, $10^5$, $10^3$, $10^1$, 1, 10, $10^{-3}$, $10^{-5}$, $10^{-10}$ or $10^{-20}$ Hz.

In one embodiment of the invention, a suitable range of temperature increase, $\Delta T$, is between 3° C. and 28° C. The minimum value of this range (3° C.) was estimated by exposing 100 µg of magnetosomes mixed in 100 µl of water to an acoustic wave of 1.5 W/cm². In some cases, this minimum value can be decreased by a factor of more than 1.5, 2, 5, 10, $10^2$, $10^5$, $10^7$, $10^9$ or $10^{20}$ by decreasing the intensity, power, or frequency of the acoustic wave by a factor of more than 1.5, 2, 5, 10, $10^2$, $10^5$, $10^7$, $10^9$ or $10^{20}$ or by decreasing the nanoparticle concentration in the body part by a factor of more than 1.5, 2, 5, 10, $10^2$, $10^5$, $10^7$, $10^9$ or $10^{20}$. The maximum value of this range (28° C.) was estimated by exposing 45 µg of magnetosomes per cm³ of tissue to an acoustic wave of 1.5 W/cm². In some cases, this maximum value can be increased by a factor of more than 1.5, 2, 5, 10, 50, $10^2$, $10^5$, $10^7$, $10^9$ or $10^{20}$ by increasing the intensity, power, or frequency of the acoustic wave by a factor of more than 1.5, 2, 5, 10, 50, $10^2$, $10^5$, $10^7$, $10^9$ or $10^{20}$ or by increasing the nanoparticle concentration in the body part by a factor of more than 1.5, 2, 5, 10, 50, $10^2$, $10^5$, $10^7$, $10^9$ or $10^{20}$.

In another embodiment of the invention, a suitable range of $T_{NPBP}$ is between 18° C. and 56° C.

The minimum value of this range (18° C.) was estimated by exposing a suspension comprising 100 µg of magnetosomes in 100 µl of water to an acoustic wave of 0.5 W/cm². In some cases, this minimum value can be decreased by a factor of more than 1.5, 2, 5, 10, 50, $10^2$, $10^5$, $10^7$, $10^9$ or $10^{20}$ by decreasing the intensity, power, or frequency of the acoustic wave by a factor of more than 1.5, 2, 5, 10, 50, $10^2$, $10^5$, $10^7$, $10^9$ or $10^{20}$ or by decreasing the nanoparticle concentration in the body part by a factor of more than 1.5, 2, 5, 10, 50, $10^2$, $10^5$, $10^7$, $10^9$ or $10^{20}$. The maximum value of this range (56° C.) was estimated by exposing 45 µg of magnetosomes per cm³ of tissue to an acoustic wave of 1.5 W/cm². In some cases, this maximum value can be increased by a factor of more than 1.5, 2, 5, 10, 50, $10^2$, $10^5$, $10^7$, $10^9$ or $10^{20}$ by increasing the intensity, power, or frequency of the acoustic wave by a factor of more than 1.5, 2, 5, 10, 50, $10^2$, $10^5$, $10^7$, $10^9$ or $10^{20}$ or by increasing the nanoparticle concentration in the body part by a factor of more than 1.5, 2, 5, 10, 50, $10^2$, $10^5$, $10^7$, $10^9$ or $10^{20}$.

In still another embodiment of the invention, a suitable range of $T_BP$ is between 13° C. and 32° C. The minimum value of this range (13° C.) was estimated by exposing a water solution to an acoustic wave of 0.5 W/cm². In some cases, this minimum value can be decreased by a factor of more than 1.5, 2, 5, 10, 50, $10^2$, $10^5$, $10^7$, $10^9$ or $10^{20}$ by decreasing the intensity, power, or frequency of the acoustic wave by a factor of more than 1.5, 2, 5, 10, 50, $10^2$, $10^5$, $10^7$, $10^9$ or $10^{20}$. The maximum of this range (32° C.) was estimated by exposing a tissue to an acoustic wave of 1 W/cm². In some cases, this maximum value can be increased by a factor of more than 1.5, 2, 5, 10, 50, $10^2$, $10^5$, $10^7$, $10^9$ or $10^{20}$ by increasing the intensity, power, or frequency of the acoustic wave by a factor of more than 1.5, 2, 5, 10, 50, $10^2$, $10^5$, $10^7$ or $10^9$.

In one embodiment of the invention, the application of the acoustic wave or radiation on nanoparticles leads to a saturating temperature (ST) or the acoustic wave or radiation is applied on the nanoparticle until ST is reached. In some cases, the saturating temperature can be the desired temperature.

In one embodiment of the invention, the application of the acoustic wave or radiation is stopped as soon as the saturating temperature is reached, preferentially to avoid overheating.

Preferentially, the saturating temperature is the maximum temperature that can be reached during the time of application of the acoustic wave or radiation or represent a temperature that does not vary by more than 1, 5, 10, 50, 75, $10^2$ or $10^3$%, during a time of application of the acoustic wave or radiation designated as $t_s$, or being $t_1$ or $t_3$.

The time $t_s$, $t_1$, $t_3$, preferentially follows the time $t_i$, which is the initial time at which the acoustic wave or radiation starts to be applied. In some cases $t_s$ is smaller than $t_i$. In still some other cases, $t_i/(t_i+t_s)$ is larger than $10^{-9}$, $10^{-7}$, $10^{-5}$, $10^{-4}$, $10^{-3}$, $10^{-2}$, $10^{-1}$, 0.5, 0.75 or 0.9. In still some other cases, $t_s/t_i$ is larger than $10^{-9}$, $10^{-6}$, $10^{-3}$, $10^{-1}$, 1, 10, $10^3$, $10^6$ or $10^9$. In still some other cases, $t_s/t_i$ is smaller than $10^9$, $10^6$, $10^3$, 10, 1, $10^{-1}$, $10^{-3}$, $10^{-6}$ or $10^{-9}$.

In another embodiment of the invention, $t_1=t_i+t_s$,

In some cases, the ST can be: i) larger than −270, −200, −100, −50, 0, 1, 10, $10^3$ or $10^{5°}$ C., or ii) more important by a factor of at least 1.00001, 1.1, 1.2, 1.5, 2, 5, 10, $10^3$, $10^5$ or $10^9$ in the presence than in the absence of the nanoparticles.

In some other cases, the ST can be: i) lower than $10^{20}$, $10^5$, $10^3$, 10, 1, −100 or −200° C., or ii) is less important by a factor of at least 1.00001, 1.1, 1.2, 1.5, 2, 5, 10, $10^3$, $10^5$ or $10^9$ in the presence than in the absence of the nanoparticles.

In still some other cases, the ST can be between −270 and $10^{50}$, −100 and $10^{20}$, 0 and $10^{10}$, 10 and $10^5$, 37 and $10^3$, or between 41 and $10^{3°}$ C.

In one embodiment of the invention, a suitable range of values of ST is between (37±4) ° C. and (73±4) ° C., as deduced from table 2 considering that the initial temperature is the physiological temperature. In some cases, the minimum value of this range, (37±4) ° C., can be decreased, for example by more than 1, 5, 10, 20, 50, or 100° C., preferentially when the temperature of the body part is decreased, for example by using an equipment or a substance such as ice that decreases the temperature of the body part or by decreasing the intensity, power, or frequency of the acoustic wave or by decreasing nanoparticle concentration. In some other cases, the maximum value of this range (73±4) ° C. can be increased, for example by more than 1, 5, 10, 20, 50, or 100° C., preferentially when the temperature of the body part is increased, for example by using an equipment or a substance that increases the temperature of the body part or by increasing the intensity, power, or frequency of the acoustic wave or by increasing nanoparticle concentration.

In an embodiment of the invention, a compound, preferentially administered to the body part, is bound or attached to the nanoparticles, preferentially before or in the absence of the application of the acoustic wave or radiation on the nanoparticles.

In one embodiment of the invention, the compound is attached to the nanoparticles or not dissociated from the nanoparticles when it is: i) located at a distance lower than $10^5$, $10^3$, 100 or 10 nm from the nanoparticles, ii) bound or linked to the nanoparticles, preferentially through Hydrogen, Van der Walls, London, covalent, metallic, or ionic bonds, iii) the compound can't be magnetically separated from the nanoparticle, iv), the percentage of compounds associated or linked to the nanoparticles or located at distance of less than 10, 1, $10^{-1}$, $10^{-3}$, $10^{-6}$ or $10^{-9}$ cm from the nanoparticles, is larger than 99, 90, 75, 50, 30, 20, 10, 5, 2 or 1%, where this percentage can be or represent the ratio between the number or mass of compounds linked or associated to the nanoparticles before magnetic separation and the number or mass of compounds linked or associated to the nanoparticles after magnetic separation.

The invention also relates to nanoparticles for use according to the invention, wherein a compound is attached to the nanoparticles and the application of the acoustic wave on the nanoparticles induces the dissociation of the compound from the nanoparticles.

In some cases, the compound can be not linked or not bound to the nanoparticle or dissociated from the nanoparticle when: i) it is located at a distance larger than $10^{-3}$, $10^{-1}$, 1, 5, 10, 100, $10^3$ or $10^5$ nm or between 1 and $10^{10}$ nm from the nanoparticles or surface of the nanoparticles or coating of the nanoparticles, ii) it is not bound or not linked to the nanoparticles through Hydrogen, Van der Walls, London, covalent, metallic, or ionic bonds, iii) the nanoparticles can be magnetically separated from the compound, preferentially by using a magnet that attracts the nanoparticles, iv) the percentage of compounds associated or linked to the nanoparticles or located at a distance of less than 10, 1, $10^{-1}$, $10^{-1}$, $10^{-6}$ or $10^{-9}$ cm from the nanoparticles, is lower than 99, 90, 75, 50, 30, 20, 10, 5, 2 or 1%.

In some cases, magnetic separation can consist to separate the compound from the nanoparticle by applying a magnetic field on the nanoparticle whose strength varies spatially, preferentially using a magnet with a lower strength than 10, 1, $10^{-1}$, $10^{-3}$ or $10^{-9}$ T, where this strength is preferentially measured at the surface or near the magnet and decreases with increasing distance away from the magnet.

In some other cases, the compound can be linked or bound to the nanoparticles or not dissociated from the nanoparticle. In this case, it can be located at a distance lower than $10^{100}$ $10^{50}$, $10^{10}$, $10^5$, $10^2$, 10, 5, 2 or 1 nm or between $10^{-3}$ and 1 nm from the nanoparticles or surface of the nanoparticles or coating of the nanoparticles.

Preferentially, the compound is attached to the nanoparticles in the absence of the application of the acoustic wave or radiation and dissociates from the nanoparticles under the application of the acoustic wave or radiation.

In one embodiment of the invention, the acoustic wave or radiation is associated with, or linked with, or induces, or produces, or results in, or is responsible for, or creates the movement, or vibration, or oscillation of the compound, preferentially after the dissociation of the compound from the nanoparticle.

In an embodiment of the invention, the compound is a therapeutic, immunogenic, metabolic, luminescent, fluorescent, radioactive, diagnostic, biologic, or chemical compound. In some cases, the compound(s) can be or represent an assembly of more than 1, 10, $10^2$, $10^3$, $10^5$, $10^7$, $10^{10}$, $10^{20}$ or $10^{50}$ compounds. It is preferentially linked or bound to the nanoparticles. In some cases, the compound can dissociate from the nanoparticles under the application of the acoustic wave or radiation. In some cases, more than $10^{-5}$, $10^{-3}$, $10^{-1}$, 1, 5, 10, 25, 50, 75, 85 or 90% of compounds is dissociated from the nanoparticles, where this percentage can represent or be the ratio between the quantity of compounds dissociated from the nanoparticles following or under the application of the acoustic wave or radiation and the quantity of compounds linked or bound to the nanoparticles before or without the application of the acoustic wave or radiation. In some cases, the number of compounds linked or bound to one nanoparticle is larger than 1, 2, 5, 10, $10^3$, $10^5$ or $10^{10}$. In some other cases, the number of compounds linked or bound to one nanoparticle is lower than 2, 5, 10, $10^3$, $10^5$ or $10^{10}$. In still some other cases, the percentage of compounds dissociated can increase by a factor of at least 1.01, 1.1, 2, 5, 7, 10, $10^2$ or $10^5$ between before and after the application of the acoustic wave or radiation on the nanoparticles.

In one embodiment of the invention, the compound is part of the nanoparticle. In this case, it can be free iron or free oxygen, preferentially in the ionic form, that preferentially dissociates or leaks or diffuses away from the nanoparticle, preferentially under or following the application of the acoustic wave or radiation on the nanoparticle or body part, preferentially following dissolution or degradation of the nanoparticle, preferentially following administration of the nanoparticle in/to the body part.

In another embodiment of the invention, the ratio between the mass, number, or weight, of the compounds, preferentially linked to a single nanoparticle, and the mass, number, or weight of a single nanoparticle is lower than $10^{20}$, $10^9$, $10^5$, $10^2$, 2, 1, $10^{-2}$, $10^{-5}$, $10^{-9}$ or $10^{-20}$.

In another embodiment of the invention, the ratio between the mass, number, or weight, of the compound, preferentially linked to a single nanoparticle, and the mass, number, or weight of a single nanoparticle is larger than $10^{20}$, $10^9$, $10^5$, $10^2$, 1, $10^{-2}$, $10^{-5}$, $10^{-9}$ or $10^{-20}$.

In one embodiment of the invention, a suitable range of values for the number of compounds preferentially linked to a single nanoparticle is between 1 and 178, where this minimum value of 1 corresponds to the minimum number of compounds that can be linked to a single nanoparticle and the maximum value of 178 corresponds to the number of RhB molecules that was linked to a single magnetosome in patent WO2017/068252 incorporated in reference, and which could dissociate at least in part from a single magnetosome. In some cases, this maximum value of 178 can be increased, preferentially by a factor of more than 5, 10, $10^3$, $10^7$, $10^{10}$, or $10^{20}$, by: i) decreasing the size, or mass of the compound linked to the nanoparticle, preferentially by a factor of more than 1.1, 2, 5, 10, $10^3$, $10^7$, $10^{10}$, or $10^{20}$, ii) changing the type of bounds between the compounds and the nanoparticle, or iii) changing the method for attaching or binding the compound to the nanoparticle.

In an important embodiment of the invention, a sequential application of the acoustic wave or radiation is used for or enables reaching temperatures or maximum temperature, preferentially during at least one sequence, which is below the maximum temperature that would be reached by using a continuous application of the radiation of acoustic wave. On the one hand, it may result in less toxicity by heating at a lower temperature compared with a continuous application of the acoustic wave or radiation. On the other hand, it may result in higher efficacy, preferentially anti-tumor or anti-cancer efficacy, by producing temperature gradients, or gradient in the speed or movement of the nanoparticles, during at least one sequence, which can more efficiently trigger at least one mechanism of treatment as disclosed in this invention than a continuous application of the acoustic wave or radiation.

The invention also relates to nanoparticles for use according to the invention, wherein the sequential application of the acoustic wave or radiation on the body part or nanoparticle induces:
 i) a series of temperature increases of the body part or nanoparticle followed by temperature decreases of the body part or nanoparticle, and/or
 ii) a series of dissociations of the compound from the nanoparticles followed by non-dissociation of the compound from the nanoparticles.

In one embodiment of the invention, the acoustic wave or radiation is applied sequentially, preferentially on the body part or nanoparticle, when: i) it is not applied continuously over time, ii) it is not applied with a continuous power, intensity, or frequency over time, or iii) it creates or is associated with or produces at least one sequence.

In some cases, the time $t_1$ is the duration of application of the acoustic wave or radiation.

In some other cases, the time $t_2$ is the duration of the non-application of the acoustic wave or radiation.

In still some other cases, the time $t_3$ is the duration of the application of the acoustic wave or radiation, whose intensity, energy, power, or frequency is/are lower than that/those applied on nanoparticles during the time $t_1$ or $t_2$.

In some cases, a sequence can correspond to or be the application of the acoustic wave or radiation during a time $t_1$ followed by the non-application of the acoustic wave or radiation during a time $t_2$.

In some other cases, a sequence can correspond to or be the application of an acoustic wave or radiation during a time $t_1$ followed by the application of another acoustic wave or radiation during a time $t_3$, wherein the intensity, power, energy, or frequency of the acoustic wave or radiation applied during the time $t_3$ is lower than the intensity, power, energy, or frequency of the acoustic wave or radiation applied during the time $t_1$.

In one embodiment of the invention, the time $t_1$ is the duration of a heating step.

In one embodiment of the invention, the heating step is a step during which the temperature of the body part or nanoparticle increases.

In one embodiment of the invention, the temperature increase of the heating step has at least one of the following properties: i) it is larger in the presence than in the absence of the nanoparticle, ii) it is larger during $t_1$ than during $t_2$ or $t_3$, iii) it is larger than or has a magnitude larger than $10^{-20}$, $10^{-5}$, $10^{-3}$, $10^{-1}$, 1, 2, 5, 10, 25, 50, 100, 200, 500, $10^3$, $10^5$ or $10^{9}$° C., iv) it leads to or is characterized by an initial temperature increase, also designated as the initial slope of the temperature increase with time, $\Delta T/\delta t$, which is larger than $10^{-40}$, $10^{-20}$, $10^{-10}$, $10^{-7}$, $10^{-5}$, $10^{-3}$, $10^{-1}$, 1, 2, 5, 10, $10^2$, $10^3$ or $10^{5}$° C./sec or ° C./sec as measured per gram of nanoparticle or body part or ° C./sec as measured per cm$^3$ of nanoparticle or body part, v), it is such that the maximum temperature reached during a heating step remains below 25, 30, 37, 39, 41, 45, 50, 100, $10^3$, $10^5$, $10^9$ or $10^{11}$° C., or vi) it is larger by at least $10^{-5}$, $10^{-3}$, $10^{-1}$, 1, 2, 5, or 10, $10^3$, $10^5$, or $10^{9}$° C. than the temperature increase reached by applying the acoustic wave or radiation in the absence of the nanoparticles.

In another embodiment of the invention, the temperature increase of the heating step has at least one of the following properties: i) it is lower or has a magnitude of less than $10^{50}$, $10^9$, $10^5$, $10^3$, 10, 5, 2, 1, $10^{-1}$, $10^{-3}$ or $10^{-5}$° C., ii) it leads to or is characterized by a value of $\Delta T/\delta t$, which is lower than $10^{50}$, $10^{20}$, $10^{10}$, $10^3$, $10^2$, 10, 5, 2, 1, $10^{-1}$, $10^{-3}$, $10^{-5}$, $10^{-7}$, $10^{-10}$, $10^{-20}$ or $10^{-40}$° C./sec or ° C./sec as measured per gram of nanoparticle or body part or ° C./sec as measured per cm$^3$ of nanoparticle or body part, iii) it is such that the maximum temperature reached during a heating step remains below $10^{11}$, $10^9$, $10^5$, $10^3$, 100, 50, 45, 41, 39, 37, 30, 25, 10, 5, 0, −100, −200 or −273° C., iv), it is lower by at least $10^{-50}$, $10^{-5}$, $10^{-3}$, $10^{-1}$, 1, 2, 5, or 10, $10^3$, $10^5$, or $10^{9}$° C. than the temperature increase reached by applying the acoustic wave or radiation in the absence of the nanoparticles, or v), it leads to or is characterized by a $\Delta T/\delta t$ value, which is lower than $10^{100}$, $10^{40}$, $10^{20}$, $10^5$, $10^3$, $10^2$, 10, 5, 2, 1, $10^{-1}$, $10^{-3}$, $10^{-5}$, $10^{-7}$, $10^{-20}$ or $10^{-40}$° C./sec or ° C./sec as measured per gram of nanoparticle or body part or ° C./sec as measured per cm$^3$ of nanoparticle or body part.

In one embodiment of the invention, the temperature increase or initial slope of this increase, preferentially of heating step, is measured or occurs above: i) the physiological temperature,
 ii) the temperature of the individual or body part without, before or after the heating step, iii) the temperature of the individual or body part during the cooling step, or
 iv) the temperature increase reached by applying the acoustic wave or radiation on the body part without the nanoparticles.

In one embodiment of the invention, the temperature increase, preferentially occurring or measured during the heating step, is the difference in temperature between the temperatures measured: i) after and before the application of the acoustic wave or radiation, ii) the beginning and end of $t_1$.

In some cases, the temperature increase, preferentially occurring or measured during the heating step, can be larger than $10^{-20}$, $10^{-3}$, $10^{-2}$, $10^{-1}$, 1, 10, $10^2$, $10^3$ or $10^{5}$° C.

In some other cases, the temperature increase, preferentially occurring or measured during the heating step, can be lower than $10^{20}$, $10^5$, $10^3$, $10^2$, 10, 1, $10^{-1}$, $10^{-2}$ or $10^{-3}$° C.

In still some other cases, the temperature increase, preferentially occurring or measured during the heating step, can be between $10^{-50}$ and $10^{50}$, $10^{-5}$ and $10^{50}$, $10^{-1}$ and $10^{10}$, $10^{-5}$ and $10^3$, or between $10^{-2}$ and $10^{3}$° C.

In still some other cases, the temperature increase, preferentially occurring or measured during the heating step, can be more than $10^{-50}$, $10^{-20}$, $10^{-5}$, $10^{-3}$, $10^{-2}$, $10^{-1}$, 1, 10, $10^2$, $10^3$ or $10^{5}$° C. larger in the presence than in the absence of the nanoparticles.

In one embodiment of the invention, a suitable range for the magnitude of the temperature increase is between 0° C. and 36° C. as deduced from table 2. In some cases, the maximum value of this range (36° C.) can be increased, for example by more than 1, 5, 10, 20, 50 or 100° C., preferentially when the temperature of the body part is increased, for example by using an equipment or a substance that increases the temperature of the body part or by increasing the intensity, power, or frequency of the acoustic wave or by increasing nanoparticle concentration.

In one embodiment of the invention, for a continuous application of the acoustic wave or radiation, $t_2$ and/or $t_3=0$ second.

In some cases, $t_1$, $t_2$, and/or $t_3$, is/are chosen or is/are such to reach a lower temperature at the end of n sequences of total duration $n \cdot (t_1+t_2)$ or $n \cdot (t_1+t_3)$, preferentially by a factor of at least 1.00001, 1.1, 2 or 5, than that reached at the end of a continuous application of the acoustic wave or radiation of duration $n \cdot t_1$, where the heating times are the same for the sequential and continuous application of the acoustic wave or radiation. n can be an integer comprised between 1 and $10^{100}$ The invention also relates to nanoparticles for use according to the invention, wherein the application of the acoustic wave or radiation on nanoparticle or body part induces a temperature increase, preferentially during at least one heating step, which is:

i) larger than $10^{-10}$, $10^{-5}$, $10^{-3}$, $10^{-1}$, 1, 5 or 10° C. in the pathological site, and/or ii) lower than $10^{10}$, $10^5$, $10^3$, 100, 50, 20, 10, 5, 2, 1, $10^{-1}$, $10^{-5}$ or $10^{-10}$° C. in the healthy site, preferentially surrounding the pathological site.

In another embodiment of the invention, the time $t_2$ or $t_3$ is the duration of a cooling step.

In one embodiment of the invention, the cooling step is a step during which the temperature of the body part decreases. In some cases, the temperature decrease of the cooling step can be the magnitude or absolute value of this decrease.

In one embodiment of the invention, the temperature decrease of the cooling step has at least one of the following properties: i) it is larger in the presence than in the absence of nanoparticles, ii) it is larger during $t_2$ or $t_3$ than during $t_1$, iii) it is larger than $10^{-20}$, $10^{-5}$, $10^{-3}$, $10^{-1}$, 1, 2, 5, 10, 25, 50, 100, 200, 500, $10^3$, $10^5$ or $10^9$° C., iv), it leads to or is characterized by an initial temperature decrease, also designated as the initial slope of the temperature decrease with time, $\Delta T/\delta t$, which is larger than $10^{-40}$, $10^{-20}$, $10^{-10}$, $10^{-7}$, $10^{-5}$, $10^{-3}$, $10^{-1}$, 1, 2, 5, 10, $10^2$, $10^3$ or $10^5$° C./sec or ° C./sec as measured per gram of nanoparticle or body part or ° C./sec as measured per cm³ of nanoparticle or body part, v) it is such that the minimum temperature reached during a cooling step remains above −273, −150, −100, −75, −50, −30, −10, 0, 5, 10, 25, 30, 37, 39, 41, 45, 50, 100, $10^3$, $10^5$, $10^9$ or $10^{11}$° C., vi) it is larger by at least $10^{-5}$, $10^{-3}$, $10^{-1}$, 1, 2, 5, 10, $10^3$, $10^5$ or $10^9$° C. than the temperature decrease reached by the non-application of the acoustic wave in the absence of the nanoparticles, or vii) it leads to or is characterized by a $\Delta T/\delta t$ value, which is larger than $10^{-40}$, $10^{-20}$, $10^{-10}$, $10^{-7}$, $10^{-5}$, $10^{-3}$, $10^{-1}$, 1, 2, 5, 10, $10^2$, $10^3$ or $10^5$ ° C./sec or ° C./sec as measured per gram of nanoparticle or body part or ° C./sec as measured per cm³ of nanoparticle or body part.

In another embodiment of the invention, the temperature of the cooling step has at least one of the following properties: i) it is lower in the presence than in the absence of nanoparticles, ii) it is lower than $10^{50}$, $10^9$, $10^5$, $10^3$, 10, 5, 2, 1, $10^{-1}$, $10^{-3}$ or $10^{-5}$° C., iii) it leads to or is characterized by a value of $\Delta T/\delta t$, which is lower than $10^{50}$, $10^{20}$, $10^{10}$, $10^3$, $10^2$, 10, 5, 2, 1, $10^{-1}$, $10^{-3}$, $10^{-5}$, $10^{-7}$, $10^{-10}$, $10^{-20}$ or $10^{-40}$° C./sec or ° C./sec as measured per gram of nanoparticle or body part or ° C./sec as measured per cm³ of nanoparticle or body part, iv) it is such that the minimum temperature reached during a cooling step remains below $10^{11}$, $10^9$, $10^5$, $10^3$, 100, 50, 45, 41, 39, 37, 30, 25, 10, 5, 0, −100, −200 or −273° C., v) it is lower by at least $10^{-50}$, $10^{-5}$, $10^{-3}$, $10^{-1}$, 1, 2, 5, or 10, $10^3$, $10^5$, or $10^9$° C. than the temperature decrease reached in the absence of the nanoparticles, or vi) it leads to or is characterized by a $\Delta T/\delta t$ value, which is lower than $10^{100}$, $10^{40}$, $10^{20}$, $10^5$, $10^3$, $10^2$, 10, 5, 2, 1, $10^{-1}$, $10^{-3}$, $10^{-5}$, $10^{-7}$, $10^{-20}$ or $10^{-40}$° C./sec or ° C./sec as measured per gram of nanoparticle or body part or ° C./sec as measured per cm³ of nanoparticle or body part.

In one embodiment of the invention, the temperature decrease, initial slope of temperature decrease, preferentially of the cooling step, is measured or occurs below: i) the temperature of the individual or body part without, before or after the cooling step, or ii) the temperature of the individual or body part during the heating step.

In one embodiment of the invention, the temperature decrease, preferentially occurring or measured during the cooling step, is the difference in temperature between the temperatures measured between the beginning and end of $t_2$ or $t_3$.

In some cases, the temperature decrease, preferentially occurring or measured during the cooling step, can be larger than $10^{-20}$, $10^{-3}$, $10^{-2}$, $10^{-1}$, 1, 10, $10^2$, $10^3$ or $10^5$° C.

In some other cases, the temperature decrease, preferentially occurring or measured during the cooling step, can be lower than $10^{20}$, $10^5$, $10^3$, $10^2$, 10, 1, $10^{-1}$, $10^{-2}$ or $10^{-3}$° C.

In still some other cases, the temperature decrease, preferentially occurring or measured during the cooling step, can be between $10^{-50}$ and $10^{50}$, $10^{-5}$ and $10^{50}$, $10^{-1}$ and $10^{10}$, $10^{-5}$ and $10^3$, or between $10^{-2}$ and $10^{3}$° C.

In still some other cases, the temperature decrease, preferentially occurring or measured during the cooling step, can be: i), in some cases more than $10^{-50}$, $10^{-20}$, $10^{-5}$, $10^{-3}$, $10^{-2}$, $10^{-1}$, 1, 10, $10^2$, $10^3$ or $10^5$° C. larger in the presence than in the absence of the nanoparticles, and/or ii), in some other cases more than $10^{-50}$, $10^{-20}$, $10^{-5}$, $10^{-3}$, $10^{-2}$, $10^{-1}$, 1, 10, $10^2$, $10^3$ or $10^5$° C. lower in the presence than in the absence of the nanoparticles.

In one embodiment of the invention, the time $t_1$ is the duration of a dissociation step, where the dissociation step is the step during which the compound dissociates from the nanoparticles.

In some cases, more than 0.01, 0.1, 1, 5, 10, 25, 50, 75, 80 or 90% of compounds are dissociated or dissociate from the nanoparticles, preferentially during the dissociation step.

In some other cases, less than 100, 99, 90, 80, 75, 50, 20, 10, 5, 2, 1 or 0.1% of compounds are dissociated or dissociate from the nanoparticles, preferentially during the dissociation step.

In still some other cases, between $10^{-1}$ and 100, 1 and 99, 1 and 50, or between 2 and 10% of compounds are dissociated or dissociate from the nanoparticles, preferentially during the dissociation step.

This percentage can be equal to the ratio between the number or concentration or mass of compounds dissociated from the nanoparticles divided by the total number or concentration or mass of compounds not dissociated from the nanoparticles and/or attached to the nanoparticles.

In another embodiment of the invention, the time $t_2$ or $t_3$ is the duration of a non-dissociation step, where the non-dissociation step is the step during which the compound does not dissociate from the nanoparticles.

In some cases, the compound does not dissociate from the nanoparticles when the percentage of compounds that are dissociated or dissociate from the nanoparticles is lower, preferentially by a factor of more than 1.00001, 1.1, 1.2, 1.5, 2, 5, 10, $10^5$ or $10^{10}$ than that reached or obtained during the dissociation step.

In some cases, the value of $t_2$ can be the same as the value of $t_1$.

In one embodiment of the invention, the time $t_1$, $t_2$, or $t_3$, is shorter than $10^{-3}$, $10^{-2}$, $10^{-1}$, 1, 10, $10^2$ or $10^3$, $10^5$, $10^{20}$, $10^{100}$ or $10^{1000}$ minute(s). In some cases, $t_1$, $t_2$, or $t_3$, is shorter than $10^{-9}$, $10^{-7}$, $10^{-5}$, $10^{-3}$, $10^{-1}$, 1, 10, $10^3$, $10^5$, $10^7$ or $10^9$ seconds.

In still another embodiment of the invention, the time $t_1$, $t_2$, or $t_3$, is longer than $10^{-3}$, $10^{-2}$, $10^{-1}$, 1, 10, $10^2$, or $10^3$ minute(s). In some cases, $t_1$, $t_2$, or $t_3$, is longer than $10^{-100}$, $10^{-50}$, $10^{-20}$, $10^{-9}$, $10^{-7}$, $10^{-5}$, $10^{-3}$, $10^{-1}$, 1, 10, $10^3$, $10^5$, $10^7$ or $10^9$ seconds.

In one embodiment of the invention, the time $t_1$, $t_2$, or $t_3$, is shorter than the time of a pulse, preferentially by a factor of at least 1.1, 1.5, 2, 5, 10, $10^2$, $10^3$, $10^5$, $10^7$, $10^9$, $10^{12}$, $10^{15}$ or $10^{20}$. In still another embodiment of the invention, the time $t_1$, $t_2$, or $t_3$, is longer than the time of a pulse, preferentially by a factor of at least 1.1, 1.5, 2, 5, 10, $10^2$, $10^3$, $10^5$, $10^7$, $10^9$, $10^{12}$, $10^{15}$ or $10^{20}$.

In still another embodiment of the invention, the pulse is defined as the application of the acoustic wave or radiation, preferentially the acoustic wave or radiation power, energy, or intensity, on the nanoparticle or body part during a time shorter than $10^6$, $10^3$, 1, $10^{-3}$, $10^{-6}$ or $10^{-9}$ seconds.

In one embodiment of the invention, the ratio $t_1/t_2$ or $t_2/t_3$ is smaller than $10^{-9}$, $10^{-6}$, $10^{-3}$, $10^{-1}$, 1, 10, $10^3$, $10^6$, $10^9$, $10^{20}$, $10^{50}$ or $10^{100}$.

In still another embodiment of the invention, the ratio $t_1/t_2$ or $t_2/t_3$ is larger than $10^{-100}$, $10^{-50}$, $10^{-20}$, $10^{-9}$, $10^{-6}$, $10^{-3}$, $10^{-1}$, 1, 10, $10^3$, $10^6$ or $10^9$.

In one embodiment of the invention, the acoustic wave or radiation intensity, energy, power, or frequency applied during $t_3$ is at least 1.1, 1.3, 1.5, 2, 5, 10, $10^2$, $10^3$, $10^5$, $10^{10}$ or $10^9$ lower than the acoustic wave or radiation intensity, energy, power, or frequency applied during $t_1$.

In an embodiment of the invention, a suitable range of values is between 0.2 and 0.43 minutes for $t_1$, and between 0.2 and 0.36 minutes for $t_2$. The minimum and maximum values of these ranges were estimated by exposing sequentially 500 µg of magnetosomes mixed in 100 µl of water to an acoustic wave of 1.5 W/cm² and frequency 3 MHz, as described in example 1(c), and by estimating the smallest and largest values of $t_1$ and $t_2$ values between two different sequences.

In another embodiment of this invention, the minimum of the range of $t_1$ or $t_2$ values can be decreased, for example by a factor of more than 1.5, 2, 5, 10, $10^3$, $10^6$ or $10^9$. This may be achieved by increasing the quantity of nanoparticles in the body part, for example by a factor of more than 1.5, 2, 5, 10, $10^3$, $10^6$ or $10^9$, by reducing nanoparticle diffusion away from the body part or nanoparticle degradation, between different sequences. This may also be achieved by increasing the power, intensity, or frequency of the acoustic wave, for example by a factor of more than 1.5, 2, 5, 10, $10^3$, $10^6$ or $10^9$. This may also be achieved by decreasing the absorption of the body part not comprising the nanoparticle, and preferentially by decreasing the temperature variation resulting from this absorption. For $t_1$ and $t_2$, this can be achieved by using an equipment, substance, preferentially different from the compound or nanoparticles, that heats the body part (to seek an effect on $t_1$) or cools down the body part (to seek the effect on $t_2$).

In another embodiment of this invention, the maximum of the range of $t_1$ or $t_2$ value can be increased, for example by a factor of more than 1.5, 2, 5, 10, $10^3$, $10^6$ or $10^9$. This may be achieved by decreasing the quantity of nanoparticles in the body part, for example by a factor of more than 1.5, 2, 5, 10, $10^3$, $10^6$ or $10^9$, by increasing nanoparticle diffusion away from the body part or by increasing nanoparticle degradation, between different sequences. This may also be achieved by decreasing the power, intensity, or frequency of the acoustic wave, for example by a factor of more than 1.5, 2, 5, 10, $10^3$, $10^6$ or $10^9$. This may also be achieved by increasing the absorption of the body part not comprising the nanoparticles, and preferentially by increasing the temperature variation resulting from this absorption. For $t_1$ and $t_2$, this can be achieved by using an equipment, substance, preferentially different from the compound or nanoparticles, that heats the body part (to seek an effect on $t_1$) or cools down the body part (to seek the effect on $t_2$).

In some cases, a heating, cooling, dissociation, or non-dissociation step, preferentially of duration $t_1$, $t_2$, or $t_3$, a sequence, preferentially of duration $t_1+t_2$ or $t_1+t_3$, can be repeated more than 1, 2, 3, 4, 5, 6, 7, 8, 9, 10, 250, 500, $10^2$, $10^3$, $10^5$, $10^7$ or $10^9$ time(s).

In some cases, the treatment can comprise more than 1, 2, 3, 4, 5, 6, 7, 8, 9, 10, 250, 500, $10^2$, $10^3$, $10^5$, $10^7$ or $10^9$ sequence(s).

In some other cases, the treatment can comprise less than 1, 2, 3, 4, 5, 6, 7, 8, 9, 10, 250, 500, $10^2$, $10^3$, $10^5$, $10^7$ or $10^9$ sequence(s).

In one embodiment of the invention, the time $t_1$, $t_2$, or $t_3$ do not vary by more than 99.9, 99, 90, 75, 50, 25, 10 or $10^{-1}$% between two sequences. In some cases, this percentage of variation can be estimated as the absolute value of $(t_1-t_1')/t_1$, $(t_2-t_2')/t_2$, or as $(t_3-t_3')/t_3$, where $t_1$ and $t_1'$, $t_2$ and $t_2'$, or $t_3$ and $t_3'$, are the durations of two different heating/dissociating steps or cooling/non-dissociating steps belonging to two different sequences.

In one embodiment of the invention, a suitable range of percentages of $(t_1-t_1')/t_1$ is between 5% and 43% and a suitable range of percentages of $(t_2-t_2')/t_2$ is between 5% and 44%. The minimum and maximum values of these ranges were estimated by exposing sequentially 500 µg of magnetosomes mixed in 100 µl of water to an acoustic wave of 1.5 W/cm² and frequency 3 MHz, as described in example 1(c), and by estimating the smallest and largest variations in $t_1$ and $t_2$ values between two different sequences.

In one embodiment of the invention, the durations $(t_1+t_2)$ or $(t_1+t_3)$ do not vary by more than 99.9, 99, 90, 75, 50, 25, 10 or $10^{-1}$% between two different sequences. In some cases, this percentage of variation can be estimated as the absolute value of $[(t_1+t_2)-(t_1+t_2)']/(t_1+t_2)$, or $[(t_1+t_3)-(t_1+t_3)']/(t_1+t_3)$, where $(t_1+t_2)$ and $(t_1+t_2)'$, or $(t_1+t_3)$ and $(t_1+t_3)'$, are the duration of two different sequences.

In one embodiment of the invention, a suitable range of percentages of $[(t_1+t_2)-(t_1+t_2)']/(t_1+t_2)$ is between 2% and 35%. The minimum and maximum values of these ranges were estimated by exposing sequentially 500 µg of magnetosomes mixed in 100 µl of water to an acoustic wave of 1.5 W/cm² and frequency 3 MHz, as described in example 1(c), and by estimating the smallest and largest variations in $(t_1+t_2)$ values between two different sequences.

In another embodiment of this invention, the minimum of the range given by the values $(t_1-t_1')/t_1$, $(t_2-t_2')/t_2$, $[(t_1+t_2)-(t_1+t_2)']/(t_1+t_2)$, can be decreased, for example by a factor of more than 1.5, 2, 5, 10, $10^3$, $10^6$ or $10^9$. This may be achieved by increasing the quantity of magnetosomes in the body part, for example by a factor of more than 1.5, 2, 5, 10, $10^3$, $10^6$ or $10^9$, by decreasing nanoparticle diffusion away from the body part or nanoparticle degradation, between different sequences. This may also be achieved by increasing the power, intensity, or frequency of the acoustic wave, for example by a factor of more than 1.5, 2, 5, 10, $10^3$, $10^6$ or $10^9$. This may also be achieved by decreasing the absorption of the body part not comprising the nanoparticles, and preferentially by decreasing the temperature increase resulting from this absorption.

In another embodiment of this invention, the maximum of the range given by the values of $(t_1-t_1')/t_1$, $(t_2-t_2')/t_2$, $[(t_1+t_2)-(t_1+t_2)']/(t_1+t_2)$, can be increased, for example up to 50, 70, 80, 90, 95, 99 or 99.9%. This may be achieved by decreasing the quantity of nanoparticles, for example by a factor of more than 1.5, 2, 5, 10, $10^3$, $10^6$ or $10^9$, by decreasing nanoparticle diffusion away from the body part or nanoparticle degradation, between different sequences. This may also be achieved by decreasing the power, intensity, or frequency of the acoustic wave, for example by a factor of more than 1.5, 2, 5, 10, $10^3$, $10^6$ or $10^9$. This may also be achieved by increasing the absorption of the body part not comprising the nanoparticles, and preferentially by increasing the temperature increase resulting from this absorption.

In one embodiment of the invention, the treatment can comprise more than 1, 2, 5, 10 or $10^3$ session(s), which consists of: i) several or more than 1, 5, 10, or 100 sequences, ii) a series of heating or dissociation steps followed by cooling or non-dissociating steps.

In some cases, a session can last more than 1, 5, 10, 20, 50, $10^2$, $10^3$ or $10^5$ minute(s).

In some other cases, a session can last less than $10^{50}$, $10^{20}$, $10^{10}$, $10^5$, $10^3$, 10, 5, 2 or 1 minute(s).

In still some other cases, each session can be separated by a lapse of time of more than 1, 5, 10, $10^2$, $10^3$, $10^5$, $10^{10}$ or $10^{50}$ minute(s).

In still some other cases, each session can be separated by a lapse of time of less than $10^{50}$, $10^{10}$, $10^5$, $10^3$, $10^3$, $10^2$, 10, 5 or 1 minute(s).

The lapse of time separating two sessions is preferentially longer than the times $t_1$, $t_2$, $t_3$, $t_1+t_2$, or $t_1+t_3$, preferentially by a factor of more or less than 1.001, 1.01, 1.1, 1.2, 1.5, 2, 5, 10, 20, 50, 100, $10^3$, $10^5$ or $10^9$.

The invention also relates to the acoustic wave medical treatment or radiation medical treatment, wherein the acoustic wave or radiation is applied, preferentially sequentially, preferentially sequentially in space, on the nanoparticle or body part, wherein:
i) the acoustic wave or radiation is applied on the volume $V_1$,
ii) the nanoparticles or body part are comprised in a volume $V_2$, and $V_2$ is smaller than $V_1$. In some cases, the volume $V_2$ can be smaller than $V_1$ by a factor $\alpha$ that is larger than 1.0001, 1.1, 1.2, 2, 5, 10, $10^3$, $10^5$ or $10^{20}$ or by a factor or volume that is larger than $10^{-5}$, $10^{-1}$, 1, 5, 10, $10^3$ or $10^5$ nm$^3$ or cm$^3$. In some other cases, the volume $V_2$ can be smaller than $V_1$ by a factor $\alpha$ that is smaller than $10^{20}$, $10^5$, 10, 5 or 2 or by a factor or volume that is smaller than $10^{100}$, $10^{50}$, $10^{10}$, $10^5$, $10^3$, 10, 1 or $10^{-5}$ nm$^3$ or cm$^3$. In still some other cases, the volume $V_2$ can be smaller than $V_1$ by a factor $\alpha$ that is between 1.0001 and $10^{20}$, 1.2 and $10^{10}$, or between 2 and $10^5$ or by a factor or volume that is between $10^{-5}$ and $10^{100}$, $10^{-1}$ and $10^{10}$, or 1 and $10^5$ nm$^3$ or cm$^3$.

In one embodiment of the invention, the acoustic wave or radiation is applied sequentially, preferentially on the nanoparticles or body part, when or where:
First, the acoustic wave or radiation is applied within a region, volume, surface, or length, which is larger than the region, volume, surface, or length comprising the nanoparticles, and
Second, the region, volume, surface or length comprising the nanoparticles absorbs the acoustic waves or radiation, produces a temperature increase, or yields anti-tumor activity or the destruction of the body part, pathological or tumor cells in the region, volume, surface or length not comprising the nanoparticles.

In still another embodiment of the invention, the heating, cooling, dissociating, or non-dissociating step preferentially occurs in less than $10^{20}$, $10^{10}$, $10^5$, $10^3$, 90, 70, 50, 20, 10 or 1% of the acoustic wave or radiation volume, preferentially when the nanoparticle region is comprised in less than $10^{20}$, $10^{10}$, $10^5$, $10^3$, 90, 70, 50, 20, 10 or 1% of the acoustic wave or radiation volume. These percentages can be: i) the volume in which the heating, cooling, dissociating, or non-dissociating step occurs and the acoustic volume, or ii) the ratio between the volume in which nanoparticles are comprised and the acoustic or radiation volume.

The invention also relates to the acoustic wave medical treatment or radiation medical treatment, wherein the acoustic wave or radiation is applied, preferentially sequentially, preferentially sequentially in space, on the nanoparticle or body part, wherein:
i) the acoustic wave or radiation is applied on the volume $V_1$,
ii) the nanoparticles or body part are comprised in a volume $V_2$, and $V_2$ is larger than $V_1$. In some cases, the volume $V_2$ can be larger than $V_1$ by a factor $\alpha$ that is larger than 1.0001, 1.1, 1.2, 2, 5, 10, $10^3$, $10^5$ or $10^{20}$ or by a factor or volume that is larger than $10^{-5}$, $10^{-1}$, 1, 5, 10, $10^3$ or $10^5$ nm$^3$ or cm$^3$. In some other cases, the volume $V_2$ can be larger than $V_1$ by a factor $\alpha$ that is smaller than $10^{20}$, $10^5$, 10, 5 or 2 or by a factor or volume that is smaller than $10^{100}$, $10^{50}$, $10^{10}$, $10^5$, $10^3$, 10, 1 or $10^{-5}$ nm$^3$ or cm$^3$. In still some other cases, the volume $V_2$ can be larger than $V_1$ by a factor $\alpha$ that is between 1.0001 and $10^{20}$, 1.2 and $10^{10}$, or between 2 and $10^5$ or by a factor or volume that is between $10^{-5}$ and $10^{100}$, $10^{-1}$ and $10^{10}$, or 1 and $10^5$ nm$^3$ or cm$^3$.

In another embodiment of the invention, the acoustic wave or radiation is applied sequentially, preferentially on the nanoparticles or body part, when or where:
First, it is applied within a region, volume, surface, length, which is smaller than the region, volume, surface, or length comprising the nanoparticles, and
Second, the region, volume, surface or length comprising the nanoparticles that have not been exposed or submitted to the application of the acoustic wave, produces a temperature increase, or yields anti-tumor activity or the destruction of body part, pathological or tumor cells, preferentially through a mechanism in which the effect induced by the application of acoustic waves on the nanoparticles such as cavitation, nanoparticle movement, temperature increase, is transmitted from the nanoparticles exposed to the acoustic wave to the nanoparticles not exposed to the acoustic wave.

In another embodiment of the invention, the heating, cooling, dissociating, or non-dissociating step preferentially occurs in more than $10^{-10}$, $10^{-5}$, $10^{-1}$, 1, 10, 20, 50, 70, 90, $10^3$, $10^5$, $10^{10}$ or $10^{20}$% of the acoustic wave or radiation volume, preferentially when the nanoparticle region is comprised in more than $10^{-10}$, $10^{-5}$, $10^{-1}$, 1, 10, 20, 50, 70, 90, $10^3$, $10^5$, $10^{10}$ or $10^{20}$% of the acoustic wave volume.

The invention also relates to the acoustic wave medical treatment or radiation medical treatment, wherein the acoustic wave or radiation is applied, preferentially sequentially, preferentially sequentially in space, on the nanoparticle or body part, wherein:
  i) the acoustic wave or radiation is applied on the volume $V_1$,
  ii) the nanoparticles or body part are comprised in a volume $V_2$, and $V_2$ is similar or equal to $V_1$. In some cases, the volume $V_2$ can be similar or equal to $V_1$ when it does not differ from $V_1$ by a factor $\alpha$ that is larger than 1.0001, 1.1, 1.2, 2, 5, 10, $10^3$, $10^5$ or $10^{20}$ or by a factor or volume that is larger than $10^{-5}$, $10^{-1}$, 1, 5, 10, $10^3$ or $10^5$ $nm^3$ or $cm^3$.

In one embodiment of the invention, the heating, cooling, dissociation, or non-dissociation step occurs in the nanoparticle region, or in more than $10^{-9}$, $10^{-5}$, $10^{-3}$, $10^{-1}$, 1, 10, 20, 50, 70, $10^9$, 90 or 99% of the nanoparticle region, and preferentially does not occur outside of this region.

This percentage can be the ratio between the volume in which the heating, cooling, dissociation, or non-dissociation step occurs and the volume of the nanoparticle region.

In one embodiment of the invention, when the acoustic wave or radiation is applied on the nanoparticles or body part, it yields the production or generation by the nanoparticles of heat, radical or reactive species, bubble, cavitation, or cavitation bubble, preferentially in the volume $V_2$ and preferentially not in the volume $V_1$ or preferentially more in the volume $V_2$ than in the volume $V_1$, preferentially by a factor $\alpha$ that is: i) in some cases larger than 1.0000001, 1.1, 1.2, 1.5, 2, 5, 10, $10^3$ or $10^5$, ii) in some other cases smaller than $10^{100}$, $10^{50}$, $10^{20}$, $10^{10}$, $10^5$, $10^2$, 10, 5, 2, 1.2 or 1.000001, iii) in still some other cases between 1.000001 and $10^{100}$, or between 1.1 and $10^5$.

In some cases, the volume(s) $V_2$ and/or $V_1$ can be or be assimilated to or be replaced by: i) surface(s) $S_2$ and/or $S_1$, respectively, or ii) length(s) $L_2$ and/or $L_1$, respectively.

In one embodiment of the invention, the acoustic wave intensity, acoustic wave power, acoustic wave power density, acoustic wave energy, acoustic wave energy density, radiation energy, radiation energy density, radiation intensity, radiation power, or radiation power density, preferentially applied during $t_1$ or $t_3$, is lower than $10^{100}$, $10^{50}$, $10^{20}$, $10^9$, $10^6$, $10^3$, 100, 10, 1, $10^{-1}$, $10^{-2}$ or $10^{-5}$ W or W/cm or W/cm$^2$ or W/cm$^3$ or W·sec or W·sec/cm, or W·sec/cm$^2$ or W·sec/cm$^3$.

In one embodiment of the invention, the acoustic wave intensity, acoustic wave power, acoustic wave power density, acoustic wave energy, acoustic wave energy density, radiation energy, radiation energy density, radiation intensity, radiation power, or radiation power density, preferentially applied during $t_1$ or $t_3$, is larger than $10^{-100}$, $10^{-50}$, $10^{-20}$, $10^{-9}$, $10^{-6}$, $10^{-2}$, 1, 10, 1 $10^2$ or $10^5$ W or W/cm or W/cm$^2$ or W/cm$^3$ or W·sec or W·sec/cm, or W·sec/cm$^2$ or W·sec/cm$^3$.

In one embodiment of the invention, the frequency of the acoustic wave or radiation, preferentially applied during $t_1$ or $t_3$, is lower than $10^{100}$, $10^{50}$, $10^{20}$, $10^{10}$, $10^5$, $10^3$, 10, 1, $10^{-3}$, $10^{-6}$, $10^{-9}$ or $10^{-20}$ GHz.

In another embodiment of the invention, the frequency of the acoustic wave or radiation, preferentially applied during $t_1$ or $t_3$, is larger than $10^{-100}$, $10^{-50}$, $10^{-20}$, $10^{-10}$, $10^{-5}$, $10^{-3}$, $10^{-1}$, 1, $10^3$, $10^6$, $10^9$ or $10^{20}$ GHz.

In some cases, the acoustic wave or radiation is applied on less than $10^{-6}$, $10^{-3}$, $10^{-1}$, 1, 10, $10^3$, $10^6$, $10^9$ or $10^{20}$ nanoparticle(s) or mg of nanoparticle(s) on a basis per cell or per mm$^3$ of body part.

In some other cases, the acoustic wave or radiation is applied on more than $10^{-6}$, $10^{-3}$, $10^{-1}$, 1, 10, $10^3$, $10^6$, $10^9$, or $10^{20}$ nanoparticle(s) or mg of nanoparticle(s) on a basis per cell or per mm$^3$ of body part.

In another embodiment of the invention, when the acoustic wave or radiation is applied on the nanoparticles or body part, it yields: i) the temperature increase of the nanoparticles or body part, ii) the dissociation of the compound from the nanoparticles, iii) the destruction or growth inhibition of cells, preferentially pathological or tumor cells preferentially belonging to the body part, iv) the death, destruction, denaturation, reduction in volume or inactivation of biological material(s) preferentially belonging to the pathological site or body part, v) a movement or vibration of the nanoparticles, vi) a pressure applied on the body part or nanoparticle, vii) the absorption of the acoustic wave or radiation by the nanoparticles, or viii) the internalization of the nanoparticles in cells.

In one embodiment of the invention, the destruction or growth inhibition of cells, preferentially of more than 1, 10, $10^3$, $10^6$, $10^9$ or $10^{20}$ cell(s) preferentially per mm$^3$ or cm$^3$ of body part, is enabled by adjusting or tuning the frequency, intensity, energy, or power of the acoustic wave or radiation.

In one embodiment of the invention, the acoustic wave or radiation induces a movement or vibration of the nanoparticles when the mass of the nanoparticles is: i) in some cases larger than $10^{-50}$, $10^{-5}$, $10^{-1}$ or 1 µg per nanoparticle or, ii) in some other cases lower than $10^{20}$, $10^{10}$, $10^5$, $10^3$, $10^2$, 1, $10^{-3}$, or $10^{-5}$ g per nanoparticle. In this case, the acoustic wave can induce either a larger or lower movement or vibration for the nanoparticles than for the other substances, atoms, ions, which are not arranged or assembled in nanoparticles, and preferentially surround the nanoparticles.

In one embodiment of the invention, the acoustic wave or radiation applies a pressure on nanoparticles or on the body part, which is: i) in some cases larger than $10^{-9}$, $10^{-5}$, $10^{-3}$, $10^{-1}$, 1, 10, $10^3$, $10^6$ or $10^9$ MPa, preferentially per cm$^3$ of body part, or ii) in some other cases lower than $10^{-9}$, $10^{-5}$, $10^{-3}$, $10^{-1}$, 1, 10, $10^3$, $10^6$ or $10^9$ MPa, preferentially per cm$^3$ of body part.

In one embodiment of the invention, the acoustic wave energy is preferentially absorbed more importantly, preferentially by a factor of at least 1.1, 2, 5, 10, 25, 50 or 100, by the nanoparticles than by the other substances, atoms, ions, which are not arranged or assembled in nanoparticles or do not consist in nanoparticles, and preferentially surround the nanoparticles or preferentially belong to the body part. In some cases, it can result in a temperature increase that is at least $10^{-9}$, $10^{-6}$, $10^{-3}$, 1, 2, 5, 10 or 20° C. larger for the nanoparticles or in the nanoparticle region than for the other substances or regions outside the nanoparticle region.

In one embodiment of the invention, internalization of nanoparticles in cells, preferentially cellular internalization of more than $10^{-6}$, $10^{-3}$, $10^{-1}$, 1, 10, $10^3$, $10^6$, $10^9$, or $10^{20}$ nanoparticle(s) or mg of nanoparticles on a basis of per cell or per mm$^3$ of body part, is enabled by adjusting or tuning the value of the frequency, intensity, energy, time of application, or power of the acoustic wave or radiation.

In one embodiment of the invention, internalization of nanoparticles in cells, preferentially of cellular internalization of more than $10^{-6}$, $10^{-3}$, $10^{-1}$, 1, 10, $10^3$, $10^6$, $10^9$ or $10^{20}$ nanoparticle(s) or mg of nanoparticles on a basis of per cell or per mm$^3$ of body part, is prevented by adjusting or tuning the frequency, intensity, energy, time of application, or power of the acoustic wave or radiation, to a different value as that of the previous embodiment.

In another embodiment of the invention, when the acoustic wave or radiation is applied on the nanoparticles or body part, it does not yield the destruction or growth inhibition of cell(s), preferentially healthy cells.

In one embodiment of the invention, the destruction or growth inhibition of cell(s), preferentially healthy cells, preferentially more than 1, 10, $10^3$, $10^6$, $10^9$ or $10^{20}$ of this/these cell(s), is prevented by adjusting or tuning the frequency, intensity, energy, time of application, or power of the acoustic wave or radiation.

In one embodiment of the invention, the acoustic wave medical treatment or its efficacy or the destruction or treatment or volume decrease of tumor, body part, or pathological site, is due to or is associated with a mechanism of treatment, preferentially a therapeutic mechanism of treatment. In some cases, this mechanism preferentially occurs under the application of an acoustic wave or radiation on the nanoparticle or body part and preferentially does not occur when the acoustic wave or radiation is not applied on the nanoparticle or body part.

In one embodiment of the invention, the mechanism of treatment, preferentially the beginning or initiation of this mechanism, involves or is due to or is associated with: i) a temperature increase, preferentially of the body part or nanoparticle, ii) the generation or production of radical or reactive species, preferentially by the nanoparticles such as radical oxygen species (ROS), iii) the dissociation of the compound from the nanoparticles, iv) a pharmaceutical effect preferentially due to the compound, v) a metabolic effect, or vi) cavitation.

In one embodiment of the invention, cavitation is associated with the production of bubbles. In some cases, cavitation can induce a mechanical stress on cells, preferentially cell membranes, and induce cell death. In the presence of the nanoparticles, the size and number of the bubbles can be changed. They can be increased or decreased by a factor larger or smaller than 1.5, 2, 10, 100, $10^3$ or $10^9$. In some cases, the size and number of the bubbles can tend to be close to that of the nanoparticles exposed to the acoustic wave or radiation and/or differ from the size and number of these nanoparticles by a factor of less than $10^9$, $10^5$, $10^3$, $10^2$ or 10.

In another embodiment of the invention, the mechanism of treatment, preferentially following or resulting from the beginning or initiation of this mechanism, involves, or is due to or is associated with: i) the immune system or activation of such system preferentially against the body part, ii) an apoptotic mechanism preferentially of pathological cells, iii) an indirect mechanism or by stander effect. In some cases, it occurs more than 1, 5, 10, $10^3$, $10^5$ or $10^{10}$ second(s) after the beginning or initiation of this mechanism.

In some cases, the indirect mechanism or by stander effect can involve, be due to, or be associated with the destruction of pathological cells at a distance from the nanoparticle or nanoparticle region, which is: i) in some cases lower than 5, 2, 1, $10^{-1}$, $10^{-3}$, $10^{-3}$, $10^{-6}$ or $10^{-9}$ m, ii) in some other cases larger than $10^{-1}$, 1, 5, 10, $10^3$ or $10^5$ nm, or iii) in still some other cases between $10^{-1}$ and $10^{20}$ nm, or between or 1 and $10^{10}$ nm, or between 1 and $10^5$ nm.

In some cases, the mechanism of treatment can involve, be due to, or be associated with the direct effect of the nanoparticle, preferentially excluding immune effects or by-stander effects, or some effects that can induce the destruction of pathological or tumor cells, or the decrease in body part volume, at some distance from the nanoparticles, at a distance preferentially larger than 1, 10, $10^3$, $10^5$, $10^{10}$, $10^{20}$, $10^{50}$ or $10^{100}$ nm from the nanoparticle.

In one embodiment of the invention, preferentially during at least one session or sequence, the mechanism of treatment is: i) activated by applying for the first the time the acoustic wave or radiation, ii) re-activated by re-applying the acoustic wave or radiation, or iii) deactivated by stopping the application of the acoustic wave or radiation following an activation or re-activation.

In one embodiment of the invention, the radiation, acoustic wave, and nanoparticle parameters are: i) the power, intensity, strength, frequency, energy, of the acoustic wave or radiation, ii) the volume or body part exposed to the acoustic wave or radiation, iii) the time of application of the acoustic wave or radiation, iv) the time $t_1$, $t_2$, or $t_3$, v) the duration of a sequence or session, vi) the time separating two sequences or sessions, and/or vii) a nanoparticle property such as the concentration, organization, distribution, size, composition of the nanoparticle.

In some other cases, the radiation, acoustic wave, and nanoparticle parameters are such, are adjusted, are fixed, are optimized, are sufficiently long or large, are sufficiently small or low, or are set at specific values chosen to reach at least one of the following treatment parameters, preferentially desired treatment parameters: i) a mechanism of treatment, ii) a desired or certain level of cavitation, iii) a desired or certain level or concentration of radical or reactive species such as radical oxygen species (ROS), iv) a desired or certain level of apoptosis or apoptotic cells, v) a desired or certain temperature during the heating step, vi) a desired or certain percentage of dissociated compounds during the dissociation step, vii) a desired or certain temperature during the cooling step, viii) a desired or certain percentage of dissociated compounds during the non-dissociation step.

In one embodiment of the invention, the desired treatment parameter is the treatment parameter that one wants to reach during the treatment. In some cases, it differs from the treatment parameter reached by applying the acoustic wave or radiation on the nanoparticle or body part by less than $10^{-20}$, $10^{-10}$, $10^{-5}$, $10^{-3}$, $10^{-1}$, 1, 5, 10, 50, 100, $10^4$, $10^5$ or $10^{10}$%. In some other cases, it differs from the treatment parameter reached by applying the acoustic wave or radiation on the nanoparticle or body part differs by more than $10^{-20}$, $10^{-10}$, $10^{-5}$, $10^{-3}$, $10^{-1}$, 1, 5, 10, 50, 100, $10^4$, $10^5$ or $10^{10}$%. In still some other cases, this percentage can be the ratio between the desired treatment parameter and the treatment parameter reached by applying the acoustic wave or radiation on the nanoparticle or body part.

In some cases, the at least one treatment parameter can be higher or larger during the time $t_1$ than during $t_2$ or $t_3$ by a factor, which is preferentially at least equal to 1, 1.2, 1.5, 2, 5, 10, $10^2$, $10^3$, $10^5$, $10^9$ or $10^{20}$.

In some cases, cavitation can be or be associated with bubbles or cavitation bubbles.

In some other cases, radical or reactive species or bubbles can be associated with or be the compound.

In some other cases, radical or reactive species or bubbles are not the compound.

In some cases, a desired temperature during the heating step can be larger than or equal to 0, 5, 10, 25, 30, 37, 39, 41, 45, 50, 100, $10^3$ or $10^{5}$° C.

In some other cases, a desired temperature during the heating step can be lower than $10^5$, $10^3$, 100, 50, 45, 41, 39, 37, 30, 25, 30 or 37° C.

In still some other cases, a desired temperature during the heating step can be between −273 and $10^{10}$, 0 and $10^3$, or 10 and 100° C.

In one embodiment of the invention, a suitable range of values for the desired temperature is between 41° C. and 100° C., where 41° C. is preferentially the minimum value that can trigger a therapeutic effect such as an antitumor activity and 100° C. is the boiling temperature of water, which preferentially constitutes the majority of the body part. In some cases, the minimum value of this range (41° C.) can be decreased, for example by more than 1, 5, 10, 50, 100, 150, 200, or 250° C., for example when the body part is cooled down. In some other cases, the maximum value of this range (100° C.) can be increased, for example by more than 1, 5, 10, 50, 100, $10^3$, or $10^{5°}$ C., for example when the body part does not mainly comprise water or when the body part is heated, or when the intensity, frequency of the acoustic wave is increased, or when the magnetosome or nanoparticle concentration is increased.

In some cases, a desired percentage of dissociated compounds during the dissociation step can be larger than 0.1, 1, 5, 10, 25, 50, 75 or 90%.

In some other cases, a desired percentage of dissociated compounds during the dissociation step can be lower than 100, 90, 75, 50, 25, 10, 5, 1 or 0.1%.

In still some other cases, a desired percentage of dissociated compounds during the dissociation step can be between 0 and 100%, 0.1 and 99%, or between 5 and 75%.

In some cases, the desired temperature during the cooling step is more than $10^{-5}$, 1, 5, $10^3$ or $10^{5°}$ C. below the temperature of the heating step.

In some other cases, the desired temperature during the cooling step is less than 10, $10^3$, 5, 1 or $10^{-5°}$ C. below the temperature of the heating step.

In some cases, the desired percentage of dissociation of the compounds is more than 0.001, 0.01, 0.1, 1, 2, 5, 10, 25, 50, 75, 80, 90 or 99% lower during the non-dissociation step than during the dissociation step.

In still some other cases, the desired percentage of dissociation of the compounds is less than 100, 90, 80, 75, 50, 25, 10, 5, 2, 1, 0.1, 0.01 or 0.001% lower during the non-dissociation step than during the dissociation step.

In one embodiment of the invention, to reach the desired temperature during the heating step or the desired level of dissociated compounds during the dissociation step, it is possible to increase, preferentially by a factor β, preferentially between time $t_2$ or $t_3$ and time $t_1$: i) the power, intensity, strength, frequency, energy, of the acoustic wave or radiation, ii) the volume or body part exposed to the acoustic wave or radiation, iii) the time of application of the acoustic wave or radiation, and/or iv) the nanoparticle concentration.

In one embodiment of the invention, to reach the desired temperature during the cooling step or the desired level of dissociated compounds during the non-dissociation step, it is possible to decrease, preferentially by a factor β, preferentially between time $t_1$ and time $t_2$ or $t_3$: i) the power, intensity, strength, frequency, energy, of the acoustic wave or radiation, ii) the volume or body part exposed to the acoustic wave or radiation, and/or iii) the time of application of the acoustic wave or radiation.

In some cases, β can be larger than 1.00001, 1.0001, 1.001, 1.01, 1.1, 1.2, 1.5, 2, 5, 10, $10^3$, $10^5$, $10^{10}$, $10^{20}$ or $10^{40}$, In some other cases, β can be lower than $10^{50}$, $10^{20}$, $10^{10}$, $10^5$, $10^3$, 10, 5, 2, 1.5, 1.2, 1.1, 1.01, 1.001, 1.000 or 1.00001, In still some other cases, β can be between 1.00001 and $10^{50}$, 1.1 and $10^5$, or 1.2 and $10^3$.

The invention also relates to nanoparticles for use in an acoustic wave medical treatment or radiation medical treatment or treatment of a body part of an individual, wherein the treatment involves or comprises at least one of the following steps:

The preparation of the suspension or composition of nanoparticles, preferentially of sufficiently large stability and concentration to enable the treatment of the body part (step 1), The administration of the nanoparticles to the body part or to the individual (step 2), The targeting of the nanoparticles towards the body part (step 3), The detection or imaging of the nanoparticles (step 4), The detection or imaging of the body part, preferentially comprising the nanoparticles (step 5), The application of the acoustic waves or radiation on the nanoparticles (Step 6), The removal of the body part, preferentially by surgery (Step 7), The treatment of the body part, using another treatment modality than the acoustic wave or radiation medical treatment, using for example surgery or chemotherapy (Step 8).

In one embodiment of the invention, the temperature, preferentially of the body part or nanoparticles, is measured during step 1 to 8, preferentially during, before, or after step 6.

In one embodiment of the invention, several of the steps 1 to 8 follow each other in the indicated order or in any other order.

In one embodiment of the invention, the method of treatment, preferentially step 4 or 5, comprises imaging of the body part, preferentially to follow the evolution or growth of the body part following the treatment, preferentially using an imaging technique such as magnetic resonance imaging (MRI), computing tomography (CT), scanner, positron emission tomography (PET), radiography, or echography. The nanoparticle concentration can in some cases be too large to enable efficient imaging of the body part. The nanoparticle can in some cases act like a screen or hide the body part and prevents efficient imaging of the body part. In some cases, the nanoparticle composition is adjusted or changed to enable imaging of the body part. To enable imaging of the body part or the treatment, the following actions can in some cases be undertaken: i) the iron oxide composition is replaced by a composition comprising another substance selected among lithium, beryllium, scandium, titanium, vanadium, chromium, manganese, iron, nickel, copper, zinc, boron, carbon, nitrogen, oxygen, fluorine, or helium family, or alkali metals, or alkaline earth metals, or coinage metals, or triels, or tetrela, or pentels, or pnictogens, or chalcogens, or halogens, or noble gases, or ii) the nanoparticle concentration is decreased, preferentially below $10^{-20}$, $10^{-9}$, $10^{-6}$, $10^{-3}$, $10^{-1}$, 1, 10, $10^3$, $10^6$, $10^9$ or $10^{20}$ mg per $cm^3$ or mg per $cm^3$ of body part.

Preferably, the radiation or acoustic waves according to the invention generate radical or reactive species, in particular when they are applied on the nanoparticles or magnetosomes.

The invention also relates to nanoparticles for use, wherein the sequential application of the acoustic wave or radiation on the body part or nanoparticles prevents a decrease of the temperature of the body part or nanoparticles.

In an embodiment of the invention, when the acoustic wave or radiation is applied on the body part or nanoparticles, it prevents a temperature decrease, preferentially under conditions in terms of nanoparticle concentration, frequency, power, and/or energy of the applied acoustic wave or radiation, in which the sequential application of the acoustic wave or radiation prevents a temperature decrease whereas a continuous application of the acoustic wave or radiation does not prevent such temperature decrease.

In some cases, the magnitude of the temperature decrease that is prevented can be larger than 0, $10^{-50}$, $10^{-20}$, $10^{-10}$, $10^{-5}$, $10^{-1}$, 1, 5, 10 or $10^{2}$° C., preferentially as measured per minute, per $cm^3$ of body part, or per gram of nanoparticle.

In some other cases, the magnitude of the temperature decrease that is prevented can be lower than $10^{50}$, $10^{20}$, $10^{10}$, $10^{5}$, $10^{2}$, 10, 5, 2, 1, $10^{-1}$ or $10^{-2}$° C., preferentially as measured per minute, per $cm^3$ of body part, or per gram of nanoparticle.

In still some other cases, the magnitude of the temperature decrease that is prevented can be between $10^{-50}$ and $10^{50}$, $10^{-20}$ and $10^{20}$, $10^{-10}$ and $10^{10}$, or between $10^{-3}$ and $10^{3}$° C., preferentially as measured per minute, per $cm^3$ of body part, or per gram of nanoparticle.

A suitable range for the temperature decrease that is a prevented can be ~2° C. for a magnetosome concentration of 500 µg/mL, sequentially exposed to an acoustic wave a power 100 W/$cm^2$ during 12 minutes. Larger prevented temperature decreases may be reached by increasing: i) magnetosome concentrations above 500 µg/mL, ii) frequency of the acoustic wave above 1 MHz, and/or iii) acoustic wave power above 100 mW/$cm^2$.

The invention also relates to nanoparticles for use according to the invention, wherein the application of the acoustic wave or radiation on the nanoparticles produces or generates radical or reactive species.

The invention also relates to a method for the generation of reactive or radical species by the nanoparticle or to the acoustic wave medical treatment, wherein:
  i) radiation or acoustic waves are sequentially applied on nanoparticles,
  ii) nanoparticles are degraded, and/or
  iii) nanoparticles are magnetosomes.

In some cases, the nanoparticles are degraded when they are dissolved, decomposed, and/or de-crystallized, preferentially by cells, body part, an organelle, or lysosome.

The invention also relates to the acoustic wave medical treatment or to the radiation medical treatment according to the invention for the generation of reactive or radical species by the nanoparticles.

In some cases, the acoustic wave medical treatment or radiation medical treatment can be or can comprise the method for the generation of reactive or radical species by the nanoparticles.

In one embodiment of the invention, reactive or radical species are superoxide, oxygen radical, hydroxyl, alkoxy-radical, peroxyl radical, nitric oxide, nitrogen monoxide, and nitrogen dioxide.

In one embodiment of the invention, reactive or radical species are associated with, derived from, originate from, or are produced by $H_2O_2$. In some cases, reactive or radical species can be derivatives of $H_2O_2$, result from a transformation of $H_2O_2$, or result from a chemical reaction involving $H_2O_2$.

In one embodiment of the invention, the radical or reactive species are free when they are detached or dissociated from the nanoparticles. In some cases, the radical or reactive species are the compound, preferentially dissociated from the nanoparticles under the application of the radiation or acoustic wave on the nanoparticle or body part.

In one embodiment of the invention, the production or generation of radical or reactive species, preferentially by the nanoparticles, is associated to or leads to or produces: i) the efficacy of the acoustic wave medical treatment, ii) the destruction of the body part, and/or iii) the reduction of the volume of the body part.

In one embodiment of the invention, the production or generation of reactive or radical species, preferentially by the nanoparticles, preferentially when the radiation or acoustic wave is applied on the nanoparticles, is due to or associated with: i) the degradation of the nanoparticles, preferentially by biological material, the cell, a cell organelle, ii) the decrease in size of the nanoparticle, preferentially by more than $10^{-5}$, $10^{-3}$, 1, 5, 10, 50 or 75%, where this percentage can be the ratio between the size of the nanoparticle following the acoustic wave medical treatment and the size of the nanoparticle before the acoustic wave medical treatment, preferentially from a size larger than 1, 5, 10, 50, 75 or 100 nm before the acoustic wave medical treatment down to a size lower than $10^5$, $10^3$, $10^2$, 50, 20, 10, 5, 2 or 1 nm following the acoustic wave medical treatment, or iii) the production by or release from or dissociation from the nanoparticles of the compound or free ions such as free oxygen, nitrogen, or iron ions.

The invention also relates to the method for the generation of reactive or radical species or to the acoustic wave medical treatment, or to the radiation medical treatment, for: i) the treatment of a disease comprising radio-resistant or acoustic-resistant cells, ii) the destruction or death of at least one radiation-resistant or acoustic-resistant cell, preferentially comprised in the body part, or iii) the decrease in the volume of the body part.

In some cases, the radio-resistant cells can be the cells that are not destroyed when radiation are applied on them in the absence of the nanoparticles and that are destroyed when radiation are applied on them in the presence of the nanoparticles, where the same or similar radiation, radiation power, radiation intensity, and/or radiation frequency, is/are preferentially applied on the nanoparticles or body part, preferentially to enable comparison between cell destruction or death in the presence and absence of nanoparticles.

In some cases, the acoustic-resistant cells can be the cells that are not destroyed when acoustic waves are applied on them in the absence of the nanoparticles and that are destroyed when acoustic waves are applied on them in the presence of the nanoparticles, where the same or similar acoustic waves, acoustic wave power, acoustic wave intensity, and/or acoustic wave frequency, is/are preferentially applied on the nanoparticles or body part, preferentially to enable comparison between cell destruction in the presence and absence of nanoparticles.

The invention also relates to the method for the generation of radical or reactive species or to the acoustic wave medical treatment, wherein the radical or reactive species:
  i) destroy pathological cells, tumor cells, bacteria, virus, or a pathological site, and/or
  ii) don't destroy healthy cells, non-pathological cells, non-tumor cells, a healthy site, or cells belonging to a healthy individual.

The invention also relates to nanoparticles for use according to the invention, wherein the nanoparticles induce the destruction of a pathological site of the body part without the destruction of a healthy site preferentially surrounding the pathological site.

In some cases, the nanoparticle can induce the destruction of more than 1, 10, $10^3$, $10^6$, $10^9$ or $10^{15}$ pathological cell(s) and/or less than 1, 10, $10^3$, $10^6$, $10^9$ or $10^{15}$ healthy cell(s).

In some cases, radical or reactive species can produce oxidative stress, preferentially producing the destruction or death of cells, preferentially of pathological cells, preferentially of tumor cells, bacteria, or virus.

The invention also relates to the method for the generation of radical or reactive species or to the acoustic wave medical treatment, wherein the quantity or concentration of radical or reactive species produced or generated, preferentially by nanoparticles, is more important, preferentially by a factor $\alpha$, when radiation or acoustic waves are applied sequentially on the nanoparticles or body part than when radiation or acoustic waves are applied continuously on the nanoparticles or body part. In some cases, the factor $\alpha$ can be larger than or equal to: i) 1.0001, 1.1, 1.2, 1.5, 2, 5, 10 or $10^3$ or, ii) 1, 2, 5, 10, $10^3$, $10^5$, $10^{10}$ or $10^{50}$ radical or reactive specie(s) or radical or reactive specie(s) per cm$^3$ of body part or radical or reactive species per gram of nanoparticle, or iii) $10^{-100}$, $10^{-50}$, $10^{-20}$, $10^{-10}$, $10^{-5}$, $10^{-3}$, $10^{-1}$, 1, 2, 5, 10, $10^3$, $10^5$, $10^{10}$ or $10^{50}$ µM of reactive or radical species. This can be the case when the application of the radiation or acoustic wave increases significantly the quantity of radical or reactive species produced or generated by the nanoparticles, for example by catalyzing or favoring or enabling the Fenton or Heber-Weiss reaction or the dissociation of ions originating from the nanoparticles such as iron or oxygen ions. In some other cases, the factor $\alpha$ can be lower than or equal to: i) $10^{100}$, $10^{10}$, $10^5$, $10^3$, 10, 5, 3 or 2, or ii) $10^{100}$, $10^{50}$, $10^{20}$, $10^{10}$, $10^5$, $10^2$, 10 or 5 radical or reactive specie(s) or radical or reactive specie(s) per cm$^3$ of body part or radical or reactive species per gram of nanoparticle, or, iii) $10^{100}$, $10^{50}$, $10^{20}$, $10^{10}$, $10^5$, 10, $10^{-5}$ or $10^{-10}$ M of radical or reactive species. This can be the case when the application of the radiation or acoustic wave on the nanoparticles does not change or increases more moderately the quantity of radical or reactive species produced or generated by the nanoparticles.

In another embodiment of the invention, the quantity or concentration of radical or reactive species produced or generated, preferentially by nanoparticles, is less important, preferentially by a factor $\alpha$, when radiation or acoustic waves are applied sequentially on the nanoparticles or body part than when radiation or acoustic waves are applied continuously on the nanoparticles or body part. In some cases, the factor $\alpha$ can be larger than or equal to: i) 1.0001, 1.1, 1.2, 1.5, 2, 5, 10 or $10^3$ or, ii) 1, 2, 5, 10, $10^3$, $10^5$, $10^{10}$ or $10^{50}$ radical or reactive specie(s) or radical or reactive specie(s) per cm$^3$ of body part or radical or reactive species per gram of nanoparticle, or iii) $10^{-100}$, $10^{-50}$, $10^{-20}$, $10^{-10}$, $10^{-5}$, $10^{-3}$, $10^{-1}$, 1, 2, 5, 10, $10^3$, $10^5$, $10^{10}$ or $10^{50}$ µM of reactive or radical species. This can be the case when the application of the radiation or acoustic wave decreases significantly the quantity of radical or reactive species, for example by preventing ions or radical or reactive species originating from the nanoparticles such as iron or oxygen ions, to dissociate or leave the nanoparticles. In some other cases, the factor $\alpha$ can be lower than or equal to: i) $10^{100}$, $10^{10}$, $10^5$, $10^3$, 10, 5, 3 or 2, or ii) $10^{100}$, $10^{50}$, $10^{20}$, $10^{10}$, $10^5$, $10^2$, 10 or 5 radical or reactive specie(s) or radical or reactive specie(s) per cm$^3$ of body part or radical or reactive species per gram of nanoparticle, or, iii) $10^{100}$, $10^{50}$, $10^{20}$, $10^{10}$, $10^5$, 10, $10^{-5}$ or $10^{-10}$ M of radical or reactive species. This can be the case when the application of the radiation or acoustic wave on the nanoparticles does not change or decreases more moderately the quantity of radical or reactive species produced or generated by the nanoparticles.

The invention also relates to the method for the generation of radical or reactive species or to the acoustic wave medical treatment, wherein the nanoparticles have at least one of the following properties:
i) a surface/volume ratio larger than $10^{-50}$ nm$^{-1}$,
ii) a composition or chemical formula that comprises: i) atoms with at least two different stoichiometric coefficients or oxidation state or reduction state such as Fe$_2$ and Fe$_3$, ii) ions with a different number of charge or oxidation sate or reduction state such as Fe$^{2+}$ and Fe$^{3+}$, iii) atoms that lead to the formation of at least two different types of ions with a different number of charges, oxidation or reduction state, such as Fe$^{2+}$ and Fe$^{3+}$,
iii) a composition and/or size and/or surface/volume ratio enabling or leading to the Fenton or Haber-Weiss reaction,
iv) a dissolution or decomposition or de-crystallization, preferentially favoring a reaction of free ions originating from or dissociated from the nanoparticles,
v) a chain arrangement, and/or
vi) a concentration that is lower than 1 mg per cm$^3$ or 1 mg per cell or 1 mg per cm$^3$ of body part,
wherein at least one of these properties preferentially leads to a quantity or concentration of radical or reactive species produced in the presence of radiation or acoustic wave applied on the nanoparticles that is larger, preferentially by a factor of more than 1.0001, 1.1, 1.5, 2, 5, 10, $10^3$ or $10^5$, than that produced in the absence of radiation or acoustic wave.

In one embodiment of the invention, the surface/volume ratio of the nanoparticles is large, preferentially larger than $10^{-100}$, $10^{-50}$, $10^{-20}$, $10^{-10}$, $10^{-5}$, $10^{-3}$, $10^{-1}$, 1, 5, 10 or 100 nm$^{-1}$. A sufficiently large surface/volume ratio of the nanoparticles can enable to have a large number of atoms at the surface of the nanoparticles exposed to the radiation or acoustic wave, where these atoms can preferentially react to form free radical or reactive species. Preferentially, atoms located in or inside the nanoparticles generate with more difficulty free radical or reactive species than atoms located at the surface of the nanoparticles, In another embodiment of the invention, the surface/volume ratio of the nanoparticles is small, preferentially smaller than $10^{100}$, $10^{50}$, $10^{20}$, $10^{10}$, $10^5$, $10^3$, 10, 5, 2, 1, $10^{-5}$, $10^{-10}$, $10^{-20}$ or $10^{-50}$ nm$^{-1}$. A sufficiently small surface/volume ratio of the nanoparticles may be desired to enable the nanoparticles to keep in three dimensional volume or geometry and/or to prevent the nanoparticles from switching from a three to a two dimensional system and/or to enable the nanoparticle to absorb or interact with the radiation or acoustic wave, where the absorption or interaction with the radiation or acoustic wave is more pronounced with a three dimensional than with a two dimensional system.

In still another embodiment of the invention, the surface/volume ratio of the nanoparticles is comprised between $10^{-5}$ nm$^{-1}$ and $10^3$ nm$^{-1}$ or between $10^{-2}$ nm$^{-1}$ and 1 nm$^{-1}$.

In one embodiment of the invention, the composition of chemical formula of the nanoparticle comprises at least one atom A$_\alpha$ with at least two different values of its coefficient or stoichiometric coefficient $\alpha$, where $\alpha$ can be equal to 0, 1, 2, 3, 4, 5, 6 7, 8, 9, 10, 11, 12, 13, 14, 15, an integer, or a decimal number.

In one embodiment of the invention, the nanoparticle leads to the Fenton reaction. In some cases, the Fenton reaction can be written as: i) Fe$^{2+}$+H$_2$O$_2$→Fe$^{3+}$+·OH+OH$^-$, and/or, ii) Fe$^{3+}$+H$_2$O$_2$→Fe$^{2+}$+·OOH+H$^+$. In some cases, the Fenton reaction is such that: i) Iron(II) is oxidized by hydrogen peroxide to iron(III), forming a hydroxyl radical and a hydroxide ion in the process, and/or ii) Iron(III) is reduced back to iron(II) by another molecule of hydrogen peroxide, forming a hydroperoxyl radical and a proton. In some cases, the Fenton reaction is favored or increased or enabled when: i) the nanoparticle or nanoparticle chemical formula comprises $Fe_2$, $Fe^{2+}$, $Fe_3$, and/or $Fe^{3+}$ ions or atoms, ii) the nanoparticle comprises maghemite and magnetite, or iii) a radiation or acoustic wave is applied on the nanoparticle or body part.

In some other cases, the Fenton reaction yields radical or reactive species.

In one embodiment of the invention, the nanoparticle leads to or undergoes the Heber-Weiss reaction that can in some cases be written as: $Fe^{3+}+\cdot O_2^- \rightarrow Fe^{2+}+O_2$, $Fe^{2+}+H_2O_2 \rightarrow Fe^{3+}+OH^-+\cdot OH$, and/or $\cdot O_2^-+H_2O_2 \rightarrow \cdot OH+OH^-+O_2$.

In some cases, the Haber-Weiss or Fenton reaction generates $\cdot OH$ (hydroxyl radicals) and/or $\cdot OOH$ (hydroperoxyl radical) from $H_2O_2$ (hydrogen peroxide) and/or superoxide ($\cdot O_2^-$). In some cases, this reaction is catalyzed by the nanoparticles or iron comprised or originating from the nanoparticles.

In one embodiment of the invention, a dissolution of the nanoparticles is the partial or total loss of the mass of the nanoparticle, preferentially a decrease of the mass of the nanoparticle larger than $10^{-50}$, $10^{-10}$, $10^{-1}$, 1, 5, 10, 50, 75 or 90%, where this percentage can be the ratio between the mass of the nanoparticle after dissolution and the mass of the nanoparticle before dissolution.

In another embodiment of the invention, a decomposition of the nanoparticles is the partial or total change of the composition of the nanoparticle, preferentially the change of the composition of the nanoparticle in more than $10^{-50}$, $10^{-10}$, $10^{-1}$, 1, 5, 10, 50, 75 or 90% of the nanoparticle, where this percentage can be the ratio between the volume or number of atoms of the nanoparticle in which compositional change occurs and the total volume or total number of all atoms of the nanoparticle.

In one embodiment of the invention, a de-crystallization of the nanoparticle is the partial or total loss of crystallinity or crystal planes or ordered atomic arrangement of the nanoparticle or the transition from a crystalline to an amorphous structure of the nanoparticle, preferentially the loss of more than 1, 10, $10^3$ or $10^5$ crystallographic plane(s) in the nanoparticles. In some cases, the loss of at least one crystallographic plane can be observed by electron microscopy or equipment enabling to obtain similar information than electron microscopy.

The invention also relates to the method for the generation of radical or reactive species or to the acoustic wave medical treatment or to the radiation medical treatment, in which:
i) First: radiation or acoustic waves are applied on the nanoparticle during a time $t_1$, until a certain quantity of radical species is reached (step 1), second: the radiation or acoustic wave is not applied on the nanoparticle during a time $t_2$ to reduce the quantity of radical or reactive species produced compared with step 1 (step 2), third: Optionally repeating steps 1 and 2 more than two times, and/or
ii) The radiation or acoustic wave applied on the nanoparticles or body part produces or generates radical or reactive species locally around the nanoparticles, where this local production or generation of radical or reactive species can preferentially be realized by using: a), a low concentration of nanoparticles, preferentially less than $10^{50}$, $10^{20}$, $10^5$, $10^3$, 10, 5, 2, 1, $10^{-2}$ or $10^{-5}$ gram of nanoparticle per $cm^3$ of body part or, ii) by using nanoparticles that occupy a part of the body part or cell such as a lysosome where they can produce reactive or radical species.

The invention also relates to the method for the generation of radical or reactive species or to the acoustic wave medical treatment or to the radiation medical treatment, wherein the quantity of radical or reactive species, preferentially produced or generated by the nanoparticles, is larger than: i) 1, 2, 5, 10, $10^3$, $10^5$, $10^{10}$ or $10^{50}$ radical or reactive specie(s) per nanoparticle or radical or reactive specie(s) per gram of nanoparticles or radical or reactive specie(s) per $cm^3$ of body part or radical or reactive species per gram of nanoparticles per $cm^3$ of body part or radical or reactive specie(s) per atom preferentially comprised at the surface or in the nanoparticle, ii) $10^{-50}$, $10^{-20}$, $10^{-10}$, $10^{-5}$, 1, 5, 10, $10^3$, $10^5$ or $10^{10}$ nanomolar (nM) or micromolar (μM) of radical or reactive specie(s) or nM or μM of radical or reactive specie(s) per gram of nanoparticles or nM or μM of radical or reactive specie(s) per $cm^3$ of body part or nM or μM of radical or reactive specie(s) per gram of nanoparticles per $cm^3$ of body part, or iii) $10^{-50}$, $10^{-20}$, $10^{-10}$, $10^{-5}$, 1, 5, 10, $10^3$, $10^5$ or $10^{10}$ nM or μM of radical or reactive species per Watt or nM or μM of radical or reactive species per Watt per $cm^3$ of body part or nM or μM of radical or reactive species per Watt per gram of nanoparticles or nM or μM of radical or reactive species per Gy or nM or μM of radical or reactive species per Gy per $cm^3$ of body part or nM or μM of radical or reactive species per Gy per gram of nanoparticle. In some cases, the production of radical or reactive species can be large, preferentially when the nanoparticles can be dissolved into free ions or when the Fenton or Heber-Weiss reaction can take place or when the surface of the nanoparticle is sufficiently large and/or reactive to yield the production of these species.

In some cases, the reactive or radical species can be $H_2O_2$.

The invention also relates to the method for the generation of radical or reactive species or to the acoustic wave medical treatment or to the radiation medical treatment, wherein the quantity or concentration of radical or reactive species, preferentially produced or generated by the nanoparticles, is lower than: i) $10^{100}$, $10^{50}$, $10^{20}$, $10^{10}$, $10^5$, $10^3$, 10, 5, 2 or 1 radical or reactive specie(s) per nanoparticle or radical or reactive specie(s) per gram of nanoparticles or radical or reactive specie(s) per $cm^3$ of body part or radical or reactive species per gram of nanoparticles per $cm^3$ of body part or radical or reactive specie(s) per atom preferentially comprised at the surface or in the nanoparticle, ii) $10^{100}$, $10^{50}$, $10^{20}$, $10^{10}$, $10^5$, $10^2$, 10, 5, 2, 1, $10^{-1}$, $10^{-3}$ or $10^{-5}$ nM or μM of radical or reactive specie(s) or nM or μM of radical or reactive specie(s) per gram of nanoparticles or nM or μM of radical or reactive specie(s) per $cm^3$ of body part or nM or μM of radical or reactive specie(s) per gram of nanoparticles per $cm^3$ of body part, or iii) $10^{100}$, $10^{50}$, $10^{20}$, $10^{10}$, $10^5$, $10^3$, 10, 5, 2, 1 or $10^{-3}$ nM or μM of radical or reactive species per Watt or nM or μM of radical or reactive species per Watt per $cm^3$ of body part or nM or μM of radical or reactive species per Watt per gram of nanoparticles or nM or M of radical or reactive species per Gy or nM or μM of radical or reactive species per Gy per $cm^3$ of body part or nM or μM of radical or reactive species per Gy per gram of nanoparticle.

In some cases, the production of radical or reactive species can be low, preferentially when the nanoparticles can't be dissolved into free ions or when the Fenton or Heber-Weiss reaction can't take place or when the surface of the nanoparticle isn't sufficiently large and/or reactive to yield the production of these species.

In one embodiment of the invention, the quantity or concentration of radical or reactive species, preferentially produced or generated by the nanoparticles, is comprised between: i) 1 and $10^{100}$, 10 and $10^{50}$, or between $10^3$ and $10^{20}$ radical or reactive specie(s) per nanoparticle or radical or reactive specie(s) per gram of nanoparticles or radical or reactive specie(s) per $cm^3$ of body part or radical or reactive species per gram of nanoparticles per $cm^3$ of body part or radical or reactive specie(s) per atom preferentially comprised at the surface or in the nanoparticle, ii) $10^{-100}$ and $10^{100}$, $10^{-50}$ and $10^{50}$, $10^{-10}$ and $10^{10}$, 1 and $10^{10}$, or 1 and $10^5$ nM or µM of radical or reactive specie(s) or nM or µM of radical or reactive specie(s) per gram of nanoparticles or nM or µM of radical or reactive specie(s) per $cm^3$ of body part or nM or µM of radical or reactive specie(s) per gram of nanoparticles per $cm^3$ of body part, or iii) $10^{-100}$ and $10^{100}$, $10^{-50}$ and $10^{50}$, $10^{-10}$ and $10^{10}$, 1 and $10^{10}$, or between 1 and $10^5$ nM or µM of radical or reactive species per Watt or nM or µM of radical or reactive species per Watt per $cm^3$ of body part or nM or µM of radical or reactive species per Watt per gram of nanoparticles or nM or µM of radical or reactive species per Gy or nM or µM of radical or reactive species per Gy per $cm^3$ of body part or nM or µM of radical or reactive species per Gy per gram of nanoparticle.

In one embodiment of the invention, the quantity or concentration of radical or reactive species is that measured, which can: i) in a first case be the same or be similar to the real quantity or concentration of radical or reactive species produced or generated by the nanoparticles, ii) in a second case be different from the real quantity or concentration of radical or reactive species produced or generated by the nanoparticles. The second case can occur when reactive or radical species have a short life, react, and are in a location where they can't be detected, are in a too small or too large number to be detected, are reacting with, interacting with or are absorbed by some compounds.

The invention also relates to the method for the generation of radical species or to the acoustic wave medical treatment or to the radiation medical treatment, by:
  i) increasing the temperature, preferentially of the nanoparticles or body part, in some cases preferentially by more than $10^{-10}$, $10^{-1}$, $10^{-1}$, 1, 5, 10, 100 or $10^{3}$° C. (degree Celsius), in some other cases preferentially by less than $10^{10}$, $10^5$, $10^3$, $10^2$, 10, 5, 2 or 1° C., in still some other cases by a value of temperature increase comprised between $10^{-10}$ and $10^{10}$° C., $10^{-5}$ and $10^{5}$° C., $10^{-3}$ and $10^{3}$° C., or between $10^{-1}$ and $10^{3}$° C.
  ii) increasing the movement of the nanoparticle, in some cases preferentially by more than $10^{-100}$, $10^{-50}$, $10^{-20}$, $10^{-10}$, $10^{-5}$, $10^{-1}$, 1, 5, 10, $10^2$, $10^3$ or $10^5$ nm per second, in some other cases by less than $10^{100}$, $10^{50}$, $10^{20}$, $10^{10}$, $10^5$, 10, 5, 2, 1, $10^{-1}$, $10^{-3}$ or $10^{-5}$ nm per second, in still some other cases by a value comprised between $10^{-100}$ and $10^{100}$, $10^{-50}$ and $10^{50}$, $10^{-5}$ and $10^{5}$, $10^{-1}$ and $10^{3}$, or between $10^{-1}$ and 10 nm per second, and/or
  iv), dissociation of the compound from the nanoparticles.

The invention also relates to a method for generating radical or reactive species by applying the acoustic wave or radiation on the nanoparticles or to the acoustic or radiation medical treatment, wherein radical oxygen species destroy at least pathological cell preferentially without destroying at least one healthy cell.

The invention also relates to a composition, preferentially a pharmaceutical composition, comprising at least one nanoparticle as defined in the invention, optionally associated with a pharmaceutically acceptable vehicle.

In one embodiment, the vehicle is the compound.

The invention also relates to a pharmaceutical composition, wherein the pharmaceutically acceptable vehicle is the compound.

The invention also relates to a diagnostic composition, comprising at least one nanoparticle as defined in this invention.

The invention also relates to a medical device comprising at least one nanoparticle as defined in this invention.

The invention also relates to a medical device, comprising at least one nanoparticle associated or bound with the compound.

The invention also relates to a composition, medical device, drug, or cosmetic composition, comprising the nanoparticle according to the invention, optionally associated or bound with the compound.

The invention also relates to the magnetosomes for use in the treatment of anemia, preferentially iron anemia.

The invention also relates to the acoustic wave medical treatment or radiation medical treatment for the generation of reactive or radical species or as a method for the generation of reactive or radical species.

The invention also relates to the acoustic wave medical treatment or radiation medical treatment as a method to:
  i) decrease the cell density of or in a body part or tumor, and/or
  ii) decrease the volume of the body part, wherein this method preferentially enables to administer the nanoparticles in the body part.

In still another embodiment of the invention, the property(ies) or features, preferentially of the nanoparticle(s) or method or treatment, described in each individual embodiment or section or sentence of this patent application can be combined to result in a combination of property(ies) or features, preferentially of the nanoparticle(s) or method or treatment.

In still another embodiment of the invention, when an entity such as the compound, substance, nanoparticle, radiation, has a property with a value of $P_1$ that is higher, longer, or larger by a factor α than a property with a value of $P_2$, it means that: $P_1=\alpha \cdot P_2$ (α>1) or $P_1=\alpha+P_2$.

In still another embodiment of the invention, when an entity such as the compound, substance, nanoparticle, radiation, has a property with a value of Pi that is lower, smaller, or shorter by a factor α than a property with a value of $P_2$, it means that: $P_1=\alpha P_2$ (α<1), $P_1=P_2/\alpha$ (α>1), $P_1=P_2-\alpha$ or $P_1=\alpha-P_2$.

DETAILED DESCRIPTION

Example 1

Materials and Methods:

Nanoparticles: We used magnetosomes extracted from magnetotactic bacteria and further purified to remove most organic material from magnetotactic bacteria, which were composed of: i) a core or mineral of maghemite with a percentage in mass of organic material originating from magnetotactic bacteria of 0.3%, and ii) a coating made of carboxy-methyl-dextran surrounding the core. Magnetosomes formed chains and were prepared using an adapted and improved protocol described in patent PCT/FR2016/000095 (Pub. Number WO2016/203121A1) incorporated in reference (example 8). These magnetosomes are designated as M-CMD. We also used i) nanoparticles composed of iron oxide of sizes 35±13 nm purchased from Sigma designated as Sigma nanoparticles (Ref: 637106-25G, Lot #MKBK2270V), ii) superparamagnetic nanoparticles composed of iron oxide of 20 nm purchased from Micromod designated as SPION20 (Nanomag®-D-spio 20, Ref: 79-02-201), iii) superparamagnetic nanoparticles composed of iron oxide of 50 nm purchased from Micromod designated as SPION50 (synomag-D50, Ref: 104-000-501), iv), superparamagnetic nanoparticles composed of iron oxide of 100 nm purchased from Micromod designated as SPION100 (Nanomag®-D-spio 100, Ref: 79-00-102).

Preparation of Samples Containing Nanoparticles Inserted in Tissue or Dispersed in Water: For heating experiments in tissues, 10 µl of suspensions containing water alone or 204 µg in iron of nanoparticles (Magnetosome(s) and Sigma or Sigma nanoparticle(s)) were inserted homogenously in 4.5 cm$^3$ of liver tissue leading to a concentration of 45 lag in iron of nanoparticles per cm$^3$ of liver tissue. For heating experiments in aqueous conditions, 100 µl of water alone or 100 µl of water mixed with 100 µg in iron of nanoparticles (Magnetosome, Sigma, SPION20, SPION50, SPION100) were dispersed in a 200 µl Eppendorf.

Heating Apparatus Generating Ultrasound: Samples made of tissues with/without nanoparticles or water with/without nanoparticles were exposed to ultrasound of intensity 0.5, 1, or 1.5 W/cm$^3$, and frequency 3 MHz, during 10 minutes. The intensity corresponds to that red on the apparatus and it is possible that there is a difference between the ultrasound intensity in the body part and the ultrasound intensity that the phyaction 190i indicates. To apply the ultrasound, we used a phyaction 190i ultrasound generator with a transducer of surface area 4 cm$^2$. The ultrasound power indicated in the example corresponds to that read on the 190i ultrasound generator and not to an ultrasound power measured with an external probe. We used an ultrasound gel (Winelec, Ref: 1741/WINELEC) located between the transducer and the samples to favor the transmission of the ultrasounds.

Measurement of Temperature: We used an infrared camera (EasIR™-2, Optophase) positioned 13 cm above the transducer to measure the spatial distribution in temperature as a function of time during the experiments. We measured the temperature distribution at the following time points: 0 sec., 30 sec., 1 min., 2 min., 3 min., 4 min., 5 min., 6 min., 7 min., 8 min., 9 min., and 10 min. We only considered the maximum temperature recorded at each time point.

Results and Discussion:

a) Non-Sequential Heating Experiment in Tissues:

FIG. 1 shows ΔT, the difference in temperature between the tissue with the nanoparticles and the tissue without the nanoparticles, measured at each time point, and for an ultrasound power of 0.5 W/cm$^2$ (FIG. 1($a$)), 1 W/cm$^2$ (FIG. 1($b$)), and 1.5 W/cm$^2$ (FIG. 1($c$)). At the three different tested powers, ΔT is positive indicating that the temperature increase is more important for the tissue containing nanoparticles than for tissue without the nanoparticles. At the lowest power of 0.5 W/cm$^2$, Sigma nanoparticles produce more heat than Magnetosomes, while at 1.5 W/cm$^2$, the opposite behavior is observed with Magnetosomes producing more heat than Sigma nanoparticles.

For the magnetosomes mixed in tissue and exposed to different ultrasound powers of 0.5, 1, or 1.5 W/cm$^2$, we have also estimated the values of $\Delta T_{10minreal(M)}$, which is equal to $\Delta T_{10min(M)} - \Delta T_{10min(W)}$, where $\Delta T_{10min(M)}$ and $\Delta T_{10min(W)}$ are the temperature increases observed after 10 minutes of ultrasound application for the samples containing tissue with the magnetosomes and tissue without the magnetosomes, respectively. We observed that $\Delta T_{10minreal(M)}$ increases from 6° C. at 0.5 W/cm$^2$ to 28° C. at 1.5 W/cm$^2$ (table 1). We also estimated the percentage in temperature rise, Temperature rise$_{(M)}$, expressed using the formula Temperature rise$_{(M)}$ = $(\Delta T_{10min(M)}/\Delta T_{10min(W)} - 1) \cdot 100$. It increases from 37% at 0.5 W/cm$^2$ to 100% at 1.5 W/cm$^2$ (table 1). We also estimated the value of the specific absorption rate of the magnetosomes inserted in tissue, $SAR_{real(M)}$, expressed in watt per gram of magnetosomes in iron (W/g$_{Fe}$), using the formula $SAR_{real(M)} = Slope_{real(M)} \cdot C_v/C_{nano}$, where $Slope_{real(M)} = Slope_{(M)} - Slope_{(W)}$, with $Slope_{(M)}$ and $Slope_{(W)}$ representing the initial slopes of the temperature variations with time deduced from the plots of FIGS. 1($a$) to 1($c$), $C_v$=4.2 J·K$^{-1}$g$^{-1}$ is the specific heat of water and $C_{nano}$ is the nanoparticle concentration in gram of nanoparticles per mL of water. $SAR_{real(M)}$ increases from 5-12 W/g$_{Fe}$ at 0.5-1 W/cm$^2$ to 71 W/g$_{Fe}$ at 1.5 W/cm$^2$ (table 1). We also estimated the percentage in slope rise, Slope rise$_{(M)}$, expressed using the formula Slope rise$_{(M)}$=$[(Slope_{(M)}/Slope_{(W)}) - 1] \cdot 100$. It increases from 9-47% at 0.5-1 W/cm$^2$ to 124% at 1.5 W/cm$^2$.

Figure 2:
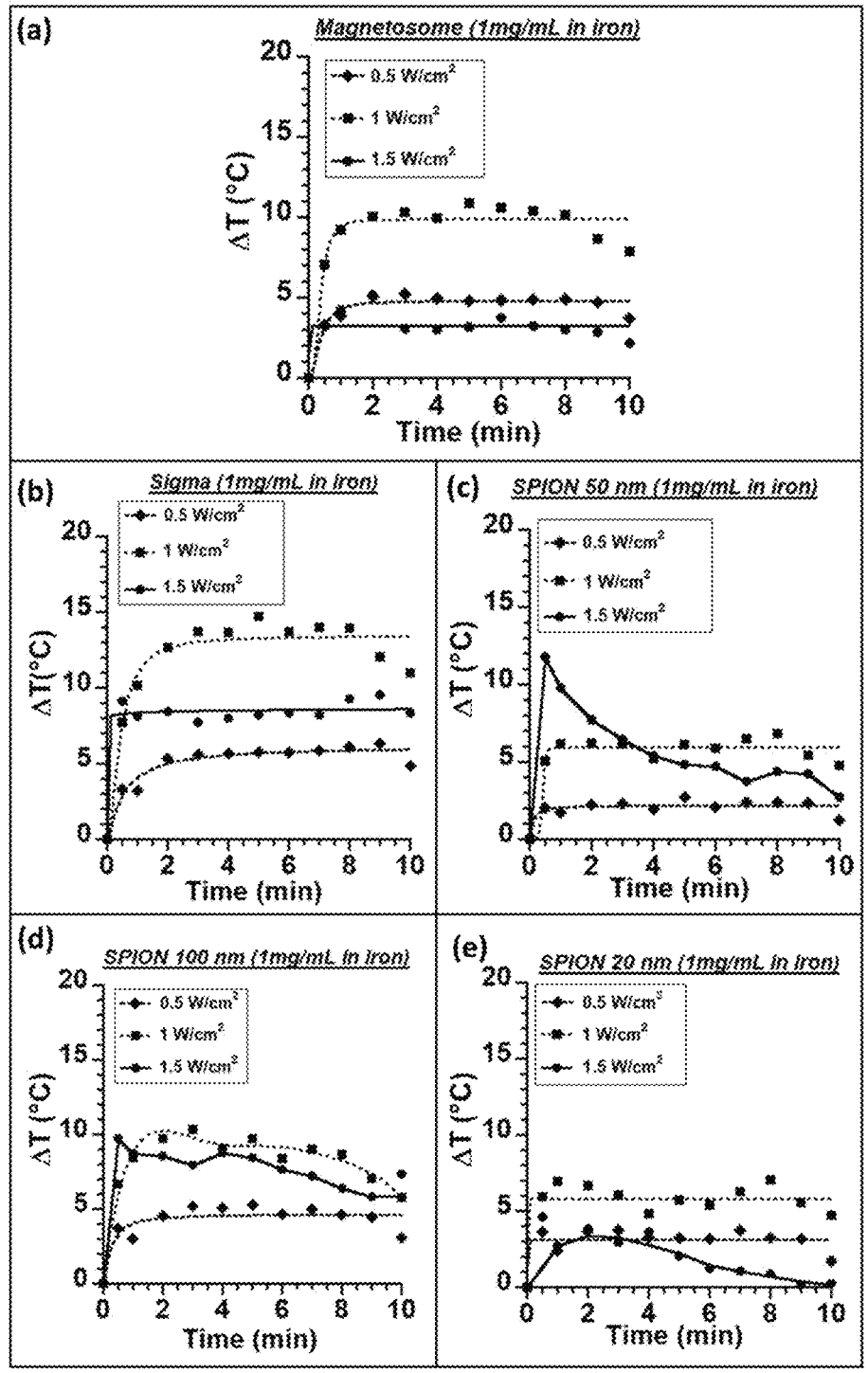
FIG. 2: (a) For 100 µg in iron of magnetosomes dispersed in 100 µl of water exposed to ultrasounds of frequency 3 MHz and power 0.5 W/cm$^2$, 1 W/cm$^2$, or 1.5 W/cm$^2$, ΔT, designing the temperature difference between the temperature measured for magnetosomes dispersed in water and the temperature measured for water without magnetosomes, as a function of duration of ultrasound application (time in minutes). (b) For 100 µg in iron of Sigma nanoparticles dispersed in 100 µl of water exposed to ultrasound of frequency 3 MHz and power 0.5 W/cm$^2$, 1 W/cm$^2$, or 1.5 W/cm$^2$, ΔT, designing the temperature difference between the temperature measured for Sigma nanoparticles dispersed in 100 µl of water and the temperature measured for 100 µl of water without Sigma nanoparticles, as a function of duration of ultrasound application (time in minutes). (c) For 100 µg in iron of SPION50 nanoparticles dispersed in 100 µl of water exposed to ultrasound of frequency 3 MHz and power 0.5 W/cm$^2$, 1 W/cm$^2$, or 1.5 W/cm$^2$, ΔT, designing the temperature difference between the temperature measured for SPION50 nanoparticles dispersed in 100 µl of water and the temperature measured for 100 µl of water without SPION50 nanoparticles, as a function of duration of ultrasound application (time in minutes). (d) For 100 µg in iron of SPION100 nanoparticles dispersed in 100 µl of water exposed to ultrasound of frequency 3 MHz and power 0.5 W/cm$^2$, 1 W/cm$^2$, or 1.5 W/cm$^2$, ΔT, designing the temperature difference between the temperature measured for SPION100 nanoparticles dispersed in 100 µl of water and the temperature measured for 100 µl of water without SPION100 nanoparticles, as a function of duration of ultrasound application (time in minutes). (e) For 100 µg in iron of SPION20 nanoparticles dispersed in 100 µl of water exposed to ultrasound of frequency 3 MHz and power 0.5 W/cm$^2$, 1 W/cm$^2$, or 1.5 W/cm$^2$, ΔT, designing the temperature difference between the temperature measured for SPION20 nanoparticles dispersed in 100 µl of water and the temperature measured for 100 µl of water without SPION20 nanoparticles, as a function of duration of ultrasound application (time in minutes).

For Sigma nanoparticles mixed in tissue and exposed to different ultrasound powers of 0.5, 1, or 1.5 W/cm$^2$, we have also estimated the values of $\Delta T_{10minreal(S)}$, which is equal to $\Delta T_{10min(S)} - \Delta T_{10min(W)}$, where $\Delta T_{10min(S)}$ and $\Delta T_{10min(W)}$ are the temperature increases observed after 10 minutes of ultrasound application for the samples containing tissue with the Sigma nanoparticles and tissue without the Sigma nanoparticles, respectively. We observed that $\Delta T_{10minreal(S)}$ decreases from 14° C. at 0.5 W/cm$^2$ to 6-7° C. at 1-1.5 W/cm$^2$ (table 1). We also estimated the percentage in temperature rise, Temperature rise$_{(S)}$, expressed using the formula Temperature rise$_{(S)}$=$(\Delta T_{10min(S)}/\Delta T_{10min(W)} - 1) \cdot 100$. It decreases from 90% at 0.5 W/cm$^2$ to 17-26% at 1-1.5 W/cm$^2$ (table 1). We also estimated the value of the specific absorption rate of the Sigma nanoparticles inserted in tissue, $SAR_{real(S)}$, expressed in watt per gram of Sigma nanoparticles in iron (W/g$_{Fe}$), using the formula $SAR_{real(S)} = Slope_{real(S)} \cdot C_v/C_{nano}$, where $Slope_{real(S)}$ represent the initial slopes of the temperature variations with time deduced from the plots of FIGS. 1($a$) to 1($c$) for sigma nanoparticles, $C_v$=4.2 J·K$^{-1}$g$^{-1}$ is the specific heat of water and $C_{nano}$ is the nanoparticle concentration in gram of Sigma nanoparticles per mL of water. $SAR_{real(S)}$ remains at 16-28 W/g$_{Fe}$ between 0.5 and 1.5 W/cm$^2$ (table 1). We also estimated the percentage in slope rise, Slope rise$_{(S)}$, expressed using the formula Slope rise$_{(S)}$=$(Slope_{(S)}/Slope_{(W)} - 1) \cdot 100$. It decreases from 118% at 0.5 W/cm$^2$ to 30-36% at 1-1.5 W/cm$^2$.

b) Non-Sequential Heating Experiments in Water:

FIGS. 2($a$), 2($b$), 2($c$), 2($d$), and 2($e$), show ΔT, the difference between the temperature of the suspension containing the different nanoparticles dispersed in water and temperature of water without the nanoparticles, when the different suspensions are exposed to ultrasounds of 0.5, 1, or 1.5 W/cm$^2$ during 10 minutes. FIGS. 2($a$), 2($b$), 2($c$), 2($d$), and 2($e$) show ΔT as a function of time for Magnetosomes, Sigma, SPION50, SPION100, and SPION20, respectively. For the different nanoparticles and the three different tested powers, ΔT is positive indicating that the temperature increase is more important for nanoparticles dispersed in water than for water alone.

For the magnetosomes mixed in water and exposed to different ultrasound powers of 0.5, 1, or 1.5 W/cm$^2$, we have estimated the values of $\Delta T_{10minreal(M)}$, which is equal to $\Delta T_{10min(M)} - \Delta T_{10min(W)}$, where $\Delta T_{10min(M)}$ and $\Delta T_{10min(W)}$ are the temperature increases observed after 10 minutes of ultrasound application for the samples containing tissue with the magnetosomes and tissue without the magnetosomes, respectively. We observed that $\Delta T_{10minreal(M)}$ remains at 3 to 9° C. between 0.5 W/cm² and 1.5 W/cm² (table 2), smaller values of $\Delta T_{10minreal(M)}$ than those observed in tissue at 1.5 W/cm² (table 1). We also estimated the percentage in temperature rise, Temperature rise$_{(M)}$, expressed using the formula Temperature rise$_{(M)}$=($\Delta T_{10min(M)}/\Delta T_{10min(W)}$−1)·100. It decreases from 37-43% at 0.5-1 W/cm² down to 10% at 1.5 W/cm² (table 2) and is also smaller than Temperature rise$_{(M)}$ measured in tissue at 1.5 W/cm² (table 1). We also estimated the value of the specific absorption rate of the magnetosomes dispersed in water, SAR$_{real(M)}$, expressed in watt per gram of magnetosomes in iron (W/g$_{Fe}$), using the formula SAR$_{real(M)}$=Slope$_{real(M)}$·C$_v$/C$_{nano}$, where Slope$_{real(M)}$ represents the initial slopes of the temperature variations with time deduced from the plots of FIG. 2(a), C$_v$=4.2 J·K$^{-1}$g$^{-1}$ is the specific heat of water and C$_{nano}$ is the Magnetosome concentration in gram of magnetosomes per mL of water. SAR$_{real(M)}$ increases from 294 W/g$_{Fe}$ at 0.5 W/cm² to 424 W/g$_{Fe}$ at 1.5 W/cm² (table 2), higher values than those measured in tissue (table 1). We also estimated the percentage in slope rise, Slope rise$_{(M)}$, expressed using the formula Slope rise$_{(M)}$=(Slope$_{(M)}$/Slope$_{(W)}$−1)·100. It remains at 16-24% at 0.5-1.5 W/cm² (table 2), smaller values than 124% deduced in tissue at 1.5 W/cm² (table 1).

For Sigma nanoparticles dispersed in water and exposed to different ultrasound powers of 0.5, 1, or 1.5 W/cm², we have also estimated the values of $\Delta T_{10minreal(S)}$, which is equal to $\Delta T_{10min(S)}-\Delta T_{10min(W)}$, where $\Delta T_{10min(S)}$ and $\Delta T_{10min(W)}$ are the temperature increases observed after 10 minutes of ultrasound application for the samples containing Sigma nanoparticles dispersed in water and water without the Sigma nanoparticles, respectively. We observed that $\Delta T_{10minreal(S)}$ remains at 6-12° C. for ultrasound energies of 0.5-1.5 W/cm² (table 2). We also estimated the percentage in temperature rise, Temperature rise$_{(S)}$, expressed using the formula Temperature rise$_{(S)}$=($\Delta T_{10min(S)}/\Delta T_{10min(W)}$−1)·100. It remains at 31-60% for powers of 0.5-1.5 W/cm² (table 2). We also estimated the value of the specific absorption rate of the Sigma nanoparticles inserted in tissue, SAR$_{real(S)}$, expressed in watt per gram of Sigma nanoparticles in iron (W/g$_{Fe}$), using the formula SAR$_{real(S)}$=Slope$_{real(S)}$·C$_v$/C$_{nano}$, where Slope$_{real(S)}$ represents the initial slopes of the temperature variations with time deduced from the plots of FIG. 2(b) for Sigma nanoparticles, C$_v$=4.2 J·K$^{-1}$g$^{-1}$ is the specific heat capacity of water and C$_{nano}$ is the nanoparticle concentration in gram of Sigma nanoparticles in iron per mL of water. SAR$_{real(S)}$ increases from 0 W/g$_{Fe}$ at 0.5 W/cm² to 2686 W/g$_{Fe}$ at 1.5 W/cm² (table 2). We also estimated the percentage in slope rise, Slope rise$_{(S)}$, expressed using the formula Slope rise$_{(S)}$=(Slope$_{(S)}$/Slope$_{(W)}$−1)·100. It increases from 0-8% at 0.5-1 W/cm² to 99% at 1.5 W/cm².

Figure 3:
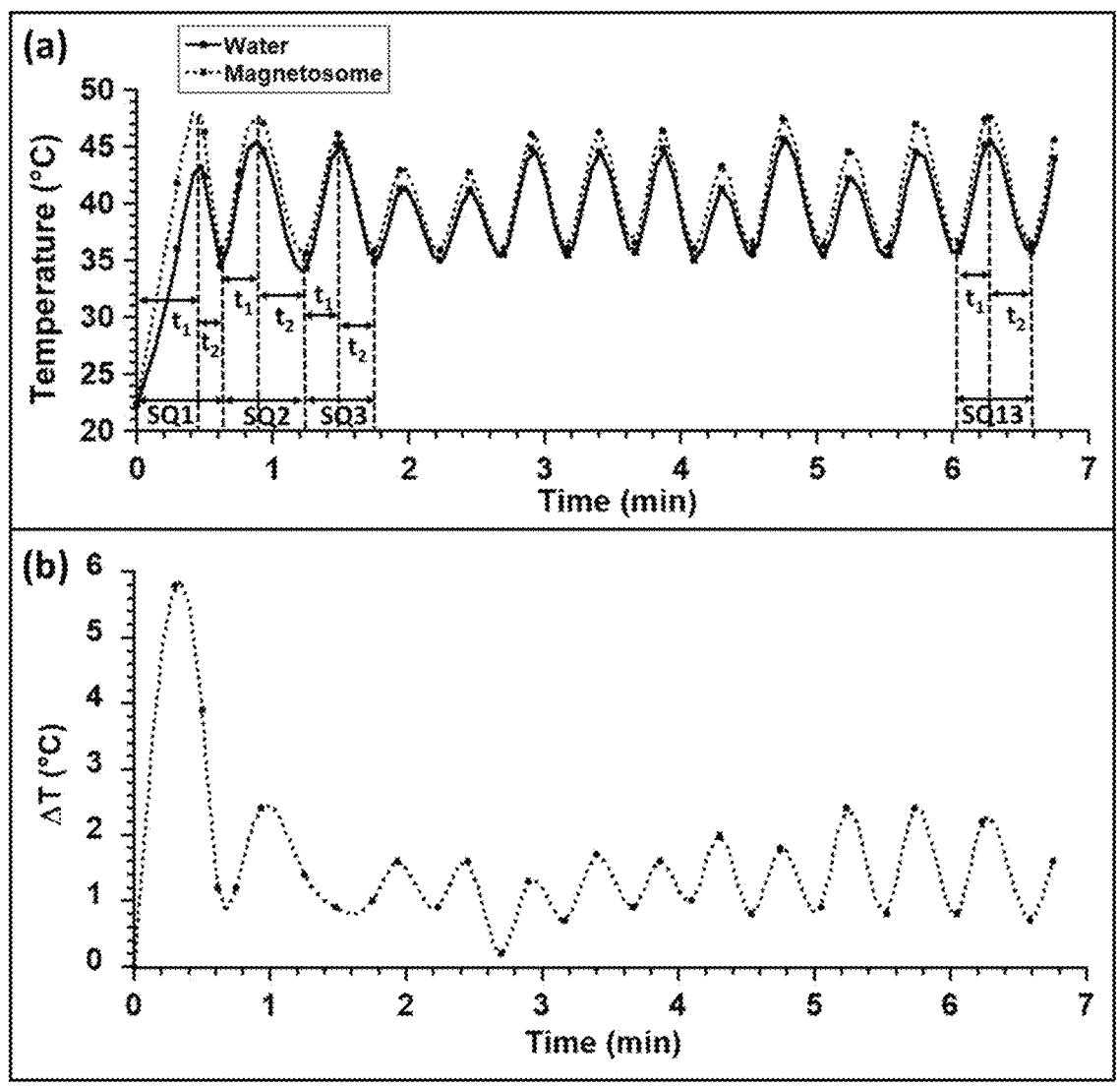
FIG. 3: (a) For 800 µg in iron of magnetosomes dispersed in 100 µl of water (magnetosomes) or 100 µl of water without magnetosomes (water) exposed to ultrasound of frequency 3 MHz and power 1.5 W/cm² during heating steps of duration $t_1$ and no exposed to ultrasound during cooling steps of duration $t_2$, where the different values of heating and cooling times ($t_1$ and $t_2$) during sequences 1 to 13 (SQ1 to SQ13) are indicated in table 3. (b) Difference between the temperature of magnetosomes dispersed in water (magnetosomes in (a)) and the temperature of water without the magnetosomes (Water in (b)) as a function of duration of ultrasound application (time in minutes) during the different sequences.

For SPION50, SPION100, and SPION20 nanoparticles dispersed in water and exposed to different ultrasound powers of 0.5, 1, or 1.5 W/cm², we have also estimated the values of $\Delta T_{10minreal(S50)}$, $\Delta T_{10minreal(S100)}$, and $\Delta T_{10minreal(S20)}$, which are equal to $\Delta T_{10min(S50)}-\Delta T_{10min(W)}$, $\Delta T_{10min(S100)}-\Delta T_{10min(W)}$ and $\Delta T_{10min(S20)}-\Delta T_{10min(W)}$, respectively. $\Delta T_{10min(S50)}$, $\Delta T_{10min(S100)}$, $\Delta T_{10min(S20)}$ and $\Delta T_{10min(W)}$ are the temperature increases observed after 10 minutes of ultrasound application for the samples containing SPION50, SPION100, and SPION20 nanoparticles dispersed in water and water without nanoparticles, respectively. We observed that $\Delta T_{10minreal(S50)}$, $\Delta T_{10minreal(S100)}$, and $\Delta T_{10minreal(S20)}$, remain at 0-7° C. for ultrasound energies of 0.5-1.5 W/cm² (table 2). We also estimated the percentage in temperature rise, Temperature rise$_{(S)}$, expressed using the formula Temperature rise$_{(S50)}$= ($\Delta T_{10min(S50)}/\Delta T_{10min(W)}$−1)·100 for SPION50, Temperature rise$_{(S100)}$=($\Delta T_{10min(S100)}/\Delta T_{10min(W)}$−1)·100 for SPION100, Temperature rise$_{(S20)}$=($\Delta T_{10min(S20)}/\Delta T_{10min(W)}$−1)·100 for SPION20. It remains at 1-35% for powers of 0.5-1.5 W/cm² for the different SPION (table 2). We also estimated the value of the specific absorption rate of the SPION50, SPION100, and SPION20 nanoparticles inserted in tissue, SAR$_{real(S50)}$, SAR$_{real(S100)}$, SAR$_{real(S20)}$, expressed in watt per gram of SPION50, SPION100, and SPION20 nanoparticles in iron (W/g$_{Fe}$). For that, we used the formula SAR$_{real(S50)}$=Slope$_{real(S50)}$·C$_v$/C$_{nano}$, SAR$_{real(S100)}$=Slope$_{real(S100)}$·C$_v$/C$_{nano}$, SAR$_{real(S20)}$=Slope$_{real(S20)}$·C$_v$/C$_{nano}$ for SPION50, SPION100, and SPION20 nanoparticles, respectively. Slope$_{real(S50)}$, Slope$_{real(S100)}$, Slope$_{real(S20)}$ represent the initial slopes of the temperature variations with time deduced from the plots of FIG. 2(c) for SPION50, of FIG. 2(d) for SPION100, and of FIG. 2(e) for SPION20, where C$_v$=4.2 J·K$^{-1}$g$^{-1}$ is the specific heat of water and C$_{nano}$ is the nanoparticle concentration in gram of SPION50, SPION20, or SPION100 nanoparticles in iron per mL of water. SAR$_{real(S20)}$, SAR$_{real(S50)}$, and SAR$_{real(S100)}$ increase from 0-677 W/g$_{Fe}$ at 0.5-1 W/cm² to 787-2795 W/g$_{Fe}$ at 1.5 W/cm² (table 2). We also estimated the percentage in slope rise, Slope rise$_{(S20)}$, Slope rise$_{(S50)}$, Slope rise$_{(S100)}$, expressed using the formula Slope rise$_{(S20)}$=(Slope$_{(S20)}$/Slope$_{(W)}$−1)·100 for SPION20, Slope rise$_{(S50)}$=(Slope$_{(S50)}$/Slope$_{(W)}$−1)·100 for SPION50 and Slope rise$_{(S100)}$= (Slope$_{(S100)}$/Slope$_{(W)}$−1)·100 for SPION100. It remains at 0-104% between 0.5 and 1.5 W/cm².

c) Sequential Heating Experiments in Water:

Eppendorf containing 500 µg of Magnetosomes dispersed in 100 µl of water were exposed sequentially to ultrasounds. FIG. 3(a) shows 13 sequences (SQ1 to SQ13) consisting for each of them in the application of an ultrasound of power 1.5 W/cm² and frequency 3 MHz during time t$_1$ followed by the non-application of an ultrasound during times t$_2$. The time t$_1$ corresponds to the time necessary to reach a desired targeted temperature of 43.5±1.5° C. during the heating step, while the time t$_2$ corresponds to the time necessary to cool down the sample from 43.5±1.5° C. to 34.5±0.5° C. during the cooling step. The values of t$_1$ and t$_2$ are given in table 3 for the different sequences. The average frequency of the sequences, 1/(t$_{1av}$+t$_{2av}$), where t$_{1av}$ and t$_{2av}$ represent the average values of t$_1$ and t$_2$ over the 13 sequences, was estimated at 33 mHz. FIG. 3(b) shows the variation of $\Delta T$, the difference in temperature between the temperature of the tube containing water with the Magnetosome and the temperature of the tube containing water without the Magnetosome, as a function of time. $\Delta T$ is positive indicating that the temperature increase is more important in the tube containing water with magnetosomes than in the tube containing water alone without magnetosomes during all 13 sequences. Furthermore, we are able to repeat the heating and cooling steps due to the presence of Magnetosome a large number of times (13) as seen in FIG. 3(b), suggesting that the ultrasound are not damaging the Magnetosomes or are not strongly undermining the heating power of the magnetosomes. The heating steps are more important in magnitude during the two first sequences, which may be attributed to better magnetosome dispersion and lower magnetosome aggregation during the first two sequences than during the other remaining sequences. We also observe that the sequences can be repeated with heating and cooling times that do not vary by more than 53% between the different sequences (table 3).

Conclusion

We can draw the following conclusion from this example:
(i) The values of ΔT, the difference in temperature between the temperature of nanoparticles in tissues or water exposed to ultrasound and the temperature of tissue or water alone exposed to ultrasound, is always positive, indicating that the different nanoparticles (Magnetosome, Sigma, SPION20, SPION50, SPION100) enhance the heating efficacy of ultrasound in the tested conditions (ultrasound frequency=3 MHz, ultrasound power=0.5-1.5 W/cm$^2$, nanoparticle concentration varied between 60 μg/mL and 8 mg/mL and nanoparticles either inserted in tissue or dispersed in water).
(ii) For water suspensions, lower SAR values observed for magnetosomes than for other nanoparticles (table 2) may be explained by more aggregation for the magnetosomes than for other nanoparticles following application of the ultrasound (as was observed by eyes).
(iii) in some cases, the SAR may have been underestimated due to the heat produced by the transducer generating the ultrasound that can heat the tissue and interfere with the heat produced by nanoparticles exposed to ultrasound. This may be the reason why some of the SAR values are reported to be 0 W/g for example.
(iv) When $SAR_{real}$ is zero, the value of $\Delta T_{10min\ real}$ is non-zero (table 2), indicating that nanoparticles increase the quantity of heat generated by the acoustic wave but that $SAR_{real}$ is underestimated, possibly due to the interference with the heat generated by the transducer.
(v) Nanoparticle SAR values estimated by applying ultrasound in tissue comprising the various nanoparticles reach the largest value for the the magnetosomes.
(vi) Using magnetosomes, we can produce sequences consisting in heating steps (application of ultrasound on magnetosomes) followed by cooling steps (non-application of ultrasound on magnetosomes), with enhanced magnitudes of heating and cooling compared with heating and cooling steps obtained without the magnetosomes (FIGS. 3(a) and 3(b)).

Example 2

Figure 4:
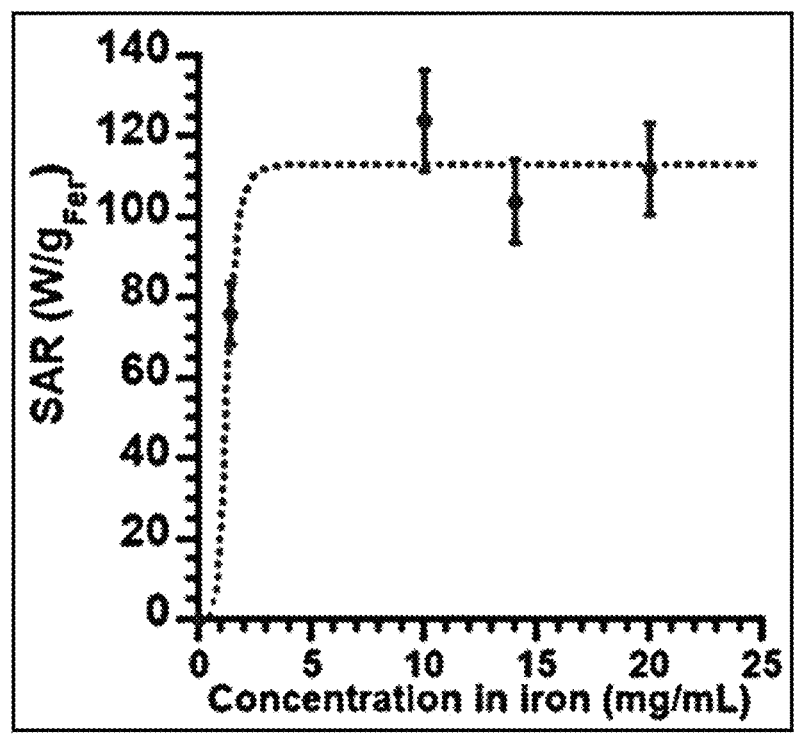
FIG. 4: For 100 µl of a suspension of BNF-Starch nanoparticles (ref Micromod: 10-00102) mixed in water, exposed to an alternating magnetic field of average strength 30 mT and frequency 196 kHz, variation of the SAR, expressed in watt per gram of iron comprised in nanoparticles, as a function of the iron concentration comprised in BNF-Starch. BNF-Starch are ferrimagnetic iron oxide nanoparticles of average sizes 18 nm.

FIG. 4 shows that when 100 μl of a suspension of BNF-Starch nanoparticles mixed in water are exposed to an alternating magnetic field of average strength 30 mT and frequency 196 kHz during 30 minutes, the SAR increases from 4 Watt per gram of iron comprised in nanoparticles for a concentration of 500 μg of iron comprised in nanoparticles per mL up to 114 Watt per gram of iron comprised in nanoparticles for a concentration of 5 mg of iron comprised in nanoparticles per mL. The SAR increases by factor of 29 for an increase in nanoparticle concentration by a factor of 10. Above 5 mg/mL, the SAR saturates at 110 Watt per gram of iron comprised in nanoparticles.

Example 3: Cellular Toxicity and Temperature Measurement of Cells Brought into Contact with Different Concentrations of Magnetosomes and Subjected (or not) to the Sequential or Continuous Application of Ultrasounds Materials and Methods:

The magnetosomes used in its example are M-CMD. U87-MG glioblastoma cells were purchased from ATCC (ATCC® HTB-14) and cultivated in High-Glucose Dulbecco's Modified Eagle's Medium (DMEM), supplemented with 1 mM pyruvate, 10% fetal calf serum, 100 units/mL of penicillin and 100 μg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 μL of cells was collected and mixed with 30 μL of 4% trypan blue to count the cells using a cell counter (Countess™ II FL Automated Cell Counter (Thermo Fisher scientific)) and thus to determine the cell concentration of the initial suspension. A volume of 2 mL of 250 000 cells was deposited per petri dish and then incubated at 37° C. with 5% CO2 for 24 hours so that the cells adhere at the surface of the petri dish. The cell medium was then removed and replaced either by a new medium without magnetosomes or by a new medium comprising magnetosomes at a concentration of 100 μg/mL or 500 μg/mL in iron. The cells were then either continuously exposed to ultrasounds or sequentially exposed to ultrasounds. The power of the ultrasounds used was 0 mW/cm$^2$, 100 mW/cm$^2$, or 500 mW/cm$^2$, and the frequency of the ultrasound used was 1 MHz.

The ultrasound was applied as follows: the surface of the transducer was oriented upward, a gel-pad coated with ultrasound gel was deposited on the surface of the transducer to reduce the heat released by the transducer. Then above the gel-pad, the petri dishes were deposited. The petri-dishes were maintained above the gel-pad for 5 minutes, so that ultrasounds can cross the different surfaces.

For the continuous application of ultrasounds, ultrasounds were applied continuously during 5 minutes to petri dishes containing cells with or without magnetosomes.

For the sequential application of ultrasounds, the ultrasounds were sequentially applied to petri dishes containing the cells with or without magnetosomes in the following way: first application of ultrasound for 1 min, no application of ultrasound during 1 min, second application of ultrasound for 1 min 24 s, no application of ultrasound during 1 min 24 s, third application of ultrasound for 1 min, no application of ultrasound during 1 min 30 s, fourth application of ultrasound for 1 min, no application of ultrasound during 1 min 18 s, fifth application of ultrasound for 1 min 12 s, no application of ultrasound during 1 min 18 s. The total time of application of the ultrasound was 5 min 36 seconds, close to the duration of 5 minutes during which the ultrasounds were continuously applied.

During the application of ultrasounds, the heating temperature was measured using the infra-red camera EasyIR-2 from the company Guide Infrared, which was positioned 20 cm above the petri dishes.

24 hours after the treatments, the medium with and without magnetosomes was removed and then replaced with a PBS buffer solution. The cells were washed twice with PBS buffer solution and then 2 ml of a solution of bromide of 3-(4,5-dimethylthiazol-2-yl)-2,5-diphenyl-tetrazolium at 1 mg/ml was brought into contact with the cells during 4 hours, the tetrazolium salt was removed and then replaced with 2 mL of isopropanol. After gentle stirring, a volume of 100 μL of each petri dish was transferred to a 96-well plate. Absorbance was measured at 620 nm. The percentage of living cells was determined by measuring the ratio between the optical density measured for the cells treated with ultrasounds with/without magnetosomes and the optical density measured for the cells treated alone without magnetosomes without the application of the ultrasounds, and the ratio was multiplied by 100.

Figure 5:
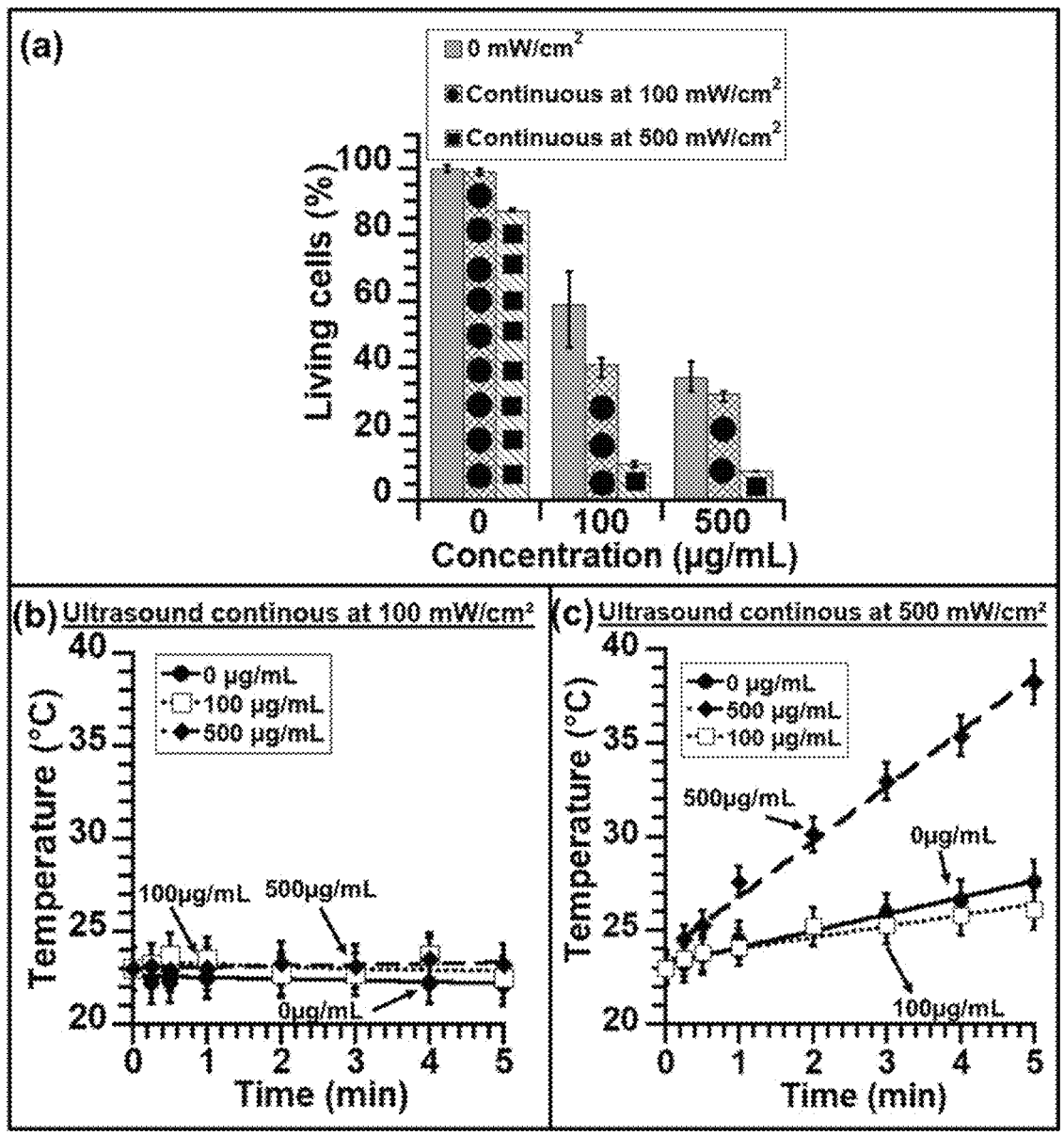
FIG. 5: (a) Histogram representing the percentage of living U87-MG cells resulting from the following treatment: $2.5 \cdot 10^5$ of U87-MG living cells are placed in the presence of three concentrations of magnetosomes (0, 100, and 500 µg in iron of magnetosomes per ml of medium and cells) and continuously exposed for 5 minutes to an ultrasound of a power of 100 mW/cm² (middle column with lines in ascending and descending directions and filled black circles), or a power of 500 mW/cm² (right column hatched with a line in a descending direction and filled black square) or without ultrasound exposure (gray left column without hatching). (b) For $2.5 \cdot 10^5$ U87-MG cells, which are brought into contact with 3 different concentrations in iron of magnetosomes, i.e. 0 mg/mL (filled black circle with a solid black line), 100 µg/mL (white square with dashed lines) and 500 µg/mL (black diamond with half a solid line), and continuously exposed to ultrasound of power 100 mW/cm² for 5 minutes, variation of temperature, measured with an IR camera, as a function of the continuous ultrasonic exposure time. (c) For $2.5 \cdot 10^5$ U87-MG cells, which are brought into contact with 3 different concentrations in iron of magnetosomes, i.e. 0 mg/ml (filled black circle with a solid black line), 100 µg/mL (white square with dashed lines) and 500 µg/mL (black diamond with half a solid line), and continuously exposed to ultrasound at a power of 500 mW/cm² for 5 minutes, variation of temperature, measured with an IR camera, as a function of the continuous ultrasonic exposure time.

Results:

FIG. 5(a) is an histogram showing the percentage of living U87-Luc cells after the following treatment: U87-Luc cells were brought into contact with 0, 100, or 500 μg in iron of magnetosomes per mL and continuously exposed (or not) to ultrasounds of power 100 mW/cm$^2$ or 500 mW/cm$^2$, where cm$^2$ represents the power of the ultrasound indicated by the equipment generating the ultrasounds.

On the one hand, it is observed that when the magnetosome concentration increases from 0 to 500 μg/mL, the percentage of living cells decreases: i) from 100% to 35% in the absence of application of the ultrasounds, and ii) from 87% to 10% in the presence of the application of the ultrasounds of power 500 mW/cm$^2$.

On the other hand, it is observed that when the power of the ultrasounds increases from 0 mW/cm$^2$ to 500 mW/cm$^2$, the percentage of living cells decreases: i) from 100% to 87% in the absence of magnetosomes and ii) from 35% to 10% in the presence of 500 μg/mL of magnetosomes.

It is observed that the percentage of living cells decreases when the power of the ultrasounds and the magnetosome concentration are increased.

FIG. 5(b) represents the temperature variation as a function of time, measured with an IR camera, of U87-Luc cells brought into contact with magnetosomes at different concentrations in iron (0, 100, or 500 μg per mL), which are exposed continuously to ultrasounds of power 100 mW/cm$^2$ and frequency 1 MHz. FIG. 5(b) shows that for a power of 100 mW/cm$^2$, there isn't any temperature increase at the different tested magnetosome concentrations.

FIG. 5(c) represents the temperature variation as a function of time, measured with an IR camera, of U87-Luc cells brought into contact with magnetosomes at different concentrations in iron (0, 100, or 500 μg par mL), continuously exposed to ultrasounds of power 500 mW/cm$^2$ and frequency 1 MHz. FIG. 5(c) shows that for the power of 500 mW/cm$^2$, the temperature increases after 5 minutes of ultrasound application by 4° C. for 0 and 100 μg/mL of magnetosomes and by 15° C. for 500 μg/mL of magnetosomes.

We can deduce from these results that:
i) In order to obtain a temperature increase by continuously applying ultrasounds on magnetosomes, it is necessary to use a sufficiently large magnetosome concentration (500 μg/mL) and a sufficiently large power of the ultrasounds of 500 mW/cm$^2$ (FIG. 5(c)). The temperature increase is the difference between the temperature increase reached in the presence of the magnetosomes and the temperature increase reached in the absence of the magnetosomes.
ii) The percentage of living cells resulting from the treatment which consists in applying ultrasounds of 100 mW/cm$^2$ and 500 mW/cm$^2$ on magnetosomes is similar for a magnetosome concentration of 100 and 500 μg/mL, at 10% for a power of the ultrasounds of 500 mW/cm$^2$ and at 32-40% for a power of the ultrasounds of 100 mW/cm$^2$, indicating that the magnetosome concentration has a limited impact on the efficacy of cellular destruction for this range of concentration (FIG. 5(a)). It suggests that a high efficacy of cellular destruction could be reached at low magnetosome concentrations.
iii) When ultrasounds of power 500 mW/cm$^2$ are applied on magnetosomes of concentrations of 100 μg/mL and 500 μg/mL, it results in a similar percentage of living cells (FIG. 5(a)). Given that for 100 μg/mL, there isn't any temperature increase while for 500 μg/mL there is a temperature increase of 15° C. (FIG. 5(c)), the presence (or not) of a temperature increase does not seem to play a role in the cellular viability under these conditions.

Figure 6:
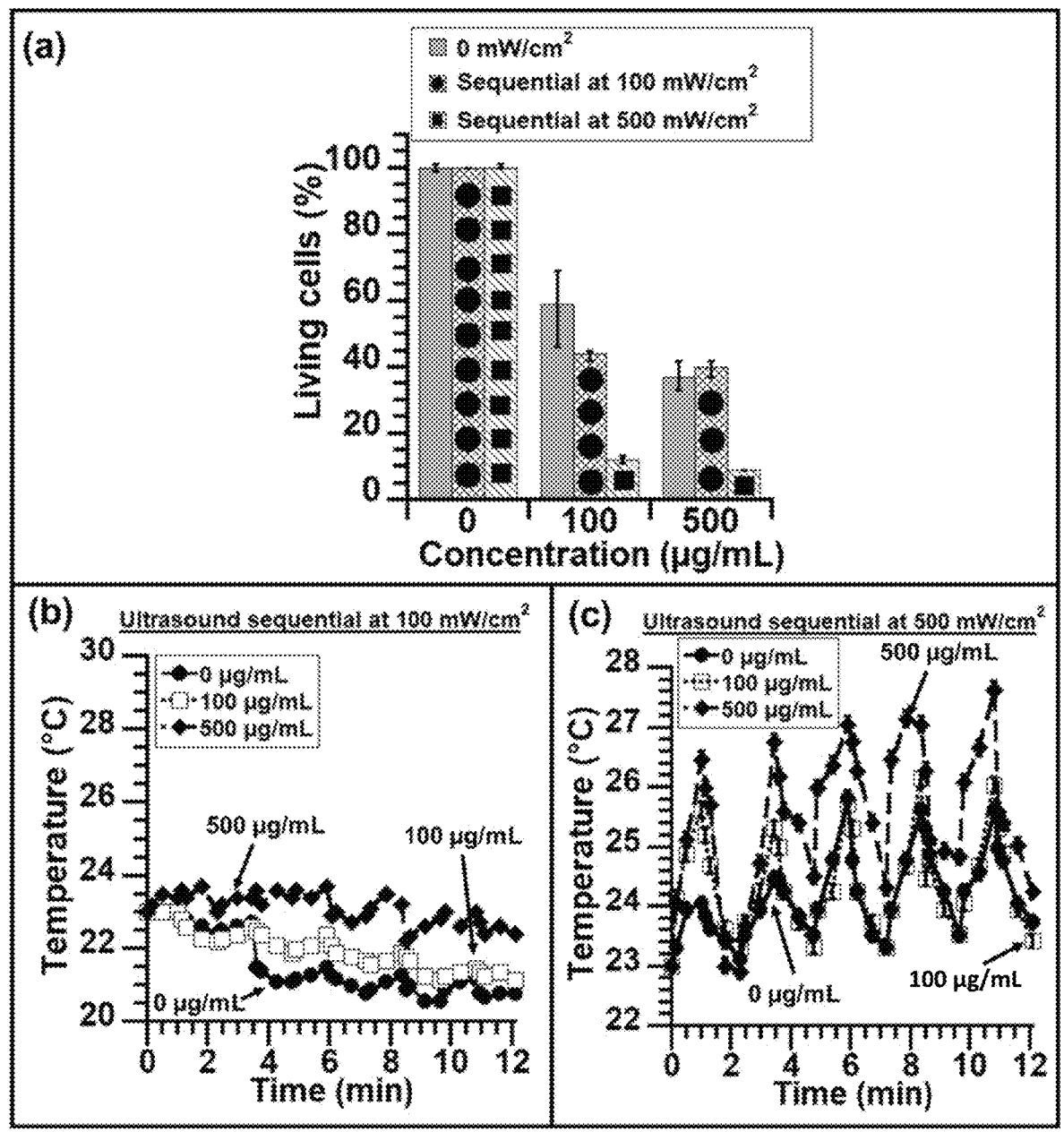
FIG. 6: (a) Histogram representing the percentage of living U87-MG cells after the following treatment: $2.5 \cdot 10^5$ U87-MG living cells are brought into contact with three concentrations of magnetosomes (0, 100 and 500 µg in iron of magnetosomes per mL), and sequentially exposed to ultrasounds. The details of the sequences are as follows: first application of ultrasound for 1 min (minute), no application of ultrasound during 1 min, second application of ultrasound for 1 min 24 s (second), no application of ultrasound during 1 min 24 s, third application of ultrasound for 1 min, no application of ultrasound during 1 min 30 s, fourth application of ultrasound for 1 min, no application of ultrasound during 1 min 18 s, fifth application of ultrasound for 1 min 12 s, no application of ultrasound during 1 min 18 s. During the time of application of the ultrasounds, the ultrasound power was set at 100 mW/cm² (middle column containing ascending and descending lines with filled black circle inside), or at a power of 500 mW/cm² (right column hatched with a descending line and containing filled black square). The percentage of living cells resulting from the treatment without ultrasound exposure is indicated by the left gray column without hatching. (b) For $2.5 \cdot 10^5$ U87-MG cells, which are brought into contact with 3 different concentrations of magnetosomes, i.e. 0 mg/ml (dot with a solid black line), 100 µg/ml (white square with dashed lines) and 500 µg/ml (black diamond with half a solid line), and sequentially exposed to ultrasound at a power of 100 mW/cm² (details of the sequences are given in the legend of (a)), temperature variation measured during treatment. (c) For $2.5 \cdot 10^5$ U87-MG cells, which are brought into contact with 3 concentrations of magnetosomes, i.e. 0 mg/ml (dot with a solid black line), 100 µg/ml (white square with dashed lines) and 500 µg/mL (black diamond with half a solid line), and sequentially exposed to ultrasound at a power of 500 mW/cm² (details of the sequences are given in the legend of (a)), temperature variation measured during treatment.

FIG. 6(a) is a histogram showing the percentage of living U87-Luc cells after the following treatment: U87-Luc cells are brought into contact with 0, 100, or 500 μg in iron of magnetosomes per mL and exposed (or not) to ultrasounds of power 100 mW/cm$^2$ or 500 mW/cm$^2$, where cm$^2$ represents the transducer surface generating ultrasounds. As a whole, the results are similar to those obtained in FIG. 5(a) for a continuous application of the ultrasounds.

FIG. 6(b) is the temperature variation as a function of time, measured with an IR camera, of U86-Luc cells brought into contact with different quantities of magnetosomes, i.e. 0, 100, or 500 μg in iron of magnetosomes par mL, exposed in a sequential manner to ultrasounds of power 100 mW/cm$^2$ and frequency 1 MHz. FIG. 6(b) shows that for 0 and 100 μg/mL of magnetosomes sequentially exposed to ultrasounds of 100 mW/cm$^2$, the temperature slightly decreases from 23° C. to 21° C., possibly due to the environment of cells that is below 23° C., while for 500 μg/mL of magnetosomes sequentially exposed to ultrasounds of 100 mW/cm$^2$, the temperature remains globally unchanged or unvaried at 23° C.

FIG. 6(c) is the temperature variation over time, measured using an IR camera, of U87-Luc cells brought into contact with different magnetosome concentrations, i.e. 0, 100, or 500 μg in iron of magnetosomes per mL, sequentially exposed to ultrasounds of power 500 mW/cm$^2$ and frequency of 1 MHz. FIG. 6(c) shows series or sequences of moderate temperature increases followed by moderate temperature decreases, whose magnitudes are: 1.2-2° C. for 0 μg/mL of magnetosomes (without magnetosomes), 2.2-6° C. for 100 μg/mL of magnetosomes, and 2.4-4° C. for 500 μg/mL of magnetosomes. Variations of temperature are slightly more important in the presence than in the absence of magnetosomes, especially at 500 μg/mL but they remain very moderate.

We have shown the possibility of efficiently destroying U87 tumor cells by applying ultrasounds on these cells in the presence of magnetosomes under conditions in terms of ultrasounds power and frequency that are such that the sole application of the ultrasounds without the magnetosomes induces limited or no cellular toxicity.

When the quantity of magnetosomes continuously exposed to ultrasounds of 500 mW/cm$^2$ is increased from 100 μg/mL to 500 μg/mL, the treatment results either in the absence of additional heating at 100 μg/mL or to an additional temperature increase of 11° C. (15-4° C.) at 500 μg/mL, compared with the condition of ultrasound application of 500 W/cm$^2$ without magnetosomes (FIG. 5(c)). Despite the difference in heating properties between 100 and 500 μg/mL, these two conditions result in a similar percentage of living cells of 10% (FIG. 5(a)). When a quantity of 500 μg/mL of magnetosomes is sequentially exposed to ultrasounds of power 500 mW/cm$^2$, it results in moderate temperature increases and temperature decreases during the different sequences of 2.4-4° C. and in a percentage of living cells of 10%, which is similar to the percentage of living cells of 10% obtained by continuously applying ultrasounds of power 500 mW/cm$^2$ on 500 µg/mL of magnetosomes, yielding a more significant temperature increase of 15° C.

These results pave the way to effective treatment obtained at low magnetosome concentration and/or in conditions of limited or no temperature increase, thus potentially reducing the toxicity of nanoparticle-based treatment often combining high nanoparticle concentrations with strong heating such as those using magnetic hyperthermia currently tested in the clinic.

Example 4: Cellular Toxicity and Temperature Measurement of Cells Brought into Contact with Magnetosomes and Subjected (or not) to the Continuous or Sequential Application of the Laser Materials and Methods:

Magnetosomes used in this example ate M-CMD. U87-MG glioblastoma cells were purchased from ATCC (ATCC® HTB-14) and cultivated in High-Glucose Dulbecco's Modified Eagle's Medium (DMEM), supplemented with 1 mM pyruvate, 10% fetal calf serum, 100 units/mL of penicillin and 100 µg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 µL of cells was collected and mixed with 30 µL of 4% trypan blue to count the cells using a cell counter (Countess™ II FL Automated Cell Counter (Thermo Fisher scientific)) and thus to determine the cell concentration of the initial suspension. A volume of 100 µL of 10$^4$ cells was inserted in each well of a 96 well plate and the cells were incubated at 37° C. with 5% CO$^2$ for 24 hours so that the cells adhere at the surface of well. The cell medium was then removed and replaced either by a new medium without magnetosomes or a new medium containing magnetosomes at a concentration of 1 mg/mL in iron of magnetosomes.

BALB/3T3 clone A31 fibroblast cells were purchased from ATCC (ATCC®CCL-163)) and cultivated in High-Glucose Dulbecco's Modified Eagle's Medium (DMEM), supplemented with 1 mM pyruvate, 10% bovine calf serum, 100 units/mL of penicillin and 100 µg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 µL of cells was collected and mixed with 30 µL of 4% trypan blue to count the cells using a cell counter (Countess™ II FL Automated Cell Counter (Thermo Fisher scientific)) and thus to determine the cell concentration of the initial suspension. A volume of 100 µL of 10$^4$ cells was deposited in each well of a 96 well plate and the cells were incubated at 37° C. with 5% CO$_2$ for 24 hours so that the cells adhere at the surface of well. The cell medium was then removed and replaced either by a new medium without magnetosomes or a new medium containing magnetosomes at a concentration of 1 mg/mL in iron of magnetosomes.

U87-MG or 3T3 cells, treated as described above, were then either continuously exposed to a laser of average power 3 W/cm$^2$ during 6 minutes or sequentially exposed to the laser. The power of the laser used was ~3 W/cm$^2$, where the power is the ratio between the laser power at the end of the fiber and the exposed surface (the surface of the well). The wavelength of the laser was 808 nm. The beam of laser light was focused at the bottom of the well containing cells with/without magnetosomes.

The laser light was applied as follows:

For the continuous application of the laser, the laser was applied continuously during 6 minutes. For the sequential application of the laser, two conditions were tested. In condition 1, the cells were brought into contact with 1 mg/mL of magnetosomes and exposed sequentially to a laser in the following way: (a) for U87-MG: First sequence: i) application of the laser of average power 3 W/cm$^2$ during 60 seconds until the temperature reaches 45° C., ii) non-application of the laser during 18 seconds resulting in a temperature decrease from 45° C. to 37° C.; Second sequence: i) application of the laser of average power 3 W/cm$^2$ during 17.5 seconds resulting in a temperature increase from 37° C. to 45° C., ii) non-application of the laser during 24 seconds resulting in a temperature decrease from 45° C. to 37° C.; Third sequence: i) application of the laser of average power 3 W/cm$^2$ during 17.5 seconds resulting in a temperature increase from 37° C. to 45° C., ii) non-application of the laser during 20 seconds resulting in a temperature decrease from 45° C. to 37° C.; Fourth sequence: i) application of the laser of average power 3 W/cm$^2$ during 15.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm$^2$ during 15 seconds resulting in a temperature increase from 37° C. to 45° C., ii) non-application of the laser during 21.5 seconds resulting in a temperature decrease from 45° C. to 37° C.; sixth sequence: i) application of the laser of average power 3 W/cm$^2$ during 14.5 seconds resulting in a temperature increase from 37° C. to 45° C., ii) non-application of the laser during 21.5 seconds resulting in a temperature decrease from 45° C. to 37° C.; seventh sequence: i) application of the laser of average power 3 W/cm$^2$ during 15 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm$^2$ during 13.5 seconds resulting in a temperature increase from 37° C. to 45° C., ii) non-application of the laser during 22 seconds resulting in a temperature decrease from 45° C. to 37° C.; ninth sequence: i) application of the laser of average power at 3 W/cm$^2$ during 13 seconds resulting in a temperature increase from 37° C. to 45° C., ii) non-application of the laser during 21 seconds resulting in a temperature decrease from 45° C. to 37° C.; tenth sequence: i) application of the laser of average power 3 W/cm$^2$ during 15 seconds resulting in a temperature increase from 37° C. to 45° C., ii) non-application of the laser during 23 seconds resulting in a temperature decrease from 45° C. to 37° C.; eleventh sequence: i) application of the laser of average power at 3 W/cm$^2$ during 14.5 seconds resulting in a temperature increase from 37° C. to 45° C., ii) non-application of the laser during 23 seconds resulting in a temperature decrease from 45° C. to 37° C.; twelfth sequence: i) application of the laser of average power 3 W/cm² during 15 seconds resulting in a temperature increase from 37° C. to 45° C., ii) non-application of the laser during 25 seconds resulting in a temperature decrease from 45° C. to 37° C.; thirteenth sequence: i) application of the laser of average power 3 W/cm² during 14.5 seconds resulting in a temperature increase from 37° C. to 45° C., ii) non-application of the laser during 24.5 seconds resulting in a temperature decrease from 45° C. to 37° C.; fourteenth sequence: i) application of the laser of average power 3 W/cm² during 12.5 seconds resulting in a temperature increase from 37° C. to 45° C., ii) non-application of the laser during 24 seconds resulting in a temperature decrease from 45° C. to 37° C.; fifteenth sequence: i) application of the laser of average power 3 W/cm2 during 12.5 seconds resulting in a temperature increase from 37° C. to 45° C., ii) non-application of the laser during 18.5 seconds resulting in a temperature decrease from 45° C. to 37° C.; sixteenth sequence: i) application of the laser of average power 3 W/cm² during 15 seconds resulting in a temperature increase from 37° C. to 45° C., ii) non-application of the laser during 23 seconds resulting in a temperature decrease from 45° C. to 37° C.; seventeenth sequence: i) application of the laser of average power 3 W/cm² during 12.5 seconds resulting in a temperature increase from 37° C. to 45° C., ii) non-application of the laser during 22.5 seconds resulting in a temperature decrease from 45° C. to 37° C.; eighteenth sequence: i) application of the laser of average power 3 W/cm² during 13.5 seconds resulting in a temperature increase from 37° C. to 45° C., ii) non-application of the laser during 24 seconds resulting in a temperature decrease from 45° C. to 37° C.; nineteenth sequence: i) application of the laser of average power 3 W/cm² during 13.5 seconds resulting in a temperature increase from 37° C. to 45° C., ii) non-application of the laser during 21.5 seconds resulting in a temperature decrease from 45° C. to 37° C.; twentieth sequence: i) application of the laser an average power at 3 W/cm² during 14 seconds resulting in a temperature increase from 37° C. to 45° C., ii) non-application of the laser during 21 seconds resulting in a temperature decrease from 45° C. to 37° C.; twenty first sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twenty second sequence: i) application of the laser of average power 3 W/cm² during 14 seconds resulting in a temperature increase from 37° C. to 45° C., ii) non-application of the laser during 16 seconds resulting in a temperature decrease from 45° C. to 37° C. The total duration of the application of the laser is 6 min 2 sec. (b), for 3T3: First sequence: i) application of the laser of average power 3 W/cm² during 90 seconds until the temperature reaches 45° C., ii) non-application of the laser during 21 seconds resulting in a temperature decrease from 45° C. to 37° C.; Second sequence: i) application of the laser of average power 3 W/cm² during 17.5 seconds resulting in a temperature increase from 37° C. to 45° C., ii) non-application of the laser during 22 seconds resulting in a temperature decrease from 45° C. to 37° C.; Third sequence: i) application of the laser of average power 3 W/cm² during 17.5 seconds resulting in a temperature increase from 37° C. to 45° C., ii) non-application of the laser during 20.5 seconds resulting in a temperature decrease from 45° C. to 37° C.; Fourth sequence: i) application of the laser of average power 3 W/cm² during 14.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm² during 15.5 seconds resulting in a temperature increase from 37° C. to 45° C., ii) non-application of the laser during 19 seconds resulting in a temperature decrease from 45° C. to 37° C.; sixth sequence: i) application of the laser of average power 3 W/cm² during 15.5 seconds resulting in a temperature increase from 37° C. to 45° C., ii) non-application of the laser during 19.5 seconds resulting in a temperature decrease from 45° C. to 37° C.; seventh sequence: i) application of the laser of average power 3 W/cm² during 18.5 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 18.5 seconds resulting in a temperature increase from 37° C. to 45° C., ii) non-application of the laser during 21 seconds resulting in a temperature decrease from 45° C. to 37° C.; ninth sequence: i) application of the laser of average power 3 W/cm² during 20 seconds resulting in a temperature increase from 37° C. to 45° C., ii) non-application of the laser during 20 seconds resulting in a temperature decrease from 45° C. to 37° C.; tenth sequence: i) application of the laser of average power 3 W/cm² during 18.5 seconds resulting in a temperature increase from 37° C. to 45° C., ii) non-application of the laser during 19.5 seconds resulting in a temperature decrease from 45° C. to 37° C.; eleventh sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; twelfth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; thirteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fourteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fifteenth sequence: i) application of the laser of average power 3 W/cm² during 19.5 seconds resulting in a temperature increase from 37° C. to 45° C., ii) non-application of the laser during 21.5 seconds resulting in a temperature decrease from 45° C. to 37° C.; sixteenth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; seventeenth sequence: i) application of the laser of average power 3 W/cm² during 17.5 seconds resulting in a temperature increase from 37° C. to 45° C., ii) non-application of the laser during 19.5 seconds resulting in a temperature decrease from 45° C. to 37° C.; eighteenth sequence: i) application of the laser of average power 3 W/cm² during 17.5 seconds resulting in a temperature increase from 37° C. to 45° C., ii) non-application of the laser during 20 seconds resulting in a temperature decrease from 45° C. to 37° C.; nineteenth sequence: i) application of the laser of average power 3 W/cm² during 19 seconds resulting in a temperature increase from 37° C. to 45° C., ii) non-application of the laser during 18.5 seconds resulting in a temperature decrease from 45° C. to 37° C. In condition 2, the cells were not brought into contact with the magnetosomes and sequentially exposed to the laser using the same sequence durations those of condition 1.

During the application of the laser, the heating temperature was measured using the infra-red camera EasyIR-2 from the company Guide Infrared, which was positioned 20 cm above the well.

24 hours after the treatments, the medium with and without magnetosomes was removed and then replaced with a PBS buffer solution. The cells were washed twice with this buffer solution and then 100 μl of a solution of bromide of 3-(4,5-dimethylthiazol-2-yl)-2,5-diphenyl-tetrazolium at 1 mg/ml was brought into contact with the cells during 4 hours, the tetrazolium salt was removed and then replaced with 100 μL of isopropanol. After gentle stirring, absorbance was measured at 620 nm using a microplate spectrophotometer system. The percentage of living cells was determined by measuring the ratio between the optical density for the cells treated with laser and magnetosomes and the optical density measured for the cells treated alone without magnetosomes without the application of the laser, and the ratio was multiplied by 100.

Results:

FIGS. 7(b) and 8(b) show the temperature variations obtained when U87-Luc and 3T3 cells are not brought into contact with magnetosomes or are brought into contact with 1 mg/mL of magnetosomes and continuously exposed to the laser of average power 3 W/cm$^2$ during 6 minutes. The initial temperature before laser application is 21° C. For the concentration of 1 mg/mL a temperature of 50-54° C. is reached after 6 minutes of laser application, while in the absence of magnetosomes, a temperature of 25° C. is reached.

FIGS. 7(c) and 8(c) show the temperature variations obtained when U87-Luc and 3T3 cells are either brought into contact with 1 mg/mL of magnetosomes or are not brought into contact with the magnetosomes, and are then sequentially exposed to a laser of average power 3 W/cm$^2$. The total heating time for the continuous application of the laser is the similar to the total heating time of the sequential application.

The details of the sequences are as follows for U87-MG cells: First sequence: i) application of the laser of average power 3 W/cm$^2$ during 60 seconds until the temperature reaches 45° C., ii) non-application of the laser during 18 seconds resulting in a temperature decrease from 45° C. to 37° C.; Second sequence: i) application of the laser of average power 3 W/cm$^2$ during 17.5 seconds resulting in a temperature increase from 37° C. to 45° C., ii) non-application of the laser during 24 seconds resulting in a temperature decrease from 45° C. to 37° C.; Third sequence: i) application of the laser of average power 3 W/cm$^2$ during 17.5 seconds resulting in a temperature increase from 37° C. to 45° C., ii) non-application of the laser during 20 seconds resulting in a temperature decrease from 45° C. to 37° C.; Fourth sequence: i) application of the laser of average power at 3 W/cm$^2$ during 15.5 seconds resulting in a temperature increase from 37° C. to 45° C., ii) non-application of the laser during resulting in a temperature decrease from 45° C. to 37° C. during 20.5 seconds; Fifth sequence: i) application of the laser of average power 3 W/cm$^2$ during 15 seconds resulting in a temperature increase from 37° C. to 45° C., ii) non-application of the laser during resulting in a temperature decrease from 45° C. to 37° C. during 21.5 seconds; sixth sequence: i) application of the laser of average power 3 W/cm$^2$ during 14.5 seconds resulting in a temperature increase from 37° C. to 45° C., ii) non-application of the laser during 21.5 seconds resulting in a temperature decrease from 45° C. to 37° C.; seventh sequence: i) application of the laser of average power 3 W/cm$^2$ during 15 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm$^2$ during 13.5 seconds resulting in a temperature increase from 37° C. to 45° C., ii) non-application of the laser during 22 seconds resulting in a temperature decrease from 45° C. to 37° C.; ninth sequence: i) application of the laser of average power 3 W/cm$^2$ during 13 seconds resulting in a temperature increase from 37° C. to 45° C., ii) non-application of the laser during 21 seconds resulting in a temperature decrease from 45° C. to 37° C.; tenth sequence: i) application of the laser of average power 3 W/cm$^2$ during 15 seconds resulting in a temperature increase from 37° C. to 45° C., ii) non-application of the laser during 23 seconds resulting in a temperature decrease from 45° C. to 37° C.; eleventh sequence: i) application of the laser of average power 3 W/cm$^2$ during 14.5 seconds resulting in a temperature increase from 37° C. to 45° C., ii) non-application of the laser during 23 seconds resulting in a temperature decrease from 45° C. to 37° C.; twelfth sequence: i) application of the laser of average power 3 W/cm$^2$ during 15 seconds resulting in a temperature increase from 37° C. to 45° C., ii) non-application of the laser during 25 seconds resulting in a temperature decrease from 45° C. to 37° C.; thirteenth sequence: i) application of the laser of average power 3 W/cm$^2$ during 14.5 seconds resulting in a temperature increase from 37° C. to 45° C., ii) non-application of the laser during 24.5 seconds resulting in a temperature decrease from 45° C. to 37° C.; fourteenth sequence: i) application of the laser of average power 3 W/cm$^2$ during 12.5 seconds resulting in a temperature increase from 37° C. to 45° C., ii) non-application of the laser during 24 seconds resulting in a temperature decrease from 45° C. to 37° C.; fifteenth sequence: i) application of the laser of average power 3 W/cm$^2$ during 12.5 seconds resulting in a temperature increase from 37° C. to 45° C., ii) non-application of the laser during 18.5 seconds resulting in a temperature decrease from 45° C. to 37° C.; sixteenth sequence: i) application of the laser of average power 3 W/cm$^2$ during 15 seconds resulting in a temperature increase from 37° C. to 45° C., ii) non-application of the laser during 23 seconds resulting in a temperature decrease from 45° C. to 37° C.; seventeenth sequence: i) application of the laser of average power 3 W/cm$^2$ during 12.5 seconds resulting in a temperature increase from 37° C. to 45° C., ii) non-application of the laser during 22.5 seconds resulting in a temperature decrease from 45° C. to 37° C.; eighteenth sequence: i) application of the laser of average power 3 W/cm$^2$ during 13.5 seconds resulting in a temperature increase from 37° C. to 45° C., ii) non-application of the laser during 24 seconds resulting in a temperature decrease from 45° C. to 37° C.; nineteenth sequence: i) application of the laser of average power 3 W/cm$^2$ during 13.5 seconds resulting in a temperature increase from 37° C. to 45° C., ii) non-application of the laser during 21.5 seconds resulting in a temperature decrease from 45° C. to 37° C.; twentieth sequence: i) application of the laser of average power 3 W/cm$^2$ during 14 seconds resulting in a temperature increase from 37° C. to 45° C., ii) non-application of the laser during 21 seconds resulting in a temperature decrease from 45° C. to 37° C.; twenty first sequence: i) application of the laser of average power 3 W/cm$^2$ during 14.5 seconds resulting in a temperature increase from 37° C. to 45° C., ii) non-application of the laser during 23 seconds resulting in a temperature decrease from 45° C. to 37° C.; twenty second sequence: i) application of the laser of average power 3 W/cm² during 14 seconds resulting in a temperature increase from 37° C. to 45° C., ii) non-application of the laser during 16 seconds resulting in a temperature decrease from 45° C. to 37° C. The total duration of laser application is 6 min 2 sec.

The details of the sequences are as follows for 3T3 cells. First sequence: i) application of the laser an average power at 3 W/cm² during 90 seconds until the temperature reaches 45° C., ii) non-application of the laser during 21 seconds resulting in a temperature decrease from 45° C. to 37° C.; Second sequence: i) application of the laser of average power at 3 W/cm² during 17.5 seconds resulting in a temperature increase from 37° C. to 45° C., ii) non-application of the laser during 22 seconds resulting in a temperature decrease from 45° C. to 37° C.; Third sequence: i) application of the laser of average power 3 W/cm² during 17.5 seconds resulting in a temperature increase from 37° C. to 45° C., ii) non-application of the laser during 20.5 seconds resulting in a temperature decrease from 45° C. to 37° C.; Fourth sequence: i) application of the laser of average power 3 W/cm² during 14.5 seconds resulting in a temperature increase from 37° C. to 45° C., ii) non-application of the laser during 20.5 seconds resulting in a temperature decrease from 45° C. to 37° C.; Fifth sequence: i) application of the laser of average power 3 W/cm² during 15.5 seconds resulting in a temperature increase from 37° C. to 45° C., ii) non-application of the laser during 19 seconds resulting in a temperature decrease from 45° C. to 37° C.; sixth sequence: i) application of the laser of average power at 3 W/cm² during 15.5 seconds resulting in a temperature increase from 37° C. to 45° C., ii) non-application of the laser during 19.5 seconds resulting in a temperature decrease from 45° C. to 37° C.; seventh sequence: i) application of the laser of average power 3 W/cm² during 18.5 seconds resulting in a temperature increase from 37° C. to 45° C., ii) non-application of the laser during 20 seconds resulting in a temperature decrease from 45° C. to 37° C.; eighth sequence: i) application of the laser of average power 3 W/cm² during 18.5 seconds resulting in a temperature increase from 37° C. to 45° C., ii) non-application of the laser during 21 seconds resulting in a temperature decrease from 45° C. to 37° C.; ninth sequence: i) application of the laser of average power 3 W/cm² during 20 seconds resulting in a temperature increase from 37° C. to 45° C., ii) non-application of the laser during 20 seconds resulting in a temperature decrease from 45° C. to 37° C.; tenth sequence: i) application of the laser of average power 3 W/cm² during 18.5 seconds resulting in a temperature increase from 37° C. to 45° C., ii) non-application of the laser during 19.5 seconds resulting in a temperature decrease from 45° C. to 37° C.; eleventh sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; twelfth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; thirteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fourteenth sequence: i) application of the laser of average power 3 W/cm² during 17.5 seconds resulting in a temperature increase from 37° C. to 45° C., ii) non-application of the laser during 18.5 seconds resulting in a temperature decrease from 45° C. to 37° C.; fifteenth sequence: i) application of the laser of average power 3 W/cm² during 19.5 seconds resulting in a temperature increase from 37° C. to 45° C., ii) non-application of the laser during 21.5 seconds resulting in a temperature decrease from 45° C. to 37° C.; sixteenth sequence: i) application of the laser of average power 3 W/cm² during 18 seconds resulting in a temperature increase from 37° C. to 45° C., ii) non-application of the laser during 19.5 seconds resulting in a temperature decrease from 45° C. to 37° C.; seventeenth sequence: i) application of the laser of average power 3 W/cm² during 17.5 seconds resulting in a temperature increase from 37° C. to 45° C., ii) non-application of the laser during 19.5 seconds resulting in a temperature decrease from 45° C. to 37° C.; eighteenth sequence: i) application of the laser of average power 3 W/cm² during 17.5 seconds resulting in a temperature increase from 37° C. to 45° C., ii) non-application of the laser during 20 seconds resulting in a temperature decrease from 45° C. to 37° C.; nineteenth sequence: i) application of the laser of average power 3 W/cm² during 19 seconds resulting in a temperature increase from 37° C. to 45° C., ii) non-application of the laser during 18.5 seconds resulting in a temperature decrease from 45° C. to 37° C. FIGS. 7(c) and 8(c) show that: i) in the presence of 1 mg/mL of magnetosomes, heating and cooling steps can be reached, and ii) in the absence of magnetosomes, the cells do not produce any heat, and heating and cooling steps can't be reached.

FIGS. 7(a) and 8(a) show the percentage of living cells for U87-MG cells (FIG. 7(a)) and 3T3 cells (FIG. 8(a)) brought into contact with 1 mg/mL of magnetosomes (right column) or not brought into contact with the magnetosomes (left column) and either not exposed to the laser (control, W/O L), exposed continuously to the laser of an average power 3 W/cm² during 6 minutes (Continuous L), or sequentially exposed to the laser of an average power 3 W/cm² during ~13 minutes (Sequential L).

FIG. 7(a) shows that when the quantity of magnetosomes brought into contact with U87-MG cells is increased from 0 to 1 mg/mL, the percentage of living cells decreases: from 100% to 65% (no laser application), 95% to 25% (continuous laser application), 95% to 10% (sequential laser application).

FIG. 8(a) shows that when the quantity of magnetosomes brought into contact with 3T3 cells is increased from 0 to 1 mg/mL, the percentage of living cells decreases: from 100% to 85% (no laser application), 95% to 40% (continuous laser application), 95% to 15% (sequential laser application).

In conclusion, we have shown that:
i) It was possible to carry out regular or periodic sequences of temperature increase up to 45° C. of average duration 16 seconds by applying the laser of an average power 3 W/cm2 followed by temperature decreases from 45° C. to 37° C. of average duration 22 seconds by not applying the laser.
ii) The sequential application of the laser enables destroying more cells than the continuous application of the laser for the two studied cell lines (U87-Luc and 3T3 cells).

Example 5: ROS Production

Materials and Methods:
Magnetosomes M-CMD were used. U87-MG glioblastoma cells and CAL-33 were purchased from ATCC and cultivated in High-Glucose Dulbecco's Modified Eagle's Medium (DMEM), supplemented with 1 mM pyruvate, 10% fetal calf serum, 100 units/mL of penicillin and 100 µg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 µL of cells was collected and mixed with 30 µL of 4% trypan blue to count the cells using a cell counter (Countess™ II FL Automated Cell Counter (Thermo Fisher scientific)) and thus to determine the cell concentration of the initial suspension. A volume of 100 µL of 104 cells was deposited per well in 96 plate well and then incubated at 37° C. with 5% CO2 for 24 hours so that the cells adhere at the surface of well. The cell medium was then removed and replaced by a new medium containing 2',7' dichlorofluoresceine diacetate (DCFH-DA) at a concentration of 100 µM. The cells were then incubated during 45 minutes at 37° C. with 5% CO2, and the medium was removed and replaced by PBS to rinse the cells and measure the production of intracellular ROS. Then PBS was replaced by a new medium without magnetosomes or a new medium containing magnetosomes at a concentration of: i) 1 mg/mL in iron of magnetosomes for U87-MG exposed to the AMF or laser or ii) 1000, 500, 250 and 16 µg/mL in iron of magnetosomes for cal33 cells exposed to gamma radiation. BALB/3T3 clone A31 fibroblast cells were purchased from ATCC (ATCC®CCL-163)) and cultivated in High-Glucose Dulbecco's Modified Eagle's Medium (DMEM), supplemented with 1 mM pyruvate, 10% bovine calf serum, 100 units/mL of penicillin and 100 µg/mL of streptomycin. The cells were seeded in a T175 flask with culture medium. When 80-90% confluence was reached, the supernatant was removed and replaced with PBS to rinse the cells. Subsequently, the PBS solution was removed and replaced with a volume of 5 mL of 0.25% trypsin-EDTA. The cells were incubated for 5 minutes at 37° C. with 5% carbon dioxide in an incubator with a humidity of 90-95%. The cells were then harvested. A volume of 10 ml of culture medium was added to deactivate the action of trypsin and the cells were homogenized. A volume of 30 µL of cells was collected and mixed with 30 µL of 4% trypan blue to count the cells using a cell counter (Countess™ II FL Automated Cell Counter (Thermo Fisher scientific)) and thus to determine the cell concentration of the initial suspension. A volume of 100 µL of 104 cells was deposited in each well of a 96 plate well and then incubated at 37° C. with 5% CO2 for 24 hours so that the cells adhere at the surface of the well. The cell medium was then removed and replaced by a new medium containing 2',7' dichlorofluoresceine diacetate (DCFH-DA) at a concentration of 100 µM. Cells were then incubated during 45 minutes at 37° C. with 5% CO2 and the medium was then removed and replaced by PBS to rinse the cells and measure the intracellular production of ROS. Then, PBS was replaced by: i) a new medium without magnetosomes, ii) a new medium containing magnetosomes at a concentration of 1 mg/mL in iron of magnetosomes for the AMF or laser treatment, or iii) 1000, 500, 250 and 16 µg/mL in iron of magnetosomes when cells are irradiated by gamma radiation. U87-MG or 3T3 cells, treated as described above, were then either continuously exposed to a laser of an average power 3 W/cm2 during 6 minutes or sequentially exposed to the laser. The power of the laser used was ~3 W/cm2 and the wavelength of the laser was 808 nm. The beam of laser light was focused at the bottom of the well containing cells with/without magnetosomes.

The laser light was applied as follows: For the continuous application of the laser, the laser was applied continuously during 6 minutes. For the sequential application of the laser, the sequences of application of the laser are described in the legend of FIG. 7(c).

The AMF was applied as follows: For the continuous application of AMF, the well containing cells with/without magnetosomes was positioned at the center of the coil and exposed to an AMF of strength of 34-47 mT and frequency 198 KHz pendant 30 minutes. For the sequential application of the laser, the details of the sequences used are given in the legend of FIG. 10(a).

During the application of the laser and AMF, the heating temperature was measured using the infra-red camera EasyIR-2 from the company Guide Infrared, which was positioned 20 cm above the well.

For gamma irradiation, the wells were placed at the center of a plate inside a GSR_D1 irradiator containing 4 sources of Cesium 137 (GSR Cs 137/° C.) of total activity 190 TBq, purchased from Gamma Service Medical GmbH. The irradiation dose was determined in real time by the time of exposure of the surface of the wells and therefore of the cells to the irradiations, whose time was comprised between 5 minutes and 1.7 hours, and irradiation doses were comprised between 5 and 80 Gy.

After 30 minutes of the treatment, the medium with and without magnetosomes was removed and then replaced with a PBS buffer solution. Fluorescence was measured at 530 nm with an excitation at 485 nm using a microplate fluorometer system. The rate of ROS production was determined by subtraction between the intensity of fluorescence measured for the cells treated with laser or AMF or gamma radiation and magnetosomes and the intensity of fluorescence measured for the cells treated alone without magnetosomes without the application of the laser or AMF or gamma radiation, and this ratio was multiplied by 100.

For MTT assay, 72 hours after the treatments, the medium with and without magnetosomes was removed and then replaced with a PBS buffer solution. The cells were washed twice with this buffer solution and then 100 µl of a solution of bromide of 3-(4,5-dimethylthiazol-2-yl)-2,5-diphenyl-tetrazolium at 1 mg/ml was brought into contact with the cells during 4 hours, the tetrazolium salt was removed and then replaced with 100 µL of isopropanol. After gentle stirring, absorbance was measured at 620 nm. The percentage of living cells was determined by measuring the ratio between the optical density measured for the cells treated with laser or AMF or gamma radiation and magnetosomes and the optical density measured for the cells treated alone without magnetosomes without the application of the laser or AMF or gamma radiation, and the ratio was multiplied by 100.

Results:

The rate of ROS production corresponds to the percentage of free radical produced such as singlet oxygen, peroxides, anion superoxide or hydroxyl that have reacted with DCFH-DA, in the presence of cells brought (or not) into contact with the magnetosomes, and continuously or sequentially exposed to the laser, AMF, or gamma radiation.

Figure 7:
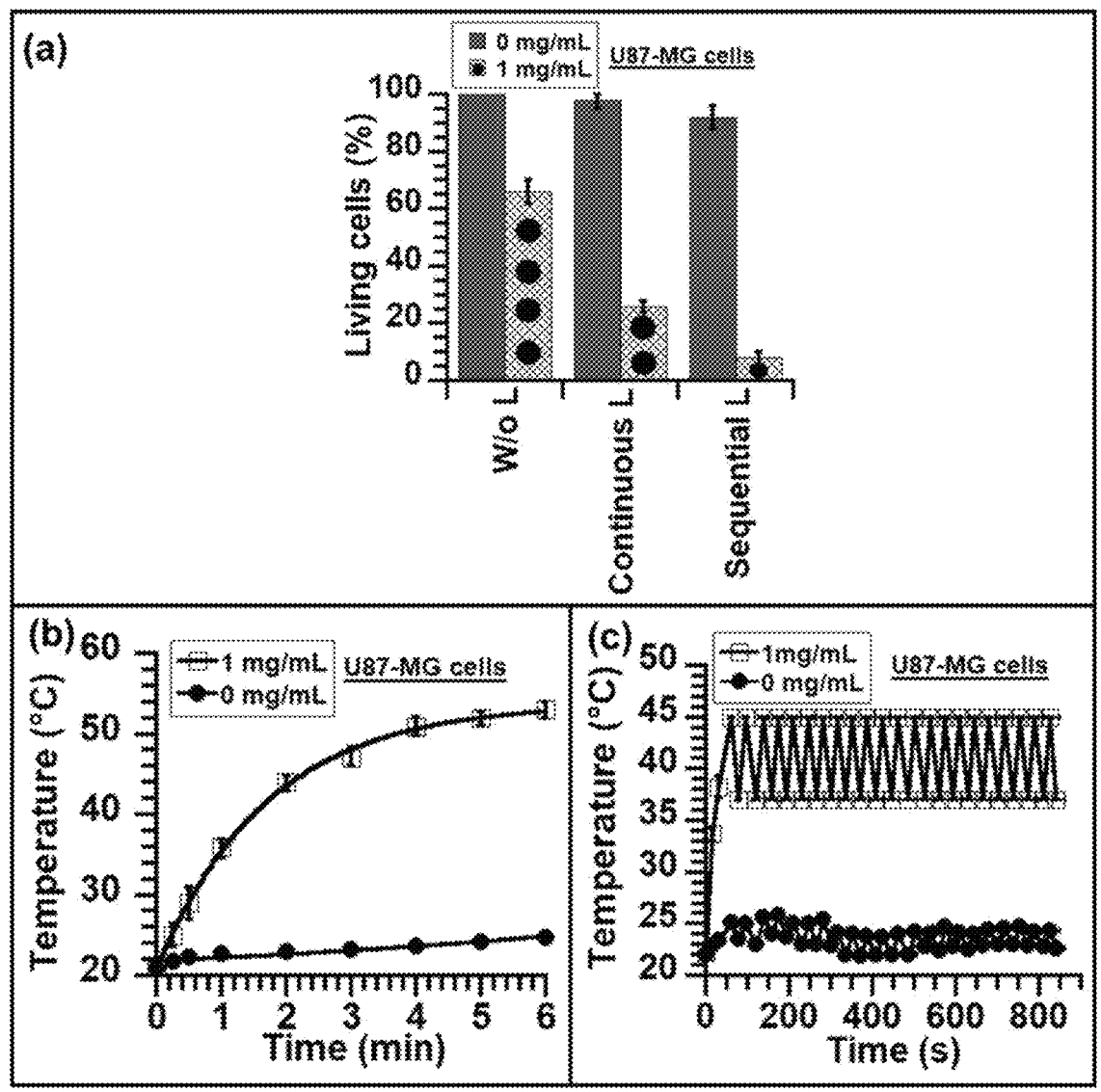
FIG. 7: (a) Percentage of living cells after the following treatment: U87-MG cells are brought into contact with 1 mg/mL in iron of magnetosomes or not brought into contact with magnetosomes (0 mg/mL) and either not exposed to the laser (W/o L), exposed sequentially to the laser with an average power at 3 W/cm², where the details of the sequences are given in the legend of (c) (Sequential L), or exposed continuously to the laser with an average power at 3 W/cm² during 6 minutes (continuous L). (b) Variation as a function of time of the temperature of U87-MG cells brought into contact with 0 mg/mL and 1 mg/mL of magnetosomes and exposed continuously to a laser with an average power at 3 W/cm² during 6 minutes. (c) Variation as a function of time of the temperature of U87-MG cells brought into contact with 0 mg/mL and 1 mg/mL of magnetosomes and sequentially exposed to a laser an average power at 3 W/cm². The details of the sequences are as follows: First sequence: i) application of the laser an average power at 3 W/cm² during 60 seconds until the temperature reaches 45° C., ii) non-application of the laser during 18 seconds resulting in a temperature decrease from 45° C. to 37° C.; Second sequence: i) application of the laser an average power at 3 W/cm2 during 17.5 seconds resulting in a temperature increase from 37° C. to 45° C., ii) non-application of the laser during resulting in a temperature decrease from 45° C. to 37° C. during 24 seconds; Third sequence: i), application of the laser of average power at 3 W/cm² during 17.5 seconds resulting in a temperature increase from 37° C. to 45° C., ii) non-application of the laser during resulting in a temperature decrease from 45° C. to 37° C. during 20 seconds; Fourth sequence: i) application of the laser an average power at 3 W/cm² during 15.5 seconds resulting in a temperature increase from 37° C. to 45° C., ii) non-application of the laser during resulting in a temperature decrease from 45° C. to 37° C. during 20.5 seconds; Fifth sequence: i) application of the laser an average power at 3 W/cm² during 15 seconds resulting in a temperature increase from 37° C. to 45° C., ii) non-application of the laser during 21.5 seconds resulting in a temperature decrease from 45° C. to 37° C.; sixth sequence: i) application of the laser an average power at 3 W/cm² during 14.5 seconds resulting in a temperature increase from 37° C. to 45° C., ii) non-application of the laser during 21.5 seconds resulting in a temperature decrease from 45° C. to 37° C.; seventh sequence: i) application of the laser an average power at 3 W/cm² during 15 seconds resulting in a temperature increase from 37° C. to 45° C., ii) non-application of the laser during 20 seconds resulting in a temperature decrease from 45° C. to 37° C.; eighth sequence: i) application of the laser an average power at 3 W/cm² during 13.5 seconds resulting in a temperature increase from 37° C. to 45° C., ii) non-application of the laser during 22 seconds resulting in a temperature decrease from 45° C. to 37° C.; ninth sequence: i) application of the laser of average power 3 W/cm² during 13 seconds resulting in a temperature increase from 37° C. to 45° C., ii) non-application of the laser during 21 seconds resulting in a temperature decrease from 45° C. to 37° C.; tenth sequence: i) application of the laser of average power 3 W/cm² during 15 seconds resulting in a temperature increase from 37° C. to 45° C., ii), non-application of the laser during 23 seconds resulting in a temperature decrease from 45° C. to 37° C.; eleventh sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twelfth sequence: i) application of the laser an average power at 3 W/cm² during 15 seconds resulting in a temperature increase from 37° C. to 45° C., ii) non-application of the laser during 25 seconds resulting in a temperature decrease from 45° C. to 37° C.; thirteenth sequence: i) application of the laser of average power at 3 W/cm² during 14.5 seconds resulting in a temperature increase from 37° C. to 45° C., ii) non-application of the laser during 24.5 seconds resulting in a temperature decrease from 45° C. to 37° C.; fourteenth sequence: i) application of the laser of average power 3 W/cm² during 12.5 seconds resulting in a temperature increase from 37° C. to 45° C., ii) non-application of the laser during 24 seconds resulting in a temperature decrease from 45° C. to 37° C.; fifteenth sequence: i) application of the laser of average power 3 W/cm² during 12.5 seconds resulting in a temperature increase from 37° C. to 45° C., ii) non-application of the laser during 18.5 seconds resulting in a temperature decrease from 45° C. to 37° C.; sixteenth sequence: i) application of the laser of average power 3 W/cm² during 15 seconds resulting in a temperature increase from 37° C. to 45° C., ii), non-application of the laser during 23 seconds resulting in a temperature decrease from 45° C. to 37° C.; seventeenth sequence: i) application of the laser of average power 3 W/cm² during 12.5 seconds resulting in a temperature increase from 37° C. to 45° C., ii) non-application of the laser during 22.5 seconds resulting in a temperature decrease from 45° C. to 37° C.; eighteenth sequence: i) application of the laser of average power 3 W/cm² during 13.5 seconds resulting in a temperature increase from 37° C. to 45° C., ii) non-application of the laser during 24 seconds resulting in a temperature decrease from 45° C. to 37° C.; nineteenth sequence: i) application of the laser of average power 3 W/cm² during 13.5 seconds resulting in a temperature increase from 37° C. to 45° C., ii) non-application of the laser during 21.5 seconds resulting in a temperature decrease from 45° C. to 37° C.; twentieth sequence: i) application of the laser of average power 3 W/cm² during 14 seconds resulting in a temperature increase from 37° C. to 45° C., ii) non-application of the laser during 21 seconds resulting in a temperature decrease from 45° C. to 37° C.; twenty first sequence: i) application of the laser of average power 3 W/cm² during 14.5 seconds resulting in a temperature increase from 37° C. to 45° C., ii) non-application of the laser during 23 seconds resulting in a temperature decrease from 45° C. to 37° C.; twenty second sequence: i) application of the laser of average power 3 W/cm² during 14 seconds resulting in a temperature increase from 37° C. to 45° C., ii) non-application of the laser during 16 seconds resulting in a temperature decrease from 45° C. to 37° C. The total duration of laser application was 6 min 2 sec.

FIGS. 9(a) and 9(b) show the rate of ROS production after the following treatment: 3T3 and U87-MG cells are brought into contact with 1 mg/mL in iron of magnetosomes (M-CMD) or not brought into contact with magnetosomes (0 mg/mL) and either not exposed to the laser (W/o L), exposed continuously to the laser of average power 3 W/cm² during 6 minutes, or exposed sequentially to the laser of average power 3 W/cm², where the details of the sequences are described in the legend of FIGS. 7 and 8.

For 3T3 cells, in the absence of the magnetosomes, cells continuously or sequentially exposed to the laser yield a similar low percentage of ROS production of ~30%. In the presence of the magnetosomes, this rate of 30% increases: i) moderately by a factor of ~3 without laser excitation up to 100%, ii) more importantly by a factor of 15 for the continuous laser excitation up to 450%, and iii) strongly by a factor of 22 for the sequential laser excitation up to 650% (FIG. 9(*a*)).

A similar behavior is observed with U87-MG cells. In the absence of the magnetosomes, U87-MG cells continuously or sequentially exposed to the laser yield a similar low percentage of ROS production of ~50%. In the presence of the magnetosomes, this rate of 50% increases: i) moderately by a factor of 3 without laser excitation up to 150%, ii) more importantly by a factor of 11 for continuous laser excitation up to 550%, and iii) strongly by a factor 16 for the sequential application up to 800% (FIG. 9(*b*)).

FIGS. 10(*a*) and 10(*b*) show the rate of ROS production after the following treatment: 3T3 and U87-MG cells are brought into contact with 1 mg/mL in iron of magnetosomes or not brought into contact with magnetosomes (0 mg/mL) and either not exposed to the AMF (W/o AMF), continuously exposed to the AMF, or sequentially exposed to the AMF, where the details of the continuous and sequential applications are given in the legend of FIG. 10.

For 3T3 cells, in the absence of the magnetosomes, cells continuously or sequentially exposed to the AMF yield a low percentage of ROS of 30-50%. In the presence of the magnetosomes, this rate of 30-50% increases: i) moderately up to 100% in the absence of AMF application, ii) more importantly up to 810% in the presence of a continuous AMF application, iii) strongly up to 1100% in the presence of a sequential AMF application (FIG. 10(*a*)).

A similar behavior is observed with U87-MG cells. In the absence of the magnetosomes, U87-MG cells continuously or sequentially exposed to the AMF yield a low percentage of ROS production of 50-80%. In the presence of the magnetosomes, this rate of 50-80% increases: i) moderately up to 200% in the absence of AMF application, ii) more importantly up to 1450% in the presence of the continuous AMF application, iii) strongly up to 1700% in the presence of a sequential AMF application.

FIG. 11(*a*) shows the percentage of living cells after the following treatment: 3T3 cells are brought into contact with 1000, 500, 250, or 16 μg/mL in iron of magnetosomes or not brought into contact with magnetosomes (0 mg/mL) and either not exposed to gamma irradiation, or exposed to different doses of gamma irradiation (5, 10, 20, 40, and 80 Gy). Cells without magnetosomes exposed to gamma radiations of 5, 10, 20, 40, and 80 Gy, yield a percentage of living cells of 80, 70, 65, 60 and 60%, respectively. Relatively similar results are obtained when the cells are brought into contact with 16 μg/mL of magnetosomes. When the magnetosome concentration is increased from 250 to 1000 μg/mL, the percentage of living cells decreases from 70% to 45%. The percentage of living cells slightly decreases in the presence of gamma radiation, but the presence of the magnetosomes at the different concentration does not seem to amplify the magnitude of this decrease.

FIG. 11(*b*) shows the rate of ROS production after the following treatment: 3T3 cells are brought into contact with 1000, 500, 250, 16 μg/mL in iron of magnetosomes or not brought into contact with magnetosomes (0 mg/mL) and either not exposed to gamma irradiation, or exposed to different doses of gamma radiation (5, 10, 20, 40, and 80 Gy). Cells without magnetosomes and exposed to different doses of gamma radiation (5, 10, 20, 40, and 80 Gy) yield a low percentage of ROS production of 200%. These results are relatively similar for the magnetosome concentration of 16 μg/mL. For magnetosome concentrations (in iron) larger than 250 μg/mL, the rate of ROS production strongly increases: i) from 50% at 0 Gy to 1050% at 80 Gy for 250 μg/mL of M-CMD, ii) from 150% at 0 Gy to 1250% at 80 Gy for 500 μg/mL of M-CMD, iii) from 200% at 0 Gy to 1600% at 80 Gy for 1000 μg/mL of M-CMD.

FIG. 12(*a*) shows the percentage of living cells after the following treatment: Cal 33 cells are brought into contact with 1000, 500, 250, 16 μg/mL in iron of magnetosomes or not brought into contact with magnetosomes (0 mg/mL) and either not exposed to gamma irradiation, or exposed to different doses of gamma irradiation (5, 10, 20, 40, and 80 Gy). Cells without magnetosomes exposed to gamma radiations 5, 10, 20, 40 and 80 Gy, yield a percentage of living cells of 98, 98, 95, 80 and 80%, respectively. The percentage of living cells strongly decreases in the presence of the magnetosomes. In the absence of irradiation, the percentage of living cells decreases from 100% at 16 μg/mL of magnetosomes down to 0% at 1000 μg/mL. Interestingly, while in the absence of magnetosomes, the percentage of living cells decreases with irradiation, in the presence of magnetosomes, the percentage of living cells can increase. Indeed, when 250 μg/mL of magnetosomes are irradiated at 5 Gy, the percentage of living cells increases from 5% (absence of irradiation) to 35% (5 Gy of irradiation).

FIG. 12(*b*) shows the rate of ROS production after the following treatment: Cal 33 cells are brought into contact with 1000, 500, 250, or 16 μg/mL in iron of magnetosomes or not brought into contact with magnetosomes (0 mg/mL) and either not exposed to gamma irradiation, or exposed to different doses of gamma radiation (5, 10, 20, 40 et 80 Gy). In the absence of magnetosomes, when Cal-33 cells alone are exposed to low power gamma radiation of 5 or 10 Gy, it does not yield ROS production. When these cells are exposed to gamma radiation of 20-80 Gy, it yields a rate of ROS production of 50-400%. In the presence of a magnetosome concentration of 250, 500, or 1000 μg/mL, the rate of ROS production strongly increases from ~50% in the absence of radiation to 1900-2400% in the presence of 80 Gy.

We can draw the following conclusions from this example:
  i) Magnetosome brought into contact with different cell lines (Cal-33, 3T3, U87-MG) produce ROS at a concentration of 1 mg/mL. For the cell lines Cal-33 and 3T3, the production of ROS is observed at 250, 500, and 1000 μg/mL, but not at 16 μg/mL, indicating that the amount of ROS produced in the absence of excitation source can be adjusted by varying the magnetosome concentration.
  ii) For the excitation sources (laser and AMF), the rate of ROS production is increased moderately by continuously applying the excitation on the magnetosomes and strongly increased by sequentially applying the excitation on the magnetosomes, both on 3T3 and U87-MG cells.
  iii) When 3T3 cells are irradiated with gamma radiation in the presence of magnetosomes (magnetosome concentration larger than 500 μg/mL), the rate of ROS production increases with increasing irradiation dose, while the cell viability does not strongly decrease with increasing irradiation dose. In the case of the healthy cells, the production of ROS does not seem to strongly affect cellular viability under gamma irradiation.

Table 1. For 210 μg in iron of nanoparticles Magnetosome inserted in 4.6 cm³ of tissue exposed to ultrasounds of frequency 3 MHz and power 0.5 W/cm², 1 W/cm², 1.5 W/cm², ($Slope_{(M)}$) designs the slope at the origin of the temperature variation with time of magnetosomes mixed with tissue ($Slope_{real(M)}$) designing the difference between slope at the origin of the temperature variation with time of magnetomes mixed with tissue ($Slope_{(M)}$) and the slope at the origin of the temperature variation with time of the tissue without the nanoparticles ($Slope_{(w)}$). $Slope_{realN(M)}$ is $Slope_{real(M)}$ divided by the magnetosome concentration in gram of iron comprised in magnetosomes per mL. Slope rise (Slope rise (M)) designates the percentage in slope rise estimated using the formula for magnetosomes: Slope rise $_{(M)}$ (%)=(($Slope_{(M)}/Slope_{(W)}$)−1)*100. The specific absorption rate of magnetosomes ($SAR_{(M)}$), estimated in watt per gram of magnetosomes is deduced from the values of $Slope_{(M)}$, using the formula: $SAR_{(M)}=C_v \cdot Slope_{(M)}/C_{nano}$, where $C_v=4.2$ $J \cdot K^{-1}$ $\mu g^{-1}$ is the specific heat of water and $C_{nano}$ is the magnetosome concentration in gram of magnetosomes per cm³ of tissue. The variation in temperature between the initial temperature measured before the application of the ultrasound and the temperature measured after 10 minutes of application of the ultrasound is designated as $\Delta T_{10min(M)}$ for magnetosomes. The difference between $\Delta T_{10min(M)}$ and $\Delta T_{10min(w)}$ is designated as $\Delta T_{10min,real(M)}$. The percentage in temperature rise is estimated for Magnetosomes using the formula: Temperature rise$_{(M)}$ (%)= (($\Delta T_{10min(M)}/\Delta T_{10min(W)}$)−1)*100 for Magnetosomes. For 210 μg in iron of Sigma nanoparticles inserted in 4.6 cm³ of tissue exposed to ultrasounds of frequency 3 MHz and power 0.5 W/cm², 1 W/cm², 1.5 W/cm², ($Slope_{(S)}$) designs the slope at the origin of the temperature variation with time of Sigma nanoparticles mixed with tissue ($Slope_{real(S)}$) designs the difference between slope at the origin of the temperature variation with time of Sigma nanoparticles mixed with tissue ($Slope_{(S)}$) and the slope at the origin of the temperature variation with time of the tissue without the nanoparticles ($Slope_{(w)}$). $Slope_{realN(S)}$ is $Slope_{real(S)}$ divided by the Sigma nanoparticle concentration in gram of iron comprised in Sigma nanoparticles per mL. Slope rise (Slope rise (S)) designates the percentage in slope rise estimated using the formula for magnetosomes: Slope rise$_{(S)}$ (%)= (($Slope_{(S)}/Slope_{(W)}$)−1)*100. The specific absorption rate of Sigma nanoparticles ($SAR_{(S)}$), estimated in watt per gram of Sigma nanoparticles is deduced from the values of Slope (s), using the formula: $SAR_{(S)}=C_v \cdot Slope_{(S)}/C_{nano}$, where $C_v=4.2$ $J \cdot K^{-11}$ $\mu g^{-1}$ is the specific heat of water and $C_{nano}$ is the Sigma nanoparticle concentration in gram of Sigma nanoparticles per cm³ of tissue. The variation in temperature between the initial temperature measured before the application of the ultrasound and the temperature measured after 10 minutes of application of the ultrasound is designated as $\Delta T_{10min(S)}$ for Sigma nanoparticles. The difference between $\Delta T_{10min(S)}$ and $\Delta T_{10min(w)}$ is designated as $\Delta T_{10min,real(S)}$. The percentage in temperature rise is estimated for Sigma nanoparticles using the formula: Temperature rise$_{(S)}$ (%)= (($\Delta T_{10min(S)}/\Delta T_{10min(W)}$)−1)*100 for Sigma nanoparticles.

TABLE 1

Heating on tissue

| | Water | | | | Magnetosome | | | | Sigma | | |
|---|---|---|---|---|---|---|---|---|---|---|---|
| | 0.5 W/cm² | 1 W/cm² | 1.5 W/cm² | | 0.5 W/cm² | 1 W/cm² | 1.5 W/cm² | | 0.5 W/cm² | 1 W/cm² | 1.5 W/cm² |
| $Slope_{(w)}$ (° C./sec) | 0.063 | 0.145 | 0.142 | $Slope_{(M)}$ (° C./sec) | 0.092 | 0.158 | 0.318 | $Slope_{(S)}$ (° C./sec) | 0.137 | 0.197 | 0.184 |
| | | | | $Slope_{real\,(M)}$ (° C./sec) | 0.029 | 0.013 | 0.177 | $Slope_{real\,(S)}$ (° C./sec) | 0.074 | 0.052 | 0.042 |
| | | | | $Slope_{real\,N(M)}$ (mL. ° C./sec/$g_{Fe}$) | 3 | 1 | 17 | $Slope_{real\,N(S)}$ (° C./sec/$g_{Fe}$) | 7 | 5 | 4 |
| | | | | Slope rise$_{(M)}$ (%) | 47 | 9 | 124 | Slope rise$_{(S)}$ (%) | 118 | 36 | 30 |
| | | | | $SAR_{(M)}$ (W/$g_{Fe}$) | 37 | 64 | 128 | $SAR_{(S)}$ (W/$g_{Fe}$) | 52 | 75 | 70 |
| | | | | $SAR_{real\,(M)}$ (W/$g_{Fe}$) | 12 | 5 | 71 | $SAR_{real\,(S)}$ (W/$g_{Fe}$) | 28 | 20 | 16 |
| $\Delta T_{10\,min\,(w)}$ (° C.) | 16 | 32 | 28 | $\Delta T_{10\,min\,(M)}$ (° C.) | 22 | 40 | 56 | $\Delta T_{10\,min\,(S)}$ (° C.) | 30 | 38 | 35 |
| | | | | $\Delta T_{10\,min\,real\,(M)}$ (° C.) | 6 | 8 | 28 | $\Delta T_{10\,min\,real\,(S)}$ (° C.) | 14 | 6 | 7 |
| | | | | Temperature rise$_{(M)}$ (%) | 37 | 25 | 100 | Temperature rise$_{(S)}$ (%) | 90 | 17 | 26 |

Table 2. For 100 μg in iron of nanoparticles (Magnetosome, Sigma, SPION20, SPION50, SPION100) dispersed in 100 μl of water exposed to ultrasounds of frequency 3 MHz and power 0.5 W/cm², 1 W/cm², 1.5 W/cm², slopes at the origin of the temperature variation with time of the different nanoparticles dispersed in water, designated as $Slope_{(M)}$ for Magnetosome, $Slope_{(S)}$ for Sigma nanoparticles, $Slope_{(S20)}$ for SPION20, $Slope_{(S50)}$ for SPION50, $Slope_{(S100)}$ for SPION100. The difference between the slope at the origin of the temperature variation with time of nanoparticles dispersed in water and the slope at the origin of the temperature variation with time of water without the nanoparticles is designated by $Slope_{real(M)}$ for Magnetosome, $Slope_{real(S)}$ for Sigma nanoparticles, $Slope_{real(S20)}$ for SPION20, $Slope_{real(S50)}$ for SPION50, $Slope_{real(S100)}$ for SPION100. Values of slope rise in percentage estimated using the formula: $Sloperise_{(M)}$=(($Slope_{(M)}/Slope_{(W)}$)−1)*100 for magnetosomes; $Sloperise_{(S20)}$=(($Slope_{(S20)}/Slope_{(W)}$)−1)*100 for SPION20; Sloperise$_{(S50)}$=((Slope$_{(S50)}$/Slope$_{(W)}$−1)*100 for SPION50; Sloperise$_{(S100)}$=((Slope$_{(S100)}$/Slope$_{(W)}$−1)*100 for SPION100. The specific absorption rate (SAR), measured in watt per gram of nanoparticles, deduced from the values of Slope, using the formula: SAR$_{(M)}$=C$_v$·Slope$_{(M)}$/C$_{nano}$ for Magnetosome, SAR$_{(S)}$=C$_v$·Slope$_{(S)}$/C$_{nano}$ for Sigma nanoparticles, SAR$_{(S20)}$=C$_v$·Slope$_{(S20)}$/C$_{nano}$ for SPION20, SAR$_{(S50)}$=C$_v$·Slope$_{(S50)}$/C$_{nano}$ for SPION50, and SAR$_{(S100)}$=C$_v$·Slope$_{(S100)}$/C$_{nano}$ for SPION100, where C$_v$=4.2 J·K$^{-1}$g$^{-1}$ is the specific heat of water, C$_{nano}$ is the nanoparticle (Magnetosome, Sigma, SPION20, SPION50, or SPION100) concentration in gram of nanoparticles per mL of water. Slope$_{(M)}$, Slope$_{(S)}$, Slope$_{(S20)}$, Slope$_{(S50)}$, Slope$_{(S100)}$ are the initial slopes of the temperature variation for Magnetosome, Sigma nanoparticles, SPION20, SPION50, and SPION100. The real specific absorption rate (SAR$_{real}$), measured in watt per gram of nanoparticles is deduced from the values of Slope$_{real}$, using the formula: SAR$_{real(M)}$=C$_v$·Slope$_{real(M)}$/C$_{nano}$ for magnetosomes, SAR$_{real(S)}$=C$_v$·Slope$_{real(S)}$/C$_{nano}$ for Sigma nanoparticles, SAR$_{real(S20)}$=C$_v$·Slope$_{real(S20)}$/C$_{nano}$ for SPION20, SAR$_{real(S50)}$=C$_v$·Slope$_{real(S50)}$/C$_{nano}$ for SPION50, SAR$_{real(S100)}$=C$_v$·Slope$_{real(S100)}$/C$_{nano}$ for SPION100, where C$_v$=4.2 J·K$^{-1}$g$^{-1}$ is the specific heat of water and C$_{nano}$ is the nanoparticle (Magnetosome, Sigma, SPION20, SPION50, or SPION100) concentration in gram of nanoparticles per mL of water. Slope$_{real(M)}$, Slope$_{real(S)}$, Slope$_{real(S20)}$, Slope$_{real(S50)}$ Slope$_{real(S100)}$ designate the difference between the initial slope of the temperature variation with time of nanoparticles dispersed in water and the initial slope of the temperature variation with time of water without nanoparticles. For nanoparticles dispersed in water, the variation in temperature between the initial temperature measured before the application of the ultrasound and the temperature measured after 10 minutes of application of the ultrasound is designated as $\Delta T_{10min(W)}$ for water alone, $\Delta T_{10min(M)}$ for Magnetosomes, $\Delta T_{10min(S)}$ for Sigma nanoparticles, $\Delta T_{10min(S20)}$ for SPION20, $\Delta T_{10min(S50)}$ for SPION50, $\Delta T_{10min(S100)}$ for SPION100. The differences between $\Delta T_{10min(M)}$ and $\Delta T_{10min(W)}$, $\Delta T_{10min(S)}$ and $\Delta T_{10min(W)}$, $\Delta T_{10min(S20)}$ and $\Delta T_{10min(W)}$, $T_{10min(S50)}$ and $\Delta T_{10min(W)}$, $\Delta T_{10min(S100)}$ and $\Delta T_{10min(W)}$, are designated as $\Delta T_{10minreal(M)}$, $\Delta T_{10minreal(S)}$, $\Delta T_{10minreal(S20)}$, $\Delta T_{10minreal(S50)}$, $\Delta T_{10minreal(S100)}$ for magnetosomes, Sigma nanoparticles, SPION20, SPION50, SPION100, respectively. The percentage in temperature rise, estimated for Sigma using the formula: Temperature rise (%)=(($\Delta T_{10min(S)}$/$\Delta T_{10min(W)}$)−1)*100, for Magnetosomes using the formula: Temperature rise (%)=(($\Delta T_{10min(S)}$/$\Delta T_{10min(W)}$)−1)*100, for SPION20 using the formula: Temperature rise (%)=(($\Delta T_{10min(S20)}$/$\Delta T_{10min(W)}$)−1)*100, for SPION50 using the formula: Temperature rise (%)= (($\Delta T_{10min(S50)}$/$\Delta T_{10min(W)}$)−1)*100, for SPION100 using the formula: Temperature rise (%)=(($\Delta T_{10min(S10)}$/$\Delta T_{10min(W)}$)−1)*100.

TABLE 2

| Heating on aqueous solutions | | | | | | | |
|---|---|---|---|---|---|---|---|
| Water | | | | Magnetosome | | | |
| | 0.5 W/cm² | 1 W/cm² | 1.5 W/cm² | | 0.5 W/cm² | 1 W/cm² | 1.5 W/cm² |
| Slope$_{(w)}$ (° C./sec) | 0.291 | 0.467 | 0.645 | Slope$_{(M)}$ (° C./sec) | 0.361 | 0.571 | 0.747 |
| | | | | Slope$_{real\,(M)}$ (° C./sec) | 0.070 | 0.104 | 0.101 |
| | | | | Slope$_{real\,N\,(M)}$ (mL. ° C./sec/g$_{Fe}$) | 70 | 104 | 101 |
| | | | | Slope rise$_{(M)}$ (%) | 24 | 22 | 16 |
| | | | | SAR$_{(M)}$ (W/g$_{Fe}$) | 1511.3 | 2389.5 | 3124.0 |
| | | | | SAR$_{real\,(M)}$ (W/g$_{Fe}$) | 294.5 | 437.0 | 424.3 |
| $\Delta T_{10\,min\,(w)}$ (° C.) | 13 | 20 | 30 | $\Delta T_{10\,min\,(M)}$ (° C.) | 18 | 29 | 33 |
| | | | | $\Delta T_{10\,min\,real\,(M)}$ (° C.) | 5 | 9 | 3 |
| | | | | Temperature rise$_{(M)}$ (%) | 37 | 43 | 10 |
| Sigma | | | | SPION 50 nm | | | |
| | 0.5 W/cm² | 1 W/cm² | 1.5 W/cm² | | 0.5 W/cm² | 1 W/cm² | 1.5 W/cm² |
| Slope$_{(S)}$ (° C./sec) | 0.275 | 0.503 | 1.287 | Slope$_{(S50)}$ (° C./sec) | 0.274 | 0.481 | 1.313 |
| Slope$_{real\,(S)}$ (° C./sec) | 0 | 0.036 | 0.642 | Slope$_{real\,(S50)}$ (° C./sec) | 0 | 0.015 | 0.668 |
| Slope$_{real\,N\,(S)}$ (mL. ° C./sec/g$_{Fe}$) | 0 | 36 | 642 | Slope$_{real\,N\,(S50)}$ (mL. ° C./sec/g$_{Fe}$) | 0 | 15 | 668 |
| Slope rise$_{(S)}$ (%) | 0 | 8 | 99 | Slope rise$_{(S50)}$ (%) | 0 | 3 | 104 |
| SAR$_{(S)}$ (W/g$_{Fe}$) | 1150.1 | 2104.7 | 5385.6 | SAR$_{(S50)}$(W/gFe) | 1145.5 | 2014.5 | 5495.0 |
| SAR$_{real\,(S)}$ (W/g$_{Fe}$) | 0 | 152.1 | 2685.9 | SAR$_{real\,(S50)}$ (W/gFe) | 0 | 62.0 | 2795.3 |
| $\Delta T_{10\,min\,(S)}$ (° C.) | 19 | 32 | 39 | $\Delta T_{10\,min\,(S50)}$ (° C.) | 15 | 26 | 34 |
| $\Delta T_{10\,min\,real\,(S)}$ (° C.) | 6 | 12 | 9 | $\Delta T_{10\,min\,real\,(S50)}$ (° C.) | 2 | 5 | 4 |
| Temperature rise$_{(S)}$ (%) | 49 | 60 | 31 | Temperature rise$_{(S50)}$ (%) | 18 | 27 | 14 |

TABLE 2-continued

| | Heating on aqueous solutions | | | | | | |
|---|---|---|---|---|---|---|---|
| | SPION 100 nm | | | | SPION 20 nm | | |
| | 0.5 W/cm² | 1 W/cm² | 1.5 W/cm² | | 0.5 W/cm² | 1 W/cm² | 1.5 W/cm² |
| Slope$_{(S100)}$ (° C./sec) | 0.300 | 0.446 | 0.992 | Slope$_{(S20)}$ (° C./sec) | 0.453 | 0.439 | 0833 |
| Slope$_{real\ (S100)}$ (° C./sec) | 0.009 | 0 | 0.346 | Slope$_{real\ (S20)}$ (° C./sec) | 0.162 | 0 | 0.188 |
| Slope$_{real\ N\ (S100)}$ (mL. ° C./sec/g$_{Fe}$) | 0 | 0 | 346 | Slope$_{real\ N\ (S20)}$ (mL. ° C./sec/g$_{Fe}$) | 162 | 0 | 188 |
| Slope rise$_{(S100)}$ (%) | 3 | 0 | 54 | Slope rise$_{(S20)}$ (%) | 56 | 0 | 29 |
| SAR$_{(S100)}$ (W/gFe) | 1253.2 | 1864.4 | 4149.1 | SAR$_{(S20)}$ (W/gFe) | 1894.2 | 1837.7 | 3486.8 |
| SAR$_{real\ (S100)}$ (W/gFe) | 36.4 | 0 | 1449.4 | SAR$_{real\ (S20)}$ (W/gFe) | 677.4 | 0 | 787.1 |
| ΔT$_{10\ min\ (S100)}$ (° C.) | 17 | 27 | 36 | ΔT$_{10\ min\ (S20)}$ (° C.) | 16 | 26 | 30 |
| ΔT$_{10\ min\ real\ (S100)}$ (° C.) | 4 | 7 | 6 | ΔT$_{10\ min\ real\ (S20)}$ (° C.) | 3 | 6 | 0 |
| Temperature rise$_{(S100)}$ (%) | 34 | 35 | 20 | Temperature rise$_{(S20)}$ (%) | 24 | 28 | 1 |

Table 3. For 500 μg of magnetosomes dispersed in 100 μl of water, exposed sequentially to ultrasounds, time $t_1$ necessary to reach the desired temperature of 43±1.5° C. during the heating step (application of an ultrasound of frequency 3 MHz and power 1.5 W/cm²), time $t_2$ necessary to reach 34.5±0.5° C. during the cooling step (non-application of ultrasound) during each of the 13 sequences, frequency of each sequence in mHz, $1/t_1+t_2$.

TABLE 3

| Utrasound sequences | Time of application of the ultrasound, $t_1$ = heating step (minuntes) | Time of non-application of the ultrasound, $t_2$ = cooling step (minutes) | f (mHz) |
|---|---|---|---|
| 1 | 0.43 | 0.2 | 26 |
| 2 | 0.26 | 0.36 | 27 |
| 3 | 0.22 | 0.27 | 34 |
| 4 | 0.21 | 0.27 | 35 |
| 5 | 0.23 | 0.23 | 36 |
| 6 | 0.22 | 0.27 | 34 |
| 7 | 0.24 | 0.26 | 33 |
| 8 | 0.2 | 0.24 | 38 |
| 9 | 0.2 | 0.21 | 41 |
| 10 | 0.24 | 0.3 | 31 |
| 11 | 0.2 | 0.25 | 37 |
| 12 | 0.24 | 0.28 | 32 |
| 13 | 0.25 | 0.29 | 31 |
| Mean | 0.24 | 0.26 | 33 |

The invention claimed is:

1. A method of medically treating a body part of an individual with an acoustic wave, consisting of:
   administering nanoparticles, optionally having a compound attached thereto, to the individual, said nanoparticles being located in a nanoparticle region selected from the group consisting of: i) a portion the body part, ii) a volume occupied by the nanoparticles in the body part, and iii) a volume occupied by the nanoparticles outside of the body part;
   applying the acoustic wave on the body part after administering the nanoparticles to the nanoparticle region, wherein the application of the acoustic wave increases an initial temperature of the body part to a temperature and corresponds to a temperature increase of the body part that has at least one property selected from the group consisting of:
   (i) the temperature increase of the body part is between 1 and 30° C.,
   (ii) the temperature increase of the body part is lower than 30° C., wherein the temperature increase of the body part is equal to $T_{NPBP}$ minus $T_{BP}$, where $T_{NPBP}$ is the temperature or the temperature increase of the body part of which the nanoparticles are exposed to the acoustic waves, and $T_{BP}$ is the temperature or temperature increase of the body part of which the nanoparticles are not exposed to the acoustic waves or the temperature or temperature increase of the body part not comprising the nanoparticles not exposed to the acoustic waves,
   wherein the application of the acoustic wave is part of at least one session, each session consists of
      more than one sequence of application of the acoustic wave, each sequence consisting of:
      a) an application of the acoustic wave for a time $t_1$; followed by non-application of the acoustic wave a time $t_2$, wherein the time $t_2$ is sufficiently short so that the temperature of the body part does not return to the initial temperature wherein the time $t_1$ is longer than one second, or
      b) an application of an acoustic wave during a time $t_1$ followed by an application of another acoustic wave during a time $t_3$, wherein the acoustic wave applied during the time $t_3$ has an intensity, a power, an energy, or a frequency lower than an intensity, a power, an energy or a frequency of the acoustic wave applied during the time $t_1$,
   wherein the time $t_1$ is longer than 1 second, wherein $t_3$ is sufficiently short so that the temperature of the body part does not return to the initial temperature,
   wherein a time lapse separating each session is longer than $t_1$, $t_2$, $t_3$, $t_1+t_2$, or $t_1+t_3$,
      wherein the acoustic wave has at least one property selected from the group consisting of:
      a) an intensity, power or power density that is lower than 10³ Watt, or Watt per a unit selected from the group consisting of: i) length or cm, ii) surface area or cm², iii) volume or cm³, iv) length or cm of body part, v) surface area or cm² of body part, vi) volume or cm³ of body part, vii) length or cm of transducer, viii) surface area or cm² of transducer, and ix) volume or cm³ of transducer, b) an intensity, a power or power density lower than $10^6$ W per gram of nanoparticles, c) an energy or energy density that is lower than $10^9$ W·sec or J, or W·sec or J per a unit selected from the group consisting of: i) length or cm, ii) surface area or cm², iii) volume or cm³, iv) length or cm of body part, v) surface area or cm² of body part, vi) volume or cm³ of body part, vii) length or cm of transducer, viii) surface area or cm² of transducer, ix) mass or gram of nanoparticles, and x) volume or cm² of transducer, and d) a frequency between 0.01 and 100 MHz.

2. The method according to claim 1, wherein $t_1$ is between 1 second and $10^{20}$ minutes and at least one of $t_2$, or $t_3$ is between $10^{-3}$ seconds and $10^{20}$ minutes.

3. The method according to claim 1, wherein the at least one session is more than two sequences.

4. The method according to claim 1,
wherein the acoustic wave is an unfocused acoustic wave having at least one property selected from the group consisting of:
i) the unfocused acoustic wave covers more than $10^{-5}\%$ by volume of the body part, using less than $10^3$ application spots,
ii) the unfocused acoustic wave is applied over an acoustic wave volume that is larger than $10^{-10}$ cm³,
iii) the unfocused acoustic wave is applied over an acoustic wave volume that is larger than the nanoparticle region to which nanoparticles have been administered, a body part, a healthy site, or a pathological site, and
iv) the unfocused acoustic wave is applied over an acoustic wave volume that is larger, than an acoustic wave volume that is reached by or exists with or results from a focused acoustic wave or the application of a focused acoustic wave,
wherein each of the application spots is defined as the acoustic volume that is covered during a single application of acoustic wave or during one sequence,
wherein the acoustic wave volume is one of a volume, that is exposed to the acoustic wave, a volume that receives the acoustic wave energy, or a volume that undergoes the effects of the acoustic wave,
wherein the healthy site is a site of the individual that comprises healthy cell(s),
wherein the pathological site is a site of the individual that comprises pathological cell(s),
wherein the acoustic volume of a focused acoustic wave is a volume that covers less than $10^5\%$ by volume of the body part, using more than 1 application spot or is a volume covered by a high intensity focused ultrasound.

5. The method according to claim 1, wherein the acoustic wave is not a focused ultrasound or is not a high intensity focused ultrasound.

6. The method according to claim 1, wherein the acoustic wave is an ultrasound.

7. The method according to claim 1, wherein the nanoparticles are administered to at least a portion of the body part.

8. The method according to claim 1, wherein the nanoparticles are sono-sensitizers.

9. The method according to claim 1, wherein the nanoparticles are magnetosomes.

10. The method according to claim 1, wherein the nanoparticles are chemical analogues of magnetosomes.

11. The method according to claim 7, wherein the nanoparticles, which are exposed to the acoustic wave, onto which the acoustic wave is applied, or which are located in the body part are at a concentration:
i) larger than $10^{-50}$ g of nanoparticles per cm³ of body part or of g of iron in nanoparticles per cm³ of body part, and/or
ii) lower than 10 g of nanoparticles per cm³ of body part or of g of iron in nanoparticles per cm³ of body part.

12. The method according to claim 1, wherein the medical treatment is a treatment of an infectious disease, a cancer, or tumor.

13. The method according to claim 12, wherein the cancer or tumor is selected from the group consisting of: cancer of an organ, cancer of blood, cancer of a system of a living organism, adrenal cancer, anal cancer, bile duct cancer, bladder cancer, bone cancer, brain cancer, breast cancer, cervical cancer, colon/rectum cancer, endometrial cancer, esophagus cancer, eye cancer, gallbladder cancer, heart cancer, kidney cancer, laryngeal and hypopharyngeal cancer, leukemia, liver cancer, lung cancer, nasal cavity and paranasal sinus cancer, nasopharyngeal cancer, neuroblastoma, non-Hodgkin lymphoma, oral cavity and oropharyngeal cancer, osteosarcoma cancer, ovarian cancer, pancreatic cancer, pancreatic penile cancer, prostate cancer, retinoblastoma, rhabdomyosarcoma, salivary gland cancer, sarcoma, skin cancer, small intestine cancer, stomach cancer, testicular cancer, thymus cancer, thyroid cancer, uterine cancer, uterine sarcoma cancer, vaginal cancer, vulvar cancer, waldenstrom macroglobulinemia wilms tumor, castleman disease ewing family of tumor, gastrointestinal carcinoid tumor, gastrointestinal stromal tumor, myelodysplastic syndrome pituitary tumor, gestational trophoblastic disease, Hodgkin's disease, kaposi sarcoma, malignant mesothelioma, and multiple myeloma.

14. The method according to claim 1, wherein the medical treatment is a treatment of a disease, which as at least one property selected from the group consisting of:
i) the disease is due to the malfunction of an organ or body part,
ii) the disease induces death, destruction, denaturation, or inactivation of at least 1 biological material selected from the group consisting of cell(s), RNA, DNA, protein(s), lipid(s), and enzyme(s), wherein the death of cell(s) can occur through apoptosis or necrosis.

15. The method according to claim 7, wherein a compound is attached to the nanoparticles, and the application of the acoustic wave on the body part to which the nanoparticles have been administered induces the dissociation of the compound from the nanoparticles.

16. The method according to claim 15, wherein the acoustic wave that is applied on the body part or onto the nanoparticles administered to the body part induces at least one dissociation of the compounder from the nanoparticle(s), optionally followed by non-dissociation(s) of the compounder from the nanoparticle(s).

17. The method according to claim 1, wherein the sequential application of the acoustic wave on the body part prevents a decrease of the temperature of the body part.

18. The method according to claim 4, wherein the application of the acoustic wave on the body part produces or generates at least one of:
i) radical or reactive species,
ii) a destruction or growth inhibition of pathological or tumor cells in the body part,
iii) death, destruction, denaturation, reduction in volume or inactivation of biological material(s) in the body part,
iv) a movement or vibration of the nanoparticles, v) an absorption of the acoustic wave or radiation by the nanoparticles, and vi) an internalization of the nanoparticles in cells, vii) bubbles, viii) cavitation, and ix) cavitation bubbles.

19. The method according to claim 1, wherein the nanoparticles are magnetosomes synthesized by, originating from, extracted from, or isolated from magnetotactic bacteria.

20. The method according to claim 7, wherein the acoustic waves is applied:

i) with a penetration depth in the body part between $10^{-5}$ and $10^5$ cm, and/or ii) on at least $10^{-5}\%$ in volume of the body part or nanoparticle(s), wherein the body part has regions with nanoparticles and/or regions without nanoparticles.

21. The method according to claim 4, wherein the acoustic wave is applied sequentially on the body part, according to a set of parameters selected from the group consisting of:

i) the acoustic wave is applied on a volume $V_1$ and the body part has a volume $V_2$, and $V_2$ that is either smaller or larger than $V_1$, ii) first, the acoustic wave is applied within a region, volume, surface, or length, which is larger than a region, volume, surface, or length comprising the nanoparticles, and second, the region, volume, surface or length comprising the nanoparticles absorbs the acoustic waves, produces a temperature increase, or yields anti-tumor activity or the destruction of the body part, pathological or tumor cells in the region, volume, surface or length not comprising the nanoparticles, and iii) first, the acoustic wave is applied within a region, volume, surface, length, which is smaller than a region, volume, surface, or length comprising the nanoparticles, and second, the region, volume, surface or length comprising the nanoparticles that have not been exposed or submitted to the application of the acoustic wave, produces a temperature increase, or yields anti-tumor activity or the destruction of body part, pathological or tumor cells.

22. The method according to claim 1, wherein the nanoparticles are administered:

i) more than $10^{-9}$ m away from the body part, and/or ii) less than 1 meter away from the body part.

23. The method according to claim 7, wherein the nanoparticles remain in the body part during more than 1 sequence.

24. The method according to claim 7, wherein the nanoparticles have sizes before administration to the body part that do not decrease by more than 100% after administration in the body part.

25. The method according to claim 4, wherein the temperature increase is at least $10^{-5}\%$ larger in the presence than in the absence of the nanoparticles in the body.

26. The method according to claim 7, wherein the thermal conductivity or density of the body part, the velocity of the acoustic wave, the attenuation of the acoustic wave, the absorption of the acoustic wave, the elasticity of the acoustic wave, or the acoustic impendence of the acoustic wave is at least 1.001 larger or lower in a portion of the body part comprising the nanoparticles than in a portion of the body part not comprising the nanoparticles.

27. The method according to claim 15, wherein the compound is selected in the group consisting of: i), a therapeutic compound, ii) a metabolic compound, iii) a luminescent compound, iv) a fluorescent compound, v) a radioactive compound, vi) a diagnostic compound, and vii) a biological compound.

28. The method according to claim 18, wherein the nanoparticles or body part produces or generates at least one radical or reactive species selected from the group consisting of:

i) radical or reactive species selected from the group consisting of superoxide, oxygen radical, hydroxyl, alkoxy radical, peroxyl radical, nitric oxide, nitrogen monoxide, and nitrogen dioxide, ii) radical or reactive species associated with, derived from, originated from, or produced by $H_2O_2$, iii) radical or reactive species that are free, detached or dissociated radical or radical species from the nanoparticles, iv) radical or reactive species that are due to or associated with: a) a degradation of the nanoparticles, b) a decrease in size of the nanoparticle, or c) production by, release from, or dissociation from the nanoparticles of free ions, v) radical or reactive species producing oxidative stress, vi) radical or reactive species due to a Fenton or Haber-Weiss reaction of the nanoparticles, vii) radical or reactive species present in a quantity or concentration that corresponds to a quantity or a concentration of radical or reactive species produced or generated by the nanoparticles, and viii) radical or reactive species present in a quantity or concentration different from a quantity or concentration produced or generated by the nanoparticles.

* * * * *